United States Patent
Chi

(10) Patent No.: US 10,100,115 B2
(45) Date of Patent: Oct. 16, 2018

(54) METHODS FOR THE TREATMENT OF VASCULARIZING CANCERS

(71) Applicant: MacroGenics, Inc., Rockville, MD (US)

(72) Inventor: Andrew S. Chi, Boston, MA (US)

(73) Assignee: MacroGenics, Inc., Rockville, MD (US)

( * ) Notice: Subject to any disclaimer, the term of this patent is extended or adjusted under 35 U.S.C. 154(b) by 0 days.

(21) Appl. No.: 15/118,010

(22) PCT Filed: Feb. 11, 2015

(86) PCT No.: PCT/US2015/015320
§ 371 (c)(1),
(2) Date: Aug. 10, 2016

(87) PCT Pub. No.: WO2015/123241
PCT Pub. Date: Aug. 20, 2015

(65) Prior Publication Data
US 2017/0008961 A1    Jan. 12, 2017

Related U.S. Application Data

(60) Provisional application No. 61/939,804, filed on Feb. 14, 2014.

(51) Int. Cl.
*C07K 16/22*     (2006.01)
*C07K 16/28*     (2006.01)
*A61K 39/00*     (2006.01)

(52) U.S. Cl.
CPC .......... *C07K 16/2827* (2013.01); *C07K 16/22* (2013.01); *A61K 2039/507* (2013.01); *A61K 2039/545* (2013.01); *C07K 2317/24* (2013.01); *C07K 2317/31* (2013.01); *C07K 2317/56* (2013.01); *C07K 2317/94* (2013.01)

(58) Field of Classification Search
CPC ................ C07K 16/22; C07K 16/2827; C07K 2317/24; C07K 2317/56; A61K 2039/507
USPC .................................... 1/1; 424/133.1, 178.1
See application file for complete search history.

(56) References Cited

U.S. PATENT DOCUMENTS

| | | |
|---|---|---|
| 4,526,938 A | 7/1985 | Churchill et al. |
| 4,676,980 A | 6/1987 | Segal et al. |
| 4,880,078 A | 11/1989 | Inoue et al. |
| 5,128,326 A | 7/1992 | Balazs et al. |
| 5,208,020 A | 5/1993 | Chari et al. |
| 5,390,540 A | 2/1995 | Mallison |
| 5,416,064 A | 5/1995 | Chari et al. |
| 5,552,391 A | 9/1996 | Coutts et al. |
| 5,624,821 A | 4/1997 | Winter |
| 5,656,444 A | 8/1997 | Webb |
| 5,679,377 A | 10/1997 | Bernstein et al. |
| 5,855,913 A | 1/1999 | Hanes et al. |
| 5,874,064 A | 2/1999 | Edwards et al. |
| 5,885,573 A | 3/1999 | Bluestone |
| 5,888,533 A | 3/1999 | Dunn |
| 5,912,015 A | 6/1999 | Bernstein et al. |
| 5,916,597 A | 6/1999 | Lee et al. |
| 5,934,272 A | 8/1999 | Lloyd et al. |
| 5,945,155 A | 8/1999 | Grill et al. |
| 5,985,309 A | 11/1999 | Edwards et al. |
| 5,985,320 A | 11/1999 | Edwards et al. |
| 5,989,463 A | 11/1999 | Tracy et al. |
| 6,019,968 A | 2/2000 | Platz et al. |
| 6,054,561 A | 4/2000 | Ring |
| 6,218,149 B1 | 4/2001 | Morrison et al. |
| 6,333,410 B1 | 12/2001 | Widdison et al. |
| 6,340,701 B1 | 1/2002 | Blatter et al. |
| 6,372,738 B2 | 4/2002 | Blattler et al. |
| 6,436,931 B1 | 8/2002 | Blattler et al. |
| 6,441,163 B1 | 8/2002 | Widdison et al. |
| 6,472,511 B1 | 10/2002 | Leung et al. |
| 6,596,757 B1 | 7/2003 | Miller et al. |
| 6,737,056 B1 | 5/2004 | Presta |
| 6,884,879 B1 | 4/2005 | Baca et al. |
| 6,891,030 B2 | 5/2005 | Chen |
| 6,946,292 B2 | 9/2005 | Kanda et al. |
| 7,060,269 B1 | 6/2006 | Baca et al. |

(Continued)

FOREIGN PATENT DOCUMENTS

| | | |
|---|---|---|
| CA | 2145985 | 9/2003 |
| CA | 2286330 | 6/2008 |

(Continued)

OTHER PUBLICATIONS

Sun et al. OncoTargets and Therapy 2014:7 1979-1986.*
International Search Report PCT/US2015/015320 (WO 2015/123241) (dated 2015) (4 pages).
Qin, X., et al., (2013) "B7-H3 is a New Cancer-Specific Endothelial Marker in Clear Cell Renal Cell Carcinoma," Onco Targets Ther. 6:1667-1673.
Written Opinion of the International Searching Authority PCT/US2015/015320 (WO 2015/123241) (dated 2015) (5 pages).
Agarwal, A et al. (2008) "*The Role of Positive Costimulatory Molecules in Transplantation and Tolerance*," Curr. Opin. Organ Transplant 13:366-372.

(Continued)

*Primary Examiner* — Lynn A Bristol
(74) *Attorney, Agent, or Firm* — William C. Schrot; AuerbachSchrot LLC

(57) ABSTRACT

The invention concerns therapeutic compositions for the treatment of vascularizing cancers, especially, glioblastoma. In particular, the invention is directed to compositions that comprise a molecule having a binding ability that is specific for B7-H3 and a molecule having a binding ability that is specific for a cell-surface factor (or its receptor) that is involved in promoting tumor angiogenesis (especially VEGF or its receptor, VEGFR). The invention is additionally directed to the use of such compositions in the treatment of such cancers, and in particular, in the treatment of glioblastoma.

10 Claims, 11 Drawing Sheets
Specification includes a Sequence Listing.

(56) References Cited

U.S. PATENT DOCUMENTS

| | | | |
|---|---|---|---|
| 7,122,637 B2 | 10/2006 | Presta | |
| 7,169,901 B2 | 1/2007 | Baca et al. | |
| 7,183,387 B1 | 2/2007 | Presta | |
| 7,276,497 B2 | 10/2007 | Widdison et al. | |
| 7,276,586 B2 | 10/2007 | Goddard et al. | |
| 7,279,567 B2 | 10/2007 | Mikesell et al. | |
| 7,297,334 B2 | 11/2007 | Baca et al. | |
| 7,317,091 B2 | 1/2008 | Dang et al. | |
| 7,332,581 B2 | 2/2008 | Presta | |
| 7,335,742 B2 | 2/2008 | Presta | |
| 7,355,008 B2 | 4/2008 | Stavenhagen et al. | |
| 7,358,354 B2 | 4/2008 | Chang et al. | |
| 7,365,166 B2 | 4/2008 | Baca et al. | |
| 7,368,554 B2 | 5/2008 | Chang et al. | |
| 7,371,826 B2 | 5/2008 | Presta | |
| 7,375,193 B2 | 5/2008 | Baca et al. | |
| 7,416,727 B2 | 8/2008 | Presta | |
| 7,521,542 B2 | 4/2009 | Huang et al. | |
| 7,527,969 B2 | 5/2009 | Mather et al. | |
| 7,585,857 B2 | 9/2009 | Blattler et al. | |
| 7,622,656 B2 | 11/2009 | Chen | |
| 7,632,497 B2 | 12/2009 | Stavenhagen | |
| 7,732,131 B2 | 6/2010 | Moretta et al. | |
| 7,847,081 B2 | 12/2010 | Chen | |
| 7,851,432 B2 | 12/2010 | Widdison et al. | |
| 7,992,748 B2 | 8/2011 | Lawrence | |
| 8,101,178 B2 | 1/2012 | Babcook et al. | |
| 8,129,347 B2 | 3/2012 | Chen | |
| 8,802,091 B2 * | 8/2014 | Johnson | C07K 16/2809 |
| | | | 424/130.1 |
| 9,150,656 B2 * | 10/2015 | Johnson | A61K 45/06 |
| 9,441,049 B2 * | 9/2016 | Johnson | C07K 16/2809 |
| 9,487,587 B2 * | 11/2016 | Koenig | C07K 16/2827 |
| 9,714,295 B2 * | 7/2017 | Johnson | C07K 16/2827 |
| 9,714,296 B2 * | 7/2017 | Johnson | C07K 16/2827 |
| 2002/0028486 A1 | 3/2002 | Morrison et al. | |
| 2002/0032315 A1 | 3/2002 | Baca et al. | |
| 2004/0259075 A1 | 12/2004 | Dimitrov et al. | |
| 2006/0099216 A1 | 5/2006 | Nicholas Cardy et al. | |
| 2007/0059302 A1 | 3/2007 | Baca et al. | |
| 2007/0196374 A1 | 8/2007 | Baca et al. | |
| 2008/0226629 A1 | 9/2008 | Baca et al. | |
| 2009/0018315 A1 | 1/2009 | Chen | |
| 2011/0052575 A1 | 3/2011 | Baca et al. | |
| 2011/0081342 A1 | 4/2011 | Baca et al. | |
| 2012/0294796 A1 * | 11/2012 | Johnson | A61K 39/39558 |
| | | | 424/1.11 |
| 2013/0058927 A1 | 3/2013 | Baca et al. | |
| 2013/0149236 A1 * | 6/2013 | Johnson | A61K 45/06 |
| | | | 424/1.11 |
| 2014/0328750 A1 * | 11/2014 | Johnson | A61K 39/39558 |
| | | | 424/1.11 |
| 2015/0259434 A1 * | 9/2015 | Johnson | A61K 45/06 |
| | | | 424/1.11 |
| 2015/0274838 A1 * | 10/2015 | Johnson | A61K 45/06 |
| | | | 424/1.11 |
| 2016/0264672 A1 * | 9/2016 | Johnson | A61K 39/39558 |
| 2017/0198045 A1 * | 7/2017 | Johnson | C07K 16/2827 |
| 2017/0362333 A1 * | 12/2017 | Johnson | G01N 33/6893 |

FOREIGN PATENT DOCUMENTS

| | | |
|---|---|---|
| EP | 0359096 | 11/1997 |
| EP | 1292619 | 2/2008 |
| WO | WO 1992/019244 | 11/1922 |
| WO | WO 1991/005548 | 5/1991 |
| WO | WO 1996/020698 | 7/1996 |
| WO | WO 1997/032572 | 9/1997 |
| WO | WO 1997/044013 | 11/1997 |
| WO | WO 1998/031346 | 7/1998 |
| WO | WO 1998/045331 | 10/1998 |
| WO | WO 1999/015154 | 4/1999 |
| WO | WO 1999/020253 | 4/1999 |
| WO | WO 1999/058572 | 11/1999 |
| WO | WO 1999/066903 | 12/1999 |
| WO | WO 2000/042072 | 7/2000 |
| WO | WO 2001/094413 | 12/2001 |
| WO | WO 2002/010187 | 2/2002 |
| WO | WO 2002/032375 | 4/2002 |
| WO | WO 2003/035835 | 5/2003 |
| WO | WO 2004/001381 | 12/2003 |
| WO | WO 2004/063351 | 7/2004 |
| WO | WO 2004/093894 | 11/2004 |
| WO | WO 2005/011542 | 2/2005 |
| WO | WO 2005/061547 | 7/2005 |
| WO | WO 2005/110474 | 11/2005 |
| WO | WO 2006/016276 | 2/2006 |
| WO | WO 2006/088494 | 8/2006 |
| WO | WO 2006/113665 | 10/2006 |
| WO | WO 2007/021841 | 2/2007 |
| WO | WO 2007/106707 | 9/2007 |
| WO | WO 2008/002933 | 1/2008 |
| WO | WO 2008/066691 | 6/2008 |
| WO | WO 2008/105886 | 9/2008 |
| WO | WO 2008/116219 | 9/2008 |
| WO | WO 2008/157379 | 12/2008 |
| WO | WO 2010/080538 | 7/2010 |
| WO | WO 2011/109400 | 9/2011 |

OTHER PUBLICATIONS

Aggarwal, C. et al. (2012) "*Antiangiogenic Agents in the Management of Non-Small Cell Lung Cancer: Where Do We Stand Now and Where Are We Headed?*" Cancer Biol. Ther. 13(5):247-263.

Alegre, M.L. et al. (1994) "*A Non Activating "Humanized" Anti-CD3 Monoclonal Antibody Retains Immunosuppressive Properties in Vivo*," Transplantation 57:1537-1543.

Anonymous (2013) "*Ramucirumab Takes Steps Forward in Gastric Cancer*," Cancer Discov. 3(12):of 4.

Aprile, G. et al. (2013) "*Critical Appraisal of Ramucirumab (IMC-1121B) For Cancer Treatment: From Benchside to Clinical Use*" Drugs 73(18):2003-2015.

Armour, K.L. et al. (1999) "*Recombinant human IgG Molecules Lacking Fcgamma Receptor I Binding and Monocyte Triggering Activities*," Eur. J. Immunol 29:2613-2624.

Aruffo, A et al. (1987) *Molecular Cloning of a CD28 cDNA by a High Efficiency COS Cell Expression System* Proc. Natl. Acad. Sci. (U.S.A.) 84:8573-8577.

Atwell et al. (1997) *Stable Heterodimers From Remodeling The Domain Interface of a Homodimer Using a Phage Display Library*, J. Mol. Biol. 270:26-35.

Baca, M. et al. (1997) "*Antibody Humanization Using Monovalent Page Display*," J. Biol. Chem. 272(16):10678-10684.

Baeuerle, P et al. (2008) "*BiTE®: A New Class OfAntibodies That Recruti T Cells*," Drugs of the Future 33:137-147.

Bargou, et al. (2008) *Tumor Regression in Cancer Patients by Very Low Doses of a T Cell-Engaging Antibody*, Science 321:974-977.

Batchelor, T.T. et al. (2007) "*AZD2171, a Pan-VEGF Receptor Tyrosine Kinase Inhibitor, Nonnalizes Tumor Vasculature and Alleviates Edema in Glioblastoma Patients*," Cancer Cell 11:83-95.

Batchelor, T.T. et al. (2013) "*Improved Tumor Oxygenation and Survival in Glioblastoma Patients Who Show Increased Blood Perfusion After Cediranib and Chemoradiation*," Proc. Natl. Acad. Sci. U.S.A. 110(47):19059-19064.

Bernard, A. et al. (2005) "*T and B Cell Cooperation: A Dance of Life and Death*," Transplantation 79:S8-S11.

Boyer, S.J. (2002) "*Small Molecule Inhibitors of KDR (VEGFR-2) Kinase: An Overview of Structure Activity Relationships*," Current Topics in Medicinal Chemistry 2:973-1000.

Buchwald et al. (1980) *Long-Term Continuous Intravenous Heparin Administration by an Implantable Infusion Pump in Ambulatory Patients With Recurrent Venous Thrombosis*, Surgery 88:507-516.

Buie, L. W. et al. (2008) "*Bevacizumab: A Treatment Option for Recurrent Glioblastoma Multiforme*," The Annals of Pharmacotherapy 42:1486-1490.

Cao, R. et al. (2010) "*VEGFRI-Mediated Pericyte Ablation Links VEGF and PLGF to Cancer-Associated Retinopathy*," Proc. Natl. Acad. Sci. (U.S.A.) 107(2):586-861.

(56) References Cited

OTHER PUBLICATIONS

Carillo, J.A. et al. (2012) "Relationship between Tumor Enhancement, Edema, IDH1 Mutational Status, MGMT Promoter Methylation, and Survival in Glioblastoma," Amer. J. Neuroradiol. 10.3174/ajnr.A2950, pp. 1-7.

Caron, P.C. et al. (1992) "Engineered Humanized Dimeric Forms of IgG Are More Effective Antibodies," J. Exp. Med. 176:1191-1195.

Carter, P. et al. (1992) "Humanization of An Anti-p185her2 Antibody for Human Cancer Therapy," Proc. Natl. Acad. Sci. (U.S.A.) 89:4285-4289.

Castriconi et al. (2004) "Identification of 4Ig-B7-H3 as a Neuroblastoma Associated Molecule That Exerts A Protective Role From an NK Cell-Mediated Lysis," Proc. Natl. Acad. Sci. (U.S.A.) 101(34):12640-12645.

Cesca, M. et al. (2013) "Tumor Delivery of Chemotherapy Combined with Inhibitors of Angiogenesis and Vascular Targeting Agents," Front Oncol. 3:259:1-7.

Chakrabarti, I. et al. (2005) "A Population-Based Description of Glioblastoma Multiforme in Los Angeles County, 1974-1999," Cancer 104(12):2798-2806.

Chapoval, A. et al. (2001) "B7-H3: A Costimulatory Molecule for T Cell Activation and IFN-γ Production," Nature Immunol. 2:269-274.

Chaudhry, I. H. et al. (2001) "Vascular Endothelial Growth Factor Expression Correlates With Tumour Grade and Vascularity in Gliomas," Histopathology 39:409-415.

Cheng, S. Y. et al. (1996) "Suppression of Glioblastoma Angiogenicity and Tumorigenicity by Inhibition of Endogenous Expression of Vascular Endothelial Growth Factor," Proc. Natl. Acad. Sci. USA 93:8502-8507.

Choi, B. D. et al. (2013) "Regulatory T Cells Are Redirected to Kill Glioblastoma by an EgfrvIII-Targeted Bispecific Antibody," OncoImmunology 2(12):e26757:1-2.

Clarke, J.M. et al. (2013) "Targeted Inhibition of VEGF Receptor 2: An Update on Ramucirumab," Expert Opin. Biol. Ther. 13(8):1187-1196.

Co, M. S. et al. (1991) "Humanized Antibodies for Antiviral Therapy," Proc. Natl. Acad. Sci. (U.S.A.) 88:2869-2873.

Co, M.S. et al. (1992) "Chimeric and Humanized Antibodies With Specificity for the CD33 Antigen," J. Immunol. 148:1149-1154.

Collins, M. et al. (2005) "The B7 Family of Immune-Regulatory Ligands," Genome Biol. 6:223.1-223.7.

Connolly, D.T. (1989) "Tumor vascular permeability factor stimulates endothelial cell growth and angiogenesis," The Journal of Clinical Investigation 84(5):1470-1478.

Coyle, A.J. et al. (2001) "The Expanding B7 Superfamily: Increasing Complexity in Costimulatory Signals Regulating T Cell Function," Nature Immunol. 2(3):203-209.

Das, S. et al. (2013) "Angiogenesis in Glioblastoma," The New England Journal of Medicine 369(16): 1561-1563.

Debinski, W. et al. (2001) "VEGF-D is an X-linked/AP-1 Regulated Putative Onco-angiogen in Human Glioblastoma Hultiforme," Molecular Medicine 7(9):598-608.

di Tomaso, E. et al. (2011) "Glioblastoma Recurrence after Cediranib Therapy in Patients: Lack of "Rebound" Revascularization as Mode of Escape," Cancer Res. 71:19-28.

Dietrich, J. et al. (2009) "Cediranib: Profile of A Novel Anti-Angiogenic Agent in Patients With Glioblastoma," Expert Opin. Investig. Drugs. 18(10):1549-1557.

Dietvorst, M.H. et al. (2013) "Current and Novel Treatment Options for Metastatic Colorectal Cancer: Emphasis on Aflibercept," Biol. Ther. 3:25-33.

Dillman et al. (1988) "Superiority of An Acid-Labile Daunorubicin Monoclonal Antibody Immunoconjugate Compared to Free Drug," Cancer Res. 48:6097-6102.

Dong, C. et al. (2003) "Immune Regulation by Novel Costimulatory Molecules," Immunolog. Res. 28(1):39-48.

Duncan, A.R. et al. (1988) "Localization of the Binding Site for The Human High-Affinity Fc Receptor on IgG," Nature 332:563-564.

During et al. (1989) "Controlled Release of Dopamine From A Polymeric Brain Implant: In Vivo Characterization," Ann. Neurol. 25:351-356.

Elkabetz et al. (2005) "Cysteines in CHI Underlie Retention of Unassembled Ig Heavy Chains," J. Biol. Chem. 280:14402-14412.

Eveno, C. et al. (2012) "VEGF Levels and The Angiogenic Potential of the Microenvironment Can Affect Surgical Strategy for Colorectal Liver Metastasis," Cell. Adh. Migr. 6(6):569-573.

Ferrara, N. et al. (1997) "The Biology of Vascular Endothelial Growth Factor," Endocrine Reviews 18:4-25.

Ferrara, N. et al. (2004) "Discovery and Development of Bevacizumab, An Anti-Vegf Antibody for Treating Cancer" Nature Reviews Drug Discovery 3:391-400.

Flies, D.B. et al. (2007) "The New B7s: Playing a Pivotal Role in Tumor Immunity," J. Immunother. 30(3):251-260.

Fuchs, C.S. et al. (2014) "Ramucirumab Monotherapy for Previously Treated Advanced Gastric or Gastro-Oesophageal Junction Adenocarcinoma (REGARD): An International, Randomised, Multicentre, Placebo-Controlled, Phase 3 Trial," Lancet 383(9911):31-39.

Fukushima, A. et al. (2007) "B7-H3 Regulates The Development of Experimental Allergic Conjunctivitis in Mice," Immunol. Lett. 113:52-57.

Gerstner, E.R. et al. (2012) "Antiangiogenic Therapy for Glioblastoma," Cancer J. 18(1):45-50.

Goldman, C. K. et al. (1993) "Epidermal Growth Factor Stimulates Vascular Endothelial Growth Factor Production by Human Malignant Glioma Cells: A Model of Glioblastoma Multiforme Pathophysiology," Molecular Biology of the Cell 4:121-133.

Gollmer, J. C. et al. (2000) "Expression of vascular endothelial growth factor-b in human astrocytoma," Neuro-Oncology 2:80-86.

Gorman, S. D. et al. (1991) "Reshaping A Therapeutic CD4 Antibody," Proc. Natl. Acad. Sci. (U.S.A.) 88:4181-4185.

Greenwald, R.J. et al. (2005) "The B7 Family Revisited," Ann. Rev. Immunol. 23:515-548.

Grossman, R. et al. (2014) "Combination of anti-VEGF therapy and temozolomide in two experimental human glioma models," J Neurooncol 116:59-65.

Hashiguchi, M. et al. (2008) "Triggering Receptor Expressed on Myeloid Cell-Like Transcript 2 (TLT-2) Is a Counter-Receptor for B7-H3 and Enhances T Cell Responses," Proc. Natl. Acad. Sci. (U.S.A.) 105(30):10495-10500.

Hofmeyer, K. et al. (2008) "The Contrasting Role of B7-H3," Proc. Natl. Acad. Sci. (U.S.A.) 105(30):10277-10278.

Holmes, K., et al. (2007) "Vascular Endothelial Growth Factor Receptor-2: Structure, Function, Intracellular Signalling and Therapeutic Inhibition," Cellular Signaling 19:2003-2012.

Houck, K.A. et al. (1991) "The Vascular Endothelial Growth Factor Family: Identification of A Fourth Molecular Species and Characterization of Alternative Splicing of RNA," Mol. Endocrinol. 5(12):1806-1814.

Howard et al. (1989) "Intracerebral Drug Delivery in Rats With Lesion Induced Memory Deficits," J. Neurosurg. 7(1):105-112.

Hutchins et al. (1995) "Improved Biodistribution, Tumor Targeting, and Reduced Immunogenicity in Mice With a Gamma 4 Variant of Campath-1H," Proc. Natl. Acad. Sci. (U.S.A.) 92:11980-84.

Ichimura, K. et al. (2009) "IDH1 Mutations are Present in the Majority of Common Adult Gliomas But Rare in Primary Glioblastomas," Neuro. Oncol. 11(4):341-347.

Idusogie, E.E. et al. (2000) "Mapping of the C1q Binding Site on Rituxan, A Chimeric Antibody With a Human IgG Fc," J. Immunol. 164:4178-4184.

Idusogie, E.E. et al. (2001) "Engineered Antibodies With Increased Activity to Recruit Complement," J. Immunol. 166:2571-2575.

Inda, M. et al. (2014) "Glioblastoma Multiforme: A Look Inside Its Heterogeneous," Cancers 6:226-239.

Ishigami, S.I. et al. (1998) "Predictive Value of Vascular Endothelial Growth Factor (VEGF) in Metastasis and Prognosis of Human Colorectal Cancer," Br. J. Cancer 78:1379-1384.

Jefferis, R. et al. (1995) "Recognition Sites on Human IgG for Fc Gamma Receptors: The Role of Glycosylation," Immunol. Lett. 44:111-117.

(56) References Cited

OTHER PUBLICATIONS

Jefferis, R. et al. (1996) "*Modulation of Fc(Gamma)R and Human Complement Activation by IgG3-Core Oligosaccharide Interactions*," Immunol. Lett. 54:101-104.
Jefferis, R. et al. (2002) "*Interaction Sites on Human IgG-Fc for FcgammaR: Current Models*," Immunol. Lett. 82:57-65.
Ji, X. et al. (2013) "*Knockdown of Nrf2 Suppresses Glioblastoma Angiogenesis by Inhibiting Hypoxia-Induced Activation of HIF-Lcx*," International Journal of Cancer 135(3):574-584.
Jin, K. et al. (2010) "*Aflibercept (VEGF Trap): one more double-edged sword of anti-VEGF therapy for cancer?*" Clin. Trans. Oncol. 12:526-532.
Johansson, M. et al. (2002) "*Spatial expression of VEGF-A in human glioma*," Journal of Neuro-Oncology 59:1-6.
Kaya, M. et al. (2000) "*Vascular Endothelial Growth Factor Expression in Untreated Osteosarcoma is Predictive of Pulmonary Metastasis and Poor Prognosis*," Clin. Cancer Res. 6:572-577.
Kettleborough, C. A. et al. (1991) "*Humanization of A Mouse Monoclonal Antibody by CDR-Grafting: The Importance of Framework Residues on Loop Conformation*," Protein Engineering 4:773-3783.
Keunen, O. et al. (2011) "*Anti-VEGF Treatment Reduces Blood Supply and Increases Tumor Cell Invasion in Glioblastoma*," Proc. Natl. Acad. Sci. U.S.A. 108(9):3749-3754.
Khawli, L.A. et al. (2008) "*Cytokine, Chemokine, and Co-Stimulatory Fusion Proteins for the Immunotherapy of Solid Tumors*," Exper. Pharmacol. 181:291-328.
Kim, K.B. (2013) "*Is There a Role for Targeting Vascular Endothelial Growth Factor/Receptor Axis in the Treatment of Patients With Metastatic Melanoma?*" Cancer 119(3):477-480.
King, R.G. et al. (2006) "*Trem-Like Transcript 2 is Expressed on Cells of the Myeloid/Granuloid and B Lymphoid Lineage and is Up-Regulated in Response to Inflammation*," J. Immunol. 176:6012-6021.
Kleihues, P. et al. (1997) "*Genetics of Glioma Progression and the Definition of Primary and Secondary Glioblastoma*," Brain Pathology 7:1131-1136.
Klement, G., et al. (2002) "*Differences in Therapeutic Indexes of Combination Metronomic Chemotherapy and an Anti-VEGFR-2 Antibody in Multidrug-resistant Human Breast Cancer Xenografts*," Clin. Cancer Res. 8:221-232.
Klesney-Tait, J. et al. (2006) "*The TREM Receptor Family and Signal Integration*," Nat. Immunol. 7:1266-1273.
Koch, S. et al. (2011) "*Signal Transduction by Vascular Endothelial Growth Factor Receptors*," Biochem. J. 437:169-183.
Korman, A.J. et al. (2007) "*Checkpoint Blockade in Cancer Immunotherapy*," Adv. Immunol. 90:297-339.
Kubota, Y. (2012) "*Tumor Angiogenesis and Anti-Angiogenic Therapy*," Keio J. Med. 61(2):47-56.
Kunkel, P. et al. (2001) "*Inhibition of Glioma Angiogenesis and Growth in Vivo by Systemic Treatment with a Monoclonal Antibody against Vascular Endothelial Growth Factor Receptor-2*," Cancer Research 61:6624-6628.
Laigle-Donadey, F. et al. (2009) "*Association of Radiotherapy and Chemotherapy-Targeted Therapies in Glioblastomas*," Bull. Cancer. 96(3):291-297 (Abstract Translation Only).
Lamelas, I. et al. (2012) "*Directed Therapies in Lung Cancer: New Hope?*," Arch. Bronconeumol. 48(10):367-371.
Lamszus, K. et al. (2003) "*Levels of Soluble Vascular Endothelial Growth Factor (VEGF) Receptor 1 in Astrocytic Tumors and Its Relation to Malignancy, Vascularity, and VEGF-A*," Clinical Cancer Research 9:1399-1405.
Langer (1990) "*New Methods of Drug Delivery*," Science 249:1527-1533.
Leder, K. et al (2014) "*Mathematical Modeling of PDGF-Driven Glioblastoma Reveals Optimized Radiation Dosing Schedules*," Cell 156:603-616.
Lenschow, D.J. et al. (1996) "*CD28/B7 System of T Cell Costimulation*," Ann. Rev. Immunol. 14:233-258.

Leung, D.W. et al. (1989) "*Vascular Endothelial Growth Factor is a Secreted Angiogenic Mitogen*," Science 246(4935):1306-1309.
Levy et al. (1985) "*Inhibition of Calcification of Bioprosthetic Heart Valves by Local Controlled-Release Diphosphonate*," Science 228:190-192.
Liang, Y. et al. (2002) "*Activation of Vascular Endothelial Growth Factor a Transcription in Tumorigenic Glioblastoma Cell Lines by an Enhancer with CellType-specific DNase I Accessibility*," The Journal of Biological Chemistry 277:20087-20094.
Lindley, P.S. et al. (2009) "*The Clinical Utility of Inhibiting CD28-Mediated Costimulation*," Immunol. Rev. 229:307-321.
Liu, L. et al. (2012) "*Prognostic Value of Vascular Endothelial Growth Factor Expression in Resected Gastric Cancer*," Asian Pac. J. Cancer Prey. 13(7):3089-3097.
LoBuglio, A.F. et al. (1989) "*Mouse/Human Chimeric Monoclonal Antibody in Man: Kinetics and Immune Response*," Proc. Natl. Acad. Sci. (U.S.A.) 86:4220-4224.
Loke, P. et al. (2004) "*Emerging Mechanisms of Immune Regulation: The Extended B7 Family and Regulatory T Cells.*" Arthritis Res. Ther. 6:208-214.
Lund et al. (1991) "*Human Fc Gamma RI and Fc Gamma RII Interact With Distinct But Overlapping Sites on Human IgG*," J. Immunol. 147:2657-2662.
Lund et al. (1992) "*Multiple Binding Sites on the CH2 Domain of IgG for Mouse Fc Gamma RII*," Mol. Immunol. 29:53-59.
Lund, J. et al. (1995) "*Oligosaccharide-Protein Interactions in IgG Can Modulate Recognition by Fc Gamma Receptors*," FASEB J. 9:115-19.
Lund, J. et al. (1996) "*Multiple Interactions of IgG With Its Core Oligosaccharide Can Modulate Recognition by Complement and Human Fc Gamma Receptor I and Influence the Synthesis of Its Oligosaccharide Chains*," J. Immunol. 157:4963-4969.
Maeda, H. et al. (1991) "*Construction of Reshaped Human Antibodies With HIV-Neutralizing Activity*," Human Antibodies Hybridoma 2:124-134.
Maeda, K. et al. (1996) "*Prognostic Value of Vascular Endothelial Growth Factor Expression in Gastric Carcinoma*," Cancer 77:858-863.
Mahato et al. (1997) "*Cationic Lipid-Based Gene Delivery Systems: Pharmaceutical Perspectives*," Pharm. Res. 14:853-859.
Martin-Orozco, N. et al. (2007) "*Inhibitory Costimulation and Anti-Tumor Immunity*," Semin. Cancer Biol. 17(4):288-298.
McNamara, M. G. et al. (2013) "*Emerging Biomarkers in Glioblastoma*," Cancers 5:1103-1109.
McNamara, M. G. et al. (2014) "*Conditional Probability of Survival and Post-Progression Survival in Patients with Glioblastoma in The Temozolomide Treatment Era*," J. Neurooncol.:8 pages.
McNamara, M. G. et al. (2014) "*Factors Impacting Survival Following Second Surgery in Patients with Glioblastoma in the Temozolomide Treatment Era, Incorporating Neutrophivlymphocyte Ratio and Time to First Progression*," J. Neurooncol.:6 pages.
Mendez, O. et al. (2010) "*Knock down of HIF-1 a in glioma cells reduces migration in vitro and invasion in vivo and impairs their ability to form tumor spheres*," Molecular Cancer 9:133:1-10.
Miyake, T.M. et al. (2013) "*Contemporary Use of Bevacizumab in Ovarian Cancer*," Expert Opin. Biol. Ther. 13(2):283-294.
Modak, S. et al. (1999) "*Disialoganglioside GD2 and Antigen 8H9: Potential Targets for Antibody-Based Immunotherapy Against Desmoplastic Small Round Cell Tumor (DSRCT) and Rhabdomyosarcoma (RMS)*," Proceedings of The American Association for Cancer Research Annual Meeting, vol. 40:474:#3133.
Modak, S. et al. (2000) "*Radioimmunotargeting to Human Rhabdomyosarcoma Using Monoclonal Antibody 8H9*," Proc. Am. Assoc. Cancer Res.41:724:#4600.
Modak, S. et al. (2001) "*Monoclonal Antibody 8H9 Targets a Novel Cell Surface Antigen Expressed by a Wide Spectrum of Human Solid Tumors*," Cancer Res. 61(10):4048-4054.
Moeini, A. et al. (2012) "*Emerging Signaling Pathways in Hepatocellular Carcinoma*," Liver Cancer 1(2):83-93.
Moradi, A. et al. (2013) "*Vascular Endothelial Growth Factor Trap-Eye (Aflibercept) For The Management of Diabetic Macular Edema*," World J. Diabetes. 4(6):303-309.

(56) References Cited

OTHER PUBLICATIONS

Mrugala, M.M. (2013) "*Advances and Challenges in the Treatment of Glioblastoma: A Clinician's Perspective*," Discov. Med. 15(83):221-230.

Narita, Y. (2013) "*Drug Review: Safety and Efficacy of Bevacizumab for Glioblastoma and Other Brain Tumors*," Jpn. J. Clin. Oncol. 43(6):587-595.

Neufeld, G., et al. (1999) "*Vascular Endothelial Growth Factor (VEGF) and Its Receptors*," The FASEB Journal 13:9-22.

Ning et al. (1996) "*Intratumoral Radioimmunotheraphy of A Human Colon Cancer Xenograft Using a Sustained Release Gel*," Radiotherapy & Oncology 39:179-189.

Pavlidis, E.T. et al. (2013) "*Role of Bevacizumab in Colorectal Cancer Growth and Its Adverse Effects: A Review*," World J. Gastroenterol. 19(31):5051-5060.

Pellegatta, S. et al. (2011) "*Brain Cancer Immunoediting: Novel Examples Provided by Immunotherapy of Malignant Gliomas*," Expert Rev. Anticancer Ther. 11(11):1759-1774.

Plate, K. H. et al. (1997) "*Vascular Endothelial Growth Factor*," Journal of Neuro-Oncology 35:365-372.

Plate, K.H. et al. (2012) "*Tumor Angiogenesis and Anti-Angiogenic Therapy in Malignant Gliomas Revisited*," Acta Neuropathol. 124(6):763-775.

Prasad, D.V. et al. (2004) "*Murine B7-H3 is a Negative Regulator of T Cells*," J. Immunol. 173:2500-2506.

Presta, L.G. et al. (1997) "*Humanization of An Anti-Vascular Endothelial Growth Factor Monoclonal Antibody for The Therapy of Solid Tumors and Other Disorders*," Cancer Res. 57(20):4593-4599.

Presta, L.G. et al. (2002) "*Engineering therapeutic antibodies for improved function*," Biochem. Soc. Trans. 30(4):487-490.

Preusser, M. et al. (2011) "*Current Concepts and Management of Glioblastoma*," Annals of Neurology 70:9-21.

Reardon, D.A. et al. (2008) "*Glioblastoma Multiforme: An Emerging Paradigm of Anti-VEGF Therapy*," Expert Opin. Biol. Ther. 8(4):541-553.

Reddy, M.P. et al. (2000) "*Elimination of Fc Receptor-Dependent Effector Functions of A Modified IgG4 Monoclonal Antibody to Human CD4*," J. Immunol. 164:1925-1933.

Ridgway et al. (1996) "'*Knobs-Into-Holes' Engineering of Antibody CH3 Domains for Heavy Chain Heterodimerization*," Protein Engr. 9:617-621.

Riechmann, L et al. (1988) "*Reshaping Human Antibodies for Therapy*," Nature 332:323-327.

Roberts, E. et al. (2013) "*The Role of Vascular Endothelial Growth Factor in Metastatic Prostate Cancer to the Skeleton*," Prostate Cancer 2013:418340.

Rubenstein, J. L. et al. (2000) "*Anti-VEGF Antibody Treatment of Glioblastoma Prolongs Survival but Results in Increased Vascular Cooption*," Nature 2(4):306-314.

Saatian, B. et al. (2004) "*Expression of Genes for B7-H3 and Other T Cell Ligands by Nasal Epithelial Cells During Differentiation and Activation*," Amer. J. Physiol. Lung Cell. Mol. Physiol. 287:L217-L225.

Saintigny, P. et al. (2012) "*Recent Advances in Non-Small Cell Lung Cancer Biology and Clinical Management*," Discov. Med. 13(71):287-297.

Saito, T., et al. (2013) "*VEGF-A Induces Its Negative Regulator, Soluble Form of VEGFR-1, by Modulating Its Alternative Splicing*," FEBS Letters 587:2179-2185.

Sandstrom, M. et al. (2008) "*Effects of the VEGFR Inhibitor ZD6474 in Combination with Radiotherapy and Temozolomide in an Orthotopic Glioma Model*," J. Neurooncol. 88:1-9.

Sanli, A. M. et al. (2010) "*Unusual Manifestations of Primary Glioblastoma Multiforme: A Report of Three Cases*" Surgical Neurology Internationa 1:87:1-5.

Sassi, F. A. et al. (2014) "*Inhibitory Activities of 1Hchostatin a in U87 Glioblastoma Cells and Thmorsphere-Derived Cells*," J. Mol. Neuro.:14 pages.

Sato, K. et al. (1993) "*Reshaping a Human Antibody to Inhibit the Interleukin 6-Dependent Tumor Cell Growth*," Cancer Res 53:851-856.

Saudek et al. (1989) "*A Preliminary Trial of The Programmable Implantable Medication System for Insulin Delivery*," N. Engl. J. Med. 321:574-579.

Sawa, H. et al. (2002) "*Histone Deacetylase Inhibitors Such As Sodium Butyrate and Trichostatin A Inhibit Vascular Endothelial Growth Factor (VEGFJ Secretion From Human Glioblastoma Cells*," Brain Tumor Pathol. 19:77-81.

Schittenhelm, J. et al. (2010) "*Glioblastoma with Granular Cell Astrocytoma Features: A Case Report and Literature Review*," Clinical Neuropathology 29(5):323-329.

Sefton, (1987) "*Implantable Pumps*," CRC Crit. Rev. Biomed. Eng. 14:201-240 (Abstract Only).

Semenza, G.L. (2003) "*Targeting HIF-1 for Cancer Therapy*," Nature Reviews 3:721-732.

Sharpe, A.H. et al. (2002) "*The B7-CD28 Superfamily*," Nature Rev. Immunol. 2:116-126.

Shen, W.C. et al. (1981) "*cis-Aconityl Spacer Between Daunomycin and Macromolecular Carriers: A Model of pH-Sensitive Linkage Releasing Drug From a Lysosomotropic Conjugate*," Biochem. Biophys. Res. Comtnun. 102:1048-1054.

Shibuya, M. (2013) "*Vascular Endothelial Growth Factor and Its Receptor System: Physiological Functions in Angiogenesis and Pathological Roles in Various Diseases*," J. Biochem. 153(1):13-19.

Shields, R.L. et al. (2001) "*High Resolution Mapping of the Binding Site on Human IgG1 for Fc gamma RI, Fc gamma RII, Fc gamma RIII, and FcRn and Design of IgG1 Variants With Improved Binding to the Fc gamma R*," J. Biol. Chem. 276(9):6591-6604.

Shields, R.L. et al. (2002) "*Lack of fucose on human IgG1 N-linked oligosaccharide improves binding to human Fcgamma RIII and antibody-dependent cellular toxicity*," J. Biol. Chem. 26;277(30):26733-26740.

Shih, S. et al. (1999) "*Role of Protein Kinase C Isoforms in Phorbol Ester-induced Vascular Endothelial Growth Factor Expression in Human Glioblastoma Cells*," The Journal of Biological Chemistry 274:15407-15414.

Shopes, B. (1992) "*A Genetically Engineered Human IgG Mutant With Enhanced Cytolytic Activity*," J. Immunol. 148(9):2918-2922.

Simpson, L. et al. (2006) "*Recurrent Glioblastoma Multiforme: Advances in Treatment and Promising Drug Candidates*," Expert Rev. Anticancer Ther. 6(11):1593-607 (Abstract Only).

Song et al. (1995) "*Antibody Mediated Lung Targeting of Long Circulating Emulsions*," PDA Journal of Pharmaceutical Science & Technology 50:372 397.

Sonoda, Y. et al. (2003) "*Overexpression of Vascular Endothelial Growth Factor Isoforms Drives Oxygenation and Growth but not Progression to Glioblastoma Multiforme in a Human Model of Gliomagenesis*," Cancer Research 63:1962-1968.

Sophie, R. et al. (2012) "*Aflibercept: A Potent Vascular Endothelial Growth Factor Antagonist for Neovascular Age-Related Macular Degeneration and Other Retinal Vascular Diseases*," Biol. Ther. 2:3:1-22.

Stefanini, M.O. (2010) "*Increase of Plasma VEGF after Intravenous Administration of Bevacizumab is Predicted by a Pharmacokinetic Model*," Cancer Res. 70(23):9886-9894.

Steinberger, P. et al. (2004) "*Molecular Characterization of Human 4Ig-B7-H3, a Member of the B7 Family with Four Ig-Like Domains*," J. Immunol. 172(4):2352-2359.

Steiner, H. et al. (2004) "*Autocrine Pathways of the Vascular Endothelial Growth Factor (VEGF) in Glioblastoma Multiforme: Clinical Relevance of Radiation-Induced Increase of VEGF Levels*," Journal of Neuro-Oncology 66:129-138.

Stephan, J. et al. (1999) "*Selective Cloning of Cell Surface Proteins Involved in Organ Development: Epithelial Glycoprotein Is Involved in Normal Epithelial Differentiation*," Endocrinol. 140:5841-5854.

Stevenson, C.E. et al. (2012) "*Bevacizumab and Breast Cancer: What Does The Future Hold?*," Future Oncol. 8(4):403-414.

Stevenson, G.T. et al. (1989) "*A Chimeric Antibody With Dual Fc Regions (bisFabFc) Prepared by Manipulations at The IgG Hinge*," Anti-Cancer Drug Design 3:219-230 (Abstract Only).

(56) References Cited

OTHER PUBLICATIONS

Stockhammer, G. et al. (2000) "*Vascular Endothelial Growth Factor (VEGF) is Elevated in Brain Tumor Cysts and Correlates with Tumor Progression*," Acta. Neurophatho. 100:101-105.

Stopschinski, B. et al. (2013) "*Glioblastoma Cancer Stem Cells—from Concept to Clinical Application*," Cancer Letters 338:32-40.

Subudhi, S.K. et al. (2005) "*The Balance of Immune Responses: Costimulation Verse Coinhibition*," J. Mol. Med. 83:193-202.

Sugimoto, H. et al. (2003) "*Neutralization of Circulating Vascular Endothelial Growth Factor (VEGF) by Anti-VEGF Antibodies and Soluble VEGF Receptor 1 (sFit-I) Induces Proteinuria*," The Journal of Biological Chemistry 278:12605-12608.

Sullivan, L.A. (2010) "*The VEGF Family in Cancer and Antibody-Based Strategies for Their Inhibition*," mAbs 2:2:165-175.

Sun, M. et al. (2002) "*Characterization of Mouse and Human B7-H3 Genes*," J. Immunol. 168:6294-6297.

Sun, W. et al. (2014) "*Interleukin-1β promotes hypoxia-induced apoptosis of glioblastoma cells by inhibiting hypoxia-inducible factor-1 mediated adrenomedullin production*," Cell Death and Disease 5:e1020.

Takahashi, S. (2011) "*Vascular Endothelial Growth Factor (VEGF), VEGF Receptors and Their Inhibitors for Antiangiogenic Tumor Therapy*," Biol. Pharm. Bull. 34(12):1785-1788.

Tanako, S. et al. (1996) "Concentration of Vascular Endothelial Growth Factor in the Serum and Tumor Tissue of Brain Tumor Patients" Cancer Research 56:2185-2190.

Tanako, S. et al. (2003) "*Anti-Vascular Endothelial Growth Factor Antibody and Nimustine As Combined Therapy: Effects on Tumor Growth and Angiogenesis in Human Glioblastoma Xenografts*," Neuro-Oncology 5(1):1-7.

Taylor, L. et al. (2010) "*Diagnosis, Treatment, and Prognosis of Glioma: Five New Things*," Neurology 75:S28-S32.

Tempest, P.R. et al. (1991) "*Reshaping a Human Monoclonal Antibody to Inhibit Human Respiratory Syncytial Virus Infection in vivo*," Bio/Technology 9:266-271.

Tischer, E. et al. (1991) "*The Human Gene for Vascular Endothelial Growth Factor*," J. Biol. Chem. 266:11947-11954.

Trevisan, E. et al. (2014) "*Antiangiogenic Therapy of Brain Tumors: The Role of Bevacizumab*," Neurol. Sci.:8 pages.

Trouet et al. (1982) "*A Covalent Linkage Between Daunorubicin and Proteins That is Stable in Serum and Reversible by Lysosomal Hydrolases, As Required for a Lysosomofropic Drug-Carrier Conjugate: In Vitro and In Vivo Studies*," Proc. Natl. Acad. Sci. (U.S.A.) 79:626-629.

Vajkoczy, P. et al. (1999) "*Inhibition of Tumor Growth, Angiogenesis, and Microcirculation by the Novel Flk-1 Inhibitor SU5416 as Assessed by Intravital Multifluorescence Videomicroscopy*," Neoplasia 1(1):31-41.

Ventrice, P. et al. (2013) "*Anti-vascular endothelial growth factor drugs safety and efficacy in ophthalmic diseases*," J. Pharmacol. Pharmacother. 4(Suppl1):S38-S42.

Verhoeyen, M. et al. (1988) "*Reshaping Human Antibodies: Grafting an Antilysozyme Activity*," Science 239:1534-1536.

Vici, P. et al. (2014) "*Emerging Biological Treatments for Uterine Cervical Carcinoma*," J. Cancer 5(2):86-97.

Viglietta, V. et al. (2007) "*Modulating Co-Stimulation*," Neurotherapeutics 4:666-675.

Wadhwa, R. et al. (2013) "*Ramucirumab: a novel antiangiogenic agent*," Future Oncol. 9(6):789-795.

Wang, E. et al. (2014) "*The Role of Factor Inhibiting HIF (FIH-1) in Inhibiting HIF-1 Transcriptional Activity in Glioblastoma Multiforme*," Plos One 9:e86102:9 pages.

Wang, R. et al. (2010) "*Glioblastoma Stem-Like Cells Give Rise to Tumour Endothelium*," Nature 468:829-835.

Wang, S. et al. (2004) "*Co-Signaling Molecules of the B7-CD28 Family in Positive and Negative Regulation of T Lymphocyte Responses*," Microbes Infect. 6:759-766.

Welti, J. et al. (2013) "*Recent Molecular Discoveries in Angiogenesis and Antiangiogenic Therapies in Cancer*," J. Clin. Invest. 123(8):3190-3200.

Wicki, A. et al. (2012) "*Targeted Therapies in Breast Cancer*," Swiss Med. Wkly. 142:w13550:1-7.

Wolff, E.A. et al. (1993) "*Monoclonal Antibody Homodimers: Enhanced Antitumor Activity in Nude Mice*," Cancer Research 53:2560-2565.

Wu et al. (1987) "*Receptor-Mediated In Vitro Gene Transformation by a Soluble DNA Carrier System*," J. Biol. Chem. 262:4429-4432.

Xiang, F. et al. (2001) "*Expression of Vascular Endothelial Growth Factor (VEGFJ and Its Two Receptors in Diffusely Infiltrating Astrocytomas and Relationship to Proliferative Activity of Tumor Cells*," Brain Tumor Pathol. 18:67-71.

Xie et al. (2005) "*A New Format of Bispecific Antibody: Highly Efficient Heterodimerization, Expression and Tumor Cell Lysis*," J. Immunol. Methods 296:95-101.

Xu, D. et al. (2000) "*In Vitro Characterization of Five Humanized OKT3 Effector Function Variant Antibodies*," Cell. Immunol. 200:16-26.

Xu, H. et al. (2009) "*MicroRNA miR-29 Modulates Expression of Immunoinhibitory Molecule B7-H3: Potential Implications for Immune Based Therapy of Human Solid Tumors*," Cancer Res. 69(15):5275-6281.

Xue, Y. et al. (2008) "*Anti-VEGF Agents Confer Survival Advantages to Tumor-Bearing Mice by Improving Cancer Associated Systemic Syndrome*," Proc. Natl. Acad. Sci. (U.S.A.) 105(47):18513-18518.

Yan, K. et al. (2013) "*The Evolving Landscape of Glioblastoma Stem Cells*," Current Opinion 26(6):701-707.

Yang et al. (1988) "*Pharmacokinetics and Mechanism of Action of A Doxorubicin-Monoclonal Antibody 9.2.27 Conjugate Directed to a Human Melanoma Proteoglycan*," J. Natl. Canc. Inst. 80:1154-1159.

Yang, Y. et al. (2013) "*Anti-VEGF- and Anti-VEGF Receptor-Induced Vascular Alteration in Mouse Healthy Tissues*," Proc. Natl. Acad. Sci. (U.S.A.) 110(29):12018-12023.

Yi. K.H. et al. (2009) "*Fine Tuning the Immune Response Through B7-H3 and B7-H4*," Immunol. Rev. 229:145-151.

Zang, X. et al. (2003) "*B7x: A Widely Expressed B7 Family Member That Inhibits T Cell Activation*," Proc. Natl. Acad. Sci. (U.S.A.) 100:10388-10392.

Zang, X. et al. (2007) "*The B7 Family and Cancer Therapy: Costimulation and Coinhibition*," Clin. Cancer Res. 13:5271-5279.

Zhang, D. et al. (2011) "*Anti Angiogenic Agents Significantly Improve Survival in Tumor-Bearing Mice by Increasing Tolerance to Chemotherapy-Induced Toxicity*," Proc. Natl. Acad. Sci. (U.S.A.) 108(10):4117-4122.

Zuo et al. (2000) "*An efficient route to the production of an IgG-like bispecific antibody*," PE 13(5):361-367.

\* cited by examiner

SEQUENCE LISTING

```
<160> NUMBER OF SEQ ID NOS: 110

<210> SEQ ID NO 1
<211> LENGTH: 316
<212> TYPE: PRT
<213> ORGANISM: Homo sapiens
<220> FEATURE:
<221> NAME/KEY: MISC_FEATURE
<222> LOCATION: (1)..(316)
<223> OTHER INFORMATION: "2Ig" form of human B7-H3

<400> SEQUENCE: 1

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45
```

```
Cys Cys Ser Phe Ser Pro Glu Pro Gly Phe Ser Leu Ala Gln Leu Asn
     50                  55                  60

Leu Ile Trp Gln Leu Thr Asp Thr Lys Gln Leu Val His Ser Phe Ala
 65                  70                  75                  80

Glu Gly Gln Asp Gln Gly Ser Ala Tyr Ala Asn Arg Thr Ala Leu Phe
                 85                  90                  95

Pro Asp Leu Leu Ala Gln Gly Asn Ala Ser Leu Arg Leu Gln Arg Val
                100                 105                 110

Arg Val Ala Asp Glu Gly Ser Phe Thr Cys Phe Val Ser Ile Arg Asp
                115                 120                 125

Phe Gly Ser Ala Ala Val Ser Leu Gln Val Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Arg Gly Tyr Pro Glu Ala Glu Val
                165                 170                 175

Phe Trp Gln Asp Gly Gln Gly Val Pro Leu Thr Gly Asn Val Thr Thr
                180                 185                 190

Ser Gln Met Ala Asn Glu Gln Gly Leu Phe Asp Val His Ser Val Leu
                195                 200                 205

Arg Val Val Leu Gly Ala Asn Gly Thr Tyr Ser Cys Leu Val Arg Asn
    210                 215                 220

Pro Val Leu Gln Gln Asp Ala His Gly Ser Val Thr Ile Thr Gly Gln
225                 230                 235                 240

Pro Met Thr Phe Pro Pro Glu Ala Leu Trp Val Thr Val Gly Leu Ser
                245                 250                 255

Val Cys Leu Ile Ala Leu Leu Val Ala Leu Ala Phe Val Cys Trp Arg
                260                 265                 270

Lys Ile Lys Gln Ser Cys Glu Glu Asn Ala Gly Ala Glu Asp Gln
    275                 280                 285

Asp Gly Glu Gly Glu Gly Ser Lys Thr Ala Leu Gln Pro Leu Lys His
    290                 295                 300

Ser Asp Ser Lys Glu Asp Asp Gly Gln Glu Ile Ala
305                 310                 315

<210> SEQ ID NO 2
<211> LENGTH: 948
<212> TYPE: DNA
<213> ORGANISM: Homo sapiens
<220> FEATURE:
<221> NAME/KEY: misc_feature
<222> LOCATION: (1)..(948)
<223> OTHER INFORMATION: Polynucleotide Sequence Encoding the "2Ig"
      Form of Human B7-H3

<400> SEQUENCE: 2
atgctgcgtc ggcggggcag ccctggcatg ggtgtgcatg tgggtgcagc cctgggagca    60
ctgtggttct gcctcacagg agccctggag gtccaggtcc ctgaagaccc agtggtggca   120
ctggtgggca ccgatgccac cctgtgctgc tccttctccc ctgagcctgg cttcagcctg   180
gcacagctca acctcatctg gcagctgaca gataccaaac agctggtgca cagctttgct   240
gagggccagg accagggcag cgcctatgcc aaccgcacgg ccctcttccc ggacctgctg   300
gcacagggca acgcatccct gaggctgcag cgcgtgcgtg tggcggacga gggcagcttc   360
acctgcttcg tgagcatccg ggatttcggc agcgctgccg tcagcctgca ggtggccgct   420
ccctactcga agcccagcat gaccctggag cccaacaagg acctgcggcc aggggacacg   480
```

-continued

```
gtgaccatca cgtgctccag ctaccggggc taccctgagg ctgaggtgtt ctggcaggat      540
gggcagggtg tgcccctgac tggcaacgtg accacgtcgc agatggccaa cgagcagggc      600
ttgtttgatg tgcacagcgt cctgcgggtg gtgctgggtg cgaatggcac ctacagctgc      660
ctggtgcgca accccgtgct gcagcaggat gcgcacggct ctgtcaccat cacagggcag      720
cctatgacat tccccccaga ggccctgtgg gtgaccgtgg ggctgtctgt ctgtctcatt      780
gcactgctgg tggccctggc tttcgtgtgc tggagaaaga tcaaacagag ctgtgaggag      840
gagaatgcag gagctgagga ccaggatggg gagggagaag gctccaagac agccctgcag      900
cctctgaaac actctgacag caaagaagat gatggacaag aaatagcc                  948
```

<210> SEQ ID NO 3
<211> LENGTH: 534
<212> TYPE: PRT
<213> ORGANISM: Homo sapiens
<220> FEATURE:
<221> NAME/KEY: MISC_FEATURE
<222> LOCATION: (1)..(534)
<223> OTHER INFORMATION: "4Ig" form of human B7-H3

<400> SEQUENCE: 3

```
Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
            20                  25                  30

Val Pro Glu Asp Pro Val Val Ala Leu Val Gly Thr Asp Ala Thr Leu
        35                  40                  45

Cys Cys Ser Phe Ser Pro Glu Pro Gly Phe Ser Leu Ala Gln Leu Asn
    50                  55                  60

Leu Ile Trp Gln Leu Thr Asp Thr Lys Gln Leu Val His Ser Phe Ala
65                  70                  75                  80

Glu Gly Gln Asp Gln Gly Ser Ala Tyr Ala Asn Arg Thr Ala Leu Phe
                85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Ile Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
            260                 265                 270
```

Glu Pro Gly Phe Ser Leu Ala Gln Leu Asn Leu Ile Trp Gln Leu Thr
        275                 280                 285

Asp Thr Lys Gln Leu Val His Ser Phe Thr Glu Gly Arg Asp Gln Gly
    290                 295                 300

Ser Ala Tyr Ala Asn Arg Thr Ala Leu Phe Pro Asp Leu Leu Ala Gln
305                 310                 315                 320

Gly Asn Ala Ser Leu Arg Leu Gln Arg Val Arg Val Ala Asp Glu Gly
                325                 330                 335

Ser Phe Thr Cys Phe Val Ser Ile Arg Asp Phe Gly Ser Ala Ala Val
            340                 345                 350

Ser Leu Gln Val Ala Ala Pro Tyr Ser Lys Pro Ser Met Thr Leu Glu
                355                 360                 365

Pro Asn Lys Asp Leu Arg Pro Gly Asp Thr Val Thr Ile Thr Cys Ser
    370                 375                 380

Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
                405                 410                 415

Gln Gly Leu Phe Asp Val His Ser Val Leu Arg Val Val Leu Gly Ala
            420                 425                 430

Asn Gly Thr Tyr Ser Cys Leu Val Arg Asn Pro Val Leu Gln Gln Asp
                435                 440                 445

Ala His Gly Ser Val Thr Ile Thr Gly Gln Pro Met Thr Phe Pro Pro
    450                 455                 460

Glu Ala Leu Trp Val Thr Val Gly Leu Ser Val Cys Leu Ile Ala Leu
465                 470                 475                 480

Leu Val Ala Leu Ala Phe Val Cys Trp Arg Lys Ile Lys Gln Ser Cys
                485                 490                 495

Glu Glu Glu Asn Ala Gly Ala Glu Asp Gln Asp Gly Glu Gly Glu Gly
                500                 505                 510

Ser Lys Thr Ala Leu Gln Pro Leu Lys His Ser Asp Ser Lys Glu Asp
    515                 520                 525

Asp Gly Gln Glu Ile Ala
    530

<210> SEQ ID NO 4
<211> LENGTH: 1602
<212> TYPE: DNA
<213> ORGANISM: Homo sapiens
<220> FEATURE:
<221> NAME/KEY: misc_feature
<222> LOCATION: (1)..(1602)
<223> OTHER INFORMATION: Polynucleotide Sequence Encoding the "4Ig"
      Form of Human B7-H3

<400> SEQUENCE: 4
atgctgcgtc ggcggggcag ccctggcatg ggtgtgcatg tgggtgcagc cctgggagca      60
ctgtggttct gcctcacagg agccctggag gtccaggtcc ctgaagaccc agtggtggca     120
ctggtgggca ccgatgccac cctgtgctgc tccttctccc ctgagcctgg cttcagcctg     180
gcacagctca acctcatctg gcagctgaca gataccaaac agctggtgca cagctttgct     240
gagggccagg accagggcag cgcctatgcc aaccgcacgg ccctcttccc ggacctgctg     300
gcacagggca acgcatccct gaggctgcag cgcgtgcgtg tggcggacga gggcagcttc     360
acctgcttcg tgagcatccg ggatttcggc agcgctgccg tcagcctgca ggtggccgct     420

```
ccctactcga agcccagcat gaccctggag cccaacaagg acctgcggcc aggggacacg    480
gtgaccatca cgtgctccag ctaccagggc taccctgagg ctgaggtgtt ctggcaggat    540
gggcagggtg tgcccctgac tggcaacgtg accacgtcgc agatggccaa cgagcagggc    600
ttgtttgatg tgcacagcat cctgcgggtg gtgctgggtg caaatggcac ctacagctgc    660
ctggtgcgca acccgtgctg cagcaggat gcgcacagct ctgtcaccat cacaccccag    720
agaagcccca caggagccgt ggaggtccag gtccctgagg accggtggt ggccctagtg    780 ggcaccgatg ccaccctgcg ctgctccttc tcccccgagc ctggcttcag cctggcacag    840
ctcaacctca tctggcagct gacagacacc aaacagctgg tgcacagttt caccgaaggc    900
cgggaccagg gcagcgccta tgccaaccgc acggccctct cccggaccct gctggcacaa    960
ggcaatgcat ccctgaggct gcagcgcgtg cgtgtggcgg acgagggcag cttcacctgc   1020
ttcgtgagca tccgggattt cggcagcgct gccgtcagcc tgcaggtggc cgctccctac   1080
tcgaagccca gcatgaccct ggagcccaac aaggacctgc ggccagggga cacggtgacc   1140
atcacgtgct ccagctaccg gggctaccct gaggctgagg tgttctggca ggatgggcag   1200
ggtgtgcccc tgactggcaa cgtgaccacg tcgcagatgg ccaacgagca gggcttgttt   1260
gatgtgcaca gcgtcctgcg ggtggtgctg ggtgcgaatg gcacctacag ctgcctggtg   1320
cgcaaccccg tgctgcagca ggatgcgcac ggctctgtca ccatcacagg gcagcctatg   1380
acattccccc cagaggccct gtgggtgacc gtggggctgt ctgtctgtct cattgcactg   1440
ctggtggccc tggctttcgt gtgctggaga aagatcaaac agagctgtga ggaggagaat   1500
gcaggagctg aggaccagga tggggaggga gaaggctcca agacagccct gcagcctctg   1560
aaacactctg acagcaaaga agatgatgga caagaaatag cc                      1602
```

<210> SEQ ID NO 5
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: Amino Acid Sequence of BRCA69D Variable Light
      Chain

<400> SEQUENCE: 5

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Asp Asn Leu Glu Gln
65                  70                  75                  80

Glu Asp Ile Ala Thr Tyr Phe Cys Gln Gln Gly Asn Thr Leu Pro Pro
                85                  90                  95

Thr Phe Gly Gly Gly Thr Lys Leu Glu Ile Lys
            100                 105

<210> SEQ ID NO 6
<211> LENGTH: 321
<212> TYPE: DNA
<213> ORGANISM: Mus musculus

```
<220> FEATURE:
<221> NAME/KEY: misc_feature
<222> LOCATION: (1)..(321)
<223> OTHER INFORMATION: Polynucleotide Sequence Encoding BRCA69D
      Variable Light Chain

<400> SEQUENCE: 6
gatatccaga tgacacagac tacatcctcc ctgtctgcct ctctgggaga cagagtcacc      60
atcagttgca gggcaagtca ggacattagt aattatttaa actggtatca gcagaaacca     120
gatggaactg ttaaactcct gatctactac acatcacgat tacactcagg agtcccatca     180
aggttcagtg gcagtgggtc tggaacagat tattctctca ccattgacaa cctggagcaa     240
gaagatattg ccacttactt ttgccaacag ggtaatacgc ttcctccgac gttcggtgga     300
ggcaccaaac tggaaatcaa a                                               321

<210> SEQ ID NO 7
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: BRCA69D Variable Light Chain CDR1

<400> SEQUENCE: 7

Arg Ala Ser Gln Asp Ile Ser Asn Tyr Leu Asn
1               5                   10

<210> SEQ ID NO 8
<211> LENGTH: 33
<212> TYPE: DNA
<213> ORGANISM: Mus musculus
<220> FEATURE:
<221> NAME/KEY: misc_feature
<222> LOCATION: (1)..(33)
<223> OTHER INFORMATION: Polynucleotide Sequence Encoding BRCA69D
      Variable Light Chain CDR1

<400> SEQUENCE: 8
agggcaagtc aggacattag taattattta aac                                   33

<210> SEQ ID NO 9
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: BRCA69D Variable Light Chain CDR2

<400> SEQUENCE: 9

Tyr Thr Ser Arg Leu His Ser
1               5

<210> SEQ ID NO 10
<211> LENGTH: 21
<212> TYPE: DNA
<213> ORGANISM: Mus musculus
<220> FEATURE:
<221> NAME/KEY: misc_feature
<222> LOCATION: (1)..(21)
<223> OTHER INFORMATION: Polynucleotide Sequence Encoding BRCA69D
      Variable Light Chain CDR2

<400> SEQUENCE: 10
tacacatcac gattacactc a                                                21
```

```
<210> SEQ ID NO 11
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: BRCA69D Variable Light Chain CDR3

<400> SEQUENCE: 11

Gln Gln Gly Asn Thr Leu Pro Pro Thr
1               5

<210> SEQ ID NO 12
<211> LENGTH: 27
<212> TYPE: DNA
<213> ORGANISM: Mus musculus
<220> FEATURE:
<221> NAME/KEY: misc_feature
<222> LOCATION: (1)..(27)
<223> OTHER INFORMATION: Polynucleotide Sequence Encoding BRCA69D
      Variable Light Chain CDR3

<400> SEQUENCE: 12
caacagggta atacgcttcc tccgacg                                          27

<210> SEQ ID NO 13
<211> LENGTH: 120
<212> TYPE: PRT
<213> ORGANISM: Mus musculus
<220> FEATURE:
<221> NAME/KEY: MISC_FEATURE
<222> LOCATION: (1)..(120)
<223> OTHER INFORMATION: Amino Acid Sequence of BRCA69D Variable Heavy
      Chain

<400> SEQUENCE: 13

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Arg Gly Ile Pro Arg Leu Trp Tyr Phe Asp Val Trp Gly Ala
            100                 105                 110

Gly Thr Thr Val Thr Val Ser Ser
        115                 120

<210> SEQ ID NO 14
<211> LENGTH: 360
<212> TYPE: DNA
<213> ORGANISM: Mus musculus
<220> FEATURE:
<221> NAME/KEY: misc_feature
<222> LOCATION: (1)..(360)
<223> OTHER INFORMATION: Polynucleotide Sequence Encoding BRCA69D
      Variable Heavy Chain
```

```
<400> SEQUENCE: 14
caggttcagc tccagcagtc tggggctgag ctggcaagac ctggggcttc agtgaagttg      60
tcctgcaagg cttctggcta cacctttact agctactgga tgcagtgggt aaaacagagg     120
cctggacagg gtctggaatg gattgggact atttatcctg gagatggtga tactaggtac     180
actcagaagt tcaagggcaa ggccacattg actgcagata atcctccag cacagcctac      240 atgcaactca gcagcttggc atctgaggac tctgcggtct attactgtgc aagaagaggg     300
attccacggc tttggtactt cgatgtctgg ggcgcaggga ccacggtcac cgtctcctca     360

<210> SEQ ID NO 15
<211> LENGTH: 5
<212> TYPE: PRT
<213> ORGANISM: Mus musculus
<220> FEATURE:
<221> NAME/KEY: MISC_FEATURE
<223> OTHER INFORMATION: BRCA69D Variable Heavy Chain CDR1

<400> SEQUENCE: 15

Ser Tyr Trp Met Gln
1               5

<210> SEQ ID NO 16
<211> LENGTH: 15
<212> TYPE: DNA
<213> ORGANISM: Mus musculus
<220> FEATURE:
<221> NAME/KEY: misc_feature
<222> LOCATION: (1)..(15)
<223> OTHER INFORMATION: Polynucleotide Sequence Encoding BRCA69D
      Variable Heavy Chain CDR1

<400> SEQUENCE: 16
agctactgga tgcag                                                       15

<210> SEQ ID NO 17
<211> LENGTH: 17
<212> TYPE: PRT
<213> ORGANISM: Mus musculus
<220> FEATURE:
<221> NAME/KEY: MISC_FEATURE
<222> LOCATION: (1)..(17)
<223> OTHER INFORMATION: BRCA69D Variable Heavy Chain CDR2

<400> SEQUENCE: 17

Thr Ile Tyr Pro Gly Asp Gly Asp Thr Arg Tyr Thr Gln Lys Phe Lys
1               5                   10                  15
Gly

<210> SEQ ID NO 18
<211> LENGTH: 51
<212> TYPE: DNA
<213> ORGANISM: Mus musculus
<220> FEATURE:
<221> NAME/KEY: misc_feature
<222> LOCATION: (1)..(51)
<223> OTHER INFORMATION: Polynucleotide Sequence Encoding BRCA69D
      Variable Heavy Chain CDR2

<400> SEQUENCE: 18
actatttatc ctggagatgg tgatactagg tacactcaga gttcaaggg c                51

<210> SEQ ID NO 19
<211> LENGTH: 11
<212> TYPE: PRT
```

```
<213> ORGANISM: Mus musculus
<220> FEATURE:
<221> NAME/KEY: MISC_FEATURE
<222> LOCATION: (1)..(11)
<223> OTHER INFORMATION: BRCA69D Variable Heavy Chain CDR3

<400> SEQUENCE: 19

Arg Gly Ile Pro Arg Leu Trp Tyr Phe Asp Val
1               5                   10

<210> SEQ ID NO 20
<211> LENGTH: 33
<212> TYPE: DNA
<213> ORGANISM: Mus musculus
<220> FEATURE:
<221> NAME/KEY: misc_feature
<222> LOCATION: (1)..(33)
<223> OTHER INFORMATION: Polynucleotide Sequence Encoding BRCA69D
      Variable Heavy Chain CDR3

<400> SEQUENCE: 20
agagggattc cacggctttg gtacttcgat gtc                               33

<210> SEQ ID NO 21
<211> LENGTH: 108
<212> TYPE: PRT
<213> ORGANISM: Mus musculus
<220> FEATURE:
<221> NAME/KEY: MISC_FEATURE
<222> LOCATION: (1)..(108)
<223> OTHER INFORMATION: Amino Acid Sequence of PRCA157 Variable Light
      Chain

<400> SEQUENCE: 21

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Ser Ile Tyr Ser Tyr
                20                  25                  30

Leu Ala Trp Tyr Gln Gln Lys Gln Gly Lys Ser Pro Gln Leu Leu Val
            35                  40                  45

Tyr Asn Thr Lys Thr Leu Pro Glu Gly Val Pro Ser Arg Phe Ser Gly
        50                  55                  60

Ser Gly Ser Gly Thr Gln Phe Ser Leu Lys Ile Asn Ser Leu Gln Pro
65                  70                  75                  80

Glu Asp Phe Gly Arg Tyr Tyr Cys Gln His Tyr Gly Thr Pro Pro
                85                  90                  95

Trp Thr Phe Gly Gly Gly Thr Asn Leu Glu Ile Lys
            100                 105

<210> SEQ ID NO 22
<211> LENGTH: 324
<212> TYPE: DNA
<213> ORGANISM: Mus musculus
<220> FEATURE:
<221> NAME/KEY: misc_feature
<222> LOCATION: (1)..(324)
<223> OTHER INFORMATION: Polynucleotide Sequence Encoding PRCA157
      Variable Light Chain

<400> SEQUENCE: 22
gacatccaga tgactcagtc tccagcctcc ctatctgtat ctgtgggaga aactgtcacc     60
attacatgtc gagcaagtga gagtatttac agttatttag catggtatca gcagaaacag    120
ggaaaatctc ctcagctcct ggtctataat acaaaaacct taccagaggg tgtgccatca    180
```

```
aggttcagtg gcagtggatc aggcacacag ttttctctga agatcaacag cctgcagcct    240
gaagattttg ggagatatta ctgtcaacat cattatggta ctcctccgtg gacgttcggt    300
ggaggcacca acctggaaat caaa                                           324
```

<210> SEQ ID NO 23
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: PRCA157 Variable Light Chain CDR1

<400> SEQUENCE: 23

```
Arg Ala Ser Glu Ser Ile Tyr Ser Tyr Leu Ala
1               5                   10
```

<210> SEQ ID NO 24
<211> LENGTH: 33
<212> TYPE: DNA
<213> ORGANISM: Mus musculus
<220> FEATURE:
<221> NAME/KEY: misc_feature
<222> LOCATION: (1)..(33)
<223> OTHER INFORMATION: Polynucleotide Sequence Encoding PRCA157
      Variable Light Chain CDR1

<400> SEQUENCE: 24

```
cgagcaagtg agagtattta cagttattta gca                                  33
```

<210> SEQ ID NO 25
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: PRCA157 Variable Light Chain CDR2

<400> SEQUENCE: 25

```
Asn Thr Lys Thr Leu Pro Glu
1               5
```

<210> SEQ ID NO 26
<211> LENGTH: 21
<212> TYPE: DNA
<213> ORGANISM: Mus musculus
<220> FEATURE:
<221> NAME/KEY: misc_feature
<222> LOCATION: (1)..(21)
<223> OTHER INFORMATION: Polynucleotide Sequence Encoding PRCA157
      Variable Light Chain CDR2

<400> SEQUENCE: 26

```
aatacaaaaa ccttaccaga g                                               21
```

<210> SEQ ID NO 27
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: PRCA157 Variable Light Chain CDR3

<400> SEQUENCE: 27

```
Gln His His Tyr Gly Thr Pro Pro Trp
```

<210> SEQ ID NO 28
<211> LENGTH: 27
<212> TYPE: DNA
<213> ORGANISM: Mus musculus
<220> FEATURE:
<221> NAME/KEY: misc_feature
<222> LOCATION: (1)..(27)
<223> OTHER INFORMATION: Polynucleotide Sequence Encoding PRCA157
    Variable Light Chain CDR3

<400> SEQUENCE: 28
caacatcatt atggtactcc tccgtgg                                          27

<210> SEQ ID NO 29
<211> LENGTH: 117
<212> TYPE: PRT
<213> ORGANISM: Mus musculus
<220> FEATURE:
<221> NAME/KEY: MISC_FEATURE
<222> LOCATION: (1)..(117)
<223> OTHER INFORMATION: Amino Acid Sequence of PRCA157 Variable Heavy
    Chain

<400> SEQUENCE: 29

Glu Val Gln Gln Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Asn Ser Gly Gly Ser Asn Thr Tyr Tyr Pro Asp Ser Leu
    50                  55                  60

Lys Gly Arg Phe Thr Ile Ser Arg Asp Asn Ala Lys Asn Thr Leu Tyr
65                  70                  75                  80

Leu Gln Met Arg Ser Leu Lys Ser Glu Asp Thr Ala Met Tyr Tyr Cys
                85                  90                  95

Ala Arg His Asp Gly Gly Ala Met Asp Tyr Trp Gly Gln Gly Thr Ser
            100                 105                 110

Val Thr Val Ser Ser
        115

<210> SEQ ID NO 30
<211> LENGTH: 351
<212> TYPE: DNA
<213> ORGANISM: Mus musculus
<220> FEATURE:
<221> NAME/KEY: misc_feature
<222> LOCATION: (1)..(351)
<223> OTHER INFORMATION: Polynucleotide Sequence Encoding PRCA157
    Variable Heavy Chain

<400> SEQUENCE: 30
gaggtgcagc aggtggagtc ggggggagac ttagtgaagc ctggagggtc cctgaaactc        60
tcctgtgcag cctctggatt cactttcagt tcctatggca tgtcttgggt tcgccagact       120
ccagacaaga ggctggagtg gtcgcaacc attaatagtg gtggaagtaa cacctactat        180
ccagacagtt tgaaggggcg attcaccatc tccagagaca atgccaagaa cacccttac        240 ctgcaaatgc gcagtctgaa gtctgaggac acagccatgt attactgtgc aagacatgac       300
gggggagcta tggactactg gggtcaagga acctcagtca ccgtctcctc a                351

```
<210> SEQ ID NO 31
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: PRCA157 Variable Heavy Chain CDR1

<400> SEQUENCE: 31

Ser Tyr Gly Met Ser
1               5

<210> SEQ ID NO 32
<211> LENGTH: 15
<212> TYPE: DNA
<213> ORGANISM: Mus musculus
<220> FEATURE:
<221> NAME/KEY: misc_feature
<222> LOCATION: (1)..(15)
<223> OTHER INFORMATION: Polynucleotide Sequence Encoding PRCA157
      Variable Heavy Chain CDR1

<400> SEQUENCE: 32
tcctatggca tgtct                                                    15

<210> SEQ ID NO 33
<211> LENGTH: 19
<212> TYPE: PRT
<213> ORGANISM: Mus musculus
<220> FEATURE:
<221> NAME/KEY: MISC_FEATURE
<222> LOCATION: (1)..(19)
<223> OTHER INFORMATION: PRCA157 Variable Heavy Chain CDR2

<400> SEQUENCE: 33

Val Ala Thr Ile Asn Ser Gly Gly Ser Asn Thr Tyr Tyr Pro Asp Ser
1               5                   10                  15

Leu Lys Gly

<210> SEQ ID NO 34
<211> LENGTH: 57
<212> TYPE: DNA
<213> ORGANISM: Mus musculus
<220> FEATURE:
<221> NAME/KEY: misc_feature
<222> LOCATION: (1)..(57)
<223> OTHER INFORMATION: Polynucleotide Sequence Encoding PRCA157
      Variable Heavy Chain CDR2

<400> SEQUENCE: 34
gtcgcaacca ttaatagtgg tggaagtaac acctactatc cagacagttt gaagggg     57

<210> SEQ ID NO 35
<211> LENGTH: 8
<212> TYPE: PRT
<213> ORGANISM: Mus musculus
<220> FEATURE:
<221> NAME/KEY: MISC_FEATURE
<222> LOCATION: (1)..(8)
<223> OTHER INFORMATION: PRCA157 Variable Heavy Chain CDR3

<400> SEQUENCE: 35

His Asp Gly Gly Ala Met Asp Tyr
1               5

<210> SEQ ID NO 36
```

```
<211> LENGTH: 24
<212> TYPE: DNA
<213> ORGANISM: Mus musculus
<220> FEATURE:
<221> NAME/KEY: misc_feature
<222> LOCATION: (1)..(24)
<223> OTHER INFORMATION: Polynucleotide Sequence Encoding PRCA157
      Variable Heavy Chain CDR3

<400> SEQUENCE: 36
catgacgggg gagctatgga ctac                                           24

<210> SEQ ID NO 37
<211> LENGTH: 107
<212> TYPE: PRT
<213> ORGANISM: Mus musculus
<220> FEATURE:
<221> NAME/KEY: MISC_FEATURE
<222> LOCATION: (1)..(107)
<223> OTHER INFORMATION: Amino Acid Sequence of BRCA84D Variable Light
      Chain

<400> SEQUENCE: 37

Asp Ile Ala Met Thr Gln Ser Gln Lys Phe Met Ser Thr Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Asn Asn Val Gln Ser
65                  70                  75                  80

Glu Asp Leu Ala Glu Tyr Phe Cys Gln Gln Tyr Asn Asn Tyr Pro Phe
                85                  90                  95

Thr Phe Gly Ser Gly Thr Lys Leu Glu Ile Lys
            100                 105

<210> SEQ ID NO 38
<211> LENGTH: 321
<212> TYPE: DNA
<213> ORGANISM: Mus musculus
<220> FEATURE:
<221> NAME/KEY: misc_feature
<222> LOCATION: (1)..(321)
<223> OTHER INFORMATION: Polynucleotide Sequence Encoding BRCA84D
      Variable Light Chain

<400> SEQUENCE: 38
gacattgcga tgacccagtc tcaaaaattc atgtccacat cagtaggaga cagggtcagc    60
gtcacctgca aggccagtca gaatgtggat actaatgtag cctggtatca acagaaacca   120
gggcaatctc ctaaagcact gatttactcg gcatcctacc ggtacagtgg agtccctgat   180
cgcttcacag gcagtggatc tgggacagat ttcactctca ccatcaacaa tgtgcagtct   240
gaagacttgg cagagtattt ctgtcagcaa tataacaact atccattcac gttcggctcg   300
gggacaaagt tggaaataaa a                                             321

<210> SEQ ID NO 39
<211> LENGTH: 11
<212> TYPE: PRT
<213> ORGANISM: Mus musculus
<220> FEATURE:
<221> NAME/KEY: MISC_FEATURE
```

```
<222> LOCATION: (1)..(11)
<223> OTHER INFORMATION: BRCA84D Variable Light Chain CDR1

<400> SEQUENCE: 39

Lys Ala Ser Gln Asn Val Asp Thr Asn Val Ala
1               5                   10

<210> SEQ ID NO 40
<211> LENGTH: 33
<212> TYPE: DNA
<213> ORGANISM: Mus musculus
<220> FEATURE:
<221> NAME/KEY: misc_feature
<222> LOCATION: (1)..(33)
<223> OTHER INFORMATION: Polynucleotide Sequence Encoding BRCA84D
      Variable Light Chain CDR1

<400> SEQUENCE: 40
aaggccagtc agaatgtgga tactaatgta gcc                                  33

<210> SEQ ID NO 41
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: BRCA84D Variable Light Chain CDR2

<400> SEQUENCE: 41

Ser Ala Ser Tyr Arg Tyr Ser
1               5

<210> SEQ ID NO 42
<211> LENGTH: 21
<212> TYPE: PRT
<213> ORGANISM: Mus musculus
<220> FEATURE:
<221> NAME/KEY: MISC_FEATURE
<222> LOCATION: (1)..(21)
<223> OTHER INFORMATION: Polynucleotide Sequence Encoding BRCA84D
      Variable Light Chain CDR2

<400> SEQUENCE: 42

Thr Cys Gly Gly Cys Ala Thr Cys Cys Thr Ala Cys Cys Gly Gly Thr
1               5                   10                  15

Ala Cys Ala Gly Thr
            20

<210> SEQ ID NO 43
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: BRCA84D Variable Light Chain CDR3

<400> SEQUENCE: 43

Gln Gln Tyr Asn Asn Tyr Pro Phe Thr
1               5

<210> SEQ ID NO 44
<211> LENGTH: 27
<212> TYPE: DNA
<213> ORGANISM: Mus musculus
<220> FEATURE:
<221> NAME/KEY: misc_feature
```

```
<222> LOCATION: (1)..(27)
<223> OTHER INFORMATION: Polynucleotide Sequence Encoding BRCA84D
      Variable Light Chain CDR3

<400> SEQUENCE: 44
cagcaatata caactatcc attcacg                                          27

<210> SEQ ID NO 45
<211> LENGTH: 122
<212> TYPE: PRT
<213> ORGANISM: Mus musculus
<220> FEATURE:
<221> NAME/KEY: MISC_FEATURE
<222> LOCATION: (1)..(122)
<223> OTHER INFORMATION: Amino Acid Sequence of BRCA84D Variable Heavy
      Chain

<400> SEQUENCE: 45
```

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Asp Ser Ser Ala Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Gly Arg Gly Arg Glu Asn Ile Tyr Tyr Gly Ser Arg Leu Asp Tyr Trp
            100                 105                 110

Gly Gln Gly Thr Thr Leu Thr Val Ser Ser
        115                 120

```
<210> SEQ ID NO 46
<211> LENGTH: 366
<212> TYPE: DNA
<213> ORGANISM: Mus musculus
<220> FEATURE:
<221> NAME/KEY: misc_feature
<222> LOCATION: (1)..(366)
<223> OTHER INFORMATION: Polynucleotide Sequence Encoding BRCA84D
      Variable Heavy Chain

<400> SEQUENCE: 46
gatgtgcagc tggtggagtc tgggggaggc ttagtgcagc ctggagggtc ccggaaactc     60
tcctgtgcag cctctggatt cactttcagt agctttggaa tgcactgggt tcgtcaggct    120
ccagagaagg ggctggagtg ggtcgcatac attagtagtg acagtagtgc catctactat    180
gcagacacag tgaagggccg attcaccatc tccagagaca atcccaagaa caccctgttc    240
ctgcaaatga ccagtctaag gtctgaggac acggccatgt attactgtgg aagagggagg    300
gaaaacattt actacggtag taggcttgac tactggggcc aaggcaccac tctcacagtc    360
tcctca                                                               366

<210> SEQ ID NO 47
<211> LENGTH: 4
<212> TYPE: PRT
<213> ORGANISM: Mus musculus
<220> FEATURE:
<221> NAME/KEY: MISC_FEATURE
```

```
<222> LOCATION: (1)..(4)
<223> OTHER INFORMATION: BRCA84D Variable Heavy Chain CDR1

<400> SEQUENCE: 47

Phe Gly Met His
1

<210> SEQ ID NO 48
<211> LENGTH: 12
<212> TYPE: DNA
<213> ORGANISM: Mus musculus
<220> FEATURE:
<221> NAME/KEY: misc_feature
<222> LOCATION: (1)..(12)
<223> OTHER INFORMATION: Polynucleotide Sequence Encoding BRCA84D
      Variable Heavy Chain CDR1

<400> SEQUENCE: 48
tttggaatgc ac                                                           12

<210> SEQ ID NO 49
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
<223> OTHER INFORMATION: BRCA84D Variable Heavy Chain CDR2

<400> SEQUENCE: 49

Tyr Ile Ser Ser Asp Ser Ser Ala Ile Tyr Tyr Ala Asp Thr Val Lys
1               5                   10                  15

<210> SEQ ID NO 50
<211> LENGTH: 48
<212> TYPE: DNA
<213> ORGANISM: Mus musculus
<220> FEATURE:
<221> NAME/KEY: misc_feature
<222> LOCATION: (1)..(48)
<223> OTHER INFORMATION: Polynucleotide Sequence Encoding BRCA84D
      Variable Heavy Chain CDR2

<400> SEQUENCE: 50
tacattagta gtgacagtag tgccatctac tatgcagaca cagtgaag                    48

<210> SEQ ID NO 51
<211> LENGTH: 13
<212> TYPE: PRT
<213> ORGANISM: Mus musculus
<220> FEATURE:
<221> NAME/KEY: MISC_FEATURE
<222> LOCATION: (1)..(13)
<223> OTHER INFORMATION: BRCA84D Variable Heavy Chain CDR3

<400> SEQUENCE: 51

Gly Arg Glu Asn Ile Tyr Tyr Gly Ser Arg Leu Asp Tyr
1               5                   10

<210> SEQ ID NO 52
<211> LENGTH: 39
<212> TYPE: DNA
<213> ORGANISM: Mus musculus
<220> FEATURE:
<221> NAME/KEY: misc_feature
<222> LOCATION: (1)..(39)
<223> OTHER INFORMATION: Polynucleotide Sequence Encoding BRCA84D
      Variable Heavy Chain CDR3
```

```
<400> SEQUENCE: 52
gggagggaaa acatttacta cggtagtagg cttgactac                                    39

<210> SEQ ID NO 53
<211> LENGTH: 107
<212> TYPE: PRT
<213> ORGANISM: Artificial Sequence
<220> FEATURE:
<223> OTHER INFORMATION: Humanized BRCA84D-1 Variable Light Chain

<400> SEQUENCE: 53

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys
            100                 105

<210> SEQ ID NO 54
<211> LENGTH: 321
<212> TYPE: DNA
<213> ORGANISM: Artificial Sequence
<220> FEATURE:
<223> OTHER INFORMATION: Polynucleotide Sequence Encoding Humanized
      BRCA84D-1 Variable Light Chain

<400> SEQUENCE: 54
gacatccagc tgacccagtc cccctccttc ctgtctgcct ccgtgggcga cagagtgacc      60
atcacatgca aggcctccca gaacgtggac accaacgtgg cctggtatca gcagaagcct     120
ggcaaggccc ctaagctgct gatctactcc gcctcctacc ggtactccgg cgtgccttcc     180
aggttctccg gctccggctc tggcaccgac ttcaccctga ccatctccag cctgcagcct     240
gaggacttcg ccacctacta ctgccagcag tacaacaact acccttcac cttcggccag      300 ggcaccaagc tggaaatcaa g                                               321

<210> SEQ ID NO 55
<211> LENGTH: 11
<212> TYPE: PRT
<213> ORGANISM: Artificial Sequence
<220> FEATURE:
<223> OTHER INFORMATION: Humanized BRCA84D-1 Variable Light Chain CDR1

<400> SEQUENCE: 55

Lys Ala Ser Gln Asn Val Asp Thr Asn Val Ala
1               5                   10

<210> SEQ ID NO 56
<211> LENGTH: 33
<212> TYPE: DNA
<213> ORGANISM: Artificial Sequence
<220> FEATURE:
<223> OTHER INFORMATION: Polynucleotide Sequence Encoding Humanized
      BRCA84D-1 Variable Light Chain CDR1
```

<400> SEQUENCE: 56
aaggccagtc agaatgtgga tactaatgta gcc                                    33

<210> SEQ ID NO 57
<211> LENGTH: 7
<212> TYPE: PRT
<213> ORGANISM: Artificial Sequence
<220> FEATURE:
<223> OTHER INFORMATION: Humanized BRCA84D-1 Variable Light Chain CDR2

<400> SEQUENCE: 57

Ser Ala Ser Tyr Arg Tyr Ser
1               5

<210> SEQ ID NO 58
<211> LENGTH: 21
<212> TYPE: DNA
<213> ORGANISM: Artificial Sequence
<220> FEATURE:
<223> OTHER INFORMATION: Polynucleotide Sequence Encoding Humanized
      BRCA84D-1 Variable Light Chain CDR2

<400> SEQUENCE: 58
tcggcatcct accggtacag t                                                 21

<210> SEQ ID NO 59
<211> LENGTH: 9
<212> TYPE: PRT
<213> ORGANISM: Artificial Sequence
<220> FEATURE:
<223> OTHER INFORMATION: Humanized BRCA84D-1 Variable Light Chain CDR3

<400> SEQUENCE: 59

Gln Gln Tyr Asn Asn Tyr Pro Phe Thr
1               5

<210> SEQ ID NO 60
<211> LENGTH: 27
<212> TYPE: DNA
<213> ORGANISM: Artificial Sequence
<220> FEATURE:
<223> OTHER INFORMATION: Polynucleotide Sequence Encoding Humanized
      BRCA84D-1 Variable Light Chain CDR3

<400> SEQUENCE: 60
cagcaatata caactatcc attcacg                                            27

<210> SEQ ID NO 61
<211> LENGTH: 122
<212> TYPE: PRT
<213> ORGANISM: Artificial Sequence
<220> FEATURE:
<223> OTHER INFORMATION: Amino Acid Sequence of Humanized BRCA84D-1
      Variable Heavy Chain

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Asp Ser Ser Ala Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
            85                  90                  95

Ala Arg Gly Arg Glu Asn Ile Tyr Tyr Gly Ser Arg Leu Asp Tyr Trp
        100                 105                 110

Gly Gln Gly Thr Thr Val Thr Val Ser Ser
        115                 120

<210> SEQ ID NO 62
<211> LENGTH: 366
<212> TYPE: DNA
<213> ORGANISM: Artificial Sequence
<220> FEATURE:
<223> OTHER INFORMATION: Polynucleotide Sequence Encoding Humanized
      BRCA84D-1 Variable Heavy Chain

<400> SEQUENCE: 62
gaggtgcagc tggtcgagtc tggcggagga ctggtgcagc ctggcggctc cctgagactg      60
tcttgcgccg cctccggctt cacctttctcc agcttcggca tgcactgggt ccgccaggct    120
ccaggcaagg gactggaatg ggtggcctac atctcctccg actcctccgc catctactac    180
gccgacaccg tgaagggcag gttcaccatc tcccgggaca cgccaagaa ctccctgtac     240 ctgcagatga actccctgcg ggacgaggac accgccgtgt actactgcgc cagaggccgg    300
gagaatatct actacggctc ccggctggat tattggggcc agggcaccac cgtgaccgtg    360
tcctct                                                                366

<210> SEQ ID NO 63
<211> LENGTH: 4
<212> TYPE: PRT
<213> ORGANISM: Artificial Sequence
<220> FEATURE:
<223> OTHER INFORMATION: Humanized BRCA84D-1 Variable Heavy Chain CDR1

<400> SEQUENCE: 63

Phe Gly Met His
1

<210> SEQ ID NO 64
<211> LENGTH: 12
<212> TYPE: DNA
<213> ORGANISM: Artificial Sequence
<220> FEATURE:
<223> OTHER INFORMATION: Polynucleotide Sequence Encoding Humanized
      BRCA84D-1 Variable Heavy Chain CDR1

<400> SEQUENCE: 64
tttggaatgc ac                                                          12

<210> SEQ ID NO 65
<211> LENGTH: 16
<212> TYPE: PRT
<213> ORGANISM: Artificial Sequence
<220> FEATURE:
<223> OTHER INFORMATION: Humanized BRCA84D Variable Heavy Chain CDR2

<400> SEQUENCE: 65

Tyr Ile Ser Ser Asp Ser Ser Ala Ile Tyr Tyr Ala Asp Thr Val Lys
1               5                   10                  15

<210> SEQ ID NO 66

```
<211> LENGTH: 48
<212> TYPE: DNA
<213> ORGANISM: Artificial Sequence
<220> FEATURE:
<223> OTHER INFORMATION: Polynucleotide Sequence Encoding Humanized
      BRCA84D-1 Variable Heavy Chain CDR2

<400> SEQUENCE: 66
tacattagta gtgacagtag tgccatctac tatgcagaca cagtgaag                    48

<210> SEQ ID NO 67
<211> LENGTH: 13
<212> TYPE: PRT
<213> ORGANISM: Artificial Sequence
<220> FEATURE:
<223> OTHER INFORMATION: Humanized BRCA84D-1 Variable Heavy Chain CDR3

<400> SEQUENCE: 67

Gly Arg Glu Asn Ile Tyr Tyr Gly Ser Arg Leu Asp Tyr
1               5                   10

<210> SEQ ID NO 68
<211> LENGTH: 39
<212> TYPE: DNA
<213> ORGANISM: Artificial Sequence
<220> FEATURE:
<223> OTHER INFORMATION: Polynucleotide Sequence Encoding Humanized
      BRCA84D-1 Variable Heavy Chain CDR3

<400> SEQUENCE: 68
gggagggaaa acatttacta cggtagtagg cttgactac                              39

<210> SEQ ID NO 69
<211> LENGTH: 107
<212> TYPE: PRT
<213> ORGANISM: Artificial Sequence
<220> FEATURE:
<223> OTHER INFORMATION: Amino Acid Sequence of hBRCA84D-2VL

<400> SEQUENCE: 69

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys
            100                 105

<210> SEQ ID NO 70
<211> LENGTH: 321
<212> TYPE: DNA
<213> ORGANISM: Artificial Sequence
<220> FEATURE:
<223> OTHER INFORMATION: Polynucleotide Encoding hBRCA84D-2VL

<400> SEQUENCE: 70
gacatccagc tgacccagtc cccctccttc ctgtctgcct ccgtgggcga cagagtgacc       60
```

```
atcacatgca aggcctccca gaacgtggac accaacgtgg cctggtatca gcagaagcct    120
ggcaaggccc ctaaggcgct gatctactcc gcctcctacc ggtactccgg cgtgccttcc    180
aggttctccg gctccggctc tggcaccgac ttcaccctga ccatctccag cctgcagcct    240
gaggacttcg ccacctacta ctgccagcag tacaacaact acccctttcac cttcggccag   300 ggcaccaagc tggaaatcaa g                                              321
```

```
<210> SEQ ID NO 71
<211> LENGTH: 107
<212> TYPE: PRT
<213> ORGANISM: Artificial Sequence
<220> FEATURE:
<223> OTHER INFORMATION: Amino Acid Sequence of hBRCA84D-3VL

<400> SEQUENCE: 71

Asp Ile Gln Leu Thr Gln Ser Pro Ser Phe Leu Ser Ala Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys
            100                 105
```

```
<210> SEQ ID NO 72
<211> LENGTH: 321
<212> TYPE: DNA
<213> ORGANISM: Artificial Sequence
<220> FEATURE:
<223> OTHER INFORMATION: Polynucleotide Encoding hBRCA84D-3VL

<400> SEQUENCE: 72
gacatccagc tgacccagtc ccctccttc ctgtctgcct ccgtgggcga cagagtgtcc      60
gtcacatgca aggcctccca gaacgtggac accaacgtgg cctggtatca gcagaagcct    120
ggcaaggccc ctaagctgct gatctactcc gcctcctacc ggtactccgg cgtgccttcc    180
aggttctccg gctccggctc tggcaccgac ttcaccctga ccatctccag cctgcagcct    240
gaggacttcg ccacctacta ctgccagcag tacaacaact acccctttcac cttcggccag   300 ggcaccaagc tggaaatcaa g                                              321
```

```
<210> SEQ ID NO 73
<211> LENGTH: 107
<212> TYPE: PRT
<213> ORGANISM: Artificial Sequence
<220> FEATURE:
<223> OTHER INFORMATION: Amino Acid Sequence of hBRCA84D-4VL

<400> SEQUENCE: 73

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30
```

```
Val Ala Trp Tyr Gln Gln Lys Pro Gly Gln Ala Pro Lys Leu Leu Ile
         35                  40                  45

Tyr Ser Ala Ser Tyr Arg Tyr Ser Gly Val Pro Ser Arg Phe Ser Gly
         50                  55                  60

Ser Gly Ser Gly Thr Asp Phe Thr Leu Thr Ile Ser Ser Leu Gln Pro
 65              70                  75                      80

Glu Asp Phe Ala Thr Tyr Tyr Cys Gln Gln Tyr Asn Asn Tyr Pro Phe
                 85                  90                  95

Thr Phe Gly Gln Gly Thr Lys Leu Glu Ile Lys
            100                 105
```

<210> SEQ ID NO 74
<211> LENGTH: 321
<212> TYPE: DNA
<213> ORGANISM: Artificial Sequence
<220> FEATURE:
<223> OTHER INFORMATION: Polynucleotide Encoding hBRCA84D-4VL

<400> SEQUENCE: 74

```
gacatccagc tgacccagtc cccctccttc ctgtctgcct ccgtgggcga cagagtgacc    60
atcacatgca aggcctccca gaacgtggac accaacgtgg cctggtatca gcagaagcct   120
ggccaggccc ctaagctgct gatctactcc gcctcctacc ggtactccgg cgtgccttcc   180
aggttctccg gctccggctc tggcaccgac ttcaccctga ccatctccag cctgcagcct   240
gaggacttcg ccacctacta ctgccagcag tacaacaact accctttcac cttcggccag   300
ggcaccaagc tggaaatcaa g                                             321
```

<210> SEQ ID NO 75
<211> LENGTH: 107
<212> TYPE: PRT
<213> ORGANISM: Artificial Sequence
<220> FEATURE:
<223> OTHER INFORMATION: Amino Acid Sequence of hBRCA84D-5VL

<400> SEQUENCE: 75

```
Asp Ile Gln Leu Thr Gln Ser Pro Ser Phe Leu Ser Ala Ser Val Gly
 1               5                  10                  15

Asp Arg Val Thr Ile Thr Cys Lys Ala Ser Gln Asn Val Asp Thr Asn
             20                  25                  30

Val Ala Trp Tyr Gln Gln Lys Pro Gly Gln Ala Pro Lys Ala Leu Ile
         35                  40                  45

Tyr Ser Ala Ser Tyr Arg Tyr Ser Gly Val Pro Ser Arg Phe Ser Gly
         50                  55                  60

Ser Gly Ser Gly Thr Asp Phe Thr Leu Thr Ile Ser Ser Leu Gln Pro
 65              70                  75                      80

Glu Asp Phe Ala Thr Tyr Tyr Cys Gln Gln Tyr Asn Asn Tyr Pro Phe
                 85                  90                  95

Thr Phe Gly Gln Gly Thr Lys Leu Glu Ile Lys
            100                 105
```

<210> SEQ ID NO 76
<211> LENGTH: 321
<212> TYPE: DNA
<213> ORGANISM: Artificial Sequence
<220> FEATURE:
<223> OTHER INFORMATION: Polynucleotide Encoding hBRCA84D-5VL

<400> SEQUENCE: 76

```
gacatccagc tgacccagtc ccctccttc ctgtctgcct ccgtgggcga cagagtgacc      60
atcacatgca aggcctccca gaacgtggac accaacgtgg cctggtatca gcagaagcct     120
ggccaggccc ctaaggcgct gatctactcc gcctcctacc ggtactccgg cgtgccttcc     180
aggttctccg gctccggctc tggcaccgac ttcaccctga ccatctccag cctgcagcct     240
gaggacttcg ccacctacta ctgccagcag tacaacaact acccttcac cttcggccag      300 ggcaccaagc tggaaatcaa g                                               321
```

<210> SEQ ID NO 77
<211> LENGTH: 107
<212> TYPE: PRT
<213> ORGANISM: Artificial Sequence
<220> FEATURE:
<223> OTHER INFORMATION: Amino Acid Sequence of hBRCA84D-6VL

<400> SEQUENCE: 77

```
Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Glu Tyr Tyr Cys Gln Gln Tyr Asn Asn Tyr Pro Phe
                85                  90                  95

Thr Phe Gly Gln Gly Thr Lys Leu Glu Ile Lys
            100                 105
```

<210> SEQ ID NO 78
<211> LENGTH: 321
<212> TYPE: DNA
<213> ORGANISM: Artificial Sequence
<220> FEATURE:
<223> OTHER INFORMATION: Polynucleotide Encoding hBRCA84D-6VL

<400> SEQUENCE: 78

```
gacatccagc tgacccagtc ccctccttc ctgtctgcct ccgtgggcga cagagtgacc      60
atcacatgca aggcctccca gaacgtggac accaacgtgg cctggtatca gcagaagcct     120
ggccaggccc ctaagctgct gatctactcc gcctcctacc ggtactccgg cgtgccttcc     180
aggttctccg gctccggctc tggcaccgac ttcaccctga ccatctccag cctgcagcct     240
gaggacttcg ccgagtacta ctgccagcag tacaacaact acccttcac cttcggccag      300 ggcaccaagc tggaaatcaa g                                               321
```

<210> SEQ ID NO 79
<211> LENGTH: 122
<212> TYPE: PRT
<213> ORGANISM: Artificial Sequence
<220> FEATURE:
<223> OTHER INFORMATION: Amino Acid Sequence of hBRCA84D-2VH

<400> SEQUENCE: 79

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
```

```
            20                  25                  30
Gly Met His Trp Val Arg Gln Ala Pro Gly Lys Gly Leu Glu Trp Val
        35                  40                  45

Ala Tyr Ile Ser Ser Asp Ser Ser Ala Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Gly Arg Gly Arg Glu Asn Ile Tyr Tyr Gly Ser Arg Leu Asp Tyr Trp
            100                 105                 110

Gly Gln Gly Thr Thr Val Thr Val Ser Ser
            115                 120

<210> SEQ ID NO 80
<211> LENGTH: 366
<212> TYPE: DNA
<213> ORGANISM: Artificial Sequence
<220> FEATURE:
<223> OTHER INFORMATION: Polynucleotide Encoding hBRCA84D-2VH

<400> SEQUENCE: 80
gaggtgcagc tggtcgagtc tggcggagga ctggtgcagc ctggcggctc cctgagactg      60
tcttgcgccg cctccggctt caccttctcc agcttcggca tgcactgggt ccgccaggct     120
ccaggcaagg gactggaatg ggtggcctac atctcctccg actcctccgc catctactac     180
gccgacaccg tgaagggcag gttcaccatc tcccgggaca cgccaagaa ctccctgtac      240 ctgcagatga actccctgcg ggacgaggac accgccgtgt actactgcgg cagaggccgg     300
gagaatatct actacggctc ccggctggat tattggggcc agggcaccac cgtgaccgtg     360
tcctct                                                                366

<210> SEQ ID NO 81
<211> LENGTH: 122
<212> TYPE: PRT
<213> ORGANISM: Artificial Sequence
<220> FEATURE:
<223> OTHER INFORMATION: Amino Acid Sequence of hBRCA84D-3VH

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Asp Ser Ser Ala Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Met Tyr Tyr Cys
                85                  90                  95

Gly Arg Gly Arg Glu Asn Ile Tyr Tyr Gly Ser Arg Leu Asp Tyr Trp
            100                 105                 110

Gly Gln Gly Thr Thr Val Thr Val Ser Ser
            115                 120
```

```
<210> SEQ ID NO 82
<211> LENGTH: 366
<212> TYPE: DNA
<213> ORGANISM: Artificial Sequence
<220> FEATURE:
<223> OTHER INFORMATION: Polynucleotide Encoding hBRCA84D-3VH

<400> SEQUENCE: 82
gaggtgcagc tggtcgagtc tggcggagga ctggtgcagc ctggcggctc cctgagactg      60
tcttgcgccg cctccggctt caccttctcc agcttcggca tgcactgggt ccgccaggct     120
ccaggcaagg gactggaatg ggtggcctac atctcctccg actcctccgc catctactac     180
gccgacaccg tgaagggcag gttcaccatc tcccgggaca cgccaagaa ctccctgtac      240 ctgcagatga actccctgcg ggacgaggac accgccatgt actactgcgg cagaggccgg     300
gagaatatct actacggctc ccggctggat tattggggcc agggcaccac cgtgaccgtg     360
tcctct                                                                366

<210> SEQ ID NO 83
<211> LENGTH: 122
<212> TYPE: PRT
<213> ORGANISM: Artificial Sequence
<220> FEATURE:
<223> OTHER INFORMATION: Amino Acid Sequence of hBRCA84D-4VH

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Asp Ser Ser Ala Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ser Glu Asp Thr Ala Val Tyr Tyr Cys
                85                  90                  95

Ala Arg Gly Arg Glu Asn Ile Tyr Tyr Gly Ser Arg Leu Asp Tyr Trp
            100                 105                 110

Gly Gln Gly Thr Thr Val Thr Val Ser Ser
        115                 120

<210> SEQ ID NO 84
<211> LENGTH: 366
<212> TYPE: DNA
<213> ORGANISM: Artificial Sequence
<220> FEATURE:
<223> OTHER INFORMATION: Polynucleotide Encoding hBRCA84D-4VH

<400> SEQUENCE: 84
gaggtgcagc tggtcgagtc tggcggagga ctggtgcagc ctggcggctc cctgagactg      60
tcttgcgccg cctccggctt caccttctcc agcttcggca tgcactgggt ccgccaggct     120
ccaggcaagg gactggaatg ggtggcctac atctcctccg actcctccgc catctactac     180
gccgacaccg tgaagggcag gttcaccatc tcccgggaca cgccaagaa ctccctgtac      240 ctgcagatga actccctgcg gagcgaggac accgccgtgt actactgcgc cagaggccgg     300
gagaatatct actacggctc ccggctggat tattggggcc agggcaccac cgtgaccgtg     360
``` tcctct                                                                366

<210> SEQ ID NO 85
<211> LENGTH: 214
<212> TYPE: PRT
<213> ORGANISM: Artificial Sequence
<220> FEATURE:
<223> OTHER INFORMATION: Amino Acid Sequence of chBRCA84D Light Chain

<400> SEQUENCE: 85

Asp Ile Ala Met Thr Gln Ser Gln Lys Phe Met Ser Thr Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Asn Asn Val Gln Ser
65                  70                  75                  80

Glu Asp Leu Ala Glu Tyr Phe Cys Gln Gln Tyr Asn Asn Tyr Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 86
<211> LENGTH: 645
<212> TYPE: DNA
<213> ORGANISM: Artificial Sequence
<220> FEATURE:
<223> OTHER INFORMATION: Polynucleotide Encoding chBRCA84D Light Chain

<400> SEQUENCE: 86
gacattgcga tgacccagtc tcaaaaattc atgtccacat cagtaggaga cagggtcagc    60
gtcacctgca aggccagtca gaatgtggat actaatgtag cctggtatca acagaaacca   120
gggcaatctc ctaaagcact gatttactcg gcatcctacc ggtacagtgg agtccctgat   180
cgcttcacag gcagtggatc tgggacagat ttcactctca ccatcaacaa tgtgcagtct   240
gaagacttgg cagagtattt ctgtcagcaa tataacaact atccattcac gttcggctcg   300
gggacaaagt tggaaataaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480

```
gagagtgtca cagagcagga cagcaaggac agcaccctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                    645
```

<210> SEQ ID NO 87
<211> LENGTH: 452
<212> TYPE: PRT
<213> ORGANISM: Artificial Sequence
<220> FEATURE:
<223> OTHER INFORMATION: Amino Acid Sequence of chBRCA84D Heavy Chain

<400> SEQUENCE: 87

```
Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Asp Ser Ala Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Gly Arg Gly Arg Glu Asn Ile Tyr Tyr Gly Ser Arg Leu Asp Tyr Trp
            100                 105                 110

Gly Gln Gly Thr Thr Leu Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335
```

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 88
<211> LENGTH: 1359
<212> TYPE: DNA
<213> ORGANISM: Artificial Sequence
<220> FEATURE:
<223> OTHER INFORMATION: Polynucleotide Encoding chBRCA84D Heavy Chain

<400> SEQUENCE: 88

```
gatgtgcagc tggtggagtc tgggggaggc ttagtgcagc ctggagggtc ccggaaactc      60
tcctgtgcag cctctggatt cactttcagt agctttggaa tgcactgggt tcgtcaggct     120
ccagagaagg ggctggagtg ggtcgcatac attagtagtg acagtagtgc catctactat     180
gcagacacag tgaagggccg attcaccatc tccagagaca atcccaagaa caccctgttc     240
ctgcaaatga ccagtctaag gtctgaggac acggccatgt attactgtgg aagagggagg     300
gaaaacattt actacggtag taggcttgac tactggggcc aaggcaccac tctcacagtc     360
tcctcagcct ccaccaaggg cccatcggtc ttccccctgg caccctcctc caagagcacc     420
tctgggggca cagcggccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga caagagagtt     660
gagcccaaat cttgtgacaa aactcacaca tgcccaccgt gcccagcacc tgaactcctg     720
gggggaccgt cagtcttcct cttcccccca aaacccaagg acaccctcat gatctcccgg     780
acccctgagg tcacatgcgt ggtggtggac gtgagccacg aagaccctga ggtcaagttc     840
aactggtacg tggacggcgt ggaggtgcat aatgccaaga caaagccgcg ggaggagcag     900
tacaacagca cgtaccgtgt ggtcagcgtc ctcaccgtcc tgcaccagga ctggctgaat     960
ggcaaggagt acaagtgcaa ggtctccaac aaagccctcc cagcccccat cgagaaaacc    1020
atctccaaag ccaaagggca gccccgagaa ccacaggtgt acaccctgcc cccatcccgg    1080
gatgagctga ccaagaacca ggtcagcctg acctgcctgg tcaaaggctt ctatcccagc    1140
gacatcgccg tggagtggga gagcaatggg cagccggaga caactacaa gaccacgcct    1200 cccgtgctgg actccgacgg ctccttcttc ctctacagca agctcaccgt ggacaagagc    1260
aggtggcagc aggggaacgt cttctcatgc tccgtgatgc atgaggctct gcacaaccac    1320
```
tacacgcaga agagcctctc cctgtctccg ggtaaatga                                    1359

<210> SEQ ID NO 89
<211> LENGTH: 191
<212> TYPE: PRT
<213> ORGANISM: Homo sapiens
<220> FEATURE:
<221> NAME/KEY: MISC_FEATURE
<222> LOCATION: (1)..(191)
<223> OTHER INFORMATION: Amino Acid Sequence of VEGF Isoform 162

<400> SEQUENCE: 89

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190

<210> SEQ ID NO 90
<211> LENGTH: 990
<212> TYPE: DNA
<213> ORGANISM: Homo sapiens
<220> FEATURE:
<221> NAME/KEY: misc_feature
<222> LOCATION: (1)..(990)
<223> OTHER INFORMATION: Polynucleotide Encoding the Amino Acid Sequence
      of VEGF Isoform 162

<400> SEQUENCE: 90
cagtgtgctg gcggcccggc gcgagccggc ccggccccgg tcgggcctcc gaaaccatga      60
actttctgct gtcttgggtg cattggagcc tcgccttgct gctctacctc caccatgcca     120
agtggtccca ggctgcaccc atggcagaag gaggagggca gaatcatcac gaagtggtga     180
agttcatgga tgtctatcag cgcagctact gccatccaat cgagaccctg gtggacatct     240
tccaggagta ccctgatgag atcgagtaca tcttcaagcc atcctgtgtg cccctgatgc     300
gatgcggggg ctgctgcaat gacgagggcc tggagtgtgt gcccactgag gagtccaaca     360
tcaccatgca gattatgcgg atcaaacctc accaaggcca gcacatagga gagatgagct     420
tcctacagca caacaaatgt gaatgcagac caaagaaaga tagagcaaga caagaaaatc     480

```
cctgtgggcc ttgctcagag cggagaaagc atttgtttgt acaagatccg cagacgtgta      540
aatgttcctg caaaaacaca gactcgcgtt gcaaggcgag gcagcttgag ttaaacgaac      600
gtacttgcag atgtgacaag ccgaggcggt gagccgggca ggaggaagga gcctccctca      660
gggtttcggg aaccagatct ctcaccagga aagactgata cagaacgatc gatacagaaa      720
ccacgctgcc gccaccacac catcaccatc gacagaacag tccttaatcc agaaacctga      780
aatgaaggaa gaggagactc tgcgcagagc actttgggtc cggagggcga gactccggcg      840
gaagcattcc cgggcgggtg acccagcacg gtccctcttg gaattggatt cgccattta      900 tttttcttgc tgctaaatca ccgagcccgg aagattagag agttttattt ctgggattcc      960
tgtagacaca ccgcggccgc cagcacactg                                      990
```

<210> SEQ ID NO 91
<211> LENGTH: 232
<212> TYPE: PRT
<213> ORGANISM: Homo sapiens
<220> FEATURE:
<221> NAME/KEY: MISC_FEATURE
<222> LOCATION: (1)..(232)
<223> OTHER INFORMATION: Amino Acid Sequence of VEGF Isoform 206

<400> SEQUENCE: 91

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205

Thr Asp Ser Arg Cys Lys Ala Arg Gln Leu Glu Leu Asn Glu Arg Thr
    210                 215                 220

Cys Arg Cys Asp Lys Pro Arg Arg
225                 230
```

<210> SEQ ID NO 92
<211> LENGTH: 1338
<212> TYPE: PRT

```
<213> ORGANISM: Homo sapiens
<220> FEATURE:
<221> NAME/KEY: MISC_FEATURE
<222> LOCATION: (1)..(1338)
<223> OTHER INFORMATION: Amino Acid Sequence of VEGF Receptor VEGFR-1

<400> SEQUENCE: 92

Met Val Ser Tyr Trp Asp Thr Gly Val Leu Leu Cys Ala Leu Leu Ser
1               5                   10                  15

Cys Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
            35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
            115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
            195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
            275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
            355                 360                 365

Trp Leu Lys Asp Gly Leu Pro Ala Thr Glu Lys Ser Ala Arg Tyr Leu
    370                 375                 380
```

```
Thr Arg Gly Tyr Ser Leu Ile Ile Lys Asp Val Thr Glu Asp Ala
385                 390                 395                 400

Gly Asn Tyr Thr Ile Leu Leu Ser Ile Lys Gln Ser Asn Val Phe Lys
            405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
            435                 440                 445

Arg Gln Ile Leu Thr Cys Thr Ala Tyr Gly Ile Pro Gln Pro Thr Ile
            450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
            515                 520                 525

Ile Ser Gly Ile Tyr Ile Cys Ile Ala Ser Asn Lys Val Gly Thr Val
530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
            565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
            595                 600                 605

Met Ala Ile Thr Lys Glu His Ser Ile Thr Leu Asn Leu Thr Ile Met
610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
            645                 650                 655

Asp Gln Glu Ala Pro Tyr Leu Leu Arg Asn Leu Ser Asp His Thr Val
            660                 665                 670

Ala Ile Ser Ser Ser Thr Thr Leu Asp Cys His Ala Asn Gly Val Pro
            675                 680                 685

Glu Pro Gln Ile Thr Trp Phe Lys Asn Asn His Lys Ile Gln Gln Glu
            690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
            725                 730                 735

Lys Gly Ser Val Glu Ser Ser Ala Tyr Leu Thr Val Gln Gly Thr Ser
            740                 745                 750

Asp Lys Ser Asn Leu Glu Leu Ile Thr Leu Thr Cys Thr Cys Val Ala
            755                 760                 765

Ala Thr Leu Phe Trp Leu Leu Leu Thr Leu Phe Ile Arg Lys Met Lys
            770                 775                 780

Arg Ser Ser Ser Glu Ile Lys Thr Asp Tyr Leu Ser Ile Ile Met Asp
785                 790                 795                 800
```

```
Pro Asp Glu Val Pro Leu Asp Glu Gln Cys Glu Arg Leu Pro Tyr Asp
            805                 810                 815

Ala Ser Lys Trp Glu Phe Ala Arg Glu Arg Leu Lys Leu Gly Lys Ser
            820                 825                 830

Leu Gly Arg Gly Ala Phe Gly Lys Val Val Gln Ala Ser Ala Phe Gly
            835                 840                 845

Ile Lys Lys Ser Pro Thr Cys Arg Thr Val Ala Val Lys Met Leu Lys
    850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
                885                 890                 895

Ala Cys Thr Lys Gln Gly Gly Pro Leu Met Val Ile Val Glu Tyr Cys
            900                 905                 910

Lys Tyr Gly Asn Leu Ser Asn Tyr Leu Lys Ser Lys Arg Asp Leu Phe
            915                 920                 925

Phe Leu Asn Lys Asp Ala Ala Leu His Met Glu Pro Lys Lys Glu Lys
            930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
                965                 970                 975

Leu Ser Asp Val Glu Glu Glu Asp Ser Asp Gly Phe Tyr Lys Glu
                980                 985                 990

Pro Ile Thr Met Glu Asp Leu Ile Ser Tyr Ser Phe Gln Val Ala Arg
            995                1000                1005

Gly Met Glu Phe Leu Ser Ser Arg Lys Cys Ile His Arg Asp Leu
            1010                1015                1020

Ala Ala Arg Asn Ile Leu Leu Ser Glu Asn Asn Val Val Lys Ile
            1025                1030                1035

Cys Asp Phe Gly Leu Ala Arg Asp Ile Tyr Lys Asn Pro Asp Tyr
            1040                1045                1050

Val Arg Lys Gly Asp Thr Arg Leu Pro Leu Lys Trp Met Ala Pro
            1055                1060                1065

Glu Ser Ile Phe Asp Lys Ile Tyr Ser Thr Lys Ser Asp Val Trp
            1070                1075                1080

Ser Tyr Gly Val Leu Leu Trp Glu Ile Phe Ser Leu Gly Gly Ser
            1085                1090                1095

Pro Tyr Pro Gly Val Gln Met Asp Glu Asp Phe Cys Ser Arg Leu
            1100                1105                1110

Arg Glu Gly Met Arg Met Arg Ala Pro Glu Tyr Ser Thr Pro Glu
            1115                1120                1125

Ile Tyr Gln Ile Met Leu Asp Cys Trp His Arg Asp Pro Lys Glu
            1130                1135                1140

Arg Pro Arg Phe Ala Glu Leu Val Glu Lys Leu Gly Asp Leu Leu
            1145                1150                1155

Gln Ala Asn Val Gln Gln Asp Gly Lys Asp Tyr Ile Pro Ile Asn
            1160                1165                1170

Ala Ile Leu Thr Gly Asn Ser Gly Phe Thr Tyr Ser Thr Pro Ala
            1175                1180                1185

Phe Ser Glu Asp Phe Phe Lys Glu Ser Ile Ser Ala Pro Lys Phe
            1190                1195                1200

Asn Ser Gly Ser Ser Asp Asp Val Arg Tyr Val Asn Ala Phe Lys
```

```
              1205                1210                1215

Phe Met Ser Leu Glu Arg Ile Lys Thr Phe Glu Leu Leu Pro
        1220                1225                1230

Asn Ala Thr Ser Met Phe Asp Asp Tyr Gln Gly Asp Ser Ser Thr
1235                1240                1245

Leu Leu Ala Ser Pro Met Leu Lys Arg Phe Thr Trp Thr Asp Ser
    1250                1255                1260

Lys Pro Lys Ala Ser Leu Lys Ile Asp Leu Arg Val Thr Ser Lys
1265                1270                1275

Ser Lys Glu Ser Gly Leu Ser Asp Val Ser Arg Pro Ser Phe Cys
    1280                1285                1290

His Ser Ser Cys Gly His Val Ser Glu Gly Lys Arg Arg Phe Thr
1295                1300                1305

Tyr Asp His Ala Glu Leu Glu Arg Lys Ile Ala Cys Cys Ser Pro
    1310                1315                1320

Pro Pro Asp Tyr Asn Ser Val Val Leu Tyr Ser Thr Pro Pro Ile
1325                1330                1335

<210> SEQ ID NO 93
<211> LENGTH: 1356
<212> TYPE: PRT
<213> ORGANISM: Homo sapiens
<220> FEATURE:
<221> NAME/KEY: MISC_FEATURE
<222> LOCATION: (1)..(1356)
<223> OTHER INFORMATION: Amino Acid Sequence of VEGF Receptor VEGFR-2

<400> SEQUENCE: 93

Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220
```

```
Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
            245                 250                 255

Asp Phe Asn Trp Glu Tyr Pro Ser Ser Lys His Gln His Lys Lys Leu
        260                 265                 270

Val Asn Arg Asp Leu Lys Thr Gln Ser Gly Ser Glu Met Lys Lys Phe
    275                 280                 285

Leu Ser Thr Leu Thr Ile Asp Gly Val Thr Arg Ser Asp Gln Gly Leu
290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Pro Glu Ile Lys Trp Tyr Lys Asn Gly
        355                 360                 365

Ile Pro Leu Glu Ser Asn His Thr Ile Lys Ala Gly His Val Leu Thr
    370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
            420                 425                 430

Asp Ser Tyr Gln Tyr Gly Thr Thr Gln Thr Leu Thr Cys Thr Val Tyr
        435                 440                 445

Ala Ile Pro Pro Pro His His Ile His Trp Tyr Trp Gln Leu Glu Glu
    450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
            500                 505                 510

Thr Val Ser Thr Leu Val Ile Gln Ala Ala Asn Val Ser Ala Leu Tyr
        515                 520                 525

Lys Cys Glu Ala Val Asn Lys Val Gly Arg Gly Glu Arg Val Ile Ser
    530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr
        595                 600                 605

Leu Trp Lys Leu Asn Ala Thr Met Phe Ser Asn Ser Thr Asn Asp Ile
    610                 615                 620

Leu Ile Met Glu Leu Lys Asn Ala Ser Leu Gln Asp Gln Gly Asp Tyr
625                 630                 635                 640
```

```
Val Cys Leu Ala Gln Asp Arg Lys Thr Lys Lys Arg His Cys Val Val
                645                 650                 655

Arg Gln Leu Thr Val Leu Glu Arg Val Ala Pro Thr Ile Thr Gly Asn
            660                 665                 670

Leu Glu Asn Gln Thr Thr Ser Ile Gly Glu Ser Ile Glu Val Ser Cys
            675                 680                 685

Thr Ala Ser Gly Asn Pro Pro Pro Gln Ile Met Trp Phe Lys Asp Asn
        690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
                740                 745                 750

Ile Ile Glu Gly Ala Gln Glu Lys Thr Asn Leu Glu Ile Ile Ile Leu
                755                 760                 765

Val Gly Thr Ala Val Ile Ala Met Phe Phe Trp Leu Leu Leu Val Ile
            770                 775                 780

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
                805                 810                 815

Cys Glu Arg Leu Pro Tyr Asp Ala Ser Lys Trp Glu Phe Pro Arg Asp
                820                 825                 830

Arg Leu Lys Leu Gly Lys Pro Leu Gly Arg Gly Ala Phe Gly Gln Val
            835                 840                 845

Ile Glu Ala Asp Ala Phe Gly Ile Asp Lys Thr Ala Thr Cys Arg Thr
850                 855                 860

Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
                885                 890                 895

Asn Val Val Asn Leu Leu Gly Ala Cys Thr Lys Pro Gly Gly Pro Leu
                900                 905                 910

Met Val Ile Val Glu Phe Cys Lys Phe Gly Asn Leu Ser Thr Tyr Leu
            915                 920                 925

Arg Ser Lys Arg Asn Glu Phe Val Pro Tyr Lys Thr Lys Gly Ala Arg
            930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ser Ala Ser Ser Gly
                965                 970                 975

Phe Val Glu Glu Lys Ser Leu Ser Asp Val Glu Glu Glu Glu Ala Pro
            980                 985                 990

Glu Asp Leu Tyr Lys Asp Phe Leu Thr Leu Glu His Leu Ile Cys Tyr
            995                 1000                1005

Ser Phe Gln Val Ala Lys Gly Met Glu Phe Leu Ala Ser Arg Lys
    1010                1015                1020

Cys Ile His Arg Asp Leu Ala Ala Arg Asn Ile Leu Leu Ser Glu
    1025                1030                1035

Lys Asn Val Val Lys Ile Cys Asp Phe Gly Leu Ala Arg Asp Ile
    1040                1045                1050

Tyr Lys Asp Pro Asp Tyr Val Arg Lys Gly Asp Ala Arg Leu Pro
```

```
           1055                1060                1065

Leu Lys Trp Met Ala Pro Glu Thr Ile Phe Asp Arg Val Tyr Thr
    1070                1075                1080

Ile Gln Ser Asp Val Trp Ser Phe Gly Val Leu Leu Trp Glu Ile
    1085                1090                1095

Phe Ser Leu Gly Ala Ser Pro Tyr Pro Gly Val Lys Ile Asp Glu
    1100                1105                1110

Glu Phe Cys Arg Arg Leu Lys Glu Gly Thr Arg Met Arg Ala Pro
    1115                1120                1125

Asp Tyr Thr Thr Pro Glu Met Tyr Gln Thr Met Leu Asp Cys Trp
    1130                1135                1140

His Gly Glu Pro Ser Gln Arg Pro Thr Phe Ser Glu Leu Val Glu
    1145                1150                1155

His Leu Gly Asn Leu Leu Gln Ala Asn Ala Gln Gln Asp Gly Lys
    1160                1165                1170

Asp Tyr Ile Val Leu Pro Ile Ser Glu Thr Leu Ser Met Glu Glu
    1175                1180                1185

Asp Ser Gly Leu Ser Leu Pro Thr Ser Pro Val Ser Cys Met Glu
    1190                1195                1200

Glu Glu Glu Val Cys Asp Pro Lys Phe His Tyr Asp Asn Thr Ala
    1205                1210                1215

Gly Ile Ser Gln Tyr Leu Gln Asn Ser Lys Arg Lys Ser Arg Pro
    1220                1225                1230

Val Ser Val Lys Thr Phe Glu Asp Ile Pro Leu Glu Glu Pro Glu
    1235                1240                1245

Val Lys Val Ile Pro Asp Asp Asn Gln Thr Asp Ser Gly Met Val
    1250                1255                1260

Leu Ala Ser Glu Glu Leu Lys Thr Leu Glu Asp Arg Thr Lys Leu
    1265                1270                1275

Ser Pro Ser Phe Gly Gly Met Val Pro Ser Lys Ser Arg Glu Ser
    1280                1285                1290

Val Ala Ser Glu Gly Ser Asn Gln Thr Ser Gly Tyr Gln Ser Gly
    1295                1300                1305

Tyr His Ser Asp Asp Thr Asp Thr Thr Val Tyr Ser Ser Glu Glu
    1310                1315                1320

Ala Glu Leu Leu Lys Leu Ile Glu Ile Gly Val Gln Thr Gly Ser
    1325                1330                1335

Thr Ala Gln Ile Leu Gln Pro Asp Ser Gly Thr Thr Leu Ser Ser
    1340                1345                1350

Pro Pro Val
    1355

<210> SEQ ID NO 94
<211> LENGTH: 214
<212> TYPE: PRT
<213> ORGANISM: Artificial Sequence
<220> FEATURE:
<223> OTHER INFORMATION: Amino Acid Sequence of the Light Chain of
      Bevacizumab

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30
```

Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
 50                      55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Glu Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 95
<211> LENGTH: 453
<212> TYPE: PRT
<213> ORGANISM: Artificial Sequence
<220> FEATURE:
<223> OTHER INFORMATION: Amino Acid Sequence of the Heavy Chain of
      Bevacizumab

<400> SEQUENCE: 95

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
 50                      55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

```
Pro Ala Val Leu Gln Ser Ser Gly Leu Tyr Ser Leu Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 96
<211> LENGTH: 218
<212> TYPE: PRT
<213> ORGANISM: Homo sapiens
<220> FEATURE:
<221> NAME/KEY: MISC_FEATURE
<222> LOCATION: (1)..(218)
<223> OTHER INFORMATION: Amino Acid Sequence of the IgG1 Fc Region

<400> SEQUENCE: 96

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Lys Phe Asn Trp
        35                  40                  45

Tyr Val Asp Gly Val Glu Val His Asn Ala Lys Thr Lys Pro Arg Glu
    50                  55                  60
```

```
Glu Gln Tyr Asn Ser Thr Tyr Arg Val Val Ser Val Leu Thr Val Leu
 65                  70                  75                  80

His Gln Asp Trp Leu Asn Gly Lys Glu Tyr Lys Cys Lys Val Ser Asn
                 85                  90                  95

Lys Ala Leu Pro Ala Pro Ile Glu Lys Thr Ile Ser Lys Ala Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Val Phe Ser Cys Ser Val Met His Glu Ala Leu His Asn His Tyr Thr
        195                 200                 205

Gln Lys Ser Leu Ser Leu Ser Pro Gly Lys
    210                 215

<210> SEQ ID NO 97
<211> LENGTH: 8
<212> TYPE: PRT
<213> ORGANISM: Artificial Sequence
<220> FEATURE:
<223> OTHER INFORMATION: Preferred Linker of VL and VH Diabody Domains

<400> SEQUENCE: 97

Gly Gly Gly Ser Gly Gly Gly Gly
1               5

<210> SEQ ID NO 98
<211> LENGTH: 24
<212> TYPE: DNA
<213> ORGANISM: Artificial Sequence
<220> FEATURE:
<223> OTHER INFORMATION: Polynucleotide Encoding Preferred Linker of VL
      and VH Diabody Domains

<400> SEQUENCE: 98
ggaggcggat ccggaggcgg aggc                                              24

<210> SEQ ID NO 99
<211> LENGTH: 4
<212> TYPE: PRT
<213> ORGANISM: Artificial Sequence
<220> FEATURE:
<223> OTHER INFORMATION: Cysteine-Containing Linker

<400> SEQUENCE: 99

Leu Gly Gly Cys
1

<210> SEQ ID NO 100
<211> LENGTH: 13
<212> TYPE: PRT
<213> ORGANISM: Artificial Sequence
<220> FEATURE:
<223> OTHER INFORMATION: Amino Acid Sequence of Hinge Domain Linker

<400> SEQUENCE: 100
```

Glu Pro Lys Ser Cys Asp Lys Thr His Thr Cys Pro Pro
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Amino Acid Sequence of Hinge Domain Linker

<400> SEQUENCE: 101

Glu Ser Lys Tyr Gly Pro Pro Cys Pro Ser
1               5                   10

<210> SEQ ID NO 102
<211> LENGTH: 6
<212> TYPE: PRT
<213> ORGANISM: Artificial Sequence
<220> FEATURE:
<223> OTHER INFORMATION: Cysteine-Containing, Heterodimer-Promoting
      Linker Derived from IgG Hinge Domain

<400> SEQUENCE: 102

Val Glu Pro Lys Ser Cys
1               5

<210> SEQ ID NO 103
<211> LENGTH: 18
<212> TYPE: DNA
<213> ORGANISM: Artificial Sequence
<220> FEATURE:
<223> OTHER INFORMATION: Polynucleotide Encoding Cysteine-Containing,
      Heterodimer-Promoting Linker Derived from IgG Hinge Domain

<400> SEQUENCE: 103
gttgagccca aatcttgt                                                  18

<210> SEQ ID NO 104
<211> LENGTH: 10
<212> TYPE: PRT
<213> ORGANISM: Artificial Sequence
<220> FEATURE:
<223> OTHER INFORMATION: Cysteine-Containing, Heterodimer-Promoting
      Linker Derived from Human Kappa Light Chain Domain

<400> SEQUENCE: 104

Leu Gly Gly Cys Phe Asn Arg Gly Glu Cys
1               5                   10

<210> SEQ ID NO 105
<211> LENGTH: 30
<212> TYPE: DNA
<213> ORGANISM: Artificial Sequence
<220> FEATURE:
<223> OTHER INFORMATION: Polynucleotide Encoding Cysteine-Containing,
      Heterodimer-Promoting Linker Derived from Human Kappa Light Chain
      Domain

<400> SEQUENCE: 105
ctgggaggct gcttcaacag gggagagtgt                                     30

<210> SEQ ID NO 106
<211> LENGTH: 6
<212> TYPE: PRT
<213> ORGANISM: Artificial Sequence
<220> FEATURE:
<223> OTHER INFORMATION: Cysteine-Containing, Heterodimer-Promoting
      Linker Derived from Human Kappa Light Chain Domain

```
<400> SEQUENCE: 106

Phe Asn Arg Gly Glu Cys
1               5

<210> SEQ ID NO 107
<211> LENGTH: 18
<212> TYPE: DNA
<213> ORGANISM: Artificial Sequence
<220> FEATURE:
<223> OTHER INFORMATION: Polynucleotide Encoding Cysteine-Containing,
      Heterodimer-Promoting Linker Derived from Human Kappa Light Chain
      Domain

<400> SEQUENCE: 107
ttcaacaggg gagagtgt                                                 18

<210> SEQ ID NO 108
<211> LENGTH: 28
<212> TYPE: PRT
<213> ORGANISM: Artificial Sequence
<220> FEATURE:
<223> OTHER INFORMATION: Amino Acid Sequence of E-coil Heterodimer-
      Promoting Domain

<400> SEQUENCE: 108

Glu Val Ala Ala Leu Glu Lys Glu Val Ala Ala Leu Glu Lys Glu Val
1               5                   10                  15

Ala Ala Leu Glu Lys Glu Val Ala Ala Leu Glu Lys
            20                  25

<210> SEQ ID NO 109
<211> LENGTH: 28
<212> TYPE: PRT
<213> ORGANISM: Artificial Sequence
<220> FEATURE:
<223> OTHER INFORMATION: Amino Acid Sequence of K-coil Heterodimer-
      Promoting Domain

<400> SEQUENCE: 109

Lys Val Ala Ala Leu Lys Glu Lys Val Ala Ala Leu Lys Glu Lys Val
1               5                   10                  15

Ala Ala Leu Lys Glu Lys Val Ala Ala Leu Lys Glu
            20                  25

<210> SEQ ID NO 110
<211> LENGTH: 5
<212> TYPE: PRT
<213> ORGANISM: Artificial Sequence
<220> FEATURE:
<223> OTHER INFORMATION: Amino Acid Sequence of Linker

<400> SEQUENCE: 110

Gly Gly Gly Asn Ser
1               5
```

METHODS FOR THE TREATMENT OF VASCULARIZING CANCERS

CROSS REFERENCE TO RELATED APPLICATIONS

This application is a § 371 National Stage Application of PCT/US2015/015320 (filed on Feb. 11, 2015) which application claims priority to U.S. Patent Appln. Serial No. 61/939,804 (filed on Feb. 12, 2014).

REFERENCE TO SEQUENCE LISTING

This application includes one or more Sequence Listings pursuant to 37 C.F.R. 1.821 et seq., which are disclosed in both paper and computer-readable media, and which paper and computer-readable disclosures are herein incorporated by reference in their entirety.

BACKGROUND OF THE INVENTION

Field of the Invention

The invention concerns therapeutic compositions for the treatment of vascularizing cancers, especially, glioblastoma. In particular, the invention is directed to compositions that comprise a molecule having a binding ability that is specific for B7-H3 and a molecule having a binding ability that is specific for a cell-surface factor (or its receptor) that is involved in promoting tumor angiogenesis (especially VEGF or its receptor, VEGFR). The invention is additionally directed to the use of such compositions in the treatment of such cancers, and in particular, in the treatment of glioblastoma.

Description of Related Art

I. The B7 Superfamily and B7-H3

The growth and metastasis of tumors depends to a large extent on their capacity to evade host immune surveillance and overcome host defenses. Most tumors express antigens that can be recognized to a variable extent by the host immune system, but in many cases, an inadequate immune response is elicited because of the ineffective activation of effector T cells (Khawli, L. A. et al. (2008) "*Cytokine, Chemokine, and Co-Stimulatory Fusion Proteins for the Immunotherapy of Solid Tumors,*" Exper. Pharmacol. 181: 291-328).

CD4+ T-lymphocytes are the essential organizers of most mammalian immune and autoimmune responses (Dong, C. et al. (2003) "*Immune Regulation by Novel Costimulatory Molecules,*" Immunolog. Res. 28(1):39-48). The activation of CD4+ helper T-cells has been found to be mediated through co-stimulatory interactions between Antigen Presenting Cells and naive CD4+ T-lymphocytes. Two interactions are required (Viglietta, V. et al. (2007) "*Modulating Co-Stimulation,*" Neurotherapeutics 4:666-675; Korman, A. J. et al. (2007) "*Checkpoint Blockade in Cancer Immunotherapy,*" Adv. Immunol. 90:297-339). In the first interaction, an Antigen Presenting Cell must display the relevant target antigen bound to the cell's major histocompatibility complex so that it can bind to the T-cell Receptor ("TCR") of a naive CD4+ T-lymphocyte. In the second interaction, a ligand of the Antigen Presenting Cell must bind to a CD28 receptor of the CD4+ T-lymphocyte (Dong, C. et al. (2003) "*Immune Regulation by Novel Costimulatory Molecules,*" Immunolog. Res. 28(1):39-48; Lindley, P. S. et al. (2009) "*The Clinical Utility Of Inhibiting CD28-Mediated Costimulation,*" Immunol. Rev. 229:307-321). CD4+ helper T-cells experiencing both stimulatory signals are then capable of responding to cytokines (such as Interleukin-2 and Interleukin-12 to develop into Th1 cells. Such cells produce interferon-gamma (IFN-γ) and tumor necrosis factor-alpha (TNF-α), which mediate inflammatory responses to target cells expressing the target antigen. B-cell activation and proliferation also occurs, resulting in antibody production specific for the target antigen (Bernard, A. et al. (2005) "*T and B Cell Cooperation: A Dance of Life and Death,*" Transplantation 79:S8-S11). In the absence of both co-stimulatory signals during TCR engagement, T cells enter a functionally unresponsive state, referred to as clonal anergy (Khawli, L. A. et al. (2008) "*Cytokine, Chemokine, and Co-Stimulatory Fusion Proteins for the Immunotherapy of Solid Tumors,*" Exper. Pharmacol. 181:291-328). In pathologic states, Th1 cells are the key players of various organ-specific autoimmune diseases, such as type I diabetes, rheumatoid arthritis, and multiple sclerosis (Dong, C. et al. (2003) "*Immune Regulation by Novel Costimulatory Molecules,*" Immunolog. Res. 28(1):39-48).

Investigations into the ligands of the CD28 receptor have led to the characterization of a set of related molecules known as the B7 Superfamily (Coyle, A. J. et al. (2001) "*The Expanding B7 Superfamily: Increasing Complexity In Costimulatory Signals Regulating T Cell Function,*" Nature Immunol. 2(3):203-209; Sharpe, A. H. et al. (2002) "*The B7-CD28 Superfamily,*" Nature Rev. Immunol. 2:116-126; Greenwald, R. J. et al. (2005) "*The B7 Family Revisited,*" Ann. Rev. Immunol. 23:515-548; Collins, M. et al. (2005) "*The B7 Family Of Immune-Regulatory Ligands,*" Genome Biol. 6:223.1-223.7; Loke, P. et al. (2004) "*Emerging Mechanisms Of Immune Regulation: The Extended B7 Family And Regulatory T Cells.*" Arthritis Res. Ther. 6:208-214; Korman, A. J. et al. (2007) "*Checkpoint Blockade in Cancer Immunotherapy,*" Adv. Immunol. 90:297-339; Flies, D. B. et al. (2007) "*The New B7s: Playing a Pivotal Role in Tumor Immunity,*" J. Immunother. 30(3):251-260; Agarwal, A. et al. (2008) "*The Role Of Positive Costimulatory Molecules In Transplantation And Tolerance,*" Curr. Opin. Organ Transplant. 13:366-372; Lenschow, D. J. et al. (1996) "*CD28/B7 System of T Cell Costimulation,*" Ann. Rev. Immunol. 14:233-258; Wang, S. et al. (2004) "*Co-Signaling Molecules Of The B7-CD28 Family In Positive And Negative Regulation Of T Lymphocyte Responses,*" Microbes Infect. 6:759-766). There are currently seven known members of the family: B7.1 (CD80), B7.2 (CD86), the inducible co-stimulator ligand (ICOS-L), the programmed death-1 ligand (PD-L1), the programmed death-2 ligand (PD-L2), B7-H3 and B7-H4 (Collins, M. et al. (2005) "*The B7 Family Of Immune-Regulatory Ligands,*" Genome Biol. 6:223.1-223.7).

B7 family members are immunoglobulin superfamily members with an immunoglobulin-V-like and an immunoglobulin-C-like domain (e.g., IgV-IgC) (Sharpe, A. H. et al. (2002) "*The B7-CD28 Superfamily,*" Nature Rev. Immunol. 2:116-126). The IgV and IgC domains of B7-family members are each encoded by single exons, with additional exons encoding leader sequences, transmembrane and cytoplasmic domains. The cytoplasmic domains are short, ranging in length from 19 to 62 amino-acid residues and can be encoded by multiple exons (Collins, M. et al. (2005) "*The B7 Family Of Immune-Regulatory Ligands,*" Genome Biol. 6:223.1-223.7). B7-H3 is unique in that the major human form contains two extracellular tandem IgV-IgC domains (i.e., IgV-IgC-IgV-IgC) (Collins, M. et al. (2005) "*The B7 Family Of Immune-Regulatory Ligands,*" Genome Biol. 6:223.1-223.7). Members of the B7 family are predicted to form back-to-back, non-covalent homodimers at the cell surface, and such dimers have been found with respect to B7-1 (CD80) and B7-2 (CD86).

B7-1 (CD80) and B7-2 (CD86) exhibit have dual specificity for the stimulatory CD28 receptor and the inhibitory CTLA-4 (CD152) receptor (Sharpe, A. H. et al. (2002) "*The B7-CD28 Superfamily*," Nature Rev. Immunol. 2:116-126).

Although initially thought to comprise only 2 Ig domains (IgV-IgC) (Chapoval, A. et al. (2001) "*B7-H3: A Costimulatory Molecule For T Cell Activation and IFN-γ Production*," Nature Immunol. 2:269-274; Sun, M. et al. (2002) "*Characterization of Mouse and Human B7-H3 Genes,*" J. Immunol. 168:6294-6297), a four immunoglobulin extracellular domain variant ("4Ig-B7-H3") has been identified and found to be more common human form of the protein (Sharpe, A. H. et al. (2002) "*The B7-CD28 Superfamily*," Nature Rev. Immunol. 2:116-126). No functional difference has been observed between these two forms, since the natural murine form (2Ig) and the human 4Ig form exhibit similar function (Hofmeyer, K. et al. (2008) "*The Contrasting Role Of B7-H3*," Proc. Natl. Acad. Sci. (U.S.A.) 105 (30):10277-10278). The 4Ig-B7-H3 molecule inhibits the natural killer cell-mediated lysis of cancer cells (Castriconi, R. et al. "*Identification Of 4Ig-B7-H3 As A Neuroblastoma-Associated Molecule That Exerts A Protective Role From An NK Cell-Mediated Lysis,*" Proc. Natl. Acad. Sci. (U.S.A.) 101(34): 12640-12645). The human B7-H3 (2Ig form) has been found to promote T-cell activation and IFN-γ production by binding to a putative receptor on activated T cells (Chapoval, A. et al. (2001) "*B7-H3: A Costimulatory Molecule For T Cell Activation and IFN-γ Production*," Nature Immunol. 2:269-274; Xu, H. et al. (2009) "*MicroRNA miR-29 Modulates Expression of Immunoinhibitory Molecule B7-H3: Potential Implications for Immune Based Therapy of Human Solid Tumors*," Cancer Res. 69(15): 5275-6281). Both B7-H4 and B7-H1 are potent inhibitors of immune function when expressed on tumor cells (Flies, D. B. et al. (2007) "*The New B7s: Playing a Pivotal Role in Tumor Immunity*," J. Immunother. 30(3):251-260).

The mode of action of B7-H3 is complex, as the protein mediates both T cell co-stimulation and co-inhibition (Hofmeyer, K. et al. (2008) "*The Contrasting Role Of B7-H3*," Proc. Natl. Acad. Sci. (U.S.A.) 105(30):10277-10278; Martin-Orozco, N. et al. (2007) "*Inhibitory Costimulation And Anti-Tumor Immunity*," Semin. Cancer Biol. 17(4):288-298; Subudhi, S. K. et al. (2005) "*The Balance Of Immune Responses: Costimulation Verse Coinhibition,*" J. Mol. Med. 83:193-202). B7-H3 binds to (TREM)-like transcript 2 (TLT-2) and co-stimulates T cell activation, but also binds to as yet unidentified receptor(s) to mediate co-inhibition of T cells. In addition, B7-H3, through interactions with unknown receptor(s), is an inhibitor for natural killer cells and osteoblastic cells (Hofmeyer, K. et al. (2008) "*The Contrasting Role Of B7-H3*," Proc. Natl. Acad. Sci. (U.S.A.) 105(30):10277-10278). The inhibition may operate through interactions with members of the major signaling pathways through which T cell receptor (TCR) regulates gene transcription (e.g., NFTA, NF-κB, or AP-1 factors).

B7-H3 co-stimulates CD4+ and CD8+ T-cell proliferation. B7-H3 also stimulates IFN-γ production and CD8+ lytic activity (Chapoval, A. et al. (2001) "*B7-H3: A Costimulatory Molecule For T Cell Activation and IFN-γ Production*," Nature Immunol. 2:269-274; Sharpe, A. H. et al. (2002) "*The B7-CD28 Superfamily*," Nature Rev. Immunol. 2:116-126). However, the protein also possibly acts through NFAT (Nuclear Factor for Activated T cells), NF-κB (Nuclear Factor kappa B), and AP-1 (Activator Protein-1) factors to inhibit T-cell activation (Yi. K. H. et al. (2009) "*Fine Tuning The Immune Response Through B7-H3 And B7-H4*," Immunol. Rev. 229:145-151). B7-H3 is also believed to inhibit Th1, Th2, or Th17 in vivo (Prasad, D. V. et al. (2004) "*Murine B7-H3 Is A Negative Regulator Of T Cells*," J. Immunol. 173:2500-2506; Fukushima, A. et al. (2007) "*B7-H3 Regulates The Development Of Experimental Allergic Conjunctivitis In Mice*," Immunol. Lett. 113:52-57; Yi. K. H. et al. (2009) "*Fine Tuning The Immune Response Through B7-H3 And B7-H4*," Immunol. Rev. 229:145-151). Several independent studies have shown that human malignant tumor cells exhibit a marked increase in expression of B7-H3 protein and that this increased expression was associated with increased disease severity (Zang, X. et al. (2007) "*The B7 Family And Cancer Therapy: Costimulation And Coinhibition,*" Clin. Cancer Res. 13:5271-5279), suggesting that B7-H3 is exploited by tumors as an immune evasion pathway (Hofmeyer, K. et al. (2008) "*The Contrasting Role Of B7-H3*," Proc. Natl. Acad. Sci. (U.S.A.) 105(30):10277-10278).

Molecules that block the ability of a B7 molecule to bind to a T-cell receptor (e.g., CD28) inhibit the immune system and have been proposed as treatments for autoimmune disease (Linsley, P. S. et al. (2009) "*The Clinical Utility Of Inhibiting CD28-Mediated Co-Stimulation*," Immunolog. Rev. 229:307-321). Neuroblastoma cells expressing 4Ig-B7-H3 treated with anti-4Ig-B7-H3 antibodies were more susceptible to NK cells. However, it is unclear whether this activity can be attributed to only antibodies against the 4Ig-B7-H3 form because all reported antibodies raised against the 4Ig-B7-H3 also bound the two Ig-like form of B7H3 (Steinberger, P. et al. (2004) "*Molecular Characterization of Human 4Ig-B7-H3, a Member of the B7 Family with Four Ig-Like Domains*," J. Immunol. 172(4): 2352-2359 and Castriconi et al. (2004) "*Identification Of 4Ig-B7-H3 As A Neuroblastoma-Associated Molecule That Exerts A Protective Role From An NK Cell-Mediated Lysis*," Proc. Natl. Acad. Sci. (U.S.A.) 101(34):12640-12645).

B7-H3 is not expressed on resting B or T cells, monocytes, or dendritic cells, but it is induced on dendritic cells by IFN-γ and on monocytes by GM-CSF (Sharpe, A. H. et al. (2002) "*The B7-CD28 Superfamily*," Nature Rev. Immunol. 2:116-126). The receptor(s) that bind B7-H3 have not been fully characterized. Early work suggested one such receptor would need to be rapidly and transiently up-regulated on T cells after activation (Loke, P. et al. (2004) "*Emerging Mechanisms Of Immune Regulation: The Extended B7 Family And Regulatory T Cells*." Arthritis Res. Ther. 6:208-214). Recently, the (TREM)-like transcript 2 (TLT-2, or TREML2) receptor (King, R. G. et al. (2006) "*Trem-Like Transcript 2 Is Expressed On Cells Of The Myeloid/Granuloid And B Lymphoid Lineage And Is Up-Regulated In Response To Inflammation*," J. Immunol. 176: 6012-6021; Klesney-Tait, J. et al. (2006) "*The TREM Receptor Family And Signal Integration,*" Nat. Immunol. 7:1266-1273; Yi. K. H. et al. (2009) "*Fine Tuning The Immune Response Through B7-H3 And B7-H4*," Immunol. Rev. 229:145-151), which is expressed on myeloid cells has been shown to be capable of binding B7-H3, and of thereby co-stimulating the activation of CD8+ T cells in particular (Zang, X. et al. (2003) "*B7x: A Widely Expressed B7 Family Member That Inhibits T Cell Activation*," Proc. Natl. Acad. Sci. (U.S.A.) 100:10388-10392; Hashiguchi, M. et al. (2008) "*Triggering Receptor Expressed On Myeloid Cell-Like Transcript 2 (TLT-2) Is A Counter-Receptor For B7-H3 And Enhances T Cell Responses*," Proc. Natl. Acad. Sci. (U.S.A.) 105(30):10495-10500; Hofmeyer, K. et al. (2008)

"*The Contrasting Role Of B7-H3*," Proc. Natl. Acad. Sci. (U.S.A.) 105(30): 10277-10278).

In addition to its expression on neuroblastoma cells, human B7-H3 is also known to be expressed on a variety of other cancer cells (e.g., gastric, ovarian and non-small cell lung cancers). B7-H3 protein expression has been immunohistologically detected in tumor cell lines (Chapoval, A. et al. (2001) "*B7-H3: A Costimulatory Molecule For T Cell Activation and IFN-γ Production*," Nature Immunol. 2:269-274; Saatian, B. et al. (2004) "*Expression Of Genes For B7-H3 And Other T Cell Ligands By Nasal Epithelial Cells During Differentiation And Activation*," Amer. J. Physiol. Lung Cell. Mol. Physiol. 287:L217-L225; Castriconi et al. (2004) "*Identification Of 4Ig-B7-H3 As A Neuroblastoma-Associated Molecule That Exerts A Protective Role From An NK Cell-Mediated Lysis*," Proc. Natl. Acad. Sci. (U.S.A.) 101(34):12640-12645); Sun, M. et al. (2002) "*Characterization of Mouse and Human B7-H3 Genes*," J. Immunol. 168:6294-6297). mRNA expression has been found in heart, kidney, testes, lung, liver, pancreas, prostate, colon, and osteoblast cells (Collins, M. et al. (2005) "*The B7 Family Of Immune-Regulatory Ligands*," Genome Biol. 6:223.1-223.7). At the protein level, B7-H3 is found in human liver, lung, bladder, testis, prostate, breast, placenta, and lymphoid organs (Hofmeyer, K. et al. (2008) "*The Contrasting Role Of B7-H3*," Proc. Natl. Acad. Sci. (U.S.A.) 105(30):10277-10278).

II. VEGF and VEGFR

Vascular endothelial growth factors (VEGFs) belong to the platelet-derived growth factor supergene family, and play central roles in the regulation of angiogenesis and lymphangiogenesis. The VEGF family is divided into five members having a homodimer structure: VEGF-A, VEGF-B, VEGF-C, VEGFD, and placental growth factor (PlGF) (Takahashi, S. (2011) "*Vascular Endothelial Growth Factor (VEGF), VEGF Receptors And Their Inhibitors For Anti-angiogenic Tumor Therapy*," Biol. Pharm. Bull. 34(12): 1785-1788; Sullivan, L. A. (2010) "*The VEGF Family In Cancer And Antibody-Based Strategies For Their Inhibition*," mAbs 2:2:165-175). These peptides are encoded by individual genes. In addition, VEGF-A exists in four isoforms. VEGF121, VEGF165, VEGF189, and VEGF206 are generated by alternative mRNA splicing (Houck, K. A. et al. (1991) "*The Vascular Endothelial Growth Factor Family: Identification Of A Fourth Molecular Species And Characterization Of Alternative Splicing Of RNA*," Mol. Endocrinol. 5(12):1806-1814; Tischer, E. et al. (1991) "*The Human Gene for Vascular Endothelial Growth Factor,*" J. Biol. Chem. 266:11947-11954). VEGF-A is generally called VEGF, because VEGF-A is a key regulator of developmental vasculogenesis, angiogenesis, and differentiation of progenitor endothelial cells. Among VEGF-A isoforms, VEGF165 is dominant from the aspect of amount and biological activity. VEGF165 is overexpressed in a variety of human tumors, and the overexpression is correlated with progression, invasion, and metastasis of tumors (Maeda, K. et al. (1996) "*Prognostic Value Of Vascular Endothelial Growth Factor Expression In Gastric Carcinoma*," Cancer 77:858-863; Ishigami, S. I. et al. (1998) "*Predictive Value Of Vascular Endothelial Growth Factor (VEGF) In Metastasis And Prognosis Of Human Colorectal Cancer*," Br. J. Cancer 78:1379-1384; Kaya, M. et al. (2000) "*Vascular Endothelial Growth Factor Expression In Untreated Osteosarcoma Is Predictive Of Pulmonary Metastasis And Poor Prognosis*," Clin. Cancer Res. 6:572-577).

VEGF-A binds to two tyrosine kinase (TK) receptors, VEGFR-1 (Flt-1) and VEGFR-2 (KDR/Flk-1), and regulates endothelial cell proliferation, migration, vascular permeability, secretion and other endothelial functions. VEGFR-2 exhibits a strong TK activity towards pro-angiogenic signals, whereas the soluble VEGFR-1 (sFlt-1) functions as an endogenous VEGF inhibitor (Shibuya, M. (2013) "*Vascular Endothelial Growth Factor And Its Receptor System: Physiological Functions In Angiogenesis And Pathological Roles In Various Diseases*," J. Biochem. 153(1):13-19; Koch, S. et al. (2011) "*Signal Transduction By Vascular Endothelial Growth Factor Receptors*," Biochem. J. 437:169-183; Sullivan, L. A. (2010) "*The VEGF Family In Cancer And Antibody-Based Strategies For Their Inhibition*," mAbs 2:2:165-175; Takahashi, S. (2011) "*Vascular Endothelial Growth Factor (VEGF), VEGF Receptors And Their Inhibitors For Antiangiogenic Tumor Therapy*," Biol. Pharm. Bull. 34(12): 1785-1788).

III. Immunotherapy

In addition to their known uses in diagnostics, antibodies have been shown to be useful as therapeutic agents. For example, immunotherapy, or the use of antibodies for therapeutic purposes has been used in recent years to treat cancer. Passive immunotherapy involves the use of monoclonal antibodies in cancer treatments (see for example, DEVITA, HELLMAN, AND ROSENBERG'S CANCER: PRINCIPLES & PRACTICE OF ONCOLOGY, EIGHTH EDITION (2008), DeVita, V. et al. Eds., Lippincott Williams & Wilkins, Philadelphia, Pa., pp. 537-547, 2979-2990). These antibodies can have inherent therapeutic biological activity both by direct inhibition of tumor cell growth or survival and by their ability to recruit the natural cell killing activity of the body's immune system. These agents can be administered alone or in conjunction with radiation or chemotherapeutic agents. Rituximab and Trastuzumab, approved for treatment of non-Hodgkin's lymphoma and breast cancer, respectively, are examples of such therapeutics. Alternatively, antibodies can be used to make antibody conjugates in which the antibody is linked to a toxic agent and directs that agent to the tumor by specifically binding to the tumor. Gemtuzumab ozogamicin is an example of an approved antibody conjugate used for the treatment of leukemia.

Monoclonal antibodies that bind to cancer cells and have potential uses for diagnosis and therapy have been disclosed (see, for example, the following patent applications which disclose, inter alia, some molecular weights of target proteins: U.S. Pat. No. 6,054,561 (200 kD c-erbB-2 (Her2), and other unknown antigens 40-200 KD in size) and U.S. Pat. No. 5,656,444 (50 kD and 55 kD oncofetal protein)). Examples of antibodies in clinical trials and/or approved for treatment of solid tumors include: Trastuzumab (antigen: 180 kD, HER2/neu), Edrecolomab (antigen: 40-50 kD, Ep-CAM), Anti-human milk fat globules (HMFG1) (antigen > 200 kD, HMW Mucin), Cetuximab (antigens: 150 kD and 170 kD, EGF receptor), Alemtuzumab (antigen: 21-28 kD, CD52), and Rituximab (antigen: 35 kD, CD20).

The antigen targets of trastuzumab (Her-2 receptor), which is used to treat breast cancer, and cetuximab (EGF receptor), which is in clinical trials for the treatment of several cancers, are present at some detectable level on a large number of normal human adult tissues including skin, colon, lung, ovary, liver, and pancreas. The margin of safety in using these therapeutics is possibly provided by the difference in the levels of antigen expression or in access of or activity of the antibody at these sites.

Another type of immunotherapy is active immunotherapy, or vaccination, with an antigen present on a specific cancer(s) or a DNA construct that directs the expression of the antigen, which then evokes the immune response in the individual, i.e., to induce the individual to actively produce antibodies against their own cancer. Active immunization has not been used as often as passive immunotherapy or immunotoxins.

Several models of disease (including cancer) progression have been suggested. Theories range from causation by a single infective/transforming event to the evolution of an increasingly "disease-like" or "cancer-like" tissue type leading ultimately to one with fully pathogenic or malignant capability. Some argue that with cancer, for example, a single mutational event is sufficient to cause malignancy, while others argue that subsequent alterations are also necessary. Some others have suggested that increasing mutational load and tumor grade are necessary for both initiation as well as progression of neoplasia via a continuum of mutation-selection events at the cellular level. Some cancer targets are found only in tumor tissues, while others are present in normal tissues and are up regulated and/or over-expressed in tumor tissues. In such situations, some researchers have suggested that the over-expression is linked to the acquisition of malignancy, while others suggest that the over-expression is merely a marker of a trend along a path to an increasing disease state.

In some cases, cancer targets, such as oncoproteins expressed or over-expressed in tumors, have been shown to be present during embryonic and fetal development and serve as a regulator of growth and differentiation. Some researchers have found that the expression of these oncoproteins during embryonic and fetal development appear to be restricted to specific tissues and also restricted to specific stages of development. In contrast, the expression of these oncoproteins in the adult has been shown to be associated with over-expression in tumor growth and/or a malfunction of tumor suppressor proteins.

An ideal diagnostic and/or therapeutic antibody would be specific for an antigen present on a large number of cancers, but absent or present only at low levels on any normal tissue. The discovery, characterization, and isolation of a novel antibody capable of binding to an antigen that is specifically associated with cancer(s) would be useful in many ways. First, the antibody would have biological activity against such cancer cells and be able to recruit the immune system's response to thereby treat the disease. The antibody could be administered as a therapeutic alone or in combination with current treatments or used to prepare immunoconjugates linked to toxic agents. An antibody with the same specificity but with low or no biological activity when administered alone could also be useful in that an antibody could be used to prepare an immunoconjugate with a radioisotope, a toxin, or a chemotherapeutic agent or liposome containing a chemotherapeutic agent, with the conjugated form being biologically active by virtue of the antibody directing the toxin to the antigen-containing cells.

As discussed above, antibodies and other molecules that that specifically bind to B7-H3 have been described (see, U.S. Pat. Nos. 7,527,969; 7,368,554; 7,358,354; and 7,279,567; United States Patent Application Publications Nos. US 20090087416; US 20090022747; US 20090018315; US2008116219; US20080081346; US 20050202536; US20030103963; US20020168762; PCT Publications Nos. WO 2008/116219; WO 2006/016276; WO 2004/093894; WO 04/001381; WO 2002/32375; WO 2002/10187 and WO 2001/094413; EP 1292619B; Modak, S. et al. (March 1999) "*Disialoganglioside GD2 And Antigen 8H9: Potential Targets For Antibody-Based Immunotherapy Against Desmoplastic Small Round Cell Tumor (DSRCT) And Rhabdomyosarcoma (RMS),*" Proceedings Of The American Association For Cancer Research Annual Meeting, Vol. 40:474 (90th Annual Meeting Of The American Association For Cancer Research; Philadelphia, Pa., US; Apr. 10-14, 1999; Modak, S. et al. (March 2000) "*Radioimmunotargeting To Human Rhabdomyosarcoma Using Monoclonal Antibody 8H9,*" Proc. Am. Assoc. Cancer Res. 41:724; Modak, S. et al. (2001) "*Monoclonal Antibody 8H9 Targets A Novel Cell Surface Antigen Expressed By A Wide Spectrum Of Human Solid Tumors,*" Cancer Res. 61(10):4048-4054; Steinberger, P. et al. (2004) "*Molecular Characterization of Human 4Ig-B7-H3, a Member of the B7 Family with Four Ig-Like Domains,*" J. Immunol. 172(4):2352-2359; Xu, H. et al. (2009) "*MicroRNA miR-29 Modulates Expression of Immunoinhibitory Molecule B7-H3: Potential Implications for Immune Based Therapy of Human Solid Tumors,*" Cancer Res. 69(15):5275-6281).

IV. Glioblastoma

Glioblastomas are the most common primary tumor of the central nervous system (CNS), and are the deadliest of human cancers (Mrugala, M. M. (2013) "*Advances And Challenges In The Treatment Of Glioblastoma: A Clinician's Perspective,*" Discov. Med. 15(83):221-230; Steiner, H.-H. et al. (2004) "*Autocrine Pathways Of The Vascular Endothelial Growth Factor (VEGF) In Glioblastoma Multiforme: Clinical Relevance Of Radiation-Induced Increase Of VEGF Levels,*" J. Neuro-Oncol. 66:129-138). Effective therapy for patients with malignant glioma remains elusive, with median survival being under 15 months following standard-of-care therapy with surgery, radiation and temozolomide (Reardon, D. A. et al. (2008) "*Glioblastoma Multiforme: An Emerging Paradigm Of Anti-VEGF Therapy,*" Expert Opin. Biol. Ther. 8(4):541-553). There is no effective therapy following recurrence (Simpson, L. et al. (2006) "*Recurrent Glioblastoma Multiforme: Advances In Treatment And Promising Drug Candidates,*" Expert Rev. Anticancer Ther. 6(11):1593-607).

The use of Anti-VEGF antibodies (Bevacizumab, e.g., AVASTIN®, an anti-angiogenic preparation) has been explored as a therapy for glioblastoma (Gerstner, E. R. et al. (2012) "*Antiangiogenic Therapy For Glioblastoma,*" Cancer J. 18(1):45-50; Pellegatta, S. et al. (2011) "*Brain Cancer Immunoediting: Novel Examples Provided By Immunotherapy Of Malignant Gliomas,*" Expert Rev. Anticancer Ther. 11(11):1759-1774; Laigle-Donadey, F. et al. (2009) "*Association Of Radiotherapy And Chemotherapy-Targeted Therapies In Glioblastomas,*" Bull. Cancer. 96(3):291-297; Reardon, D. A. et al. (2008) "*Glioblastoma Multiforme: An Emerging Paradigm Of Anti-VEGF Therapy,*" Expert Opin. Biol. Ther. 8(4):541-553; Narita, Y. (2013) "*Drug Review: Safety And Efficacy Of Bevacizumab For Glioblastoma And Other Brain Tumors,*" Jpn. J. Clin. Oncol. 43(6):587-595. Bevacizumab (AVASTIN®) is described in United States Patent Publications No. US20020032315A1, US20030190317A1, US20050112126A1, US20070059302A1, US20070059312A1, US20070196374A1, US20070248610A1, US20080187534A1, US20080226629A1, US20110052575A1, US20110081342A1, US20130058927A1; U.S. Pat. Nos. 6,884,879; 7,060,269; 7,169,901; 7,297,334; 7,365,166; 7,375,193; CA Patents No. 2,286,330 and 2,145,985; and PCT Publication No. WO 1998/045331; Baca, M. et al. (1997) "*Antibody Humanization Using Monovalent Phage Display,*" J. Biol. Chem. 272(16):10678-10684; Presta, L. G. et al. (1997) "*Humanization Of An Anti-Vascular Endothelial Growth Factor Monoclonal Antibody For The Therapy Of Solid Tumors*

*And Other Disorders,*" Cancer Res. 57(20):4593-4599; each of which documents is herein incorporated by reference in its entirety.

Unfortunately, recurrent glioblastomas (rGBM) invariably relapse after initial response to anti-VEGF therapy (di Tomaso, E. et al. (2011) *"Glioblastoma Recurrence after Cediranib Therapy in Patients: Lack of "Rebound" Revascularization as Mode of Escape,"* Cancer Res. 71:19-28.

Thus, despite all prior advances, a need remains for improved compositions for treating vascularizing cancers, and glioblastoma, in particular. The present invention is directed to such compositions and to their use in the treatment of glioblastoma and other cancers involving vascularization.

SUMMARY OF THE INVENTION

The invention concerns therapeutic compositions for the treatment of vascularizing cancers, especially, glioblastoma. In particular, the invention is directed to compositions that comprise a molecule having a binding ability that is specific for B7-H3 and a molecule having a binding ability that is specific for a cell-surface factor (or its receptor) that is involved in promoting tumor angiogenesis (especially VEGF or its receptor, VEGFR). The invention is additionally directed to the use of such compositions in the treatment of such cancers, and in particular, in the treatment of glioblastoma.

In detail, the invention provides a method of treating a vascularizing cancer comprising administering to a recipient patient in need thereof, a molecule having a binding ability that is specific for B7-H3 and a molecule having a binding ability that is specific for a cell-surface factor, or a receptor therefor, that promotes tumor angiogenesis.

The invention particularly concerns the embodiment of such method wherein the molecule having the binding ability that is specific for B7-H3 is:
 (A) an anti-B7-H3 antibody;
 (B) a B7-H3-binding fragment of (A); or
 (C) a diabody that binds B7-H3.

The invention particularly concerns the embodiment of such methods wherein the molecule having the binding ability that is specific for a cell-surface factor, or a receptor therefor, that promotes tumor angiogenesis is:
 (A) an anti-VEGF antibody or a VEGF antagonist; or
 (B) an anti-VEGFR antibody or a VEGFR antagonist.

The invention particularly concerns the embodiment of such methods wherein the molecule having the binding ability that is specific for B7-H3:
 A. competes for B7-H3 binding with antibodies BRCA84D, BRCA69D, or PRCA157; or
 B. has the three heavy chain CDRs and the three light chain CDRs of antibody BRCA84D, of antibody BRCA69D, or of antibody PRCA157.

The invention additionally concerns the embodiment of such methods wherein the molecule having the binding ability that is specific for a cell-surface factor, or a receptor therefor, that promotes tumor angiogenesis:
 A. competes for VEGF binding with bevacizumab; or
 B. has the three heavy chain CDRs and the three light chain CDRs of bevacizumab.

The invention additionally concerns the embodiment of such methods wherein the molecule having the binding ability that is specific for B7-H3 is an anti-B7-H3 antibody having:

(A) a light chain variable domain that comprises the CDR1, CDR2 and CDR3 of the light chain of BRCA$_{84}$D;
 (B) a heavy chain variable domain that comprises the CDR1 CDR2 and CDR$_3$ of the heavy chain of BRCA84D; and
 (C) an Fc region that comprises the substitutions: L235V, F243L, R292P, Y300L, and P396L.

The invention concerns the embodiment of such methods wherein the molecule having the binding ability that is specific for B7-H3 is a humanized anti-B7-H3 antibody that comprises:
 (A) a variable light chain having the amino acid sequence of hBRCA84D-2 VL (SEQ ID NO:69); and
 (B) a variable heavy chain having the amino acid sequence of hBRCA84D-2 VH (SEQ ID NO:79);
and the molecule having the binding ability that is specific for a cell-surface factor, or a receptor therefor, that promotes tumor angiogenesis is bevacizumab.

The invention additionally concerns the embodiment of such methods wherein the molecule having the B7-H3 binding ability and the molecule having the VEGF-binding ability are administered to the patient, and the two molecules are administered concurrently.

The invention additionally concerns the embodiment of such methods wherein the second of the administered molecules is administered to the patient within 5 half-lives after the administration of the first of the molecule.

The invention additionally concerns the embodiment of such methods wherein the vascularizing cancer is glioblastoma.

The invention additionally concerns the embodiment of such methods wherein the molecule has the binding ability that is specific for B7-H3 and the molecule having the binding ability that is specific for a cell-surface factor, or a receptor therefor, that promotes tumor angiogenesis are the same molecule, the molecule being a bi-specific antibody or a bi-specific diabody.

DETAILED DESCRIPTION OF THE INVENTION

Figure 1:
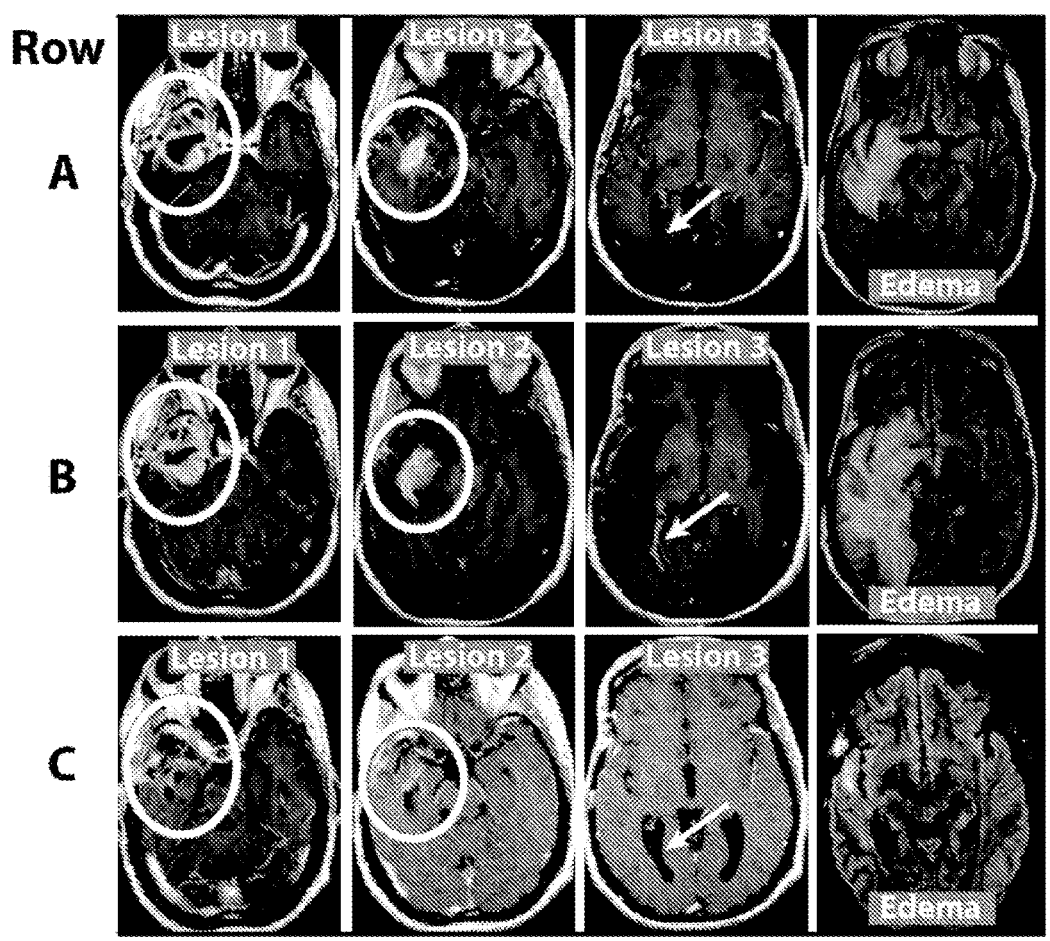
FIG. 1 shows MM scans of glioblastoma Patient NF. The first, second and third columns are, respectively, MRI scans of a first, second and third observed lesion. Row A shows the status of the patient's lesions at baseline. Row B shows the status of the patient's lesions prior to the initiation of a second planned cycle of anti-B7-H3 antibody (hBRCA84D) administration. Row C shows the status of the patient's lesions after 3 doses of bevacizumab and one dose of CCNU.

The invention concerns therapeutic compositions for the treatment of vascularizing cancers, especially, glioblastoma. In particular, the invention is directed to compositions that comprise a molecule having a binding ability that is specific for B7-H3 and a molecule having a binding ability that is specific for a cell-surface factor (or its receptor) that is involved in promoting tumor angiogenesis (especially VEGF or its receptor, VEGFR). The invention is additionally directed to the use of such compositions in the treatment of such cancers, and in particular, in the treatment of glioblastoma.

In accordance with the present invention, the B7-H3-specific binding ability is capable of binding to B7-H3 molecules that are present on the surface of cancer cells, and particularly glioblastoma cancer cells, and of facilitating or mediating an immune response against such cells through such binding. The binding ability that is specific for a cell-surface factor (or receptor) involved in promoting tumor angiogenesis (i.e., an "anti-tumor angiogenesis activity") is capable of binding to such factor (or receptor) so as to reduce or suppress, through such binding, the angiogenesis mediated by the interaction between such factor and such receptor. In a first embodiment, the B7-H3-specific binding ability and the binding ability that is specific for a cell-surface factor (or receptor) involved in promoting tumor angiogenesis are present on different molecules, such as for example an anti-B7-H3 antibody and an anti-angiogenesis factor antibody, or the B7-H3-binding fragment and anti-angiogenesis factor-binding fragment of such antibodies. In a second aspect of the invention, such binding affinities will be possessed by a single molecule (suahc as a bi-specific antibody, a diabody, a BiTE®, or other single-chain or multi-chain variants thereof that are capable of simultaneously binding to both B7-H3 and an anti-angiogenesis factor or receptor. The invention is directed to the use of such compositions in the treatment of cancer, and in particular, in the treatment of glioblastoma.

I. GENERAL TECHNIQUES

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as: MOLECULAR CLONING: A LABORATORY MANUAL, Third Edition (Sambrook et al. Eds., 2001) Cold Spring Harbor Press, Cold Spring Harbor, N.Y.; OLIGONUCLEOTIDE SYNTHESIS: METHODS AND APPLICATIONS (Methods in Molecular Biology), Herdewijn, P., Ed., Humana Press, Totowa, N.J.; OLIGONUCLEOTIDE SYNTHESIS (Gait, M. J., Ed., 1984); METHODS IN MOLECULAR BIOLOGY, Humana Press, Totowa, N.J.; CELL BIOLOGY: A LABORATORY NOTEBOOK (Cellis, J. E., Ed., 1998) Academic Press, New York, N.Y.; ANIMAL CELL CULTURE (Freshney, R. I., Ed., 1987); INTRODUCTION TO CELL AND TISSUE CULTURE (Mather, J. P. and Roberts, P. E., Eds., 1998) Plenum Press, New York, N.Y.; CELL AND TISSUE CULTURE: LABORATORY PROCEDURES (Doyle, A. et al., Eds., 1993-8) John Wiley and Sons, Hoboken, N.J.; METHODS IN ENZYMOLOGY (Academic Press, Inc.) New York, N.Y.; WEIR'S HANDBOOK OF EXPERIMENTAL IMMUNOLOGY (Herzenberg, L. A. et al. Eds. 1997) Wiley-Blackwell Publishers, New York, N.Y.; GENE TRANSFER VECTORS FOR MAMMALIAN CELLS (Miller, J. M. et al. Eds., 1987) Cold Spring Harbor Press, Cold Spring Harbor, N.Y.; CURRENT PROTOCOLS IN MOLECULAR BIOLOGY (Ausubel, F. M. et al., Eds., 1987) Greene Pub. Associates, New York, N.Y.; PCR: THE POLYMERASE CHAIN REACTION, (Mullis, K. et al., Eds., 1994) Birkhäuser, Boston Mass.; CURRENT PROTOCOLS IN IMMUNOLOGY (Coligan, J. E. et al., eds., 1991) John Wiley and Sons, Hoboken, N.J.; SHORT PROTOCOLS IN MOLECULAR BIOLOGY (John Wiley and Sons, 1999) Hoboken, N.J.; IMMUNOBIOLOGY 7 (Janeway, C. A. et al. 2007) Garland Science, London, UK; Antibodies (P. Finch, 1997) Stride Publications, Devoran, UK; ANTIBODIES: A PRACTICAL APPROACH (D. Catty., ed., 1989) Oxford University Press, USA, New York N.Y.); MONOCLONAL ANTIBODIES: A PRACTICAL APPROACH (Shepherd, P. et al. Eds., 2000) Oxford University Press, USA, New York N.Y.; USING ANTIBODIES: A LABORATORY MANUAL (Harlow, E. et al. Eds., 1998) Cold Spring Harbor Laboratory Press, Cold Spring Harbor, N.Y.; THE ANTIBODIES (Zanetti, M. et al. Eds. 1995) Harwood Academic Publishers, London, UK); and DEVITA, HELLMAN, AND ROSENBERG'S CANCER: PRINCIPLES & PRACTICE OF ONCOLOGY, EIGHTH EDITION, DeVita, V. et al. Eds. 2008, Lippincott Williams & Wilkins, Philadelphia, Pa.

II. DEFINITIONS

As used herein, an "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$ Fv), single chain (ScFv), mutants thereof, naturally occurring variants, fusion proteins comprising an antibody portion with an antigen recognition site of the required specificity, humanized antibodies, chimeric antibodies, "BiTEs," "DART™" molecules and any other modified configuration of the immunoglobulin molecule that comprises an antigen recognition site of the required specificity.

The term "BiTEs" (bi-specific T-cell engagers) refers to a single polypeptide chain molecule that having two antigen binding domains, one of which binds to a T-cell antigen and the second of which binds to an antigen present on the surface of a target (WO 05/061547; Baeuerle, P et al. (2008) "*BiTE®: A New Class Of Antibodies That Recruit T Cells*," Drugs of the Future 33: 137-147; Bargou, et al. 2008) "*Tumor Regression in Cancer Patients by Very Low Doses of a T Cell-Engaging Antibody*," Science 321: 974-977).

The term "DART™" (dual affinity retargeting reagent) refers to an immunoglobulin molecule that comprises at least two polypeptide chains that associate (especially through a covalent interaction) to form at least two epitope binding sites, which may recognize the same or different epitopes. Each of the polypeptide chains of a DART™ comprise an immunoglobulin light chain variable region and an immunoglobulin heavy chain variable region, but these regions do not interact to form an epitope binding site. Rather, the immunoglobulin heavy chain variable region of one (e.g., the first) of the DART™ polypeptide chains interacts with the immunoglobulin light chain variable region of a different (e.g., the second) DART™ polypeptide chain to form an epitope binding site. Similarly, the immunoglobulin light chain variable region of one (e.g., the first) of the DART™ polypeptide chains interacts with the immunoglobulin heavy chain variable region of a different (e.g., the second) DART™ polypeptide chain to form an epitope binding site. DART™ s may be monospecific, bispecific, trispecific, etc., thus being able to simultaneously bind one, two, three or more different epitopes (which may be of the same or of different antigens). DART™s may additionally be monovalent, bivalent, trivalent, tetravalent, pentavalent, hexavelent, etc., thus being able to simultaneously bind one, two, three, four, five, six or more molecules. These two attributes of DART™s (i.e., degree of specificity and valency may be combined, for example to produce bispecific antibodies (i.e., capable of binding two epitopes) that are tetravalent (i.e., capable of binding four sets of epitopes), etc. DART™ molecules are disclosed in PCT Publications WO 2006/113665, WO 2008/157379, and WO 2010/080538.

The term "monoclonal antibody" refers to a homogeneous antibody population wherein the monoclonal antibody is comprised of amino acids (naturally occurring and non-naturally occurring) that are involved in the selective binding of an antigen. Monoclonal antibodies are highly specific, being directed against a single antigenic site. The term "monoclonal antibody" encompasses not only intact monoclonal antibodies and full-length monoclonal antibodies, but also fragments thereof (such as Fab, Fab', F(ab')$_2$, Fv), single chain (ScFv), mutants thereof, fusion proteins comprising an antibody portion, humanized monoclonal antibodies, chimeric monoclonal antibodies, and any other modified configuration of the immunoglobulin molecule that comprises an antigen recognition site of the required specificity and the ability to bind to an antigen. It is not intended to be limited as regards to the source of the antibody or the manner in which it is made (e.g., by hybridoma, phage selection, recombinant expression, transgenic animals, etc.). The term includes whole immunoglobulins as well as the fragments etc. described above under the definition of "antibody."

The term "humanized antibody" refer to a chimeric molecule, generally prepared using recombinant techniques, having an antigen binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the complementarity determining regions (CDRs) grafted onto appropriate framework regions in the variable domains. Antigen binding sites may be wild-type or modified by one or more amino acid substitutions. This eliminates the constant region as an immunogen in human individuals, but the possibility of an immune response to the foreign variable region remains (LoBuglio, A. F. et al. (1989) "*Mouse/Human Chimeric Monoclonal Antibody In Man: Kinetics And Immune Response*," Proc. Natl. Acad. Sci. (U.S.A.) 86:4220-4224). Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the antigens in question and determine binding capability, flanked by four framework regions (FRs) which are relatively conserved in a given species and which putatively provide a scaffolding for the CDRs. When nonhuman antibodies are prepared with respect to a particular antigen, the variable regions can be "reshaped" or "humanized" by grafting CDRs derived from a non-human antibody on the FRs present in the human antibody to be modified. Application of this approach to various antibodies has been reported by Sato, K. et al. (1993) "*Reshaping A Human Antibody To Inhibit The Interleukin 6-Dependent Tumor Cell Growth*," Cancer Res 53:851-856. Riechmann, L. et al. (1988) "*Reshaping Human Antibodies for Therapy*," Nature 332:323-327; Verhoeyen, M. et al. (1988) "*Reshaping Human Antibodies: Grafting An Antilysozyme Activity*," Science 239:1534-1536; Kettleborough, C. A. et al. (1991) "*Humanization Of A Mouse Monoclonal Antibody By CDR-Grafting: The Importance Of Framework Residues On Loop Conformation*," Protein Engineering 4:773-3783; Maeda, H. et al. (1991) "*Construction Of Reshaped Human Antibodies With HIV-Neutralizing Activity*," Human Antibodies Hybridoma 2:124-134; Gorman, S. D. et al. (1991) "*Reshaping A Therapeutic CD4 Antibody*," Proc. Natl. Acad. Sci. (U.S.A.) 88:4181-4185; Tempest, P. R. et al. (1991) "*Reshaping A Human Monoclonal Antibody To Inhibit Human Respiratory Syncytial Virus Infection in vivo*," Bio/Technology 9:266-271; Co, M. S. et al. (1991) "*Humanized Antibodies For Antiviral Therapy*," Proc. Natl. Acad. Sci. (U.S.A.) 88:2869-2873; Carter, P. et al. (1992) "*Humanization Of An Anti-p185her2 Antibody For Human Cancer Therapy*," Proc. Natl. Acad. Sci. (U.S.A.) 89:4285-4289; and Co, M. S. et al. (1992) "*Chimeric And Humanized Antibodies With Specificity For The CD33 Antigen*," J. Immunol. 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five or six) which are altered with respect to the original antibody, which are also termed one or more CDRs "derived from" one or more CDRs from the original antibody.

As used herein, an antibody or a polypeptide is said to "specifically" bind a region of another molecule (i.e., an epitope) if it reacts or associates more frequently, more rapidly, with greater duration and/or with greater affinity with that epitope relative to alternative epitopes. For example, an antibody that specifically binds to a B7-H3 epitope is an antibody that binds such B7-H3 epitope with greater affinity, avidity, more readily, and/or with greater duration than it binds to other B7-H3 epitopes or to a non-B7-H3 epitope. Likewise, an antibody that specifically binds to an epitope of VEGF or VEGFR binds such epitope with greater affinity, avidity, more readily, and/or with greater duration than it binds to other VEGF or VEGFR epitopes or to a non-VEGF or VEGFR epitope. It is also understood by reading this definition that, for example, an antibody (or moiety or epitope) that specifically binds to a first target may or may not specifically or preferentially bind to a second target. As such, "specific binding" does not necessarily require (although it can include) exclusive binding. Generally, but not necessarily, reference to binding means "specific" binding.

As used herein, the term "immunologically active" in reference to an epitope being or "remaining immunologically active" refers to the ability of an antibody (e.g., an anti-B7-H3 antibody or anti-VEGF or anti-VEGFR antibody) to bind to the epitope under different conditions, for example, after the epitope has been subjected to reducing and denaturing conditions.

Different biological functions may be associated with anti-B7-H3 antibodies, including, but not limited to one or more of: an ability to specifically bind to B7-H3 (and in particular B7-H3 molecules that are expressed on the surfaces of cancer cells, including but not limited to kidney, prostate, or lung, cancer cells); an ability to competitively inhibit preferential binding of a known anti-B7-H3 antibody to B7-H3, including the ability to preferentially bind to the same B7-H3 epitope to which the original antibody preferentially binds; an ability to bind to a portion of B7-H3 that is exposed on the surface of a living cell in vitro or in vivo; an ability to bind to a portion of B7-H3 that is exposed on the surface of living cancer cells, such as but not limited to prostate, lung or kidney cancer cells; an ability to deliver a chemotherapeutic agent to cancerous cells (such as kidney, prostate, or lung cancer cells) expressing B7-H3 on their surface; and/or an ability to deliver a therapeutic agent or detectable marker into cancer cells expressing B7-H3 on their surface. Likewise, different biological functions may be associated with anti-VEGF or anti-VEGFR antibodies including, but not limited to one or more of: an ability to interfere with the binding of VEGF to VEGFR (and in particular VEGFR molecules that are expressed on the surfaces of cells; an ability to competitively inhibit preferential binding of a known anti-VEGF or anti-VEGFR antibody to VEGF or VEGFR, including the ability to preferentially bind to the same epitope to which the original antibody preferentially binds; an ability to bind to a portion of VEGFR that is exposed on the surface of a living cell in vitro or in vivo; and/or an ability to deliver a chemotherapeutic agent to VEGFR-expressing cells. The polypeptides (including antibodies) of the invention may have any one or more of these characteristics.

An "anti-B7-H3 equivalent antibody" or "anti-B7-H3 equivalent polypeptide" refers to an antibody or a polypeptide having one or more biological functions associated with an anti-B7-H3 antibody, such as, for example, binding specificity. An "anti-VEGF equivalent antibody" or "anti-VEGF equivalent polypeptide" refers to an antibody or a polypeptide having one or more biological functions associated with an anti-VEGF antibody, such as, for example, an ability to interfere with the binding of VEGF to VEGFR.

As used herein, the term "agent" refers to a biological, pharmaceutical, or chemical compound. Non-limiting examples include simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like.

Agents that are employed in the methods of this invention can be randomly selected or rationally selected or designed. As used herein, an agent is said to be randomly selected when the agent is chosen without prior consideration or knowledge of the specific amino acid or other chemical moieties involved in the association of the molecule with its native binding partner(s) or known antibodies. An example of a randomly selected agent is an agent that is identified through the use and screening of a chemical library or a peptide combinatorial library.

As used herein, an agent is said to be rationally selected or designed when the agent is chosen on a non-random basis that takes into account the sequence of the target site and/or its conformation in connection with the agent's action. With respect to anti-B7-H3 agents, it is currently believed that there are at least three epitopes on B7-H3 against which antibodies can be raised and therefore at least three sites of action for agents that block B7-H3/anti-B7-H3 interaction. This invention also encompasses agents that act at the sites of interaction between B7-H3 and its native binding partner, although other ligands and their active B7-H3-interactive sites are also encompassed within the scope of this invention, whether currently known or later identified. Agents can be rationally selected or rationally designed by utilizing the peptide sequences that make up the contact sites of the receptor/ligand and/or B7-H3/anti-B7-H3 antibody complex. For example, a rationally selected peptide agent can be a peptide whose amino acid sequence is identical to an epitope appearing on B7-H3 as it is exposed on the surface of a living cell in its native environment. Such an agent will reduce or block the association of the anti-B7-H3 antibody with B7-H3, or the association of B7-H3 with its native ligand, as desired, by binding to the anti-B7-H3 antibody or to the native ligand.

As used herein, the term "labeled," with regard to an antibody, is intended to encompass direct labeling of the antibody by coupling (i.e., physically linking) a detectable substance, such as a radioactive agent or a fluorophore (e.g. phycoerythrin (PE) or fluorescein isothiocyanate (also known as fluoroisothiocyanate or FITC)) to the antibody, as well as indirect labeling of the probe or antibody by reactivity with a detectable substance.

As used herein, the term "association", with regard to an antibody, includes covalent and non-covalent attachment or binding of an agent (e.g., chemotherapeutic agent) to the antibody. The antibody can be associated with an agent (e.g., chemotherapeutic agent) by direct binding or indirect binding via attachment to a common platform, such that the antibody directs the localization of the agent to the cancerous cell to which the antibody binds and wherein the antibody and agent do not substantially dissociate under physiological conditions such that the agent is not targeted to the same cancerous cell to which the antibody binds or such that the agent's potency is not decreased.

The term "biological sample" encompasses a variety of sample types obtained from an individual and can be used in a diagnostic or monitoring assay. The definition encompasses saliva, blood and other liquid samples of biological origin, solid tissue samples such as a biopsy specimen or tissue cultures or cells derived therefrom, and the progeny thereof, for example, cells obtained from a tissue sample collected from an individual suspected of having cancer, in preferred embodiments from ovary, lung, prostate, pancreas, colon, and breast tissue. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples.

The term "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, the term "delaying development of metastasis" means to defer, hinder, slow, retard, stabilize, and/or postpone development of metastasis. This delay can be of varying lengths of time, depending on the history of the cancer and/or individual being treated. As is evident to one skilled in the art, a sufficient or significant delay can, in effect, encompass prevention, in that the individual does not develop the metastasis.

As used herein, an "effective amount" of a pharmaceutical composition, in one embodiment, is an amount sufficient to effect beneficial or desired results including, without limitation, clinical results such as shrinking the size of the tumor (in the cancer context, for example, breast or prostate cancer), retardation of cancerous cell growth, delaying the development of metastasis, decreasing symptoms resulting from the disease, increasing the quality of life of those suffering from the disease, decreasing the dose of other medications required to treat the disease, enhancing the effect of another medication such as via targeting and/or internalization, delaying the progression of the disease, and/or prolonging survival of individuals. An effective amount can be administered in one or more administrations. For purposes of this invention, an effective amount of drug, compound, or pharmaceutical composition is an amount sufficient to reduce the proliferation of (or destroy) cancerous cells and to reduce and/or delay the development, or growth, of metastases of cancerous cells, either directly or indirectly. In some embodiments, an effective amount of a drug, compound, or pharmaceutical composition may or may not be achieved in conjunction with another drug, compound, or pharmaceutical composition. Thus, an "effective amount" may be considered in the context of administering one or more chemotherapeutic agents, and a single agent may be considered to be given in an effective amount if, in conjunction with one or more other agents, a desirable result may be or is achieved. While individual needs vary, determination of optimal ranges of effective amounts of each component is within the skill of the art. Typical dosages are discussed below.

As used herein, a nucleic acid molecule or agent, antibody, composition or cell, etc., is said to be "isolated" when that nucleic acid molecule, agent, antibody, composition, or cell, etc. is substantially separated from contaminant nucleic acid molecules, antibodies, agents, compositions, or cells, etc. naturally present in its original source.

The term "individual" refers to a vertebrate animal, preferably a mammal. Mammals include, but are not limited to, humans, farm animals, sport animals, pets, primates, mice and rats. In the most preferred embodiment, the term individual denotes a human.

The terms "polypeptide," "oligopeptide," "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or as associated chains.

Also encompassed within the scope of the invention are peptidomimetics of the B7-H3 peptide agonists, antagonists and modulators (including anti-B7-H3 antibodies) described herein. Such peptidomimetics include peptides wherein at least one amino acid residue is substituted with an amino acid residue that is not commonly found in nature, such as the D isomer of the amino acid or an N-alkylated species of the amino acid. In other embodiments, peptidomimetics are constructed by replacing at least one amide bond (—C(=O)—NH—) in a B7-H3 peptide agonist, antagonist or modulators with an amide isostere. Suitable amide isosteres include —CH$_2$—NH—, —CH$_2$—S—, —CH$_2$—S(O)—, —CH$_2$—S(O)$_2$—, —CH$_2$—CH$_2$—, —CH=CH— (E or Z form), —C(=O)—CH$_2$—, —CH(CN)—NH—, —C(OH)—CH$_2$—, and —O—C(=O)—NH—. The amide bonds in a B7-H3 peptide agonist, antagonist or modulator that are suitable candidates for replacement with amide isosteres include bonds that are hydrolyzable by the endogenous esterases or proteases of the intended subject of B7-H3 peptide agonist, antagonist or modulator treatment.

As used herein, the term "substantially pure" refers to material that is at least 50% pure (i.e., free from contaminants), more preferably at least 90% pure, more preferably at least 95% pure, more preferably at least 98% pure, more preferably at least 99% pure, and most preferably greater than 99% pure.

As used herein, the term "toxin" refers to any substance, which effects an adverse response within a cell. For example, a toxin directed to a cancerous cell would have an adverse, sometimes deleterious effect, on the cancerous cell. Examples of toxins include, but are not limited to, a taxane, a maytansinoid, an auristatin (e.g., monomethyl auristatin (MMAE), monomethyl auristatin F (MMAF), auristatin E (AE), etc.) (such as those disclosed in U.S. Pat. Nos. 5,208,020; 5,416,064; 6,333,410; 6,340,701; 6,372,738; 6,436,931; 6,441,163; 6,596,757; 7,276,497; 7,585,857; or 7,851,432), a calicheamicin, an anthracycline (e.g., doxorubicin), a CC-1065 analog, docetaxel; cathepsin B or E; ricin, gelonin, Pseudomonas exotoxin, diphtheria toxin, and RNase; radiolabeled antibodies (e.g., tiuxetan-conjugated or labeled with a toxic radioisotope (for example, $^{90}$Y; $^{131}$I, $^{177}$Lu, $^{186}$Re, $^{188}$Re, $^{211}$At, $^{212}$Bi, $^{213}$Bi, $^{225}$Ac, etc.).

As used herein, the terms "treatment" or "treating" denote an approach for obtaining a beneficial or desired result including and preferably a beneficial or desired clinical result. Such beneficial or desired clinical results include, but are not limited to, one or more of the following: reducing the proliferation of (or destroying) cancerous cells or other diseased, reducing metastasis of cancerous cells found in cancers, shrinking the size of the tumor, decreasing symptoms resulting from the disease, increasing the quality of life of those suffering from the disease, decreasing the dose of other medications required to treat the disease, delaying the progression of the disease, and/or prolonging survival of individuals.

As used herein, the term "cancer" is intended to encompass cancers characterized by the presence of a cancer cell selected from the group consisting of a cell of an adrenal gland tumor, an AIDS-associated cancer, an alveolar soft part sarcoma, an astrocytic tumor, bladder cancer (squamous cell carcinoma and transitional cell carcinoma), bone cancer (adamantinoma, aneurismal bone cysts, osteochondroma, osteosarcoma), a brain and spinal cord cancer, a metastatic brain tumor, a breast cancer, a carotid body tumors, a cervical cancer, a chondrosarcoma, a chordoma, a chromophobe renal cell carcinoma, a clear cell carcinoma, a colon cancer, a colorectal cancer, a cutaneous benign fibrous histiocytoma, a desmoplastic small round cell tumor, an ependymoma, a Ewing's tumor, an extraskeletal myxoid chondrosarcoma, a fibrogenesis imperfecta ossium, a fibrous dysplasia of the bone, a gallbladder or bile duct cancer, gastric cancer, a gestational trophoblastic disease, a germ cell tumor, a glioblastoma, a head and neck cancer, hepatocellular canrcinoma, an islet cell tumor, a Kaposi's Sarcoma, a kidney cancer (nephroblastoma, papillary renal cell carcinoma), a leukemia, a lipoma/benign lipomatous tumor, a liposarcoma/malignant lipomatous tumor, a liver cancer (hepatoblastoma, hepatocellular carcinoma), a lymphoma, a lung cancer, a medulloblastoma, a melanoma, a meningioma, a multiple endocrine neoplasia, a multiple myeloma, a myelodysplastic syndrome, a neuroblastoma, a neuroendocrine tumors, an ovarian cancer, a pancreatic cancer, a papillary thyroid carcinoma, a parathyroid tumor, a pediatric cancer, a peripheral nerve sheath tumor, a phaeochromocytoma, a pituitary tumor, a prostate cancer, a posterior uveal melanoma, a rare hematologic disorder, a renal metastatic cancer, a rhabdoid tumor, a rhabdomysarcoma, a sarcoma, a skin cancer, a soft-tissue sarcoma, a squamous cell cancer, a stomach cancer, a synovial sarcoma, a testicular cancer, a thymic carcinoma, a thymoma, a thyroid metastatic cancer, and a uterine cancer (carcinoma of the cervix, endometrial carcinoma, and leiomyoma).

III. B7-H3 AND ANTI-B7-H3 ANTIBODIES

The present invention encompasses compositions, including pharmaceutical compositions, comprising anti-B7-H3 antibodies, polypeptides derived from anti-B7-H3 antibodies, polynucleotides comprising sequence encoding anti-B7-H3 antibodies, and other agents as described herein. As used herein, compositions further comprises one or more antibodies, polypeptides and/or proteins that bind to B7-H3, B7-H3 agonists, antagonists, modulators, and/or one or more polynucleotides comprising sequences encoding one or more antibodies, polypeptides and proteins that bind to B7-H3.

The invention further provides for conjugates of any B7-H3 peptide agonist, antagonist or modulator, and additional chemical structures that support the intended function or functions of the particular B7-H3 peptide agonist, antagonist or modulator.

These conjugates include B7-H3 peptide agonist, antagonist or modulator covalently bound to a macromolecule such as any insoluble, solid support matrix used in the diagnostic, screening or purification procedures discussed herein. Suitable matrix materials include any substance that is chemically inert, has high porosity and has large numbers of functional groups capable of forming covalent linkages with peptide ligands. Examples of matrix materials and procedures for preparation of matrix-ligand conjugates are described in Dean et al. (Eds) AFFINITY CHROMATOGRAPHY: A PRACTICAL APPROACH, IRL Press (1985); Lowe, "*An Introduction to Affinity Chromatography*", in Work et al. (eds) LABORATORY TECHNIQUES IN BIOCHEMISTRY AND MOLECULAR BIOLOGY, Vol. 7, Part II, North-Holland (1979); Porath et al., "*Biospecific Affinity Chromatography*", in Neurath, H. et al. (eds), THE PROTEINS, 3rd ed., Vol. 1, pp. 95-178 (1975); and Schott, H. AFFINITY CHROMATOGRAPHY, Macel Dekker, Inc. NY (1984).

Also provided herein are conjugates of B7-H3 peptide agonist, antagonist or modulator and any reporter moiety used in the diagnostic procedures discussed herein. The B7-H3 peptide agonist, antagonist or modulator agents, polypeptides and proteins of this invention, including anti-B7-H3 antibodies, are further identified and characterized by any (one or more) of the following criteria:
- (a) an ability to specifically bind to B7-H3 (and in particular B7-H3 molecules that are expressed on the surfaces of cancer cells, including but not limited to kidney, prostate, or lung, cancer cells);
- (b) an ability to competitively inhibits preferential binding of a known anti-B7-H3 antibody to B7-H3, including the ability to preferentially bind to the same B7-H3 epitope to which the original antibody preferentially binds;
- (c) an ability to bind to a portion of B7-H3 that is exposed on the surface of a living cell in vitro or in vivo;
- (d) an ability to bind to a portion of B7-H3 that is exposed on the surface of living cancer cells that express B7-H3;
- (e) an ability to deliver a chemotherapeutic agent to cancerous cells (such as kidney, prostate, or lung cancer cells) expressing B7-H3 on their surface; and/or
- (f) an ability to deliver a therapeutic agent or detectable marker into cancer cells (such as but not limited to prostate cancer cells) expressing B7-H3 on their surface.

A preferred antibody of the invention will exhibit differential IHC staining of tumor tissue relative to normal, non-cancerous tissue, and will moreover be capable of testing in primate (and particularly cynomolgus monkey) models of antibody efficacy. Preferred antibodies of the present invention will additionally exhibit desirable levels of affinity and antigen specificity. Preferred antibodies of the present invention will additionally exhibit desirable levels of immunomodulatory activity and cellular internalization.

In some embodiments, the antibody of the invention is an antibody that is produced by hybridoma BRCA84D, BRCA69D, or PRCA157, or progeny thereof. The present invention also encompasses various formulations of antibodies produced by these deposited hybridomas and equivalent antibodies or polypeptide fragments (e.g., Fab, Fab', F(ab')$_2$ Fv, Fc, etc.), chimeric antibodies, single chain (scFv), mutants thereof, fusion proteins comprising an antibody portion, humanized antibodies, and any other modified configuration of any of these or equivalent antibodies that comprises an antigen (B7-H3), recognition site of the required specificity. The invention also provides human antibodies displaying one or more of the biological characteristics of an anti-B7-H3 family member. The equivalent antibodies of the anti-B7-H3 family (including humanized antibodies and human antibodies), polypeptide fragments, and polypeptides comprising any of these fragments are identified and characterized by any (one or more) of the five criteria described above. Murine and exemplary humanized variable domain sequences of an anti-B7-H3 antibody are provided in PCT Publication WO 2008/066691. Such sequences are provided by way of illustration not limitation, and different sequences as well as fragments and variants of the provided sequences, are encompassed within the scope of this invention.

A. B7-H3

As used herein, the term "B7-H3" refers to a member of the human B7 family of proteins, a type I membrane protein with Ig-like domains also known as CD276. The term "2Ig-B7-H3" denotes the B7-H3 form that comprises only two Ig-like domains; the term "4Ig-B7-H3" denotes the B7-H3 form that comprises four Ig-like domains (see, Sun, M. et al. (2002) "*Characterization of Mouse and Human B7-H3 Genes,*" J. Immunol. 168:6294-6297; Steinberger et al. (2004), "*Molecular Characterization Of Human 4Ig-B7-H3, A Member Of The B7 Family With Four Ig-Like Domains,*" J. Immunol. 2004, 172(4):2352-2359 and Castriconi et al. (2004) "*Identification Of 4Ig-B7-H3 As A Neuroblastoma-Associated Molecule That Exerts A Protective Role From An NK Cell-Mediated Lysis,*" Proc. Natl. Acad. Sci. (U.S.A.) 101(34):12640-12645). The antigen "TES7" (WO 2008/066691) is an antigen sharing characteristics of the 4Ig-B7-H3. Accordingly, antibodies that specifically bind to TES7 bind to 4Ig-B7-H3. The TES7 antigen may have more than one different epitope, and epitopes may be non-linear. Several anti-B7-H3 antibodies are known to bind to non-linear epitopes, including some only present on the 4Ig-B7-H3 isoform. It is currently believed that TES7 may be over-expressed in certain cancer cells in comparison to their normal tissue counterparts.

The amino acid sequence of the "2Ig" form of human B7-H3 is (SEQ ID NO:1):

```
MLRRRGSPGM GVHVGAALGA LWFCLTGALE VQVPEDPVVA

LVGTDATLCC SFSPEPGFSL AQLNLIWQLT DTKQLVHSFA

EGQDQGSAYA NRTALFPDLL AQGNASLRLQ RVRVADEGSF

TCFVSIRDFG SAAVSLQVAA PYSKPSMTLE PNKDLRPGDT

VTITCSSYRG YPEAEVFWQD GQGVPLTGNV TTSQMANEQG

LFDVHSVLRV VLGANGTYSC LVRNPVLQQD AHGSVTITGQ

PMTFPPEALW VTVGLSVCLI ALLVALAFVC WRKIKQSCEE

ENAGAEDQDG EGEGSKTALQ PLKHSDSKED DGQEIA
```

A cDNA sequence encoding the "2Ig" form of human B7-H3 is (SEQ ID NO:2):

```
atgctgcgtc ggcggggcag ccctggcatg ggtgtgcatg tgggtgcagc cctgggagca ctgtggttct gcctcacagg agccctggag gtccaggtcc ctgaagaccc agtggtggca
```

```
ctggtgggca ccgatgccac cctgtgctgc tccttctccc ctgagcctgg cttcagcctg gcacagctca acctcatctg gcagctgaca gataccaaac agctggtgca cagctttgct gagggccagg accagggcag cgcctatgcc aaccgcacgg ccctcttccc ggacctgctg gcacagggca acgcatccct gaggctgcag cgcgtgcgtg tggcggacga gggcagcttc acctgcttcg tgagcatccg ggatttcggc agcgctgccg tcagcctgca ggtgccgct ccctactcga agcccagcat gaccctggag cccaacaagg acctgcggcc aggggacacg gtgaccatca cgtgctccag ctaccgggc taccctgagg ctgaggtgtt ctggcaggat gggcagggtg tgccctgac tggcaacgtg accacgtcgc agatggccaa cgagcagggc ttgtttgatg tgcacagcgt cctgcgggtg gtgctgggtg cgaatggcac ctacagctgc ctggtgcgca accccgtgct gcagcaggat gcgcacggct ctgtcaccat cacagggcag cctatgacat tcccccaga ggccctgtgg gtgaccgtgg ggctgtctgt ctgtctcatt gcactgctgg tggccctggc tttcgtgtgc tggagaaaga tcaaacagag ctgtgaggag gagaatgcag gagctgagga ccaggatggg gagggagaag gctccaagac agccctgcag cctctgaaac actctgacag caaagaagat gatggacaag aaatagcc
```

The amino acid sequence of the "2Ig" form of human B7-H3 (SEQ ID NO:1) (shown in bold and underline below) is completely embraced within the "4Ig" form of human B7-H3 (SEQ ID NO:3):

```
MLRRRGSPGM GVHVGAALGA LWFCLTGALE VQVPEDPVVA

LVGTDATLCC SFSPEPGFSL AQLNLIWQLT DTKQLVHSFA

EGQDQGSAYA NRTALFPDLL AQGNASLRLQ RVRVADEGSF

TCFVSIRDFG SAAVSLQVAA PYSKPSMTLE PNKDLRPGDT

VTITCSSYQG YPEAEVFWQD GQGVPLTGNV TTSQMANEQG

LFDVHSILRV VLGANGTYSC LVRNPVLQQD AHSSVTITPQ

RSPTGAVEVQ VPEDPVVALV GTDATLRCSF SPEPGFSLAQ

LNLIWQLTDT KQLVHSFTEG RDQGSAYANR TALFPDLLAQ

GNASLRLQRV RVADEGSFTC FVSIRDFGSA AVSLQVAAPY

SKPSMTLEPN KDLRPGDTVT ITCSSYRGYP EAEVFWQDGQ

GVPLTGNVTT SQMANEQGLF DVHSVLRVVL GANGTYSCLV

RNPVLQQDAH GSVTITGQPM TFPPEALWVT VGLSVCLIAL

LVALAFVCWR KIKQSCEEEN AGAEDQDGEG EGSKTALQPL

KHSDSKEDDG QEIA
```

A cDNA sequence encoding the "4Ig" form of human B7-H3 is (SEQ ID NO:4); residues encoding the "2Ig" form of B&-H3 are shown in bold and underlined:

```
atgctgcgtc ggcggggcag ccctggcatg ggtgtgcatg
tgggtgcagc cctgggagca ctgtggttct gcctcacagg
agccctggag gtccaggtcc ctgaagaccc agtggtggca
ctggtgggca ccgatgccac cctgtgctgc tccttctccc
ctgagcctgg cttcagcctg gcacagctca acctcatctg
gcagctgaca gataccaaac agctggtgca cagctttgct
gagggccagg accagggcag cgcctatgcc aaccgcacgg
ccctcttccc ggacctgctg gcacagggca acgcatccct
gaggctgcag cgcgtgcgtg tggcggacga gggcagcttc
acctgcttcg tgagcatccg ggatttcggc agcgctgccg
tcagcctgca ggtggccgct ccctactcga agcccagcat
gaccctggag cccaacaagg acctgcggcc aggggacacg
gtgaccatca cgtgctccag ctaccagggc taccctgagg
ctgaggtgtt ctggcaggat gggcagggtg tgcccctgac
tggcaacgtg accacgtcgc agatggccaa cgagcagggc
ttgtttgatg tgcacagcat cctgcgggtg gtgctgggtg
caaatggcac ctacagctgc ctggtgcgca accccgtgct
gcagcaggat gcgcacagct ctgtcaccat cacacccag
agaagcccca caggagccgt ggaggtccag gtcctgagg
acccggtggt ggcctagtg ggcaccgatg ccacctgcg
ctgctccttc tccccgagc ctggcttcag cctggcacag
ctcaacctca tctggcagct gacagacacc aaacagctgg
tgcacagttt caccgaaggc cgggaccagg gcagcgccta
tgccaaccgc acggccctct tcccggacct gctggcacaa
ggcaatgcat ccctgaggct gcagcgcgtg cgtgtggcgg
acgagggcag cttcacctgc ttcgtgagca tccgggattt
cggcagcgct gccgtcagcc tgcaggtggc cgctccctac
tcgaagccca gcatgaccct ggagcccaac aaggacctgc
ggccagggga cacggtgacc atcacgtgct ccagctaccg
gggctaccct gaggctgagg tgttctggca ggatgggcag
ggtgtgcccc tgactggcaa cgtgaccacg tcgcagatgg
ccaacgagca gggcttgttt gatgtgcaca gcgtcctgcg
ggtggtgctg ggtgcgaatg gcacctacag ctgcctggtg
cgcaacccccg tgctgcagca ggatgcgcac ggctctgtca
ccatcacagg gcagcctatg acattcccc cagaggccct
gtgggtgacc gtggggctgt ctgtctgtct cattgcactg
ctggtggccc tggctttcgt gtgctggaga aagatcaaac
agagctgtga ggaggagaat gcaggagctg aggaccagga
tggggaggga gaaggctcca agacagccct gcagcctctg
aaacactctg acagcaaaga agatgatgga caagaaatag
cc
```

B7-H3 and its native ligands or an anti-B7-H3 antibody; (2) is capable of binding to human B7-H3 and its native ligands or an anti-B7-H3 antibody; (3) contains an antigenic site that can be used in the raising of antibodies capable of binding to human B7-H3 and its native ligands or an anti-B7-H3 antibody; (4) contains an antigenic site that can be used in the screening of antibodies capable of binding to human B7-H3 and its native ligands or an anti-B7-H3 antibody; (5) contains an antigenic site that can be used in the raising of antibodies capable of disrupting or blocking the interaction between human B7-H3 and its native ligands or an anti-B7-H3 antibody; (6) contains an antigenic site that can be used in the screening of antibodies capable of disrupting or blocking the interaction between human B7-H3 and its native ligands or an anti-B7-H3 antibody. B7-H3 modulators may be "B7-H3 agonists" or "B7-H3 antagonists" depending on whether their activity enhances T cell activation or inhibits Tcell activation, respectively.

B7-H3 agonists, antagonists and modulators include B7-H3 variants, B7-H3 peptide antagonists, peptidomimetics, and small molecules, anti-B7-H3 antibodies and immunoglobulin variants, amino acid variants of human B7-H3 including amino acid substitution, deletion, and addition variants, or any combination thereof, and chimeric immunoglobulins. The B7-H3 agonists, antagonists and modulators of this invention are based on the identification of the B7-H3 domains involved in the binding of human B7-H3 to its native ligands or anti-B7-H3 antibodies. Thus, the invention provides B7-H3 agonists, antagonists and modulators with molecular structures that duplicate or mimic one or more of the anti-B7-H3 binding domains of human B7-H3.

As used herein, the term "B7-H3 variant" denotes any amino acid variant of human B7-H3, including amino acid substitution, deletion, and addition variants, or any combination thereof. The definition encompasses chimeric molecules such as human B7-H3/non-human chimeras and other hybrid molecules. Also included in the definition is any fragment of a B7-H3 variant molecule that comprises the variant or hybrid region(s) of the molecule.

B. Anti-B7-H3 Antibodies

Several methods may be used to screen polypeptides and monoclonal antibodies that bind to B7-H3. It is understood that "binding" refers to biologically or immunologically relevant specific binding, and does not refer to non-specific binding that may occur, for example, when an immunoglobulin is used at a very high concentration against a non-specific target. In one embodiment, monoclonal antibodies are screened for binding to B7-H3 using standard screening techniques. In this manner, anti-B7-H3 monoclonal antibody was obtained. Methods for obtaining such antibodies are described in United States Patent Publication No. 2013/0149236 and WO 2011/109400.

The invention also provides polypeptides comprising an amino acid sequence of the antibodies of the invention. In some embodiments, the polypeptide comprises one or more of the light chain and/or heavy chain variable regions of the antibody. In some embodiments, the polypeptide comprises one or more of the light chain and/or heavy chain CDRs of the antibody. In some embodiments, the polypeptide comprises three CDRs of the light chain and/or heavy chain of the antibody. In some embodiments, the polypeptide comprises an amino acid sequence of the antibody that has any of the following: at least 5 contiguous amino acids of a sequence of the original antibody, at least 8 contiguous amino acids, at least about 10 contiguous amino acids, at least about 15 contiguous amino acids, at least about 20 contiguous amino acids, at least about 25 contiguous amino acids, at least about 30 contiguous amino acids, wherein at least 3 of the amino acids are from a variable region of the antibody. In one embodiment, the variable region is from a light chain of the original antibody. In another embodiment, the variable region is from a heavy chain of the antibody. In another embodiment, the 5 (or more) contiguous amino acids are from a complementarity-determining region (CDR) of the antibody.

The preferred anti-B7-H3 antibodies of the present invention are BRCA84D, BRCA69D and PRCA157, all of which antibodies are murine antibodies reactive toward the human B7-H3 molecule. The amino acid and encoding polynucleotide sequences of the variable light chain and variable heavy chain of BRCA84D, BRCA69D and PRCA157 are shown below along with the respective $CDR_1$, $CDR_2$ and $CDR_3$ domains of each such chain. Those of skill in the art will therefore be able to construct antibodies having such CDRs, as well as derivatives thereof, capable of binding to the epitopes recognized by BRCA84D, BRCA69D and PRCA157.

1. Sequences of BRCA69D (a) BRCA69D Light Chain Sequences

Amino Acid Sequence of BRCA69D Variable Light Chain (SEQ ID NO:5):

```
DIQMTQTTSS LSASLGDRVT ISCRASQDIS NYLNWYQQKP
DGTVKLLIYY TSRLHSGVPS RFSGSGSGTD YSLTIDNLEQ
EDIATYFCQQ GNTLPPTFGG GTKLEIK
```

Polynucleotide Sequence Encoding BRCA69D Variable Light Chain (SEQ ID NO:6):

```
gatatccaga tgacacagac tacatcctcc ctgtctgcct
ctctgggaga cagagtcacc atcagttgca gggcaagtca
ggacattagt aattatttaa actggtatca gcagaaacca
gatggaactg ttaaactcct gatctactac acatcacgat
tacactcagg agtcccatca aggttcagtg gcagtgggtc
tggaacagat tattctctca ccattgacaa cctggagcaa
gaagatattg ccacttactt ttgccaacag ggtaatacgc
ttcctccgac gttcggtgga ggcaccaaac tggaaatcaa a
```

BRCA69D Variable Light Chain $CDR_1$ (SEQ ID NO:7):

```
RASQDISNYLN
```

Polynucleotide Sequence Encoding BRCA69D Variable Light Chain $CDR_1$ (SEQ ID NO:8):

```
agggcaagtc aggacattag taattattta aac
```

BRCA69D Variable Light Chain $CDR_2$ (SEQ ID NO:9):
YTSRLHS

Polynucleotide Sequence Encoding BRCA69D Variable Light Chain $CDR_2$ (SEQ ID NO:10):

```
tacacatcac gattacactc a
```

BRCA69D Variable Light Chain CDR₃ (SEQ ID NO:11):

```
QQGNTLPPT
```

Polynucleotide Sequence Encoding BRCA69D Variable Light Chain CDR₃ (SEQ ID NO:12):

```
caacagggta atacgcttcc tccgacg
```

(b) BRCA69D Heavy Chain Sequences
Amino Acid Sequence of BRCA69D Variable Heavy Chain (SEQ ID NO:13):

```
QVQLQQSGAE LARPGASVKL SCKASGYTFT SYWMQWVKQR
PGQGLEWIGT IYPGDGDTRY TQKFKGKATL TADKSSSTAY
MQLSSLASED SAVYYCARRG IPRLWYFDVW GAGTTVTVSS
```

Polynucleotide Sequence Encoding BRCA69D Variable Heavy Chain (SEQ ID NO:14):

```
caggttcagc tccagcagtc tggggctgag ctggcaagac
ctggggcttc agtgaagttg tcctgcaagg cttctggcta
cacctttact agctactgga tgcagtgggt aaaacagagg
cctggacagg gtctggaatg gattgggact atttatcctg
gagatggtga tactaggtac actcagaagt tcaagggcaa
ggccacattg actgcagata atcctccag cacagcctac
atgcaactca gcagcttggc atctgaggac tctgcggtct
attactgtgc aagaagaggg attccacggc tttggtactt
cgatgtctgg ggcgcaggga ccacggtcac cgtctcctca
```

BRCA69D Variable Heavy Chain CDR₁ (SEQ ID NO:15): SYWMQ

Polynucleotide Sequence Encoding BRCA69D Variable Heavy Chain CDR₁ (SEQ ID NO:16):

```
agctactgga tgcag
```

BRCA69D Variable Heavy Chain CDR₂ (SEQ ID NO:17):

```
TIYPGDGDTR YTQKFKG
```

Polynucleotide Sequence Encoding BRCA69D Variable Heavy Chain CDR₂ (SEQ ID NO:18):

```
actatttatc ctggagatgg tgatactagg tacactcag
aagttcaagg gc
```

BRCA69D Variable Heavy Chain CDR₃ (SEQ ID NO:19):

```
RGIPRLWYFD V
```

Polynucleotide Sequence Encoding BRCA69D Variable Heavy Chain CDR₃ (SEQ ID NO:20):

```
agagggattc cacggctttg gtacttcgat gtc
```

2. Sequences of PRCA157
(a) PRCA157 Light Chain Sequences
Amino Acid Sequence of PRCA157 Variable Light Chain (SEQ ID NO:21):

```
DIQMTQSPAS LSVSVGETVT ITCRASESIY SYLAWYQQKQ
GKSPQLLVYN TKTLPEGVPS RFSGSGSGTQ FSLKINSLQP
EDFGRYYCQH HYGTPPWTFG GGTNLEIK
```

Polynucleotide Sequence Encoding PRCA157 Variable Light Chain (SEQ ID NO:22):

```
gacatccaga tgactcagtc tccagcctcc ctatctgtat
ctgtgggaga aactgtcacc attacatgtc gagcaagtga
gagtatttac agttatttag catggtatca gcagaaacag
ggaaaatctc ctcagctcct ggtctataat acaaaaacct
taccagaggg tgtgccatca aggttcagtg gcagtggatc
aggcacacag ttttctctga agatcaacag cctgcagcct
gaagattttg ggagatatta ctgtcaacat cattatggta
ctcctccgtg gacgttcggt ggaggcacca acctggaaat
caaa
```

PRCA157 Variable Light Chain CDR₁ (SEQ ID NO:23):

```
RASESIYSYLA
```

Polynucleotide Sequence Encoding PRCA157 Variable Light Chain CDR₁ (SEQ ID NO:24):

```
cgagcaagtg agagtattta cagttattta gca
```

PRCA157 Variable Light Chain CDR₂ (SEQ ID NO:25):

```
NTKTLPE
```

Polynucleotide Sequence Encoding PRCA157 Variable Light Chain CDR₂ (SEQ ID NO:26):

```
aatacaaaaa ccttaccaga g
```

PRCA157 Variable Light Chain CDR₃ (SEQ ID NO:27):

```
QHHYGTPPW
```

Polynucleotide Sequence Encoding PRCA157 Variable Light Chain CDR₃ (SEQ ID NO:28):

```
caacatcatt atggtactcc tccgtgg
```

(b) PRCA157 Heavy Chain Sequences
Amino Acid Sequence of PRCA157 Variable Heavy Chain (SEQ ID NO:29):

```
EVQQVESGGD LVKPGGSLKL SCAASGFTFS SYGMSWVRQT
PDKRLEWVAT INSGGSNTYY PDSLKGRFTI SRDNAKNTLY
LQMRSLKSED TAMYYCARHD GGAMDYWGQG TSVTVSS
```

Polynucleotide Sequence Encoding PRCA157 Variable Heavy Chain (SEQ ID NO:30):

```
gaggtgcagc aggtggagtc ggggggagac ttagtgaagc
ctggagggtc cctgaaactc tcctgtgcag cctctggatt
cactttcagt tcctatggca tgtcttgggt tcgccagact
ccagacaaga ggctggagtg ggtcgcaacc attaatagtg
gtggaagtaa cacctactat ccagacagtt tgaaggggcg
attcaccatc tccagagaca atgccaagaa cacccttac
ctgcaaatgc gcagtctgaa gtctgaggac acagccatgt
attactgtgc aagacatgac ggggagcta tggactactg
gggtcaagga acctcagtca ccgtctcctc a
```

PRCA157 Variable Heavy Chain CDR₁ (SEQ ID NO:31):

SYGMS

Polynucleotide Sequence Encoding PRCA157 Variable Heavy Chain CDR₁ (SEQ ID NO:32):

```
tcctatggca tgtct
```

PRCA157 Variable Heavy Chain CDR₂ (SEQ ID NO:33):

VATINSGGSN TYYPDSLKG

Polynucleotide Sequence Encoding PRCA157 Variable Heavy Chain CDR₂ (SEQ ID NO:34):

```
gtcgcaacca ttaatagtgg tggaagtaac acctactatc
cagacagttt gaagggg
```

PRCA157 Variable Heavy Chain CDR₃ (SEQ ID NO:35):

HDGGAMDY

Polynucleotide Sequence Encoding PRCA157 Variable Heavy Chain CDR₃ (SEQ ID NO:36):

```
catgacgggg gagctatgga ctac
```

2. Sequences of BRCA84D
(a) BRCA84D Light Chain Sequences
Amino Acid Sequence of BRCA84D Variable Light Chain (SEQ ID NO:37):

```
DIAMTQSQKF MSTSVGDRVS VTCKASQNVD TNVAWYQQKP
GQSPKALIYS ASYRYSGVPD RFTGSGSGTD FTLTINNVQS
EDLAEYFCQQ YNNYPFTFGS GTKLEIK
```

Polynucleotide Sequence Encoding BRCA84D Variable Light Chain (SEQ ID NO:38):

```
gacattgcga tgacccagtc tcaaaaattc atgtccacat
cagtaggaga cagggtcagc gtcacctgca aggccagtca
gaatgtggat actaatgtag cctggtatca acagaaacca
gggcaatctc ctaaagcact gatttactcg gcatcctacc
ggtacagtgg agtccctgat cgcttcacag gcagtggatc
tgggacagat ttcactctca ccatcaacaa tgtgcagtct
gaagacttgg cagagtattt ctgtcagcaa tataacaact
atccattcac gttcggctcg gggacaaagt tggaaataaa
a
```

BRCA84D Variable Light Chain CDR₁ (SEQ ID NO:39):

KASQNVDTNVA

Polynucleotide Sequence Encoding BRCA84D Variable Light Chain CDR₁ (SEQ ID NO:40):

```
aaggccagtc agaatgtgga tactaatgta gcc
```

BRCA84D Variable Light Chain CDR₂ (SEQ ID NO:41):

SASYRYS

Polynucleotide Sequence Encoding BRCA84D Variable Light Chain CDR₂ (SEQ ID NO:42):

```
tcggcatcct accggtacag t
```

BRCA84D Variable Light Chain CDR₃ (SEQ ID NO:43):

QQYNNYPFT

Polynucleotide Sequence Encoding BRCA84D Variable Light Chain CDR₃ (SEQ ID NO:44):

```
cagcaatata caactatcc attcacg
```

(b) BRCA84D Heavy Chain Sequences
Amino Acid Sequence of BRCA84D Variable Heavy Chain (SEQ ID NO:45):

```
DVQLVESGGG LVQPGGSRKL SCAASGFTFS SFGMHWVRQA
PEKGLEWVAY ISSDSSAIYY ADTVKGRFTI SRDNPKNTLF
LQMTSLRSED TAMYYCGRGR ENIYYGSRLD YWGQGTTLTV
SS
```

Polynucleotide Sequence Encoding BRCA84D Variable Heavy Chain (SEQ ID NO:46):

```
gatgtgcagc tggtggagtc tgggggaggc ttagtgcagc
ctggagggtc ccggaaactc tcctgtgcag cctctggatt
cactttcagt agctttggaa tgcactgggt tcgtcaggct
ccagagaagg ggctggagtg ggtcgcatac attagtagtg
acagtagtgc catctactat gcagacacag tgaagggccg
```

```
        attcaccatc tccagagaca atcccaagaa caccctgttc ctgcaaatga ccagtctaag gtctgaggac acggccatgt attactgtgg aagagggagg gaaaacattt actacggtag taggcttgac tactgggggcc aaggcaccac tctcacagtc tcctca
```

BRCA84D Variable Heavy Chain CDR$_1$ (SEQ ID NO:47):

```
                            FGMH
```

Polynucleotide Sequence Encoding BRCA84D Variable Heavy Chain CDR$_1$ (SEQ ID NO:48):

```
        tttggaatgcac
```

BRCA84D Variable Heavy Chain CDR$_2$ (SEQ ID NO:49):

```
                     YISSDSSAIYYADTVK
```

Polynucleotide Sequence Encoding BRCA84D Variable Heavy Chain CDR$_2$ (SEQ ID NO:50):

```
        tacattagta gtgacagtag tgccatctac tatgcagaca cagtgaag
```

BRCA84D Variable Heavy Chain CDR$_3$ (SEQ ID NO:51):

```
                      GRENIYYGSRLDY
```

Polynucleotide Sequence Encoding BRCA84D Variable Heavy Chain CDR$_3$ (SEQ ID NO:52):

```
        gggagggaaa acatttacta cggtagtagg cttgactac
```

Monoclonal antibody BRCA84D was humanized in order to produce antibodies (generically designated herein as "hBRCA84D") offering improved human therapeutic potential. The sequences of the variable light chain, and the variable heavy chain, and their respective amino acid and polynucleotide sequences of a resulting humanized antibody (designated herein as "hBRCA84D-1") are provided below:

Humanized BRCA84D-1 Variable Light Chain (SEQ ID NO:53):

```
        DIQLTQSPSF LSASVGDRVT ITCKASQNVD TNVAWYQQKP

GKAPKLLIYS ASYRYSGVPS RFSGSGSGTD FTLTISSLQP

EDFATYYCQQ YNNYPFTFGQ GTKLEIK
```

Polynucleotide Sequence Encoding Humanized BRCA84D-1 Variable Light Chain (SEQ ID NO:54):

```
        gacatccagc tgacccagtc ccctcttc ctgtctgcct ccgtgggcga cagagtgacc atcacatgca aggcctccca
```

```
        gaacgtggac accaacgtgg cctggtatca gcagaagcct ggcaaggccc ctaagctgct gatctactcc gcctcctacc ggtactccgg cgtgccttcc aggttctccg gctccggctc tggcaccgac ttcaccctga ccatctccag cctgcagcct gaggacttcg ccacctacta ctgccagcag tacaacaact accctttcac cttcggccag ggcaccaagc tggaaatcaa g
```

Humanized BRCA84D-1 Variable Light Chain CDR$_1$ (SEQ ID NO:55):

```
                        KASQNVDTNVA
```

Polynucleotide Sequence Encoding Humanized BRCA84D-1 Variable Light Chain CDR$_1$ (SEQ ID NO:56):

```
        aaggccagtc agaatgtgga tactaatgta gcc
```

Humanized BRCA84D-1 Variable Light Chain CDR$_2$ (SEQ ID NO:57):

```
                           SASYRYS
```

Polynucleotide Sequence Encoding Humanized BRCA84D-1 Variable Light Chain CDR$_2$ (SEQ ID NO:58):

```
        tcggcatcct accggtacag t
```

Humanized BRCA84D-1 Variable Light Chain CDR$_3$ (SEQ ID NO:59):

```
                          QQYNNYPFT
```

Polynucleotide Sequence Encoding Humanized BRCA84D-1 Variable Light Chain CDR$_3$ (SEQ ID NO:60):

```
        cagcaatata caactatcc attcacg
```

Amino Acid Sequence of Humanized BRCA84D-1 Variable Heavy Chain (SEQ ID NO:61):

```
        EVQLVESGGG LVQPGGSLRL SCAASGFTFS SFGMHWVRQA

PGKGLEWVAY ISSDSSAIYY ADTVKGRFTI SRDNAKNSLY

LQMNSLRDED TAVYYCARGR ENIYYGSRLD YWGQGTTVTV SS
```

Polynucleotide Sequence Encoding Humanized BRCA84D-1 Variable Heavy Chain (SEQ ID NO:62):

```
        gaggtgcagc tggtcgagtc tggcggagga ctggtgcagc ctggcggctc cctgagactg tcttgcgccg cctccggctt caccttctcc agcttcggca tgcactgggt ccgccaggct ccaggcaagg gactggaatg ggtggcctac atctcctccg actcctccgc catctactac gccgacaccg tgaagggcag gttcaccatc tcccgggaca acgccaagaa ctccctgtac
```

-continued
```
ctgcagatga actccctgcg ggacgaggac accgccgtgt actactgcgc cagaggccgg gagaatatct actacggctc ccggctggat tattggggcc agggcaccac cgtgaccgtg tcctct
```

Humanized BRCA84D-1 Variable Heavy Chain CDR$_1$ (SEQ ID NO:63):

```
                FGMH
```

Polynucleotide Sequence Encoding Humanized BRCA84D-1 Variable Heavy Chain CDR$_1$ (SEQ ID NO:64):

```
            tttggaatgcac
```

Humanized BRCA84D Variable Heavy Chain CDR$_2$ (SEQ ID NO:65):

```
          YISSDSSAIYYADTVK
```

Polynucleotide Sequence Encoding Humanized BRCA84D-1 Variable Heavy Chain CDR$_2$ (SEQ ID NO:66):

```
    tacattagta gtgacagtag tgccatctac tatgcagaca cagtgaag
```

Humanized BRCA84D-1 Variable Heavy Chain CDR$_3$ (SEQ ID NO:67):

```
           GRENIYYGSRLDY
```

Polynucleotide Sequence Encoding Humanized BRCA84D-1 Variable Heavy Chain CDR$_3$ (SEQ ID NO:68):

```
    gggagggaaa acatttacta cggtagtagg cttgactac
```

In order to obtain hBRCA84D species that exhibit improved affinity for human B7-H3, polynucleotides encoding the light or heavy chains of hBRCA84D-1 (i.e., hBRCA84D-1VL or hBRCA84D-1VH, respectively) were subjected to mutagenesis, and mutated hBRCA84D-1 light chain derivatives hBRCA84D-2VL, hBRCA84D-3VL, hBRCA84D-4VL, hBRCA84D-5VL, and hBRCA84D-6VL and mutated hBRCA84D-1 heavy chain derivatives hBRCA84D-2VH, hBRCA84D-3VH, and hBRCA84D-4VH were isolated and characterized. The amino acid and polynucleotide sequences of the variable light and heavy chains of these antibodies are presented below:

Amino Acid Sequence of hBRCA84D-2VL (SEQ ID NO:69):

```
    DIQLTQSPSF LSASVGDRVT ITCKASQNVD TNVAWYQQKP

GKAPKALIYS ASYRYSGVPS RFSGSGSGTD FTLTISSLQP

EDFATYYCQQ YNNYPFTFGQ GTKLEIK
```

Polynucleotide Encoding hBRCA84D-2VL (SEQ ID NO:70):

```
    gacatccagc tgacccagtc cccctccttc ctgtctgcct ccgtgggcga cagagtgacc atcacatgca aggcctccca gaacgtggac accaacgtgg cctggtatca gcagaagcct ggcaaggccc ctaaggcgct gatctactcc gcctcctacc ggtactccgg cgtgccttcc aggttctccg gctccggctc tggcaccgac ttcaccctga ccatctccag cctgcagcct gaggacttcg ccacctacta ctgccagcag tacaacaact acccttcac cttcggccag ggcaccaagc tggaaatcaa g
```

Amino Acid Sequence of hBRCA84D-3VL (SEQ ID NO:71):

```
    DIQLTQSPSF LSASVGDRVS VTCKASQNVD TNVAWYQQKP

GKAPKLLIYS ASYRYSGVPS RFSGSGSGTD FTLTISSLQP

EDFATYYCQQ YNNYPFTFGQ GTKLEIK
```

Polynucleotide Encoding hBRCA84D-3VL (SEQ ID NO:72):

```
    gacatccagc tgacccagtc cccctccttc ctgtctgcct ccgtgggcga cagagtgtcc gtcacatgca aggcctccca gaacgtggac accaacgtgg cctggtatca gcagaagcct ggcaaggccc ctaagctgct gatctactcc gcctcctacc ggtactccgg cgtgccttcc aggttctccg gctccggctc tggcaccgac ttcaccctga ccatctccag cctgcagcct gaggacttcg ccacctacta ctgccagcag tacaacaact acccttcac cttcggccag ggcaccaagc tggaaatcaa g
```

Amino Acid Sequence of hBRCA84D-4VL (SEQ ID NO:73):

```
    DIQLTQSPSF LSASVGDRVT ITCKASQNVD TNVAWYQQKP

GQAPKLLIYS ASYRYSGVPS RFSGSGSGTD FTLTISSLQP

EDFATYYCQQ YNNYPFTFGQ GTKLEIK
```

Polynucleotide Encoding hBRCA84D-4VL (SEQ ID NO:74):

```
    gacatccagc tgacccagtc cccctccttc ctgtctgcct ccgtgggcga cagagtgacc atcacatgca aggcctccca gaacgtggac accaacgtgg cctggtatca gcagaagcct ggccaggccc ctaagctgct gatctactcc gcctcctacc ggtactccgg cgtgccttcc aggttctccg gctccggctc tggcaccgac ttcaccctga ccatctccag cctgcagcct gaggacttcg ccacctacta ctgccagcag tacaacaact acccttcac cttcggccag ggcaccaagc tggaaatcaa g
```

Amino Acid Sequence of hBRCA84D-5VL (SEQ ID NO:75):

```
DIQLTQSPSF LSASVGDRVT ITCKASQNVD TNVAWYQQKP
GQAPKALIYS ASYRYSGVPS RFSGSGSGTD FTLTISSLQP
EDFATYYCQQ YNNYPFTFGQ GTKLEIK
```

Polynucleotide Encoding hBRCA84D-5VL (SEQ ID NO:76):

```
gacatccagc tgacccagtc ccctccttc ctgtctgcct
ccgtgggcga cagagtgacc atcacatgca aggcctccca
gaacgtggac accaacgtgg cctggtatca gcagaagcct
ggccaggccc ctaaggcgct gatctactcc gcctcctacc
ggtactccgg cgtgccttcc aggttctccg gctccggctc
tggcaccgac ttcaccctga ccatctccag cctgcagcct
gaggacttcg ccacctacta ctgccagcag tacaacaact
accctttcac cttcggccag ggcaccaagc tggaaatcaa
g
```

Amino Acid Sequence of hBRCA84D-6VL (SEQ ID NO:77):

```
DIQLTQSPSF LSASVGDRVT ITCKASQNVD TNVAWYQQKP
GKAPKLLIYS ASYRYSGVPS RFSGSGSGTD FTLTISSLQP
EDFAEYYCQQ YNNYPFTFGQ GTKLEIK
```

Polynucleotide Encoding hBRCA84D-6VL (SEQ ID NO:78):

```
gacatccagc tgacccagtc ccctccttc ctgtctgcct
ccgtgggcga cagagtgacc atcacatgca aggcctccca
gaacgtggac accaacgtgg cctggtatca gcagaagcct
ggcaaggccc ctaagctgct gatctactcc gcctcctacc
ggtactccgg cgtgccttcc aggttctccg gctccggctc
tggcaccgac ttcaccctga ccatctccag cctgcagcct
gaggacttcg ccgagtacta ctgccagcag tacaacaact
accctttcac cttcggccag ggcaccaagc tggaaatcaa
g
```

Amino Acid Sequence of hBRCA84D-2VH (SEQ ID NO:79):

```
EVQLVESGGG LVQPGGSLRL SCAASGFTFS SFGMHWVRQA
PGKGLEWVAY ISSDSSAIYY ADTVKGRFTI SRDNAKNSLY
LQMNSLRDED TAVYYCGRGR ENIYYGSRLD YWGQGTTVTV
SS
```

Polynucleotide Encoding hBRCA84D-2VH (SEQ ID NO:80):

```
gaggtgcagc tggtcgagtc tggcggagga ctggtgcagc
ctggcggctc cctgagactg tcttgcgccg cctccggctt
caccttctcc agcttcggca tgcactgggt ccgccaggct
ccaggcaagg gactggaatg ggtggcctac atctcctccg
actcctccgc catctactac gccgacaccg tgaagggcag
gttcaccatc tcccgggaca cgccaagaa ctccctgtac
ctgcagatga actccctgcg ggacgaggac accgccgtgt
actactgcgg cagaggccgg gagaatatct actacggctc
ccggctggat tattggggcc agggcaccac cgtgaccgtg
tcctct
```

Amino Acid Sequence of hBRCA84D-3VH (SEQ ID NO:81):

```
EVQLVESGGG LVQPGGSLRL SCAASGFTFS SFGMHWVRQA
PGKGLEWVAY ISSDSSAIYY ADTVKGRFTI SRDNAKNSLY
LQMNSLRDED TAMYYCGRGR ENIYYGSRLD YWGQGTTVTV
SS
```

Polynucleotide Encoding hBRCA84D-3VH (SEQ ID NO:82):

```
gaggtgcagc tggtcgagtc tggcggagga ctggtgcagc
ctggcggctc cctgagactg tcttgcgccg cctccggctt
caccttctcc agcttcggca tgcactgggt ccgccaggct
ccaggcaagg gactggaatg ggtggcctac atctcctccg
actcctccgc catctactac gccgacaccg tgaagggcag
gttcaccatc tcccgggaca cgccaagaa ctccctgtac
ctgcagatga actccctgcg ggacgaggac accgccatgt
actactgcgg cagaggccgg gagaatatct actacggctc
ccggctggat tattggggcc agggcaccac cgtgaccgtg
tcctct
```

Amino Acid Sequence of hBRCA84D-4VH (SEQ ID NO:83):

```
EVQLVESGGG LVQPGGSLRL SCAASGFTFS SFGMHWVRQA
PGKGLEWVAY ISSDSSAIYY ADTVKGRFTI SRDNAKNSLY
LQMNSLRSED TAVYYCARGR ENIYYGSRLD YWGQGTTVTV SS
```

Polynucleotide Encoding hBRCA84D-4VH (SEQ ID NO:84):

```
gaggtgcagc tggtcgagtc tggcggagga ctggtgcagc
ctggcggctc cctgagactg tcttgcgccg cctccggctt
caccttctcc agcttcggca tgcactgggt ccgccaggct
ccaggcaagg gactggaatg ggtggcctac atctcctccg
```

```
actcctccgc catctactac gccgacaccg tgaagggcag gttcaccatc tcccgggaca acgccaagaa ctccctgtac ctgcagatga actccctgcg gagcgaggac accgccgtgt actactgcgc cagaggccgg gagaatatct actacggctc ccggctggat tattggggcc agggcaccac cgtgaccgtg tcctct
```

Table 1 lists the hBRCA84D variable light chain and variable heavy chain mutations studied; numbers refer to the Kabat numbering system.

TABLE 1

| Variable Light Chain | | | | | | Variable Heavy Chain | | | |
|---|---|---|---|---|---|---|---|---|---|
| Kabat Position | 20 | 21 | 42 | 46 | 85 | Kabat Position | 84 | 89 | 93 |
| BRCA84D | S | V | Q | A | E | BRCA84D | S | M | G |
| hBRCA84D-1VL | T | I | K | L | T | hBRCA84D-1VH | D | V | A |
| hBRCA84D-2VL | T | I | K | A | T | hBRCA84D-2VH | D | V | G |
| hBRCA84D-3VL | S | V | K | L | T | hBRCA84D-3VH | D | M | G |
| hBRCA84D-4VL | T | I | Q | L | T | hBRCA84D-4VH | S | V | A |
| hBRCA84D-5VL | T | I | Q | A | T | | | | |
| hBRCA84D-6VL | T | I | K | L | E | | | | |

The relative binding affinities of the hBRCA84D light chain derivatives hBRCA84D-3VL, hBRCA84D-4VL and hBRCA84D-5VL for human B7-H3 were determined by forming antibodies containing these light chain variable regions and a chimeric BRCA84D-1VH heavy chain. BRCA84D-5VL (K42Q, L46A) was found to have the highest binding affinity of the hBRCA84D-VL tested. BRCA84D-5VL was therefore used as the light chain to investigate the relative binding affinities of the hBRCA84D heavy chains of hBRCA84D-1VH, hBRCA84D-2VH, hBRCA84D-3VH and hBRCA84D-4VH for human B7-H3. hBRCA84D-2VH (A93G) was found to have the highest binding affinity of the hBRCA84D-VH tested.

The amino acid and encoding polynucleotide sequences of the chimeric BRCA84D-1 are as follows:

Amino Acid Sequence of chBRCA84D Light Chain (SEQ ID NO:85):

```
DIAMTQSQKF MSTSVGDRVS VTCKASQNVD TNVAWYQQKP

GQSPKALIYS ASYRYSGVPD RFTGSGSGTD FTLTINNVQS

EDLAEYFCQQ YNNYPFTFGS GTKLEIKRTV AAPSVFIFPP

SDEQLKSGTA SVVCLLNNFY PREAKVQWKV DNALQSGNSQ

ESVTEQDSKD STYSLSSTLT LSKADYEKHK VYACEVTHQG

LSSPVTKSFN RGEC
```

Polynucleotide Encoding chBRCA84D Light Chain (SEQ ID NO:86):

```
gacattgcga tgacccagtc tcaaaaattc atgtccacat cagtaggaga cagggtcagc gtcacctgca aggccagtca gaatgtggat actaatgtag cctggtatca acagaaacca gggcaatctc ctaaagcact gatttactcg gcatcctacc ggtacagtgg agtccctgat cgcttcacag gcagtggatc tgggacagat ttcactctca ccatcaacaa tgtgcagtct gaagacttgg cagagtattt ctgtcagcaa tataacaact atccattcac gttcggctcg gggacaaagt tggaaataaa acgtacggtg gctgcaccat ctgtcttcat cttcccgcca tctgatgagc agttgaaatc tggaactgcc tctgttgtgt gcctgctgaa taacttctat cccagagagg ccaaagtaca gtggaaggtg gataacgccc tccaatcggg taactcccag gagagtgtca cagagcagga cagcaaggac agcacctaca gcctcagcag caccctgacg ctgagcaaag cagactacga gaaacacaaa gtctacgcct gcgaagtcac ccatcagggc ctgagctcgc ccgtcacaaa gagcttcaac aggggagagt gttag
```

Amino Acid Sequence of chBRCA84D Heavy Chain (SEQ ID NO:87):

```
DVQLVESGGG LVQPGGSRKL SCAASGFTFS SFGMHWVRQA

PEKGLEWVAY ISSDSSAIYY ADTVKGRFTI SRDNPKNTLF

LQMTSLRSED TAMYYCGRGR ENIYYGSRLD YWGQGTTLTV

SSASTKGPSV FPLAPSSKST SGGTAALGCL VKDYFPEPVT

VSWNSGALTS GVHTFPAVLQ SSGLYSLSSV VTVPSSSLGT

QTYICNVNHK PSNTKVDKRV EPKSCDKTHT CPPCPAPELL

GGPSVFLFPP KPKDTLMISR TPEVTCVVVD VSHEDPEVKF

NWYVDGVEVH NAKTKPREEQ YNSTYRVVSV LTVLHQDWLN

GKEYKCKVSN KALPAPIEKT ISKAKGQPRE PQVYTLPPSR

DELTKNQVSL TCLVKGFYPS DIAVEWESNG QPENNYKTTP

PVLDSDGSFF LYSKLTVDKS RWQQGNVFSC SVMHEALHNH

YTQKSLSLSP GK
```

Polynucleotide Encoding chBRCA84D Heavy Chain (SEQ ID NO:88):

```
gatgtgcagc tggtggagtc tgggggaggc ttagtgcagc ctggagggtc ccggaaactc tcctgtgcag cctctggatt cactttcagt agctttggaa tgcactgggt tcgtcaggct ccagagaagg ggctggagtg ggtcgcatac attagtagtg acagtagtgc catctactat gcagacacag tgaagggccg attcaccatc tccagagaca tccccaagaa cacctgttc ctgcaaatga ccagtctaag gtctgaggac acggccatgt attactgtgg aagagggagg gaaaacattt actacggtag taggcttgac tactggggcc aaggcaccac tctcacagtc tcctcagcct ccaccaaggg cccatcggtc ttccccctgg caccctcctc caagagcacc tctgggggca gcggccct
```

```
gggctgcctg gtcaaggact acttccccga accggtgacg gtgtcgtgga actcaggcgc cctgaccagc ggcgtgcaca ccttcccggc tgtcctacag tcctcaggac tctactccct cagcagcgtg gtgaccgtgc cctccagcag cttgggcacc cagacctaca tctgcaacgt gaatcacaag cccagcaaca ccaaggtgga caagagagtt gagcccaaat cttgtgacaa aactcacaca tgcccaccgt gcccagcacc tgaactcctg gggggaccgt cagtcttcct cttcccccca aaacccaagg acaccctcat gatctcccgg acccctgagg tcacatgcgt ggtggtggac gtgagccacg aagaccctga ggtcaagttc aactggtacg tggacggcgt ggaggtgcat aatgccaaga caaagccgcg ggaggagcag tacaacagca cgtaccgtgt ggtcagcgtc ctcaccgtcc tgcaccagga ctggctgaat ggcaaggagt acaagtgcaa ggtctccaac aaagccctcc cagcccccat cgagaaaacc atctccaaag ccaaagggca gccccgagaa ccacaggtgt acaccctgcc cccatcccgg gatgagctga ccaagaacca ggtcagcctg acctgcctgg tcaaaggctt ctatcccagc gacatcgccg tggagtggga gagcaatggg cagccggaga caactacaa gaccacgcct cccgtgctgg actccgacgg ctccttcttc ctctacagca agctcaccgt ggacaagagc aggtggcagc aggggaacgt cttctcatgc tccgtgatgc atgaggctct gcacaaccac tacacgcaga agagcctctc cctgtctccg ggtaaatga
```

IV. VEGF AND VEGFR AND ANTI-VEGF AND ANTI-VEGFR ANTIBODIES

A. VEGF and VEGFR

As used herein, the term "VEGF" refers to vascular endothelial growth factor A (Leung, D. W. et al. (1989) "*Vascular Endothelial Growth Factor Is A Secreted Angiogenic Mitogen,*" Science 246(4935):1306-1309). VEGF exists in multiple isoforms, reflecting alternative promoter usage, alternative splicing and alternative initiation. The initially discovered form is now designated isoform 162 (SEQ ID NO:89):

```
MNFLLSWVHW SLALLLYLHH AKWSQAAPMA EGGGQNHHEV

VKFMDVYQRS YCHPIETLVD IFQEYPDEIE YIFKPSCVPL

MRCGGCCNDE GLECVPTEES NITMQIMRIK PHQGQHIGEM

SFLQHNKCEC RPKKDRARQE NPCGPCSERR KHLFVQDPQT

CKCSCKNTDS RCKARQLELN ERTCRCDKPR R
``` and is encoded by a cDNA sequence (SEQ ID NO:90):

```
cagtgtgctg gcggcccggc gcgagccggc ccggcccggg tcgggcctcc gaaaccatga actttctgct gtcttgggtg cattggagcc tcgccttgct gctctacctc caccatgcca agtggtccca ggctgcaccc atggcagaag gaggagggca gaatcatcac gaagtggtga agttcatgga tgtctatcag cgcagctact gccatccaat cgagaccctg gtggacatct tccaggagta ccctgatgag atcgagtaca tcttcaagcc atcctgtgtg ccctgatgc gatgcggggg ctgctgcaat gacgagggcc tggagtgtgt gcccactgag gagtccaaca tcaccatgca gattatgcgg atcaaacctc accaaggcca gcacatagga gagatgagct tcctacagca caacaaatgt gaatgcagac aaagaaaga tagagcaaga caagaaaatc cctgtgggcc ttgctcagag cggagaaagc atttgtttgt acaagatccg cagacgtgta aatgttcctg caaaaacaca gactcgcgtt gcaaggcgag gcagcttgag ttaaacgaac gtacttgcag atgtgacaag ccgaggcggt gagccgggca ggaggaagga gcctccctca gggtttcggg aaccagatct ctcaccagga aagactgata cagaacgatc gatacagaaa ccacgctgcc gccaccacac catcaccatc gacagaacag tccttaatcc agaaacctga aatgaaggaa gaggagactc tgcgcagagc actttgggtc cggagggcga gactccggcg gaagcattcc cgggcgggtg acccagcacg gtccctcttg gaattggatt cgccatttta ttttcttgc tgctaaatca ccgagcccgg aagattagag agttttattt ctgggattcc tgtagacaca ccgcggccgc cagcacactg
```

The VEGF 206 isoform (Houck, K. A. et al. (1991) "*The Vascular Endothelial Growth Factor Family: Identification Of A Fourth Molecular* Species *And Characterization Of Alternative Splicing Of RNA,*" Mol. Endocrinol. 5(12):1806-1814) has been selected as the canonical sequence (SEQ ID NO:91):

```
MNFLLSWVHW SLALLLYLHH AKWSQAAPMA EGGGQNHHEV

VKFMDVYQRS YCHPIETLVD IFQEYPDEIE YIFKPSCVPL

MRCGGCCNDE GLECVPTEES NITMQIMRIK PHQGQHIGEM

SFLQHNKCEC RPKKDRARQE KKSVRGKGKG QKRKRKKSRY

KSWSVYVGAR CCLMPWSLPG PHPCGPCSER RKHLFVQDPQ

TCKCSCKNTD SRCKARQLEL NERTCRCDKP RR
```

As indicated above, three VEGF receptors have been described: VEGFR-1 (Flt-1), VEGFR-2 (Flk-1/KDR) and VEGFR-3 (Flt-4). Only VEGFR-1 and VEGFR-2 are capable of binding to VEGF-A (Shibuya, M. (2013) "*Vascular Endothelial Growth Factor And Its Receptor System: Physiological Functions In Angiogenesis And Pathological Roles In Various Diseases,*" J. Biochem. 153(1):13-19; Koch, S. et al. (2011) "*Signal Transduction By Vascular Endothelial Growth Factor Receptors,*" Biochem. J. 437: 169-183).

The amino acid sequence of VEGFR-1 is (SEQ ID NO:92):

```
MVSYWDTGVL LCALLSCLLL TGSSSGSKLK DPELSLKGTQ
HIMQAGQTLH LQCRGEAAHK WSLPEMVSKE SERLSITKSA
CGRNGKQFCS TLTLNTAQAN HTGFYSCKYL AVPTSKKKET
ESAIYIFISD TGRPFVEMYS EIPEIIHMTE GRELVIPCRV
TSPNITVTLK KFPLDTLIPD GKRIIWDSRK GFIISNATYK
EIGLLTCEAT VNGHLYKTNY LTHRQTNTII DVQISTPRPV
KLLRGHTLVL NCTATTPLNT RVQMTWSYPD EKNKRASVRR
RIDQSNSHAN IFYSVLTIDK MQNKDKGLYT CRVRSGPSFK
SVNTSVHIYD KAFITVKHRK QQVLETVAGK RSYRLSMKVK
AFPSPEVVWL KDGLPATEKS ARYLTRGYSL IIKDVTEEDA
GNYTILLSIK QSNVFKNLTA TLIVNVKPQI YEKAVSSFPD
PALYPLGSRQ ILTCTAYGIP QPTIKWFWHP CNHNHSEARC
DFCSNNEESF ILDADSNMGN RIESITQRMA IIEGKNKMAS
TLVVADSRIS GIYICIASNK VGTVGRNISF YITDVPNGFH
VNLEKMPTEG EDLKLSCTVN KFLYRDVTWI LLRTVNNRTM
HYSISKQKMA ITKEHSITLN LTIMNVSLQD SGTYACRARN
VYTGEEILQK KEITIRDQEA PYLLRNLSDH TVAISSSTTL
DCHANGVPEP QITWFKNNHK IQQEPGIILG PGSSTLFIER
VTEEDEGVYH CKATNQKGSV ESSAYLTVQG TSDKSNLELI
TLTCTCVAAT LFWLLLTLFI RKMKRSSSEI KTDYLSIIMD
PDEVPLDEQC ERLPYDASKW EFARERLKLG KSLGRGAFGK
VVQASAFGIK KSPTCRTVAV KMLKEGATAS EYKALMTELK
ILTHIGHHLN VVNLLGACTK QGGPLMVIVE YCKYGNLSNY
LKSKRDLFFL NKDAALHMEP KKEKMEPGLE QGKKPRLDSV
TSSESFASSG FQEDKSLSDV EEEEDSDGFY KEPITMEDLI
SYSFQVARGM EFLSSRKCIH RDLAARNILL SENNVVKICD
FGLARDIYKN PDYVRKGDTR LPLKWMAPES IFDKIYSTKS
DVWSYGVLLW EIFSLGGSPY PGVQMDEDFC SRLREGMRMR
APEYSTPEIY QIMLDCWHRD PKERPRFAEL VEKLGDLLQA
NVQQDGKDYI PINAILTGNS GFTYSTPAFS EDFFKESISA
PKFNSGSSDD VRYVNAFKFM SLERIKTFEE LLPNATSMFD
DYQGDSSTLL ASPMLKRFTW TDSKPKASLK IDLRVTSKSK
ESGLSDVSRP SFCHSSCGHV SEGKRRFTYD HAELERKIAC
CSPPPDYNSV VLYSTPPI
```

The amino acid sequence of VEGFR-2 is (SEQ ID NO:93):

```
MQSKVLLAVA LWLCVETRAA SVGLPSVSLD LPRLSIQKDI
LTIKANTTLQ ITCRGQRDLD WLWPNNQSGS EQRVEVTECS
DGLFCKTLTI PKVIGNDTGA YKCFYRETDL ASVIYVYVQD
YRSPFIASVS DQHGVVYITE NKNKTVVIPC LGSISNLNVS
LCARYPEKRF VPDGNRISWD SKKGFTIPSY MISYAGMVFC
EAKINDESYQ SIMYIVVVVG YRIYDVVLSP SHGIELSVGE
KLVLNCTART ELNVGIDFNW EYPSSKHQHK KLVNRDLKTQ
SGSEMKKFLS TLTIDGVTRS DQGLYTCAAS SGLMTKKNST
FVRVHEKPFV AFGSGMESLV EATVGERVRI PAKYLGYPPP
EIKWYKNGIP LESNHTIKAG HVLTIMEVSE RDTGNYTVIL
TNPISKEKQS HVVSLVVYVP PQIGEKSLIS PVDSYQYGTT
QTLTCTVYAI PPPHHIHWYW QLEEECANEP SQAVSVTNPY
PCEEWRSVED FQGGNKIEVN KNQFALIEGK NKTVSTLVIQ
AANVSALYKC EAVNKVGRGE RVISFHVTRG PEITLQPDMQ
PTEQESVSLW CTADRSTFEN LTWYKLGPQP LPIHVGELPT
PVCKNLDTLW KLNATMFSNS TNDILIMELK NASLQDQGDY
VCLAQDRKTK KRHCVVRQLT VLERVAPTIT GNLENQTTSI
GESIEVSCTA SGNPPPQIMW FKDNETLVED SGIVLKDGNR
NLTIRRVRKE DEGLYTCQAC SVLGCAKVEA FFIIEGAQEK
TNLEIIILVG TAVIAMFFWL LLVIILRTVK RANGGELKTG
YLSIVMDPDE LPLDEHCERL PYDASKWEFP RDRLKLGKPL
GRGAFGQVIE ADAFGIDKTA TCRTVAVKML KEGATHSEHR
ALMSELKILI HIGHHLNVVN LLGACTKPGG PLMVIVEFCK
FGNLSTYLRS KRNEFVPYKT KGARFRQGKD YVGAIPVDLK
RRLDSITSSQ SSASSGFVEE KSLSDVEEEE APEDLYKDFL
TLEHLICYSF QVAKGMEFLA SRKCIHRDLA ARNILLSEKN
VVKICDFGLA RDIYKDPDYV RKGDARLPLK WMAPETIFDR
VYTIQSDVWS FGVLLWEIFS LGASPYPGVK IDEEFCRRLK
EGTRMRAPDY TTPEMYQTML DCWHGEPSQR PTFSELVEHL
GNLLQANAQQ DGKDYIVLPI SETLSMEEDS GLSLPTSPVS
CMEEEEVCDP KFHYDNTAGI SQYLQNSKRK SRPVSVKTFE
DIPLEEPEVK VIPDDNQTDS GMVLASEELK TLEDRTKLSP
SFGGMVPSKS RESVASEGSN QTSGYQSGYH SDDTDTTVYS
SEEAELLKLI EIGVQTGSTA QILQPDSGTT LSSPPV
```

B. Anti-VEGF and Anti-VEGFR Antibodies

As indicated above, anti-VEGF antibodies have been considered in the treatment of glioblastomas. VEGR and its treceptor have additionally been considered with regard to numerous other types of vascularizing cancers, such as breast cancer, glioblastoma, uterine cervical carcinoma, metastatic colorectal cancer, gastric cancer, hepatocellular carcinoma, leukemia, lung cancer, metastatic melanoma, vascularizing pancreatic cancer, and metastatic prostate cancer (Roberts, E. et al. (2013) "*The Role of Vascular Endothelial Growth Factor in Metastatic Prostate Cancer to the Skeleton,*" Prostate Cancer 2013:418340; Vici, P. et al. (2014) "*Emerging Biological Treatments for Uterine Cervical Carcinoma,*" J. Cancer 5(2):86-97; Dietvorst, M. H. et al. (2013) "*Current and Novel Treatment Options for Metastatic Colorectal Cancer: Emphasis on Aflibercept,*" Biol. Ther. 3:25-33; Moeini, A. et al. (2012) "*Emerging Signaling Pathways in Hepatocellular Carcinoma,*" Liver Cancer 1(2):83-93; Cesca, M. et al. (2013) "*Tumor Delivery of Chemotherapy Combined with Inhibitors of Angiogenesis and Vascular Targeting Agents*," Front Oncol. 3:259:1-7; Pavlidis, E. T. et al. (2013) "*Role Of Bevacizumab In Colorectal Cancer Growth And Its Adverse Effects: A Review*," World J. Gastroenterol. 19(31):5051-5060; Welti, J. et al. (2013) "*Recent Molecular Discoveries In Angiogenesis And Antiangiogenic Therapies In Cancer*," J. Clin. Invest. 123(8):3190-3200; Eveno, C. et al. (2012) "*VEGF Levels And The Angiogenic Potential Of The Microenvironment Can Affect Surgical Strategy For Colorectal Liver Metastasis*," Cell. Adh. Migr. 6(6):569-573; Miyake, T. M. et al. (2013) "*Contemporary Use Of Bevacizumab In Ovarian Cancer*," Expert Opin. Biol. Ther. 13(2):283-294; Plate, K. H. et al. (2012) "*Tumor Angiogenesis And Anti-Angiogenic Therapy In Malignant Gliomas Revisited*," Acta Neuropathol. 124(6):763-775; Liu, L. et al. (2012) "*Prognostic Value Of Vascular Endothelial Growth Factor Expression In Resected Gastric Cancer*," Asian Pac. J. Cancer Prev. 13(7): 3089-3097; Kim, K. B. (2013) "*Is There A Role For Targeting Vascular Endothelial Growth Factor/Receptor Axis In The Treatment Of Patients With Metastatic Melanoma?*," Cancer 119(3):477-480; Kubota, Y. (2012) "*Tumor Angiogenesis And Anti-Angiogenic Therapy*," Keio J. Med. 61(2): 47-56; Wicki, A. et al. (2012) "*Targeted Therapies In Breast Cancer*," Swiss Med. Wkly. 142:w13550:1-7; Parente Lamelas, I. et al. (2012) "*Directed Therapies In Lung Cancer: New Hope?*," Arch. Bronconeumol. 48(10):367-371; Saintigny, P. et al. (2012) "*Recent Advances In Non-Small Cell Lung Cancer Biology And Clinical Management*," Discov. Med. 13(71):287-297; Stevenson, C. E. et al. (2012) "*Bevacizumab And Breast Cancer: What Does The Future Hold?*," Future Oncol. 8(4):403-414; Aggarwal, C. et al. (2012) "*Antiangiogenic Agents In The Management Of Non-Small Cell Lung Cancer: Where Do We Stand Now And Where Are We Headed?*," Cancer Biol. Ther. 13(5):247-263).

Particularly preferred is the humanized anti-VEGF antibody (bevacizumab) sold as AVASTIN®, an anti-angiogenic preparation (Genentech US, Inc.). Bevacizumab (AVASTIN®) is described in United States Patent Publications No. 2002/0032315, 2003/0190317, 2005/0112126, 2007/0059302, 2007/0059312, 2007/0196374, 2007/0248610, 2008/0187531, 2008/0226629, 2011/0052575, 2011/0081342, 2013/0058927; U.S. Pat. Nos. 6,884,879; 7,060,269; 7,169,901; 7,297,334; 7,365,166; 7,375,193; CA Patents No. 2,286,330 and 2,145,985; and PCT Publication No. WO 1998/045331; Baca, M. et al. (1997) "*Antibody Humanization Using Monovalent Phage Display*," J. Biol. Chem. 272(16):10678-10684; Presta, L. G. et al. (1997) "*Humanization Of An Anti-Vascular Endothelial Growth Factor Monoclonal Antibody For The Therapy Of Solid Tumors And Other Disorders*," Cancer Res. 57(20):4593-4599; each of which documents is herein incorporated by reference in its entirety.

The amino acid sequence of the light chain of bevacizumab is (SEQ ID NO:94):

```
DIQMTQSPSS LSASVGDRVT ITCSASQDIS NYLNWYQQKP

GKAPKVLIYF TSSLHSGVPS RFSGSGSGTD FTLTISSLQP

EDFATYYCQQ YSTVPWTFGQ GTKVEIKRTV AAPSVFIFPP

SDEQLKSGTA SVVCLLNNFY PREAKVQWKV DNALQSGNSQ

ESVTEEDSKD STYSLSSTLT LSKADYEKHK VYACEVTHQG

LSSPVTKSFN RGEC
```

The amino acid sequence of the heavy chain of bevacizumab is (SEQ ID NO:95):

```
EVQLVESGGG LVQPGGSLRL SCAASGYTFT NYGMNWVRQA

PGKGLEWVGW INTYTGEPTY AADFKRRFTF SLDTSKSTAY

LQMNSLRAED TAVYYCAKYP HYYGSSHWYF DVWGQGTLVT

VSSASTKGPS VFPLAPSSKS TSGGTAALGC LVKDYFPEPV

TVSWNSGALT SGVHTFPAVL QSSGLYSLSS VVTVPSSSLG

TQTYICNVNH KPSNTKVDKK VEPKSCDKTH TCPPCPAPEL

LGGPSVFLFP PKPKDTLMIS RTPEVTCVVV DVSHEDPEVK

FNWYVDGVEV HNAKTKPREE QYNSTYRVVS VLTVLHQDWL

NGKEYKCKVS NKALPAPIEK TISKAKGQPR EPQVYTLPPS

REEMTKNQVS LTCLVKGFYP SDIAVEWESN GQPENNYKTT

PPVLDSDGSF FLYSKLTVDK SRWQQGNVFS CSVMHEALHN

HYTQKSLSLS PGK
```

A particularly preferred anti-VEGFR antibody is ramucirumab (a humanized antihuman VEGFR-2 neutralizing monoclonal antibody) (Yang, Y. et al. (2013) "*Anti-VEGF- And Anti-VEGF Receptor-Induced Vascular Alteration In Mouse Healthy Tissues*," Proc. Natl. Acad. Sci. (U.S.A.) 110(29):12018-12023; Anonymous (2013) "*Ramucirumab Takes Steps Forward In Gastric Cancer*," Cancer Discov. 3(12):OF4; Aprile, G. et al. (2013) "*Critical Appraisal Of Ramucirumab (IMC-1121B) For Cancer Treatment: From Benchside To Clinical Use*," Drugs 73(18):2003-2015; *Ramucirumab Monotherapy For Previously Treated Advanced Gastric Or Gastro-Oesophageal Junction Adenocarcinoma (REGARD): An International, Randomised, Multicentre, Placebo-Controlled, Phase 3 Trial*; Fuchs, C. S. et al. (2014) "*Ramucirumab Monotherapy For Previously Treated Advanced Gastric Or Gastro-Oesophageal Junction Adenocarcinoma (REGARD): An International, Randomised, Multicentre, Placebo-Controlled, Phase 3 Trial*," Lancet 383(9911):31-39; Clarke, J. M. et al. (2013) "*Targeted Inhibition Of VEGF Receptor 2: An Update On Ramucirumab*," Expert Opin. Biol. Ther. 13(8):1187-1196; Wadhwa, R. et al. (2013) "*Ramucirumab: a novel antiangiogenic agent*," Future Oncol. 9(6):789-795).

Other anti-VEGFR antibodies include the rat anti-mouse VEGFR-1 neutralizing monoclonal antibody (MF-1) and the rat anti-mouse VEGFR-2 neutralizing monoclonal antibody (DC101) (Xue, Y. et al. (2008) "*Anti-VEGF Agents Confer Survival Advantages To Tumor-Bearing Mice By Improving Cancer-Associated Systemic Syndrome*," Proc. Natl. Acad. Sci. (U.S.A.) 105(47):18513-18518; Zhang, D. et al. (2011) "*Anti-Angiogenic Agents Significantly Improve Survival In Tumor-Bearing Mice By Increasing Tolerance To Chemotherapy-Induced Toxicity*," Proc. Natl. Acad. Sci. (U.S.A.) 108(10):4117-4122; Cao, R. et al. (2010) "*VEGFR1-Mediated Pericyte Ablation Links VEGF And Plgf To Cancer-Associated Retinopathy*," Proc. Natl. Acad. Sci. (U.S.A.) 107(2):856-861).

Alternatively, the invention contemplates the use of a VEGFR antagonist (for example, Aflibercept (VEGF-Trap), a soluble fusion protein of the extracelluar domain of VEGFR-1 and VEGFR-2 (Dietvorst, M. H. et al. (2013) "*Current and Novel Treatment Options for Metastatic Colorectal Cancer: Emphasis on Aflibercept*," Biol. Ther. 3:25-33; Moradi, A. et al. (2013) "*Vascular Endothelial Growth Factor Trap-Eye (Aflibercept) For The Management Of Diabetic Macular Edema*," World J. Diabetes. 4(6):303-309; Ventrice, P. et al. (2013) "Anti-vascular endothelial growth factor drugs safety and efficacy in ophthalmic diseases," J. Pharmacol. Pharmacother. 4(Suppl1):538-542; Sophie, R. et al. (2012) "*Aflibercept: a Potent Vascular Endothelial Growth Factor Antagonist for Neovascular Age-Related Macular Degeneration and Other Retinal Vascular Diseases*," Biol. Ther. 2:3:1-22) or the pan-VEGFR tyrosine kinase inhibitor, cediranib (AstraZeneca) (Dietrich, J. et al. (2009) "*Cediranib: Profile Of A Novel Anti-Angiogenic Agent In Patients With Glioblastoma*," Expert Opin. Investig. Drugs. 18(10):1549-1557).

V. FC-ENGINEERED ANTIBODIES

In traditional immune function, the interaction of antibody-antigen complexes with cells of the immune system results in a wide array of responses, ranging from effector functions such as antibody-dependent cytotoxicity, mast cell degranulation, and phagocytosis to immunomodulatory signals such as regulating lymphocyte proliferation and antibody secretion. All of these interactions are initiated through the binding of the Fc domain of antibodies or immune complexes to specialized cell surface receptors on hematopoietic cells. The diversity of cellular responses triggered by antibodies and immune complexes results from the structural heterogeneity of the three Fc receptors: FcγRI (CD64), FcγRII (CD32), and FcγRIII (CD16). FcγRI (CD64), FcγRIIA (CD32A) and FcγRIII (CD16) are activating (i.e., immune system enhancing) receptors; FcγRIIB (CD32B) is an inhibiting (i.e., immune system dampening) receptor. The amino acid sequence of the IgG1 Fc region is shown below (as SEQ ID NO:96, numbered according to Kabat et al., SEQUENCE OF PROTEINS OF IMMUNOLOGICAL INTEREST, 5$^{th}$ Ed. Public Health Service, NIH, MD (1991), expressly incorporated herein by reference, and hereafter referred to as "Kabat EU") (SEQ ID NO:96):

```
PAPELLGGPS  VFLFPPKPKD  TLMISRTPEV  TCVVVDVSHE
230         240         250         260

DPEVKFNWYV  DGVEVHNAKT  KPREEQYNST  YRVVSVLTVL
270         280         290         300

HQDWLNGKEY  KCKVSNKALP  APIEKTISKA  KGQPREPQVY
310         320         330         340

TLPPSREEMT  KNQVSLTCLV  KGFYPSDIAV  EWESNGQPEN
350         360         370         380

NYKTTPPVLD  SDGSFFLYSK  LTVDKSRWQQ  GNVFSCSVMH
390         400         410         420

EALHNHYTQK  SLSLSPGK
430         440
```

Residues 230-341 are the Fc CH2 region. Residues 342-447 are the Fc CH3 region.

The present invention includes anti-B7-H3 antibodies and/or anti-tumor angiogenesis antibodies (such as an anti-VEGF or anti-VEGFR antibody) that comprise a variant Fc region having one or more amino acid modifications (e.g., substitutions, deletions, insertions) in one or more portions, which modifications increase the affinity and avidity of the variant Fc region for an FcγR (including activating and inhibitory FcγRs). In some embodiments, said one or more amino acid modifications increase the affinity of the variant Fc region for FcγRIIIA and/or FcγRIIA. In another embodiment, the variant Fc region further specifically binds FcγRIIB with a lower affinity than does the Fc region of the comparable parent antibody (i.e., an antibody having the same amino acid sequence as the antibody of the invention except for the one or more amino acid modifications in the Fc region). In some embodiments, such modifications increase the affinity of the variant Fc region for FcγRIIIA and/or FcγRIIA and also enhance the affinity of the variant Fc region for FcγRIIB relative to the parent antibody. In other embodiments, said one or more amino acid modifications increase the affinity of the variant Fc region for FcγRIIIA and/or FcγRIIA but do not alter the affinity of the variant Fc regions for FcγRIIB relative to the Fc region of the parent antibody. In another embodiment, said one or more amino acid modifications enhance the affinity of the variant Fc region for FcγRIIIA and FcγRIIA but reduce the affinity for FcγRIIB relative to the parent antibody. Increased affinity and/or avidity results in detectable binding to the FcγR or FcγR-related activity in cells that express low levels of the FcγR when binding activity of the parent molecule (without the modified Fc region) cannot be detected in the cells. In other embodiments, the modified molecule exhibits detectable binding in cells which express non-FcγR receptor target antigens at a density of 30,000 to 20,000 molecules/cell, at a density of 20,000 to 10,000 molecules/cell, at a density of 10,000 to 5,000 molecules/cell, at a density of 5,000 to 1,000 molecules/cell, at a density of 1,000 to 200 molecules/cell or at a density of 200 molecules/cell or less (but at least 10, 50, 100 or 150 molecules/cell).

In another embodiment, said one or more modifications to the amino acids of the Fc region reduce the affinity and avidity of the antibody for one or more FcγR receptors. In a specific embodiment, the invention encompasses antibodies comprising a variant Fc region, wherein said variant Fc region comprises at least one amino acid modification relative to a wild type Fc region, which variant Fc region only binds one FcγR, wherein said FcγR is FcγRIIIA. In another specific embodiment, the invention encompasses antibodies comprising a variant Fc region, wherein said variant Fc region comprises at least one amino acid modification relative to a wild type Fc region, which variant Fc region only binds one FcγR, wherein said FcγR is FcγRIIA.

Preferably, the binding properties of the above-described anti-B7-H3 antibodies and/or anti-tumor angiogenesis antibodies of the invention are characterized by in vitro functional assays for determining one or more FcγR mediator effector cell functions. The affinities and binding properties of the molecules, e.g., antibodies, of the invention for an FcγR can be determined using in vitro assays (biochemical or immunological based assays) known in the art for determining antibody-antigen or Fc-FcγR interactions, i.e., specific binding of an antigen to an antibody or specific binding of an Fc region to an FcγR, respectively, including but not limited to ELISA assay, surface plasmon resonance assay, immunoprecipitation assays. In most preferred embodiments, the molecules of the invention have similar binding properties in in vivo models (such as those described and disclosed herein) as those in in vitro based assays. However, the present invention does not exclude molecules of the invention that do not exhibit the desired phenotype in in vitro based assays but do exhibit the desired phenotype in vivo.

In some embodiments, the above-described includes anti-B7-H3 antibodies and/or anti-tumor angiogenesis antibodies of the invention comprising a variant Fc region comprise at least one amino acid modification (for example, possessing 1, 2, 3, 4, 5, 6, 7, 8, 9, or more amino acid modifications) in the CH3 domain of the Fc region, which is defined as extending from amino acids 342-447. In other embodiments, the molecules of the invention comprising a variant Fc region comprise at least one amino acid modification (for example, possessing 1, 2, 3, 4, 5, 6, 7, 8, 9, or more amino acid modifications) in the CH2 domain of the Fc region, which is defined as extending from amino acids 231-341. In some embodiments, the molecules of the invention comprise at least two amino acid modifications (for example, possessing 2, 3, 4, 5, 6, 7, 8, 9, or more amino acid modifications), wherein at least one such modification is in the CH3 region and at least one such modification is in the CH2 region. The invention further encompasses amino acid modification in the hinge region. In a particular embodiment, the invention encompasses amino acid modification in the CH1 domain of the Fc region, which is defined as extending from amino acids 216-230.

In particularly preferred embodiments, the invention encompasses anti-B7-H3 antibodies and/or anti-tumor angiogenesis antibodies that comprise a variant Fc region wherein said variant confers or has an increased ADCC activity and/or an increased binding to FcγRIIA (CD32A), as measured using methods known to one skilled in the art and exemplified herein. The ADCC assays used in accordance with the methods of the invention may be NK dependent or macrophage dependent.

In particularly preferred embodiments, the invention encompasses anti-B7-H3 antibodies and/or anti-tumor angiogenesis antibodies comprising a variant Fc region wherein said variant confers or has an increased ADCC activity and/or an increased binding to FcγRIIIA (CD16A), as measured using methods known to one skilled in the art and exemplified herein. The ADCC assays used in accordance with the methods of the invention may be NK dependent or macrophage dependent.

The Fc variants of the present invention may be combined with other Fc modifications, such as those disclosed in U.S. Pat. Nos. 7,632,497; 7,521,542; 7,425,619; 7,416,727; 7,371,826; 7,355,008; 7,335,742; 7,332,581; 7,183,387; 7,122,637; and 6,737,056; in PCT Publications Nos. WO 2008/105886; WO 2008/002933; WO 2007/021841; WO 2007/106707; WO 06/088494; WO 05/115452; WO 05/110474; WO 04/1032269; and in WO 04/063351; and in Presta, L. G. et al. (2002) "*Engineering therapeutic antibodies for improved function*," Biochem. Soc. Trans. 30(4): 487-490; Shields, R. L. et al. (2002) "*Lack of fucose on human IgG1 N-linked oligosaccharide improves binding to human Fcgamma RIII and antibody-dependent cellular toxicity*," J. Biol. Chem. 26; 277(30):26733-26740 and Shields, R. L. et al. (2001) "*High Resolution Mapping Of The Binding Site On Human IgG1 For Fc gamma RI, Fc gamma RII, Fc gamma RIII, And FcRn And Design Of IgG1 Variants With Improved Binding To The Fc gamma R*," J. Biol. Chem. 276(9):6591-6604). The invention encompasses combining an Fc variant of the invention with other Fc modifications to provide additive, synergistic, or novel properties to the modified antibody. Preferably, the Fc variants of the invention enhance the phenotype of the modification with which they are combined. For example, if an Fc variant of the invention is combined with a mutant known to bind FcγRIIIA with a higher affinity than a comparable wild type Fc region; the combination with a mutant of the invention results in a greater fold enhancement in FcγRIIIA affinity.

The invention encompasses anti-B7-H3 antibodies and/or anti-tumor angiogenesis antibodies that comprise a variant Fc region, wherein the variant Fc region comprises at least one amino acid modification (for example, possessing 1, 2, 3, 4, 5, 6, 7, 8, 9, or more amino acid modifications) relative to a wild-type Fc region, such that the molecule has an enhanced effector function relative to a molecule comprising a wild-type Fc region, provided that the variant Fc region does not have or is not solely a substitution at any one or more of positions 243, 255, 256, 258, 267, 268, 269, 270, 272, 276, 278, 280, 283, 285, 286, 289, 290, 292, 293, 294, 295, 296, 298, 300, 301, 303, 305, 307, 309, 312, 320, 322, 326, 329, 330, 332, 331, 333, 334, 335, 337, 338, 339, 340, 359, 360, 373, 376, 416, 419, 430, 434, 435, 437, 438, 439. In a specific embodiment, the invention encompasses such antibodies comprising a variant Fc region, wherein the variant Fc region comprises at least one amino acid modification (for example, possessing 1, 2, 3, 4, 5, 6, 7, 8, 9, or more amino acid modifications) relative to a wild-type Fc region, such that the molecule binds an FcγR with an altered affinity relative to a molecule comprising a wild-type Fc region, provided that the variant Fc region does not have or is not solely a substitution at any one or more of positions 243, 255, 258, 267, 269, 270, 276, 278, 280, 283, 285, 289, 292, 293, 294, 295, 296, 300, 303, 305, 307, 309, 320, 322, 329, 332, 331, 337, 338, 340, 373, 376, 416, 419, 434, 435, 437, 438, 439 and does not have an alanine at any of positions 256, 290, 298, 312, 326, 333, 334, 359, 360, or 430; an asparagine at position 268; a glutamine at position 272; a glutamine, serine, or aspartic acid at position 286; a serine at position 290; a methionine at position 301; a methionine, glutamine, glutamic acid, or arginine at position 320; a glutamic acid at position 322; an asparagine, serine, glutamic acid, or aspartic acid at position 326; a lysine at position 330; a glutamine at position 334; a glutamic acid at position 334; a methionine at position 334; a histidine at position 334; a valine at position 334; a leucine at position 334; a glutamine at position 335; a lysine at position 335; or a threonine at position 339.

The invention also encompasses anti-B7-H3 antibodies and/or anti-tumor angiogenesis antibodies that comprise a variant Fc region, wherein the variant Fc region comprises such antibodies comprising a variant Fc region, wherein the variant Fc region does not have or is not solely a substitution at any one or more of positions 268, 269, 270, 272, 276, 278, 283, 285, 286, 289, 292, 293, 301, 303, 305, 307, 309, 320, 331, 333, 334, 335, 337, 338, 340, 360, 373, 376, 416, 419, 430, 434, 435, 437, 438 or 439 and does not have a histidine, glutamine, or tyrosine at position 280; a serine, glycine, threonine or tyrosine at position 290, an asparagine at position 294, a lysine at position 295; a proline at position 296; a proline, asparagine, aspartic acid, or valine at position 298; or a leucine or isoleucine at position 300. In another embodiment, the invention encompasses such antibodies comprising a variant Fc region, wherein the variant Fc region comprises at least one amino acid modification relative to a wild-type Fc region, such that the molecule binds an FcγR with a reduced affinity relative to molecule comprising a wild-type Fc region provided that the variant Fc region does not have or is not solely a substitution at any one or more of positions 243, 252, 254, 265, 268, 269, 270, 278, 289, 292, 293, 294, 295, 296, 298, 300, 301, 303, 322, 324, 327, 329, 333, 335, 338, 340, 373, 376, 382, 388, 389, 414, 416, 419, 434, 435, 437, 438, or 439. In yet another embodiment, the invention encompasses such antibodies comprising a variant Fc region, wherein the variant Fc region comprises at least one amino acid modification relative to a wild-type Fc region, such that the molecule binds an FcγR with an enhanced affinity relative to a molecule comprising a wild-type Fc region provided that the variant Fc region does not have or is not solely a substitution at any one or more of positions 280, 283, 285, 286, 290, 294, 295, 298, 300, 301, 305, 307, 309, 312, 315, 331, 333, 334, 337, 340, 360, 378, 398, or 430.

The invention also encompasses anti-B7-H3 antibodies and/or anti-tumor angiogenesis antibodies that comprise a variant Fc region, wherein the variant Fc region does not include or are not solely a substitution at any one or more of positions 330, 243, 247, 298, 241, 240, 244, 263, 262, 235, 269, or 328 and does not have a leucine at position 243, an asparagine at position 298, a leucine at position 241, and isoleucine or an alanine at position 240, a histidine at position 244, a valine at position 330, or an isoleucine at position 328.

The invention particularly encompasses anti-B7-H3 antibodies and/or anti-tumor angiogenesis antibodies that comprise a variant Fc region with enhanced effector function and/or altered affinities for activating and/or inhibitory receptors, wherein the variant Fc region comprises: (a) any 1, 2, 3, 4, 5, or 6 of the following substitutions: S239D, S298A, A330L, I332E, E333A, or K334A; or (b) any of the combinations of substitutions: (1) S298A, E333A, and K334A; (2) S239D and I332E; or (3) S239D, A330L and I332E.

The invention particularly encompasses such antibodies that comprise a variant Fc region with enhanced effector function and/or altered affinities for activating and/or inhibitory receptors, wherein the variant Fc region comprises a substitution:
(1) at position 288 with asparagine, at position 330 with serine and at position 396 with leucine;
(2) at position 334 with glutamic acid, at position 359 with asparagine, and at position 366 with serine;
(3) at position 316 with aspartic acid, at position 378 with valine, and at position 399 with glutamic acid;
(4) at position 247 with leucine, and a substitution at position 421 with lysine;
(5) at position 392 with threonine, and at position 396 with leucine;
(6) at position 221 with glutamic acid, at position 270 with glutamic acid, at position 308 with alanine, at position 311 with histidine, at position 396 with leucine, and at position 402 with aspartic acid;
(7) at position 419 with histidine, and a substitution at position 396 with leucine;
(8) at position 240 with alanine, and at position 396 with leucine;
(9) at position 410 with histidine, and at position 396 with leucine;
(10) at position 243 with leucine, at position 305 with isoleucine, at position 378 with aspartic acid, at position 404 with serine, and at position 396 with leucine;
(11) at position 255 with isoleucine, and at position 396 with leucine;
(12) at position 370 with glutamic acid and at position 396 with leucine;
(13) at position 270 with glutamic acid; or
(14) any combination of the foregoing (1)-(12) substitutions.

In a specific embodiment, the invention encompasses anti-B7-H3 antibodies and/or anti-tumor angiogenesis antibodies that comprise a variant Fc region which comprises the substitution: F243L, R292P, and Y300L. In a further specific embodiment, the invention encompasses anti-B7-H3 antibodies and/or anti-tumor angiogenesis antibodies that comprise a variant Fc region which comprises the substitution: L235V, F243L, R292P, Y300L, and P396L. In yet a further specific embodiment, the invention encompasses anti-B7-H3 antibodies and/or anti-tumor angiogenesis antibodies that comprise a variant Fc region which comprises the substitution F243L, R292P, Y300L, V305I, and P396L.

In a further specific embodiment, the invention encompasses anti-B7-H3 antibodies and/or anti-tumor angiogenesis antibodies that comprise a variant Fc region which comprises a substitution at position 396 with leucine, at position 270 with glutamic acid and at position 243 with leucine. In another specific embodiment the molecule further comprises one or more amino acid modification such as those disclosed herein.

The invention particularly encompasses antibodies that anti-B7-H3 antibodies and/or anti-tumor angiogenesis antibodies that comprise a variant Fc region with enhanced effector function and/or altered affinities for activating and/or inhibitory receptors, that have an amino acid modification at one or more of the following positions: 119, 125, 132, 133, 141, 142, 147, 149, 162, 166, 185, 192, 202, 205, 210, 214, 215, 216, 217, 218, 219, 221, 222, 223, 224, 225, 227, 229, 231, 232, 233, 235, 240, 241, 242, 243, 244, 246, 247, 248, 250, 251, 252, 253, 254, 255, 256, 258, 261, 262, 263, 268, 269, 270, 272, 274, 275, 276, 279, 280, 281, 282, 284, 287, 288, 289, 290, 291, 292, 293, 295, 298, 301, 303, 304, 305, 306, 307, 308, 309, 310, 311, 312, 313, 315, 316, 317, 318, 319, 320, 323, 326, 327, 328, 330, 333, 334, 335, 337, 339, 340, 343, 344, 345, 347, 348, 352, 353, 354, 355, 358, 359, 360, 361, 362, 365, 366, 367, 369, 370, 371, 372, 375, 377, 378, 379, 380, 381, 382, 383, 384, 385, 386, 387, 388, 389, 390, 392, 393, 394, 395, 396, 397, 398, 399, 400, 401, 402, 404, 406, 407, 408, 409, 410, 411, 412, 414, 415, 416, 417, 419, 420, 421, 422, 423, 424, 427, 428, 431, 433, 435, 436, 438, 440, 441, 442, 443, 446, or 447. Preferably such mutations result in molecules that have been conferred an effector cell mediated function and, optionally, have an altered affinity for an FcγR as determined using methods disclosed and exemplified herein and known to one skilled in the art.

The invention particularly encompasses anti-B7-H3 antibodies and/or anti-tumor angiogenesis antibodies that comprise a variant Fc region with altered effector function and/or altered affinities for activating and/or inhibitory receptors, that have:
(I) an amino acid modification at one or more of the following positions: 235, 240, 241, 243, 244, 247, 262, 263, 269, 298, 328, or 330 and more preferably one or more of the following modifications: V240A, V240I, F241L, F243L, P244H, S298N, L328I, A330V; wherein such antibodies exhibit altered effector function relative to antibodies having a wild-type Fc region that lacks such modification;
(II) an amino acid modification at one or more of the following positions: 268, 269, 270, 272, 276, 278, 283, 285, 286, 289, 292, 293, 301, 303, 305, 307, 309, 331, 333, 334, 335, 337, 338, 340, 360, 373, 376, 416, 419, 430, 434, 435, 437, 438 or 439 and more preferably one or more of the following modifications: D280H, D280Q, D280Y, K290G, K290S, K290T, K290Y, E294N, Q295K, Y296P, S298D, S298N, S298P, S298V, Y300I, Y300L; wherein such antibodies exhibit altered effector function relative to antibodies having a wild-type Fc region that lacks such modification;

(III) an amino acid modification at one or more of the following positions: 255, 256, 258, 267, 268, 269, 270, 272, 276, 278, 280, 283, 285, 286, 289, 290, 292, 293, 294, 295, 296, 298, 300, 301, 303, 305, 307, 309, 312, 320, 322, 326, 329, 330, 332, 331, 333, 334, 335, 337, 338, 339, 340, 359, 360, 373, 376, 416, 419, 430, 434, 435, 437, 438, 439, and more preferably one or more of the following modifications: T256A, H268N, E272Q, N286D, N286Q, N286S, K290A, K290S, S298A, R301M, D312A, K320E, K320M, K320Q, K320R, K322E, K326A, K326D, K326E, K326N, K326S, A330K, A339T, E333A, K334A, K334E, K334H, K334L, K334M, K334Q, K334V, T335K, T335Q, T359A, K360A, E430A; wherein such antibodies exhibit altered effector function relative to antibodies having a wild-type Fc region that lacks such modification;

(IV) an amino acid modification at one or more of the following positions: 252, 254, 265, 268, 269, 270, 278, 289, 292, 293, 294, 295, 296, 298, 300, 301, 303, 322, 324, 327, 329, 333, 335, 338, 340, 373, 376, 382, 388, 389, 414, 416, 419, 434, 435, 437, 438, or 439; wherein such antibodies exhibit reduced effector function relative to antibodies having a wild-type Fc region that lacks such modification;

(V) an amino acid modification at one or more of the following positions: 280, 283, 285, 286, 290, 294, 295, 298, 300, 301, 305, 307, 309, 312, 315, 331, 333, 334, 337, 340, 360, 378, 398, or 430; wherein such antibodies exhibit enhanced effector function relative to antibodies having a wild-type Fc region that lacks such modification; or (VI) an amino acid modification at one or more of the following positions: R255A, T256A, E258A, S267A, H268A, H268N, E272A, E272Q, N276A, D280A, E283A, H285A, N286A, N286D, N286Q, N286S, K290A, K290S, R301M, K320E, K320M, K320Q, K320R, K322E, K326A, K326D, K326E, K326S, A330K, P331A, T335Q, S337A, E430A; wherein such antibodies exhibit enhanced effector function relative to antibodies having a wild-type Fc region that lacks such modification.

In other embodiments, the invention encompasses the use of any Fc variant known in the art, such as those disclosed in Jefferis, B. J. et al. (2002) "*Interaction Sites On Human IgG-Fc For FcgammaR: Current Models*," Immunol. Lett. 82:57-65; Presta, L. G. et al. (2002) "*Engineering Therapeutic Antibodies For Improved Function*," Biochem. Soc. Trans. 30:487-90; Idusogie, E. E. et al. (2001) "*Engineered Antibodies With Increased Activity To Recruit Complement*," J. Immunol. 166:2571-75; Shields, R. L. et al. (2001) "*High Resolution Mapping Of The Binding Site On Human IgG1 For Fc Gamma RI, Fc Gamma RII, Fc Gamma RIII, And FcRn And Design Of IgG1 Variants With Improved Binding To The Fc gamma R*," J. Biol. Chem. 276:6591-6604; Idusogie, E. E. et al. (2000) "*Mapping Of The C1q Binding Site On Rituxan, A Chimeric Antibody With A Human IgG Fc*," J. Immunol. 164:4178-84; Reddy, M. P. et al. (2000) "*Elimination Of Fc Receptor-Dependent Effector Functions Of A Modified IgG4 Monoclonal Antibody To Human CD4*," J. Immunol. 164:1925-1933; Xu, D. et al. (2000) "*In Vitro Characterization of Five Humanized OKT3 Effector Function Variant Antibodies*," Cell. Immunol. 200:16-26; Armour, K. L. et al. (1999) "*Recombinant human IgG Molecules Lacking Fcgamma Receptor I Binding And Monocyte Triggering Activities*," Eur. J. Immunol. 29:2613-24; Jefferis, R. et al. (1996) "*Modulation Of Fc(Gamma)R And Human Complement Activation By IgG3-Core Oligosaccharide Interactions*," Immunol. Lett. 54:101-04; Lund, J. et al. (1996) "*Multiple Interactions Of IgG With Its Core Oligosaccharide Can Modulate Recognition By Complement And Human Fc Gamma Receptor I And Influence The Synthesis Of Its Oligosaccharide Chains*," J. Immunol. 157:4963-4969; Hutchins et al. (1995) "*Improved Biodistribution, Tumor Targeting, And Reduced Immunogenicity In Mice With A Gamma 4 Variant Of Campath-1H*," Proc. Natl. Acad. Sci. (U.S.A.) 92:11980-84; Jefferis, R. et al. (1995) "*Recognition Sites On Human IgG For Fc Gamma Receptors: The Role Of Glycosylation*," Immunol. Lett. 44:111-17; Lund, J. et al. (1995) "*Oligosaccharide-Protein Interactions In IgG Can Modulate Recognition By Fc Gamma Receptors*," FASEB J. 9:115-19; Alegre, M. L. et al. (1994) "*A Non-Activating "Humanized" Anti-CD3 Monoclonal Antibody Retains Immunosuppressive Properties In Vivo*," Transplantation 57:1537-1543; Lund et al. (1992) "*Multiple Binding Sites On The CH2 Domain Of IgG For Mouse Fc Gamma RII*," Mol. Immunol. 29:53-59; Lund et al. (1991) "*Human Fc Gamma RI And Fc Gamma RII Interact With Distinct But Overlapping Sites On Human IgG*," J. Immunol. 147:2657-2662; Duncan, A. R. et al. (1988) "*Localization Of The Binding Site For The Human High-Affinity Fc Receptor On IgG*," Nature 332:563-564; U.S. Pat. Nos. 5,624,821; 5,885,573; 6,194,551; 7,276,586; and 7,317,091; and PCT Publications WO 00/42072 and PCT WO 99/58572.

The invention encompasses molecules comprising variant Fc regions consisting of or comprising any of the mutations listed in the table below in Table 2.

TABLE 2

Exemplary Fc Modifications

Substitutions of a Single Site

| S132I | F241W | D265N | D280Q | Y296T | D312A | L328I | K334E |
|---|---|---|---|---|---|---|---|
| A162V | F241Y | D265Q | D280Y | N297D | W313F | L328K | K334H |
| S219Y | F241Y | D265T | G281D | N297E | N315I | L328M | K334I |
| K222N | F243D | D265V | G281K | N297I | E318K | L328N | K334L |
| H224L | F243H | D265Y | G281P | N297S | K320E | L328P | K334M |
| T225S | F243L | V266A | G281Y | S298A | K320M | L328Q | K334N |
| P228E | F243L | V266I | V282M | S298D | K320Q | L328R | K334Q |
| P228G | F243Q | V266M | E283A | S298N | K320R | L328S | K334V |
| P228K | F243R | V266T | V284E | S298N | K322E | L328T | T335K |
| P228Y | F243W | S267A | V284L | S298N | V323I | L328V | T335Q |
| P230A | F243Y | H268A | V284N | S298P | N325A | L328W | I336E |
| P230E | P244H | H268N | V284T | S298V | N325D | L328Y | I336K |
| P230G | P245A | D270E | V284Y | T299A | N325E | A330I | I336Y |
| P230Y | P247G | P271A | H285A | T299D | N325F | A330K | S337A |

TABLE 2-continued

| Exemplary Fc Modifications | | | | | | | |
|---|---|---|---|---|---|---|---|
| A231E | P247L | P271D | N286A | T299E | N325G | A330L | A339T |
| A231G | P247V | P271E | N286D | T299F | N325H | A330S | M352L |
| A231K | K248M | P271F | N286S | T299G | N325I | A330V | T359A |
| A231P | R255A | P271G | K288N | T299H | N325K | A330Y | T359N |
| A231Y | T256A | P271H | K290A | T299I | N325L | P331A | K360A |
| P232E | E258A | P271I | K290G | T299K | N325M | I332A | T366N |
| P232G | V262A | P271K | K290S | T299L | N325P | I332D | T366S |
| P232K | V262E | P271L | K290T | T299M | N325R | I332E | F372Y |
| P232Y | V262F | P271M | K290Y | T299N | N325S | I332F | F372Y |
| E233D | V262I | P271N | P291D | T299P | N325T | I332G | I377F |
| E233G | V262T | P271Q | P291E | T299Q | N325V | I332H | I377N |
| L234I | V263A | P271R | P291G | T299R | N325W | I332K | V379L |
| L235D | V263I | P271S | P291H | T299S | N325Y | I332L | V379M |
| S239D | V263M | P271T | P291I | T299V | K326A | I332M | K392R |
| S239E | V263T | P271V | P291Q | T299W | K326D | I332N | P396H |
| S239N | V264A | P271W | P291T | T299Y | K326E | I332P | P396L |
| S239Q | V264E | P271Y | R292G | Y300I | K326E | I332Q | L398V |
| V240A | V264F | E272A | R292L | Y300L | K326N | I332R | S400P |
| V240I | V264I | E272Q | E294N | R301M | K326S | I332S | D401V |
| V240M | V264R | V273I | Q295K | R301M | K326T | I332T | S407I |
| V240T | V264T | F275L | Y296D | V302I | L328A | I332V | K414N |
| F241E | V264W | F275W | Y296E | S304D | L328D | I332W | E430A |
| V241I | D265F | F275Y | Y296H | S304H | L328E | I332Y | |
| F241L | D265H | N276A | Y296N | S304L | L328F | E333A | |
| F241R | D265I | D280A | Y296P | S304N | L328G | K334A | |
| F241S | D265L | D280H | Y296Q | S304T | L328H | K334E | |

| Substitutions of Two Sites | | | | |
|---|---|---|---|---|
| I332E, A330L | S239N/I332Q | V279L, P395S | P396L, P217S | |
| I332E, L328D | S239Q/I332D | V284A, F372L | P396L, P227S | |
| I332E, L328E | S239Q/I332E | K288N, K326N | P396L, V323I | |
| I332E, L328H | S239Q/I332N | K288N, A330S | P396L, V240A | |
| I332E, L328I | S239Q/I332Q | K290E, L142P | P396L, L242F | |
| I332E, L328M | V240I, V281M | K290E, P227S | P396L, P244H | |
| I332E, L328N | F241L, E258T | K290T, G371D | P396L, T250A | |
| I332E, L328Q | F241L/V262I | P291S, P353Q | P396L, R255L | |
| I332E, L328T | F243L, E318K | R292P, V305I | P396L, E258D | |
| I332E, L328V | F243I, V379L | S298A/I332E | P396L, H268D | |
| I332E, N297D | P243L/V264I | S298N, W381R | P396L, H268N | |
| I332E, N297E | K246T, Y319F | S298N, S407R | P396L, V303I | |
| I332E, N297S | K246T, P396H | K317N, F423-DEL | P396L, K326I | |
| S166N, K409R | P247H, G285E | K326E, K320E | P396L, V305L | |
| P232S, S304G | P247L, I377F | K326E, A330T | P396L, L358P | |
| S239D/I332D | P247L, E389G | K326E, G385E | P396L, K370E | |
| S239D/I332E | P247S, P396L | A330V, Q419H | P396L, S375C | |
| S239D/I332N | P247L, L398Q | K334E, E233D | P396L, V379M | |
| S239D/I332Q | P247L, L406F | K334N, K246I | P396L, N384K | |
| S239D/D265N | P247L, N421K | K334E, K288M | P396L, K392T | |
| S239E/D265Q | L251F, F372L | K334E, R292L | P396L, S400F | |
| S239E/I332D | L251F, S415I | K334E, E308D | P396L, L410H | |
| S239E/I332E | R255L, E318K | K334E, E380D | P396L, Q419H | |
| S239E/I332N | R255Q, K326E | K334N, P396L | P396L, Q419L | |
| S239E/I332Q | E258D, N384K | A339V, Q347H | P396L, V427A | |
| S239N/I332D | V263Q, E272D | K370N, S440N | D399E, G402D | |
| S239N/I332E | V264I/I332E | T394M, V397M | D399E, M428L | |
| S239N/I332N | H268D, E318D | P396L, K210M | | |

| Substitutions of Three Sites | | |
|---|---|---|
| V185M, R292L, D399E | P217S, A378V, S408R | K218R, G281D, G385R |
| S192T, M252L, R301C | P247L, I253N, K334N | P247L, A330T, S440G |
| V125L, V215I, S408I | D312E, K327N, I378S | T355N, P387S, H435Q |
| R292L, T359N, P396L | E216D, E345K, S375I | P247L, A431V, S442F |
| F275I, K334N, V348M | K288N, A330S, P396L | A378V, N390I, V422I |
| F243L, R255L, E318K | G316D, A378V, D399E | V282E, V369I, L406F |
| K334E, T359N, T366S | N315I, V379M, T394M | V397M, T411A, S415N |
| K288N, A330S, P396L | P247L, W313R, E388G | T223I, T256S, L406F |
| F243I, V379L, G420V | R301H, K340E, D399E | K246N, P396L, Q419R |
| A231V, Q386H, V412M | K326I, P396L, S408N | P217A, T359A, P396L |
| E216D, K334R, S375I | K210M, K261N, P396L | V215I, K290V, P396L |
| T335N, P387S, H435Q | A330V, G427M, K438R | V263Q, E272D, Q419H |
| K246I, Q362H, K370E | K222E, V263Q, S298N | N276Y, T393N, W417R |
| K334E, E380D, G446V | E233G, P247S, L306P | D270E, G316D, R416G |
| V303I, V369F, M428L | S219T, T225K, D270E | D270E, K392T, P396L |
| K246E, V284M, V308A | R292P, F243L, V305I | R255L, D270E, P396L |
| E293V, Q295E, A327T | V284M, R292L, K370N | V240A, D270E, P396L |
| Y319F, P352L, P396L | D270E, K370E, P396L | 270E, P396L, Q419HD |

TABLE 2-continued

| Exemplary Fc Modifications | | |
|---|---|---|
| K290T, N390I, P396L | P247L, D270E, N421K | S239D, A330L, I332E |
| N297D, A330Y, I332E | Y296D, N297D, I332E | S239D, A330Y, I332E |
| N297D, T299L, I332E | Y296E, N297D, I332 E | S239D, I332E, A330I |
| N297D, T299I, I332E | Y296H, N297D, I332E | S239D, N297D, I332E |
| N297D, T299L, I332E | Y296N, N297D, I332E | S239D, S298A, I332E |
| N297D, T299V, I332E | Y296Q, N297I, I332E | S239D, V264II, I332E |
| F243L, V262I, V264W | Y296T, N297D, I332E | S239E, N297D, I332E |
| D265F, N297E, I332E | P230A, E233D, I332E | S239E, V264I, I332 E |
| D265Y, N297D, I332E | P244H, P245A, P247V | S239N, A330L, I332E |
| V264E, N297D, I332E | V264I, A330Y, I332E | S239N, A330Y, I332E |
| V264I, A330L, I332E | V264I, S298A, I332E | S239Q, V264I, I332E |

| Substitutions of Four Sites | |
|---|---|
| A141V, H268L, K288E, P291S | T256S, V305I, K334E, N390S |
| E258D, T289A, H310Y, Y407V | D280E, S354F, A431D, L441I |
| K334E, T359N, T366S, Q386R | P343S, P353L, S375I, S383N |
| K326Q, K334E, T359N, T366S | E269K, K290N, Q311R, H433Y |
| K288R, T307A, K344E, P396L | K290E, V369A, T393A, P396L |
| V273I, K326E, L328I, P396L | K210N, K222I, K320M, P396L |
| F275L, Q362H, N384K, P396L | S219T, T225K, D270E, K360R |
| V282L, A330V, H433Y, T436R | P243L, S254T, A330V, N361D |
| R255L, D270E, Y300L, P396L, | F243L, D270E, K392N, P396L |
| R255L, D270E, R292G, P396L | F243L, R255L, D270E, P396L |
| V284M, S298N, K334E, R355W | S239D, D265F, N297D, I332E |
| D265Y, N297D, T299L, I332E | S239D, D265H, N297D, I332E |
| F241E, F2430, V262T, V264F | S239D, D265I, N297D, I332E |
| F241E, F243R, V262E, V264R | S239D, 0265L, N297D, I332E |
| F241E, F243Y, V262T, V264R | S239D, D265T, N297D, I332E |
| F241L, F243L, V262I, V264I | S239D, D265V, N297D, I332E |
| F241R, F2430, V262T, V264R | S239D, D265Y, N297D, I332E |
| F241W, F243W, V262A, V264A | S239D, N297D, I332E, A330Y |
| F241Y, F243Y, V262T, V264T | S239D, N297D, I332E, K326E |
| N297D, I332E, S239D, A330L | S239D, N297D, I332E, L235D |
| N297D, S298A, A330Y, I 332E | S239D, V264I, A330L, I332E |
| S239D, A330Y, I332E, K326E | S239D, V264I, S298A, I332E |
| S239D, A330Y, I332E, K326T | S239E, V264I, A330Y, I332 E |
| S239D, A330Y, I332E, L234I | S239D, A330Y, I332E, V264T |
| S239D, A330Y, I332E, L235D | S239D, A330Y, I332E, V266I |
| S239D, A330Y, I332E, V240I | |

| Substitutions of Five Sites | |
|---|---|
| V284M, S298N, K334E, R355W, R416T | K147T, Y202M, F275I, K334N, V348M |
| P217S, V305I, I309L, N390H, P396L | T335N, K370E, A378V, T394M, S424L |
| F243L, V305I, A378D, P396L, F404S | P244H, L358M, V379M, N384K, V397M |
| K222N, T335N, K370E, A378V, T394M | P244A, K326I, C367R, S375I, K447T |
| L235P, S304G, V305I, V323I, V382M | C229Y, A287T, V379M, P396L, L443V |
| F241E, F2430, V262T, V264E, I332E | F241R, F243Q, V262T, V264R, I332E |
| F241E, F243R, V262E, V264R, I332E | S239E, V264I, S298A, A330Y, I332E |
| F241E, F243Y, V262T, V264R, I332E | |

| Substitutions of More Than Five Sites |
|---|
| D221E, D270E, V308A, Q311H, P396L, G402D |
| T215P, K274N, A287G, K334N, L365V, P396L |
| F241Y, F243Y, V262T, V264T, N297D, I332E |
| N297D, T299F, I332E, N297D, T299H, I332E |
| D221Y, M252I, A330G, A339T, T359N, V422I, H433L |
| S239D, N297D, I332E, A330Y, F241S, F243H, V262T, V264T |
| K133M, F149Y, K205E, R214I, K218E, S383N, N384K, T256N, V262L |

In specific embodiments, the variant Fc region of such anti-B7-H3 antibodies and/or anti-tumor angiogenesis antibodies has:
(1) a leucine at position 247, a lysine at position 421 and a glutamic acid at position 270;
(2) a threonine at position 392, a leucine at position 396, a glutamic acid at position 270, and a leucine at position 243
(3) a histidine at position 419, a leucine at position 396, and a glutamic acid at position 270;
(4) a histidine at position 419, a leucine at position 396, a glutamic acid at position 270, and a leucine at position 243;
(5) an alanine at position 240, a leucine at position 396, and a glutamic acid at position 270;
(6) a lysine at position 255 and a leucine at position 396;
(7) a lysine at position 255, a leucine at position 396, and a glutamic acid at position 270;
(8) a lysine at position 255, a leucine at position 396, a glutamic acid at position 270, and a lysine at position 300;
(9) a lysine at position 255, a leucine at position 396, a glutamic acid at position 270, and a glycine at position 292;
(10) a lysine at position 255, a leucine at position 396, a glutamic acid at position 270, and a leucine at position 243;

(11) a glutamic acid at position 370, a leucine at position 396, and a glutamic acid at position 270;
(12) a glutamic acid at position 270, an aspartic acid at position 316, and a glycine at position 416;
(13) a leucine at position 243, a proline at position 292, an isoleucine at position 305, and a leucine at position 396;
(14) a leucine at position 243, a glutamic acid at position 270, an asparagine at position 392 and a leucine at position 396;
(15) a leucine at position 243, a leucine at position 255, a glutamic acid at position 270 and a leucine at position 396;
(16) a glutamine at position 297;
or
(17) any combination of the foregoing (1)-(16) substitutions.

In some embodiments, the molecules of the invention further comprise one or more glycosylation sites, so that one or more carbohydrate moieties are covalently attached to the molecule. Preferably, the molecules of the invention with one or more glycosylation sites and/or one or more modifications in the Fc region confer or have an enhanced antibody mediated effector function, e.g., enhanced ADCC activity, compared to a parent antibody. In some embodiments, the invention further comprises molecules comprising one or more modifications of amino acids that are directly or indirectly known to interact with a carbohydrate moiety of the antibody, including but not limited to amino acids at positions 241, 243, 244, 245, 245, 249, 256, 258, 260, 262, 264, 265, 296, 299, and 301. Amino acids that directly or indirectly interact with a carbohydrate moiety of an antibody are known in the art, see, e.g., Jefferis et al., 1995 *Immunology Letters*, 44: 111-7, which is incorporated herein by reference in its entirety.

In another embodiment, the invention encompasses molecules that have been modified by introducing one or more glycosylation sites into one or more sites of the molecules, preferably without altering the functionality of the molecules, e.g., binding activity to target antigen or FcγR. Glycosylation sites may be introduced into the variable and/or constant region of the molecules of the invention. As used herein, "glycosylation sites" include any specific amino acid sequence in an antibody to which an oligosaccharide (i.e., carbohydrates containing two or more simple sugars linked together) will specifically and covalently attach. Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. The molecules of the invention may comprise one or more glycosylation sites, including N-linked and O-linked glycosylation sites. Any glycosylation site for N-linked or O-linked glycosylation known in the art may be used in accordance with the instant invention. An exemplary N-linked glycosylation site that is useful in accordance with the methods of the present invention is the amino acid sequence: Asn-X-Thr/Ser, wherein X may be any amino acid and Thr/Ser indicates a threonine or a serine. Such a site or sites may be introduced into a molecule of the invention using methods well known in the art to which this invention pertains (see for example, *IN VITRO* MUTAGENESIS, RECOMBINANT DNA: A SHORT COURSE, J. D. Watson, et al. W. H. Freeman and Company, New York, 1983, chapter 8, pp. 106-116, which is incorporated herein by reference in its entirety. An exemplary method for introducing a glycosylation site into a molecule of the invention may comprise: modifying or mutating an amino acid sequence of the molecule so that the desired Asn-X-Thr/Ser sequence is obtained.

In some embodiments, the invention encompasses methods of modifying the carbohydrate content of a molecule of the invention by adding or deleting a glycosylation site. Methods for modifying the carbohydrate content of antibodies are well known in the art and encompassed within the invention, see, e.g., U.S. Pat. No. 6,218,149; EP 0 359 096 B1; U.S. Publication No. US 2002/0028486; WO 03/035835; U.S. Publication No. 2003/0115614; U.S. Pat. No. 6,218,149; U.S. Pat. No. 6,472,511; all of which are incorporated herein by reference in their entirety. In other embodiments, the invention encompasses methods of modifying the carbohydrate content of a molecule of the invention by deleting one or more endogenous carbohydrate moieties of the molecule. In a specific embodiment, the invention encompasses shifting the glycosylation site of the Fc region of an antibody, by modifying positions adjacent to 297. In a specific embodiment, the invention encompasses modifying position 296 so that position 296 and not position 297 is glycosylated.

Effector function can also be modified by techniques such as by introducing one or more cysteine residues into the Fc region, thereby allowing interchain disulfide bond formation in this region to occur, resulting in the generation of a homodimeric antibody that may have improved internalization capability and/or increased complement-mediated cell killing and ADCC (Caron, P. C. et al. (1992) "*Engineered Humanized Dimeric Forms Of IgG Are More Effective Antibodies*," J. Exp. Med. 176:1191-1195; Shopes, B. (1992) "*A Genetically Engineered Human IgG Mutant With Enhanced Cytolytic Activity*," J. Immunol. 148(9):2918-2922. Homodimeric antibodies with enhanced anti-tumor activity may also be prepared using heterobifunctional cross-linkers as described in Wolff, E. A. et al. (1993) "*Monoclonal Antibody Homodimers: Enhanced Antitumor Activity In Nude Mice*," Cancer Research 53:2560-2565. Alternatively, an antibody can be engineered which has dual Fc regions and may thereby have enhanced complement lysis and ADCC capabilities (Stevenson, G. T. et al. (1989) "*A Chimeric Antibody With Dual Fc Regions (bisFabFc) Prepared By Manipulations At The IgG Hinge*," Anti-Cancer Drug Design 3:219-230).

VI. B7-H3/ANTI-TUMOR ANGIOGENESIS DIABODIES

As discussed above, the present invention additionally encompasses diabody (especially, "DART™" (dual affinity retargeting reagent)) molecules that comprise at least two covalently bonded polypeptide chains which form at least two epitope binding sites, one of which specifically binds to B7-H3 and a second of which binds to a cell-surface factor (or its receptor) that is involved in promoting tumor angiogenesis. Most preferably, such diabodies will bind to B7-H3 and VEGF or to B7-H3 and VEGFR.

In preferred embodiments, the first polypeptide chain of the diabody comprises:
  (i) a domain (A) comprising a binding region of a light chain variable domain of a first immunoglobulin (VL1) specific for an epitope of B7-H3;
  (ii) a domain (B) comprising a binding region of a heavy chain variable domain of a second immunoglobulin (VH2) specific for an epitope of either VEGF or VEGFR; and
  (iii) optionally, a domain (C).

The second polypeptide chain of such a diabody comprises:
(i) a domain (D) comprising a binding region of a light chain variable domain of the second immunoglobulin (VL2) specific for such epitope of either VEGF or VEGFR epitope;
(ii) a domain (E) comprising a binding region of a heavy chain variable domain of the first immunoglobulin (VH1) specific for such epitope of B7-H3; and
(iii) optionally, a domain (F).

The variable domains of the first and second polypeptide chains may alternatively be reversed, such that the first polypeptide chain of the diabody comprises:
(i) a domain (A) comprising a binding region of a light chain variable domain of the second immunoglobulin (VL2) specific for such epitope of either VEGF or VEGFR epitope;
(ii) a domain (B) comprising a binding region of a heavy chain variable domain of the first immunoglobulin (VH1) specific for such epitope of B7-H3; and
(iii) optionally, a domain (C);
and the second polypeptide chain of such a diabody comprises:
(i) a domain (D) comprising a binding region of a light chain variable domain of a first immunoglobulin (VL1) specific for an epitope of B7-H3;
(ii) a domain (E) comprising a binding region of a heavy chain variable domain of a second immunoglobulin (VH2) specific for an epitope of either VEGF or VEGFR; and
(iii) optionally, a domain (F).

The diabody domains (A) and (B) do not associate with one another to form an epitope binding site. Similarly, the diabody domains (D) and (E) do not associate with one another to form an epitope binding site. Rather, diabody domains (A) and (E) associate to form a binding site that binds the B7-H3 epitope and the diabody domains (B) and (D) associate to form a binding site that binds the VEGF or VEGFR epitope.

Neither the VH or VL domain of either polypeptide chain is constrained to any position within the polypeptide chain, i.e., restricted to the amino (N) or carboxy (C) terminus, nor are the domains restricted in their relative positions to one another, i.e., the VL domain may be N-terminal to the VH domain and vice-versa. The only restriction is that a complimentary polypeptide chain be available in order to form the functional diabody.

When present, Domains (C) and (F) are covalently associated together. Domains (C) and (F) may be an Fc domain or portion thereof (e.g. a CH2 domain, or CH3 domain). The Fc domain or portion thereof may be derived from any immunoglobulin isotype or allotype including, but not limited to, IgA, IgD, IgG, IgE and IgM. In preferred embodiments, the Fc domain (or portion thereof) is derived from IgG. In specific embodiments, the IgG isotype is IgG1, IgG2, IgG3 or IgG4 or an allotype thereof. In one embodiment, the diabody molecule comprises an Fc domain, which Fc domain comprises a CH2 domain and CH3 domain independently selected from any immunoglobulin isotype (i.e., an Fc domain comprising the CH2 domain derived from IgG and the CH3 domain derived from IgE, or the CH2 domain derived from IgG1 and the CH3 domain derived from IgG2, etc.). The Fc domain may be engineered into a polypeptide chain comprising the diabody molecule of the invention in any position relative to other domains or portions of said polypeptide chain (e.g., the Fc domain, or portion thereof, may be C-terminal to both the VL and VH domains of the polypeptide of the chain; may be N-terminal to both the VL and VH domains; or may be N-terminal to one domain and c-terminal to another (i.e., between two domains of the polypeptide chain)).

The Fc domains in the polypeptide chains of the diabody molecules preferentially dimerize, resulting in the formation of a diabody molecule that exhibits immunoglobulin-like properties, e.g., Fc-FcγR, interactions. Fc comprising diabodies may be dimers, e.g., comprised of two polypeptide chains, each comprising a VH domain, a VL domain and an Fc domain. Dimerization of said polypeptide chains results in a bivalent diabody comprising an Fc domain, albeit with a structure distinct from that of an unmodified bivalent antibody. Such diabody molecules will exhibit altered phenotypes relative to a wild-type immunoglobulin, e.g., altered serum half-life, binding properties, etc. In other embodiments, diabody molecules comprising Fc domains may be tetramers. Such tetramers comprise two 'heavier' polypeptide chains, i.e., a polypeptide chain comprising a VL, a VH and an Fc domain, and two 'lighter' polypeptide chains, i.e., polypeptide chain comprising a VL and a VH. The lighter and heavier chains interact to form a monomer, and said monomers interact via their unpaired Fc domains to form an Ig-like molecule. Such an Ig-like diabody is tetravalent.

Formation of a tetraspecific diabody molecule as described supra requires the interaction of four differing polypeptide chains. Such interactions are difficult to achieve with efficiency within a single cell recombinant production system, due to the many variants of potential chain mispairings. One solution to decrease the probability of mispairings, is to engineer "knobs-into-holes" type mutations into the desired polypeptide chain pairs. Such mutations favor heterodimerization over homodimerization. For example, with respect to Fc-Fc-interactions, an amino acid substitution (preferably a substitution with an amino acid comprising a bulky side group forming a 'knob', e.g., tryptophan) can be introduced into the CH2 or CH3 domain such that steric interference will prevent interaction with a similarly mutated domain and will obligate the mutated domain to pair with a domain into which a complementary, or accommodating mutation has been engineered, i.e., 'the hole' (e.g., a substitution with glycine). Such sets of mutations can be engineered into any pair of polypeptides comprising the diabody molecule, and further, engineered into any portion of the polypeptides chains of said pair. Methods of protein engineering to favor heterodimerization over homodimerization are well known in the art, in particular with respect to the engineering of immunoglobulin-like molecules, and are encompassed herein (see e.g., Ridgway et al. (1996) "'*Knobs-Into-Holes' Engineering Of Antibody CH3 Domains For Heavy Chain Heterodimerization*," Protein Engr. 9:617-621, Atwell et al. (1997) "*Stable Heterodimers From Remodeling The Domain Interface Of A Homodimer Using A Phage Display Library*," J. Mol. Biol. 270: 26-35, and Xie et al. (2005) "*A New Format Of Bispecific Antibody: Highly Efficient Heterodimerization, Expression And Tumor Cell Lysis*," J. Immunol. Methods 296:95-101; each of which is hereby incorporated herein by reference in its entirety.

The invention also encompasses diabody molecules comprising variant Fc or variant hinge-Fc domains (or portion thereof), which variant Fc domain comprises at least one amino acid modification (e.g. substitution, insertion deletion) relative to a comparable wild-type Fc domain or hinge-Fc domain (or portion thereof). Molecules comprising variant Fc domains or hinge-Fc domains (or portion thereof) (e.g., antibodies) normally have altered phenotypes relative to molecules comprising wild-type Fc domains or hinge-Fc domains or portions thereof. The variant phenotype may be expressed as altered serum half-life, altered stability, altered susceptibility to cellular enzymes or altered effector function as assayed in an NK dependent or macrophage dependent assay. Fc domain modifications identified as altering effector function are disclosed above.

The present invention also encompasses molecules comprising a hinge domain. The hinge domain be derived from any immunoglobulin isotype or allotype including IgA, IgD, IgG, IgE and IgM. In preferred embodiments, the hinge domain is derived from IgG, wherein the IgG isotype is IgG1, IgG2, IgG3 or IgG4, or an allotpye thereof. Said hinge domain may be engineered into a polypeptide chain comprising the diabody molecule together with an Fc domain such that the diabody molecule comprises a hinge-Fc domain. In certain embodiments, the hinge and Fc domain are independently selected from any immunoglobulin isotype known in the art or exemplified herein. In other embodiments the hinge and Fc domain are separated by at least one other domain of the polypeptide chain, e.g., the VL domain. The hinge domain, or optionally the hinge-Fc domain, may be engineered in to a polypeptide of the invention in any position relative to other domains or portions of said polypeptide chain. In certain embodiments, a polypeptide chain of the invention comprises a hinge domain, which hinge domain is at the C-terminus of the polypeptide chain, wherein said polypeptide chain does not comprise an Fc domain. In yet other embodiments, a polypeptide chain of the invention comprises a hinge-Fc domain, which hinge-Fc domain is at the C-terminus of the polypeptide chain. In further embodiments, a polypeptide chain of the invention comprises a hinge-Fc domain, which hinge-Fc domain is at the N-terminus of the polypeptide chain.

Each domain of the polypeptide chain of the diabody, i.e., the VL, VH and Fc domain may be separated by a peptide linker. The peptide linker may be 0, 1, 2, 3, 4, 5, 6, 7, 8, or 9 amino acids in length. In certain embodiments the amino acid linker sequence is GGGSGGGG (SEQ ID NO:97) encoded by the nucleic acid sequence ggaggcggat ccggaggcgg aggc (SEQ ID NO:98). The polypeptide chains of the diabody molecule may be engineered to comprise at least one cysteine residue that will interact with a counterpart cysteine residue on a second polypeptide chain of the diabody to form an inter-chain disulfide bond. Such inter-chain disulfide bonds serve to stabilize the diabody molecule, thereby improving expression and recovery in recombinant systems, resulting in a stable and consistent formulation and improving the stability of the isolated and/or purified product in vivo. The cysteine residue may be introduced as a single amino acid or as part of larger amino-acid sequence, e.g. a hinge domain, in any portion of the polypeptide chain. In a specific embodiment, the cysteine residue may be engineered to occur at the C-terminus of the polypeptide chain. In some embodiments, the cysteine residue is introduced into the polypeptide chain within the amino acid sequence: LGGC (SEQ ID NO:99). In a specific embodiment, the C-terminus of the polypeptide chains comprising the diabody molecules of the invention comprises the amino acid sequence LGGC (SEQ ID NO:99). In another embodiment, the cysteine residue is introduced into the polypeptide within an amino acid sequence comprising a hinge domain, e.g. EPKSCDKTHTCPP (SEQ ID NO:100) or ESKYGPPCPS (SEQ ID NO:101). In a specific embodiment, the C-terminus of a polypeptide chain of the diabody molecule of the invention comprises the amino acid sequence of an IgG hinge domain, e.g. SEQ ID NO:100 or SEQ ID NO:101. In another embodiment, the C-terminus of a polypeptide chain of a diabody molecule of the invention comprises the amino acid sequence VEPKSC (SEQ ID NO:102), which can be encoded by nucleotide sequence gttgagccca aatcttgt (SEQ ID NO:103). In other embodiments, the cysteine residue in introduced into the polypeptide chain within the amino acid sequence LGGCFNRGEC (SEQ ID NO:104), which can be encoded by the nucleotide sequence ctgggaggct gcttcaacag gggagagtgt (SEQ ID NO:105). In a specific embodiment, the C-terminus of a polypeptide chain comprising a diabody of the invention comprises the amino acid sequence LGGCFNRGEC (SEQ ID NO:104). In yet other embodiments, the cysteine residue in introduced into the polypeptide chain within the amino acid sequence FNRGEC (SEQ ID NO:106), which can be encoded by the nucleotide sequence ttcaacaggg gagagtgt (SEQ ID NO:107). In a specific embodiment, the C-terminus of a polypeptide chain comprising a diabody of the invention comprises the amino acid sequence FNRGEC (SEQ ID NO:106).

In certain embodiments, the diabody molecule comprises at least two polypeptide chains, each of which comprise the amino acid sequence LGGC (SEQ ID NO:99) and are covalently linked by a disulfide bond between the cysteine residues in the LGGC (SEQ ID NO:99) sequences. In another specific embodiment, the diabody molecule comprises at least two polypeptide chains, one of which comprises the sequence FNRGEC (SEQ ID NO:106) while the other comprises a hinge domain (containing at least one cysteine residue), wherein said at least two polypeptide chains are covalently linked by a disulfide bond between the cysteine residue in FNRGEC (SEQ ID NO:106) and a cysteine residue in the hinge domain. In particular aspects, the cysteine residue responsible for the disulfide bond located in the hinge domain is Cys-128 (as numbered according to Kabat EU; located in the hinge domain of an unmodified, intact IgG heavy chain) and the counterpart cysteine residue is Cys-214 (as numbered according to Kabat EU; located at the C-terminus of an unmodified, intact IgG light chain) (Elkabetz et al. (2005) "*Cysteines In CH1 Underlie Retention Of Unassembled Ig Heavy Chains*," J. Biol. Chem. 280:14402-14412). In yet other embodiments, the at least one cysteine residue is engineered to occur at the N-terminus of the amino acid chain. In still other embodiments, the at least one cysteine residue is engineered to occur in the linker portion of the polypeptide chain of the diabody molecule. In further embodiments, the VH or VL domain is engineered to comprise at least one amino acid modification relative to the parental VH or VL domain such that said amino acid modification comprises a substitution of a parental amino acid with cysteine.

In still another aspect of this embodiment, the Domain (C) of the first polypeptide chain comprises the amino acid sequence VEPKSC (SEQ ID NO:102), derived from the hinge domain of a human IgG, and which can be encoded by the nucleotide sequence gttgagccca aatcttgt (SEQ ID NO:103). In another aspect of this embodiment, the Domain (F) of the second polypeptide chain comprises the amino acid sequence VEPKSC (SEQ ID NO:102). In certain aspects of this embodiment, Domain (C) of the first polypeptide chain comprises the C-terminal 6 amino acids of the human kappa light chain, FNRGEC (SEQ ID NO:106); and Domain (F) of the second polypeptide chain comprises the amino acid sequence VEPKSC (SEQ ID NO:102) or a hinge domain. In other aspects of this embodiment, Domain (F) of the second polypeptide chain comprises the C-terminal 6 amino acids of the human kappa light chain, FNRGEC (SEQ ID NO:106); and Domain (C) of the first polypeptide chain comprises the amino acid sequence VEPKSC (SEQ ID NO:102) or a hinge domain.

As will be appreciated in view of the foregoing, the individual polypeptides of a bispecific diabody can form two species of homodimers and one species of heterodimer. In one embodiment of the present invention, a charged polypeptide can be added to the C-terminus of one, or more preferably, both diabody polypeptides. By selecting charged polypeptides of opposite charge for the individual polypeptides of the bispecific diabody, the inclusion of such charged polypeptides favors formation of heterodimers and lessens formation of homodimers. Preferably, a positively charged polypeptide will contain a substantial content of arginine, glutamine, histidine and/or lysine (or mixtures of such amino acids) and a negatively charged polypeptide will contain a substantial content of aspartate or glutamate (or a mixture of such amino acids). Positively charged polypeptides containing a substantial content of lysine and negatively charged polypeptides containing a substantial content of glutamate are particularly preferred. In order to maximize the electrostatic attraction between such oppositely charged polypeptides, it is preferred to employ polypeptides capable of spontaneously assuming a helical conformation.

Thus, in a preferred embodiment, a positively charged, "E-coil" will be appended to one of the polypeptides being used to form a bispecific diabody and a negatively charged "K-coil" will be appended to the second of the diabody's polypeptides. A particularly preferred E-coil will have the sequence: $(EVAALEK)_4$ [i.e. (SEQ ID NO:108) EVAALEKEVAALEKEVAALEKEVAALEK]. A particularly preferred K-coil will have the sequence: $(KVAALKE)_4$ [i.e. (SEQ ID NO:109) KVAALKEKVAALKEKVAALKEKVAALKE].

A preferred diabody polypeptide possessing such an E-coil will have the general sequence: [VL Domain]-[GGGSGGGG]-[VH Domain]-[(EVAALEK)$_4$]-GGGNS, where VL is the diabody's variable light Ig domain, GGGSGGGG is SEQ ID NO:97, VH is the diabody's variable heavy Ig domain, $(EVAALEK)_4$ is SEQ ID NO:108, and GGGNS is SEQ ID NO:110. A preferred diabody polypeptide possessing such a K-coil will have the general sequence: [VL Domain]-[GGGSGGGG]-[VH Domain]-[(KVAALKE)$_4$]-GGGNS, where VL is the diabody's variable light Ig domain, GGGSGGGG is SEQ ID NO:97, VH is the diabody's variable heavy Ig domain, $(KVAALKE)_4$ is SEQ ID NO:109, and GGGNS is SEQ ID NO:110.

In a further embodiment, Fc-regions can be linked to the E and/or K coils of E-coil or K-coil diabodies. Furthering the separation between the Fc regions and the diabody VH domain of an Fc-containing diabody is desirable in cases in which a less separated arrangement of such domains results in diminished interaction between such domains and their binding ligands or otherwise interferes with diabody assembly. Although separators of any amino acid sequence may be employed, it is preferable to employ a separator that forms an α helix coil, so as to maximally extend and project the Fc domain away from the variable domains. Because the above-described coiled polypeptides of opposing charge additionally function to promote heterodimer formation, such molecules are particularly preferred separators. Such coil-containing Fc-diabody molecules provide benefits similar to those of Fc-diabodies, including improved serum half-life and effector function recruitment. The above-described E-coil and K-coil polypeptides are particularly preferred for this purpose. Thus, in a preferred embodiment, the E-coil Fc-containing diabody will have the general sequence: [VL Domain]-[GGGSGGGG]-[VH Domain]-[(EVAALEK)$_4$]-GGG-Fc domain starting with D234 (Kabat numbering), where VL is the diabody's variable light Ig domain, GGGSGGGG is SEQ ID NO:97, VH is the diabody's variable heavy Ig domain and $(EVAALEK)_4$ is SEQ ID NO:108. Similarly, in a preferred embodiment, the K-coil Fc-containing diabody will have the general sequence: [VL Domain]-[GGGSGGGG]-[VH Domain]-[(KVAALKE)$_4$]-GGG-Fc domain starting with D234 (Kabat numbering), where VL is the diabody's variable light Ig domain, GGGSGGGG is SEQ ID NO:97, VH is the diabody's variable heavy Ig domain and $(KVAALKE)_4$ is SEQ ID NO:109.

As indicated above, a coil-containing diabody molecule or a coil-containing Fc-containing diabody molecule may contain only a single such coil separator, or it may contain more than one such separators (e.g., two separators, preferably of opposite charge, of which one is linked to each of the VH domain of the diabody's polypeptides). By linking the Fc region to such separator molecule(s), the ability to make bivalent, tetravalent, etc. versions of the Fc-diabody molecules by chain swapping is enhanced. Fc-diabody molecules can thus be produced that form monomers or dimers depending upon whether the Fc domain is linked to one or both of the diabody VH domains

VII. THERAPEUTIC METHODS

Antibodies (or diabodies) that specifically bind to B7-H3 or a cell-surface factor (or its receptor) that is involved in promoting tumor angiogenesis (especially VEGF or its receptor, VEGFR) may be used for therapeutic purposes in individuals with cancer or other diseases. In one embodiment, molecule(s) providing such binding activities are administered concurrently. As used herein, such "concurrent" administration is intended to denote:

A. the administration of a single pharmaceutical composition that contains both a molecule having a binding ability specific for B7-H3 and a molecule having a binding ability that is specific for a cell-surface factor (or its receptor) that is involved in promoting tumor angiogenesis (especially VEGF or its receptor, VEGFR). Such molecules may be the same molecule (e.g., a diabody, or may be distinct (e.g., an anti-B7-H3 antibody, or antigen-binding fragment thereof, and an anti-VEGF-antibody, or antigen-binding fragment thereof.

or

B. the separate administration of two or more pharmaceutical compositions, one composition of which contains a molecule having a binding ability specific for B7-H3 and another composition of which contains a molecule having a binding ability that is specific for a cell-surface factor (or its receptor) that is involved in promoting tumor angiogenesis (especially VEGF or its receptor, VEGFR), wherein the second administered composition is administered within 1 biological half-life after the administration of the first administered molecule, or within 2, 3, 4, 5, 6, 7, 8, 9, or 10 half-lives after the administration of the first administered composition. Bevacizumab has an estimated half-life of approximately 20 days. The estimated half-life of humanized anti-B7-H3 is 2-3 weeks.

In a second embodiment, two distinct molecules are employed, and the molecules are administered "sequentially" (e.g., an anti-VEGF antibody is administered and, at a later time, an anti-B7-H3 antibody is provided, or vice versa). In such sequential administration, the second administered composition is administered at least 10 half-lives after the administration of the first administered composition.

Therapy with such molecules can involve the formation of complexes both in vitro and in vivo. In one embodiment, a monoclonal anti-B7-H3 antibody and a monoclonal anti-VEGF antibody (especially chimeric or humanized variants thereof) can be used for immunotherapy directed at vascularizing cancerous cells of different tissues, and particularly cancerous cells such as breast cancer, glioblastoma, uterine cervical carcinoma, metastatic colorectal cancer, gastric cancer, hepatocellular carcinoma, leukemia, lung cancer, metastatic melanoma, vascularizing pancreatic cancer, and metastatic prostate cancer. Such immunotherapy may, for example, be sufficient to reduce cell division in the cancer cell, delay the development (e.g., onset and extent) of metastasis, or provide palliative treatment for the cancer. Palliative treatment of a cancer individual involves treating or lessening the adverse symptoms of the disease, or iatrogenic symptoms resulting from other treatments given for the disease without directly affecting the cancer progression. This includes treatments for easing of pain, nutritional support, sexual problems, psychological distress, depression, fatigue, psychiatric disorders, nausea, vomiting, etc.

It is understood that the antibody is administered at a concentration that promotes binding at physiological (e.g., in vivo) conditions. The antibodies (or diabodies) may be administered with additional agents that enhance or direct an individual's own immune response, such as an agent that strengthens ADCC.

In yet another embodiment, one or more of such antibodies or diabodies may be conjugated to or associated with a radioactive molecule, toxin (e.g., calicheamicin), chemotherapeutic molecule, liposomes or other vesicles containing chemotherapeutic compounds and administered to an individual in need of such treatment to target these compounds to the cancer cell containing the antigen recognized by the antibody and thus eliminate cancerous or diseased cells. Without being limited to any particular theory, the antibody (e.g., the anti-B7-H3 antibody) is internalized by the cell bearing B7-H3 at its surface, thus delivering the conjugated moiety to the cell to induce the therapeutic effect and the antibody (or diabody) that specifically binds to a cell-surface factor (or its receptor) that is involved in promoting tumor angiogenesis (especially VEGF or its receptor, VEGFR) inhibits tumor vascularization.

In yet another embodiment, such antibodies or diabodies can be employed as an adjuvant therapy at the time of the surgical removal of a tumor in order to delay, suppress or prevent the development of metastasis. The antibody can also be administered before surgery (neoadjuvant therapy) in order to decrease the size of the tumor and thus enable or simplify surgery, spare tissue during surgery, and/or decrease any resulting disfigurement.

Cell cycle dosing is contemplated in the practice of this invention. In such embodiments, a chemotherapeutic agent is used to synchronize the cell cycle of the tumor or other target diseased cells at a pre-determined stage. Subsequently, administration of the antibodies of this invention (alone or with additional therapeutic moieties) is made. In alternative embodiments, an anti-B7-H3 antibody is used to synchronize the cell cycle and reduce cell division prior to administration of a second round of treatment; the second round may be administration of an anti-B7-H3 antibody and the antibody (or diabody) that specifically binds to a cell-surface factor (or its receptor) that is involved in promoting tumor angiogenesis (especially VEGF or its receptor, VEGFR), alone or with an additional therapeutic moiety.

Chemotherapeutic agents include radioactive molecules, toxins, also referred to as cytotoxins or cytotoxic agents, which includes any agent that is detrimental to the viability of cancerous cells, agents, and liposomes or other vesicles containing chemotherapeutic compounds. Examples of suitable chemotherapeutic agents include but are not limited to 1-dehydrotestosterone, 5-fluorouracil decarbazine, 6-mercaptopurine, 6-thioguanine, actinomycin D, adriamycin, aldesleukin, alkylating agents, allopurinol sodium, altretamine, amifostine, anastrozole, anthramycin (AMC)), antimitotic agents, cis-dichlorodiamine platinum (II) (DDP) cisplatin), diaminodichloroplatinum, anthracyclines, antibiotics, antimetabolites, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxyanthracindione, Docetaxel, dolasetronmesylate, doxorubicin HCL, dronabinol, *E. coli* L-asparaginase, emetine, epoetin alpha, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluoropyrimidine-irinotecan, fluoropyrimidine-oxaliplatin, fluorouracil, flutamide, folinic acid, gemcitabine HCL, glucocorticoids, goserelin acetate, gramicidin D, granisetron HCL, hydroxyurea, idarubicin HCL, ifosfamide, interferon alpha-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 (with carmustine implant), porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate. Use of one or more of: fluoropyrimidine-irinotecan or fluoropyrimidine-oxaliplatin, temozolomide, procarbazine, carmustine (BCNU), lomustine (CCNU), vincristine, PVC (procarbazine, lomustine and vincristine), irinotecan, cisplatin, carboplatin, methotrexate, etoposide, bleomycin, vinblastine, actinomycin (dactinomycin), cyclophosphamide and ifosfamide is particularly preferred.

In a preferred embodiment, the cytotoxin is especially effective in dividing or rapidly dividing cells, such that non-dividing cells are relatively spared from the toxic effects.

The antibodies of the invention can be internalized within the diseased or carcinoma cells to which they bind and are therefore particularly useful for therapeutic applications, for example, delivering into the cells toxins that need to be internalized for their adverse activity. Examples of such toxins include, but are not limited to, saporin, calicheamicin, auristatin, and maytansinoid.

The antibodies or polypeptides of the invention can be associated (including conjugated or linked) to a radioactive molecule, a toxin, or other therapeutic agents, or to liposomes or other vesicles containing therapeutic agents covalently or non-covalently, directly or indirectly. The antibody may be linked to the radioactive molecule, the toxin, or the chemotherapeutic molecule at any location along the antibody so long as the antibody is able to bind its target.

A toxin or a chemotherapeutic agent may be administered concurrently with (before, after, or during administration), or coupled (e.g., covalently bonded) to a suitable monoclonal antibody either directly or indirectly (e.g., via a linker group, or, alternatively, via a linking molecule with appropriate attachment sites, such as a platform molecule as described in U.S. Pat. No. 5,552,391). The toxin and chemotherapeutic agent of the present invention can be coupled directly to the particular targeting proteins using methods known in the art. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

The antibodies or polypeptides can also be linked to a chemotherapeutic agent via a microcarrier. The term "microcarrier" refers to a biodegradable or a non-biodegradable particle which is insoluble in water and which has a size of less than about 150 μm, 120 μm or 100 μm in size, more commonly less than about 50-60 μm, preferably less than about 10, 5, 2.5, 2 or 1.5 μm. Microcarriers include "nanocarriers", which are microcarriers have a size of less than about 1 μm, preferably less than about 500 nm. Such particles are known in the art. Solid phase microcarriers may be particles formed from biocompatible naturally occurring polymers, synthetic polymers or synthetic copolymers, which may include or exclude microcarriers formed from agarose or cross-linked agarose, as well as other biodegradable materials known in the art. Biodegradable solid phase microcarriers may be formed from polymers which are degradable (e.g., poly(lactic acid), poly(glycolic acid) and copolymers thereof) or erodible (e.g., poly(ortho esters), such as 3,9-diethylidene-2,4,8,10-tetraoxaspiro[5.5]undecane (DETOSU) or poly(anhydrides), such as poly(anhydrides) of sebacic acid) under mammalian physiological conditions. Microcarriers may also be liquid phase (e.g., oil or lipid based), such as liposomes, iscoms (immune-stimulating complexes, which are stable complexes of cholesterol, and phospholipid, adjuvant-active saponin) without antigen, or droplets or micelles found in oil-in-water or water-in-oil emulsions, provided the liquid phase microcarriers are biodegradable. Biodegradable liquid phase microcarriers typically incorporate a biodegradable oil, a number of which are known in the art, including squalene and vegetable oils. Microcarriers are typically spherical in shape, but microcarriers that deviate from spherical shape are also acceptable (e.g., ellipsoid, rod-shaped, etc.). Due to their insoluble nature (with respect to water), microcarriers are filterable from water and water-based (aqueous) solutions.

The antibody or polypeptide conjugates of the present invention may include a bifunctional linker that contains both a group capable of coupling to a toxic agent or chemotherapeutic agent and a group capable of coupling to the antibody. A linker can function as a spacer to distance an antibody from an agent in order to avoid interference with binding capabilities. A linker can be cleavable or non-cleavable. A linker can also serve to increase the chemical reactivity of a substituent on an agent or an antibody, and thus increase the coupling efficiency. An increase in chemical reactivity may also facilitate the use of agents, or functional groups on agents, which otherwise would not be possible. The bifunctional linker can be coupled to the antibody by means that are known in the art. For example, a linker containing an active ester moiety, such as an N-hydroxysuccinimide ester, can be used for coupling to lysine residues in the antibody via an amide linkage. In another example, a linker containing a nucleophilic amine or hydrazine residue can be coupled to aldehyde groups produced by glycolytic oxidation of antibody carbohydrate residues. In addition to these direct methods of coupling, the linker can be indirectly coupled to the antibody by means of an intermediate carrier such as an aminodextran. In these embodiments the modified linkage is via either lysine, carbohydrate, or an intermediate carrier. In one embodiment, the linker is coupled site-selectively to free thiol residues in the protein. Moieties that are suitable for selective coupling to thiol groups on proteins are well known in the art. Examples include disulfide compounds, α-halocarbonyl and α-halocarboxyl compounds, and maleimides. When a nucleophilic amine function is present in the same molecule as an α-halo carbonyl or carboxyl group the potential exists for cyclization to occur via intramolecular alkylation of the amine. Methods to prevent this problem are well known to one of ordinary skill in the art, for example by preparation of molecules in which the amine and α-halo functions are separated by inflexible groups, such as aryl groups or trans-alkenes, that make the undesired cyclization stereochemically disfavored. See, for example, U.S. Pat. No. 6,441,163 for preparation of conjugates of maytansinoids and antibody via a disulfide moiety.

One of the cleavable linkers that can be used for the preparation of antibody-drug conjugates is an acid-labile linker based on cis-aconitic acid that takes advantage of the acidic environment of different intracellular compartments such as the endosomes encountered during receptor mediated endocytosis and the lysosomes. See, for example, Shen, W. C. et al. (1981) ("*cis-Aconityl Spacer Between Daunomycin And Macromolecular Carriers: A Model Of pH-Sensitive Linkage Releasing Drug From A Lysosomotropic Conjugate*," Biochem. Biophys. Res. Comtnun. 102:1048-1054 (1981)) for the preparation of conjugates of daunorubicin with macromolecular carriers; Yang et al. (1988) ("*Pharmacokinetics And Mechanism Of Action Of A Doxorubicin-Monoclonal Antibody 9.2.27 Conjugate Directed To A Human Melanoma Proteoglycan*," J. Natl. Canc. Inst. 80:1154-1159) for the preparation of conjugates of daunorubicin to an anti-melanoma antibody; Dillman et al. (1988) ("*Superiority Of An Acid-Labile Daunorubicin-Monoclonal Antibody Immunoconjugate Compared To Free Drug*," Cancer Res. 48:6097-6102) for using an acid-labile linker in a similar fashion to prepare conjugates of daunorubicin with an anti-T cell antibody; and Trouet et al. (1982) "*A Covalent Linkage Between Daunorubicin And Proteins That Is Stable In Serum And Reversible By Lysosomal Hydrolases, As Required For A Lysosomotropic Drug-Carrier Conjugate: In Vitro And In Vivo Studies*," Proc. Natl. Acad. Sci. (U.S.A.) 79:626-629) for linking daunorubicin to an antibody via a peptide spacer arm.

An antibody (or polypeptide) of this invention may be conjugated (linked) to a radioactive molecule or toxin by any method known to the art. For a discussion of methods for radiolabeling antibody (see, CANCER THERAPY WITH MONOCLONAL ANTIBODIES, D. M. Goldenberg (Ed.) CRC Press, Boca Raton, 1995). Suitable toxins include taxanes, maytansinoids, auristatins (e.g., monomethyl auristatin (MMAE), monomethyl auristatin F (MMAF), auristatin E (AE), etc.) (such as those disclosed in U.S. Pat. Nos. 5,208,020; 5,416,064; 6,333,410; 6,340,701; 6,372,738; 6,436,931; 6,441,163; 6,596,757; 7,276,497; 7,585,857; or 7,851,432), calicheamicin, anthracyclines (e.g., doxorubicin), CC-1065 analog, docetaxel; cathepsin B or E; ricin, gelonin, *Pseudomonas* exotoxin, diphtheria toxin, and RNase; tiuxetan or toxic radioisotope such as $^{90}$Y; $^{131}$I, $^{177}$Lu; $^{186}$Re; $^{188}$Re; $^{211}$At; $^{212}$Bi; $^{213}$Bi, $^{225}$Ac, etc.).

Alternatively, an antibody can be conjugated to a second antibody to form an antibody heteroconjugate as described in U.S. Pat. No. 4,676,980. The formation of cross-linked antibodies can target the immune system to specific types of cells, for example, cancer or diseased cells expressing B7-H3.

In yet another embodiment, any of the B7-H3 binding compositions described herein can bind to B7-H3-expressing cancerous cells and induce an active immune response against the cancerous cells expressing B7-H3. In some cases, the active immune response can cause the death of the cancerous cells (e.g., antibody binding to cancer cells inducing apoptotic cell death), or inhibit the growth (e.g., block cells cycle progression) of the cancerous cells. In other cases, any of the novel antibodies described herein can bind to cancerous cells and antibody dependent cellular cytotoxicity (ADCC) can eliminate cancerous cells to which anti-B7-H3 binds. Accordingly, the invention provides methods of stimulating an immune response comprising administering any of the compositions described herein.

In some cases, antibody binding can also activate both cellular and humoral immune responses and recruit more natural killer cells or increased production of cytokines (e.g., IL-2, IFN-gamma, IL-12, TNF-alpha, TNF-beta, etc.) that further activate an individual's immune system to destroy cancerous cells. In yet another embodiment, the anti-B7-H3 antibodies can bind to cancerous cells, and macrophages or other phagocytic cell can opsonize the cancerous cells.

Various formulations of antibodies or fragments thereof or diabodies may be used for administration. In some embodiments, such molecules may be administered neat. In addition to the pharmacologically active agent, the compositions of the present invention may contain suitable pharmaceutically acceptable carriers comprising excipients and auxiliaries that are well known in the art and are relatively inert substances that facilitate administration of a pharmacologically effective substance or which facilitate processing of the active compounds into preparations that can be used pharmaceutically for delivery to the site of action. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers.

Suitable formulations for parenteral administration include aqueous solutions of the active compounds in water-soluble form, for example, water-soluble salts. In addition, suspensions of the active compounds as appropriate for oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances that increase the viscosity of the suspension and include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulation may be used simultaneously to achieve systemic administration of the active ingredient. Excipients as well as formulations for parenteral and nonparenteral drug delivery are set forth in REMINGTON: THE SCIENCE AND PRACTICE OF PHARMACY, 21st Edition, Lippincott Williams & Wilkins Publishing (2005). Suitable formulations for oral administration include hard or soft gelatin capsules, pills, tablets, including coated tablets, elixirs, suspensions, syrups or inhalations and controlled release forms thereof. Generally, these agents are formulated for administration by injection (e.g., intraperitoneally, intravenously, subcutaneously, intramuscularly, etc.), although other forms of administration (e.g., oral, mucosal, etc.) can be also used. Accordingly, anti-B7-H3 antibodies are preferably combined with pharmaceutically acceptable vehicles such as saline, Ringer's solution, dextrose solution, and the like.

The precise dose to be employed in the formulations of the present invention will depend on the route of administration, and the seriousness of the condition, and should be decided according to the judgment of the practitioner and each patient's circumstances and can be determined by standard clinical techniques. Effective doses (i.e., doses sufficient to be effective in the treatment, prevention or amelioration of one or more symptoms associated with a disorder) may be extrapolated from dose-response curves derived from in vitro or animal model test systems. The particular dosage regimen, i.e., dose, timing and repetition, will thus depend on the particular individual and that individual's medical history, as well as the route of administration. The dosage and frequency of administration of the molecules of the invention may be reduced or altered by enhancing their uptake and/or tissue penetration, such as, for example, by lipidation.

The dosage of such molecules administered to a patient is typically at least about 0.01 µg/kg body weight, at least about 0.05 µg/kg body weight, at least about 0.1 µg/kg body weight, at least about 0.2 µg/kg body weight, at least about 0.5 µg/kg body weight, at least about 1 µg/kg body weight, at least about 2 µg/kg body weight, at least about 3 µg/kg body weight, at least about 5 µg/kg body weight, at least about 10 µg/kg body weight, at least about 20 µg/kg body weight, at least about 30 µg/kg body weight, at least about 50 µg/kg body weight, at least about 100 µg/kg body weight, at least about 250 µg/kg body weight, at least about 750 µg/kg body weight, at least about 1.5 mg/kg body weight, at least about 3 mg/kg body weight, at least about 5 mg/kg body weight, or at least about 10 mg/kg body weight. The calculated dose will be administered based on the patient's body weight at baseline. Significant (>10%) change in body weight from baseline or established plateau weight should prompt recalculation of dose.

Empirical considerations, such as the half-life, generally will contribute to the determination of the dosage. Antibodies, which are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is based on reducing the number of cancerous cells, maintaining the reduction of cancerous cells, reducing the proliferation of cancerous cells, or delaying the development of metastasis. Alternatively, sustained continuous release formulations of anti-B7-H3 antibodies may be appropriate. Various formulations and devices for achieving sustained release are known in the art.

Although, as discussed above, various dosing and administration routes may be employed in order to provide anti-B7-H3 antibody therapy to recipient patients, the following dosing and administrative route is preferred. Anti-B7-H3 antibody (preferably humanized, if to be administered to human subjects) is preferably administered by intravenous (IV) infusion on Study Days 1, 8, 15, and 22 of a (50 day) Cycle 1. Additional anti-B7-H3 antibody is administered in subsequent cycles for eligible patients on Study Days 1, 8, and 15 of each subsequent 28-day cycle. The IV infusion is preferably delivered over a period of 120 minutes if the patient does not exhibit signs or symptoms of an infusion reaction. Occurrence of infusion reaction will necessitate rate reduction, interruption, or discontinuation. It is preferred that the anti-B7-H3 antibody not be administered as an IV push or bolus, and that an in-line filter or non-polyolefin IV infusion bags not be used. The antibody should not be mixed or diluted with other drugs. Infusion or allergic reactions may occur. Premedications for the prevention of infusion reactions are recommended and precautions for anaphylaxis should be observed during antibody administration. Supportive measures may include, but are not limited to: epinephrine, antihistamines, corticosteroids, IV fluids, vasopressors, oxygen, bronchodilators, diphenhydramine, and acetaminophen. IV saline, acetaminophen and emergency drugs, including epinephrine sub-cutaneous (0.3 to 0.5 mg (0.3 to 0.5 mL of a 1:1000 solution)), diphenhydramine (25 to 50 mg IV), and Decadron (10 mg IV push or equivalent) to treat hypersensitivity reactions should be available. Should symptoms of fever or chills develop, the drug infusion should be stopped and acetaminophen and diphenhydramine hydrochloride should be given.

Although, as discussed above, various dosing and administration routes may be employed in order to provide anti-VEGF antibody therapy to recipient patients, the following dosing and administrative route is preferred. Anti-VEGF antibody (bevacizumab) is preferably administered by intravenous (IV) infusion. Bevacizumab is preferably not to be administered as an intravenous push or bolus. Bevacizumab treatment should not be initiated until at least 28 days following major surgery, and only after the surgical incision has fully healed. The first IV infusion is preferably delivered over a period of 90 minutes if the patient does not exhibit signs or symptoms of an infusion reaction. Occurrence of infusion reaction will necessitate rate reduction, interruption, or discontinuation. If the initial infusion is tolerated, the second IV infusion is preferably delivered over a period of 60 minutes. Subsequent infusions may be delivered over a period of 30 minutes, if infusion over 60 minutes is tolerated. Patients should continue treatment until disease progression or unacceptable toxicity. The recommended dosages are: 5 mg/kg body weight or 10 mg/kg body weight every 2 weeks when used in combination with intravenous 5-FU-based chemotherapy; 5 mg/kg body weight when used in combination with bolus-IFL (irinotecan, leucovorin (folinic acid), and fluorouracil); 10 mg/kg body weight when used in combination with FOLFOX4 (leucovorin (folinic acid), fluorouracil (5-FU), oxaliplatin (ELOXATIN®, a platinum-based anti-cancer preparation); 15 mg/kg body weight every 3 weeks in combination with carboplatin and paclitaxel. The composition is preferably administered at a dose of 5 mg/kg body weight every 2 weeks or 7.5 mg/kg body weight every 3 weeks when used in combination with a fluoropyrimidine-irinotecan or fluoropyrimidine-oxaliplatin based chemotherapy regimen in patients who have progressed on a first-line bevacizumab-containing regimen. For the treatment of glioblastoma, the recommended dosage is 10 mg/kg every 2 weeks.

In one embodiment, dosages for antibodies may be determined empirically in individuals who have been given one or more administration(s). Individuals are given incremental dosages of an antibody. To assess efficacy of anti-B7-H3 antibodies, a marker of the specific cancer disease state can be followed. These include direct measurements of tumor size via palpation or visual observation, indirect measurement of tumor size by x-ray or other imaging techniques; an improvement as assessed by direct tumor biopsy and microscopic examination of the tumor sample; the measurement of an indirect tumor marker (e.g., PSA for prostate cancer), a decrease in pain or paralysis; improved speech, vision, breathing or other disability associated with the tumor; increased appetite; or an increase in quality of life as measured by accepted tests or prolongation of survival. It will be apparent to one of skill in the art that the dosage will vary depending on the individual, the type of cancer, the stage of cancer, whether the cancer has begun to metastasize to other location in the individual, and the past and concurrent treatments being used.

Other formulations include suitable delivery forms known in the art including, but not limited to, carriers such as liposomes. See, for example, Mahato et al. (1997) "Cationic Lipid-Based Gene Delivery Systems: Pharmaceutical Perspectives," Pharm. Res. 14:853-859. Liposomal preparations include, but are not limited to, cytofectins, multilamellar vesicles and unilamellar vesicles.

In some embodiments, more than one antibody may be present. The antibodies can be monoclonal or polyclonal. Such compositions may contain at least one, at least two, at least three, at least four, at least five different antibodies that are reactive against carcinomas, adenocarcinomas, sarcomas, or adenosarcomas. Anti-B7-H3 antibody can be admixed with one or more antibodies reactive against carcinomas, adenocarcinomas, sarcomas, or adenosarcomas in organs including but not limited to ovary, breast, lung, prostate, colon, kidney, skin, thyroid, bone, upper digestive tract, and pancreas. In one embodiment, a mixture of different anti-B7-H3 antibodies is used. A mixture of antibodies, as they are often denoted in the art, may be particularly useful in treating a broader range of population of individuals.

VIII. METHODS OF ADMINISTRATION

The compositions of the present invention may be provided for the treatment, prophylaxis, and amelioration of one or more symptoms associated with a disease, disorder or infection by administering to a subject an effective amount of a pharmaceutical composition of the invention. In a preferred aspect, such compositions are substantially purified (i.e., substantially free from substances that limit its effect or produce undesired side-effects). In a specific embodiment, the subject is an animal, preferably a mammal such as non-primate (e.g., bovine, equine, feline, canine, rodent, etc.) or a primate (e.g., monkey such as, a cynomolgous monkey, human, etc.). In a preferred embodiment, the subject is a human.

Various delivery systems are known and can be used to administer the compositions of the invention, e.g., encapsulation in liposomes, microparticles, microcapsules, recombinant cells capable of expressing the antibody or fusion protein, receptor-mediated endocytosis (See, e.g., Wu et al. (1987) "Receptor-Mediated In Vitro Gene Transformation By A Soluble DNA Carrier System," J. Biol. Chem. 262: 4429-4432), construction of a nucleic acid as part of a retroviral or other vector, etc.

Methods of administering the molecules of the present invention include, but are not limited to, parenteral administration (e.g., intradermal, intramuscular, intraperitoneal, intravenous and subcutaneous), epidural, and mucosal (e.g., intranasal and oral routes). In a specific embodiment, the molecules of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety.

The invention also provides that the pharmaceutical compositions of the invention are packaged in a hermetically sealed container such as an ampoule or sachette indicating the quantity of such molecules. In one embodiment, the antibodies, antibody fragments or diabodies of such pharmaceutical compositions are supplied as a dry sterilized lyophilized powder or water free concentrate in a hermetically sealed container and can be reconstituted, e.g., with water or saline to the appropriate concentration for administration to a subject. Preferably, the molecules of the invention are supplied as a dry sterile lyophilized powder in a hermetically sealed container at a unit dosage of at least 5 µg, more preferably at least 10 µg, at least 15 µg, at least 25 µg, at least 50 µg, at least 100 µg, or at least 200 µg.

The lyophilized molecules of the invention should be stored at between 2 and 8° C. in their original container and the molecules should be administered within 12 hours, preferably within 6 hours, within 5 hours, within 3 hours, or within 1 hour after being reconstituted. In an alternative embodiment, such molecules of the invention are supplied in liquid form in a hermetically sealed container indicating the quantity and concentration of the molecule, fusion protein, or conjugated molecule. Preferably, the liquid form of such bi-specific monovalent diabodies or bi-specific monovalent Fc diabodies is supplied in a hermetically sealed container in which the molecules are present at a concentration of least 1 µg/ml, more preferably at least 2.5 µg/ml, at least 5 µg/ml, at least 10 µg/ml, at least 50 µg/ml, or at least 100 µg/ml.

In a specific embodiment, it may be desirable to administer the pharmaceutical compositions of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering a molecule of the invention, care must be taken to use materials to which the molecule does not absorb.

In another embodiment, the compositions can be delivered in a vesicle, in particular a liposome (See Langer (1990) "New Methods Of Drug Delivery," Science 249:1527-1533); Treat et al., in Liposomes in the Therapy of Infectious Disease and Cancer, Lopez-Berestein and Fidler (eds.), Liss, New York, pp. 353-365 (1989); Lopez-Berestein, pp. 3 17-327; see generally ibid.).

In yet another embodiment, the compositions can be delivered in a controlled release or sustained release system. Any technique known to one of skill in the art can be used to produce sustained release formulations comprising one or more molecules of the invention. See, e.g., U.S. Pat. No. 4,526,938; PCT publication WO 91/05548; PCT publication WO 96/20698; Ning et al. (1996) "Intratumoral Radioimmunotherapy Of A Human Colon Cancer Xenograft Using A Sustained-Release Gel," Radiotherapy & Oncology 39:179-189, Song et al. (1995) "Antibody Mediated Lung Targeting Of Long-Circulating Emulsions," PDA Journal of Pharmaceutical Science & Technology 50:372-397; Cleek et al. (1997) "Biodegradable Polymeric Carriers For A bFGF Antibody For Cardiovascular Application," Pro. Int'l. Symp. Control. Rel. Bioact. Mater. 24:853-854; and Lam et al. (1997) "Microencapsulation Of Recombinant Humanized Monoclonal Antibody For Local Delivery," Proc. Int'l. Symp. Control Rel. Bioact. Mater. 24:759-760, each of which is incorporated herein by reference in its entirety. In one embodiment, a pump may be used in a controlled release system (See Langer, supra; Sefton, (1987) "Implantable Pumps," CRC Crit. Rev. Biomed. Eng. 14:201-240; Buchwald et al. (1980) "Long-Term, Continuous Intravenous Heparin Administration By An Implantable Infusion Pump In Ambulatory Patients With Recurrent Venous Thrombosis," Surgery 88:507-516; and Saudek et al. (1989) "A Preliminary Trial Of The Programmable Implantable Medication System For Insulin Delivery," N. Engl. J. Med. 321:574-579). In another embodiment, polymeric materials can be used to achieve controlled release of antibodies (see e.g., MEDICAL APPLICATIONS OF CONTROLLED RELEASE, Langer and Wise (eds.), CRC Pres., Boca Raton, Fla. (1974); CONTROLLED DRUG BIOAVAILABILITY, DRUG PRODUCT DESIGN AND PERFORMANCE, Smolen and Ball (eds.), Wiley, New York (1984); Levy et al. (1985) "Inhibition Of Calcification Of Bioprosthetic Heart Valves By Local Controlled-Release Diphosphonate," Science 228:190-192; During et al. (1989) "Controlled Release Of Dopamine From A Polymeric Brain Implant: In Vivo Characterization," Ann. Neurol. 25:351-356; Howard et al. (1989) "Intracerebral Drug Delivery In Rats With Lesion-Induced Memory Deficits," J. Neurosurg. 7(1):105-112); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253). Examples of polymers used in sustained release formulations include, but are not limited to, poly(-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In yet another embodiment, a controlled release system can be placed in proximity of the therapeutic target (e.g., the lungs), thus requiring only a fraction of the systemic dose (see, e.g., Goodson, in MEDICAL APPLICATIONS OF CONTROLLED RELEASE, supra, vol. 2, pp. 115-138 (1984)). In another embodiment, polymeric compositions useful as controlled release implants are used according to Dunn et al. (See U.S. Pat. No. 5,945,155). This particular method is based upon the therapeutic effect of the in situ controlled release of the bioactive material from the polymer system. The implantation can generally occur anywhere within the body of the patient in need of therapeutic treatment. In another embodiment, a non-polymeric sustained delivery system is used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (See U.S. Pat. No. 5,888,533).

Controlled release systems are discussed in the review by Langer (1990, "New Methods Of Drug Delivery," Science 249:1527-1533). Any technique known to one of skill in the art can be used to produce sustained release formulations comprising one or more therapeutic agents of the invention. See, e.g., U.S. Pat. No. 4,526,938; International Publication Nos. WO 91/05548 and WO 96/20698; Ning et al. (1996) "Intratumoral Radioimmunotheraphy Of A Human Colon Cancer Xenograft Using A Sustained-Release Gel," Radiotherapy & Oncology 39:179-189, Song et al. (1995) "Antibody Mediated Lung Targeting Of Long-Circulating Emulsions," PDA Journal of Pharmaceutical Science & Technology 50:372-397; Cleek et al. (1997) "Biodegradable Polymeric Carriers For A bFGF Antibody For Cardiovascular Application," Pro. Int'l. Symp. Control. Rel. Bioact. Mater. 24:853-854; and Lam et al. (1997) "Microencapsulation Of Recombinant Humanized Monoclonal Antibody For Local Delivery," Proc. Int'l. Symp. Control Rel. Bioact. Mater. 24:759-760, each of which is incorporated herein by reference in its entirety.

Treatment of a subject can include a single treatment or, preferably, can include a series of treatments. In a preferred example, a subject is treated with molecules of the invention one time per week for between about 1 to 10 weeks, preferably between 2 to 8 weeks, more preferably between about 3 to 7 weeks, and even more preferably for about 4, 5, or 6 weeks. In other embodiments, the pharmaceutical compositions of the invention are administered once a day, twice a day, or three times a day. In other embodiments, the pharmaceutical compositions are administered once a week, twice a week, once every two weeks, once a month, once every six weeks, once every two months, twice a year or once per year. It will also be appreciated that the effective dosage of the molecules used for treatment may increase or decrease over the course of a particular treatment.

Having now generally described the invention, the same will be more readily understood through reference to the following examples, which are provided by way of illustration and are not intended to be limiting of the present invention unless specified.

Example 1

Treatment of Recurrent Glioblastoma Multiforme (GBM) with Anti-B7-H3 Antibody and Anti-VEGF Antibody In order to demonstrate the ability of a combined therapy involving agents that provide a binding ability that is specific for B7-H3 and a second binding ability that is specific for a cell-surface factor (or its receptor) that is involved in promoting tumor angiogenesis, patients suffering from glioblastoma multiforme (GBM) were treated with a humanized anti-B7-H3 antibody and with bevacizumab (AVASTIN®, an anti-angiogenic preparation).

Overview:

Six patients (4 males and 2 females), ranging in age from 26-68 were treated. Four of the patients were experiencing their third recurrence of cancer, one patient was experiencing a second recurrence of cancer, and one patient was experiencing a first recurrence of cancer. Four of the patients received bevacizumab. One patient received an alternative anti-VEGF therapy and one patient was naïve for anti-VEGF therapy. One patient had been on high-dose dexamethasone (8 mg/day) at baseline; one patient had been on a replacement dose prednisone (5 mg/day) for a secondary adrenal insufficiency; and the remaining four patients had not received steroids. Antibody treatment was designed to include one or more 50-day cycles in which antibody would be administered on days 1, 8, 15, and 22. The profiles of the patients are reported in Table 3.

TABLE 3

| Patient Code | Age | Gender | Recurrence | Anti-VEGF Therapy at baseline | Dexamethasone |
|---|---|---|---|---|---|
| NF | 42 | M | At $2^{nd}$ Recurrence; Recurred 15 months after diagnosis | None | No Dexamethasone at Baseline |
| MR | 42 | F | At $3^{rd}$ Recurrence; Recurred 8 months after second recurrence | Bevacizumab + CCNU for 7 months | No Dexamethasone At Baseline |
| GC | 68 | M | At $1^{st}$ Recurrence; Recurred 26 months after diagnosis | Cediranib for 26 months | Baseline Replacement Dose Prednisone |
| DK | 46 | M | At $3^{rd}$ Recurrence; Recurred 5 months after diagnosis | Bevacizumab + CCNU for 3 months | No Dexamethasone At Baseline |
| JK | 45 | F | At $3^{rd}$ Recurrence; Recurred 9 months after diagnosis | Bevacizumab for 1 year | No Dexamethasone At Baseline |
| DW | 60 | M | Recurrent disease; Recurred 3 months after diagnosis | Bevacizumab + CCNU for 2 months | High Dexamethasone At Baseline |

Patient NF

FIG. 1 shows the clinical progression of Patient NF. MRI scans of the patient's brain revealed 3 lesions. An initial cycle of humanized anti-B7-H3 antibody was administered at baseline. Row A shows the status of the patient's lesions at baseline (note that for Lesion 3, the arrow in Row A points to the site where the lesion is seen in Row B of the Figure; no evidence of Lesion 3 is seen in Row A of the figure). Row B shows the status of the patient's lesions prior to the initiation of a second planned cycle of anti-B7-H3 antibody administration. Row B reveals that the three lesions appear to have increased in size (a phenomenon known as "pseudo-progression"). Concurrent with such pseudo-progression, the patient experienced increased edema in the brain (fourth column), headaches and increased seizures. Anti-B7-H3 antibody therapy was stopped and the patient was provided with 3 doses of bevacizumab and one dose of CCNU (Row C).

Significantly, the administered anti-B7-H3 antibody had a biological half-life of 2-3 weeks. Thus, at the time of the MRI analysis of Row C, the patient's level of bevacizumab had decreased to approximately 25% of maximum. As seen in Row C, of FIG. 1, a dramatic reduction in lesion size and edema was observed, along with the resolution of the patient's headaches and seizures.

The data are interpreted as indicating that the combination treatment of bevacizumab and anti-B7-H3 antibody acted synergistically to improve the patient's condition. After 1 cycle of anti-B7-H3 antibody treatment, a significant increase in lesion enhancement with headaches and increased seizures was observed. However, after receiving 3 doses of bevacizumab+CCNU, a marked reduction of all MRI findings was observed. The patient has been clinically stable for more than 10 months after the last dose of anti-B7-H3 antibody. The patient's overall survival is more than 2 years, 7 months from the date of diagnosis.

Patient MR

Figure 2A:
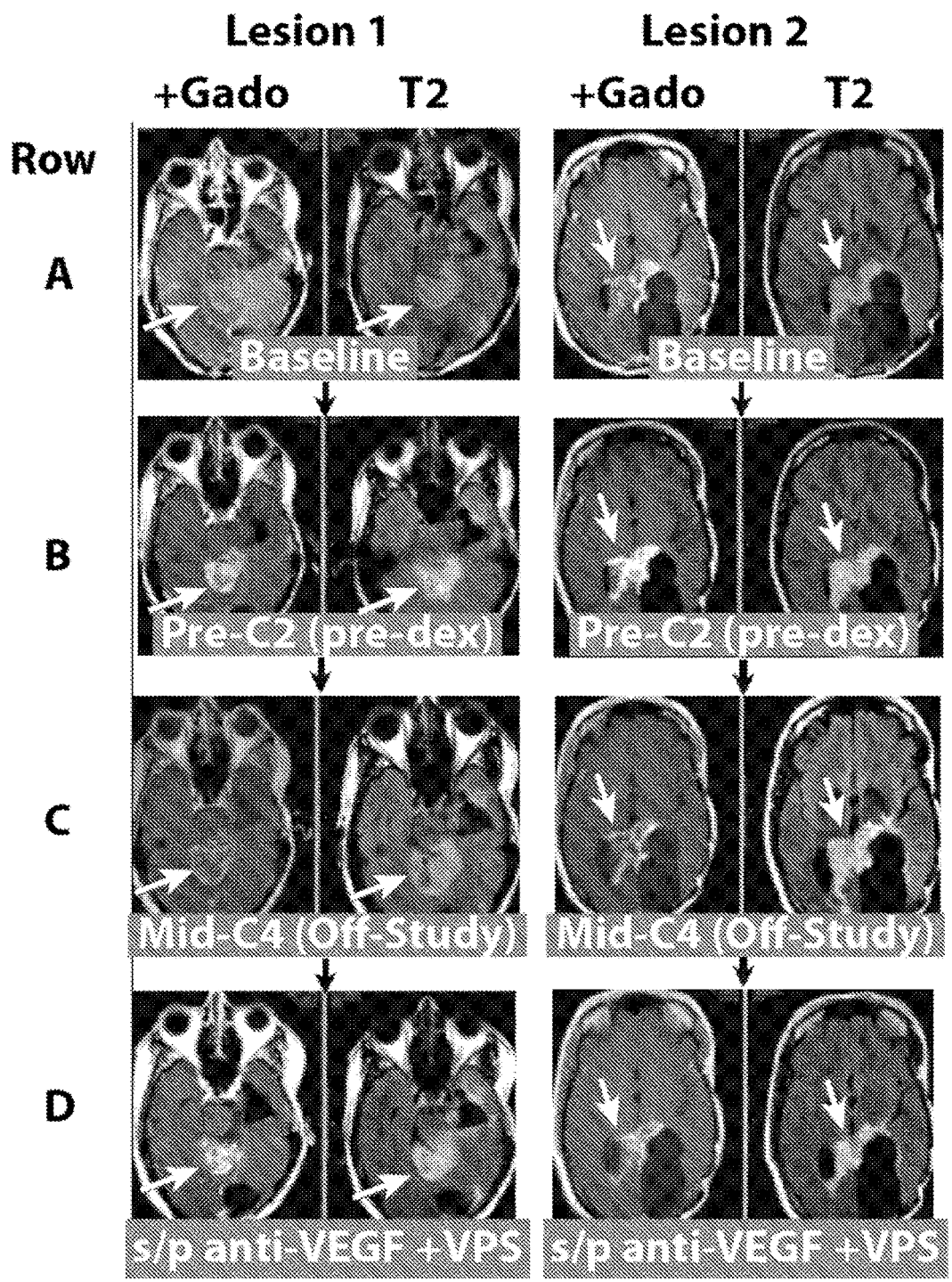
FIGS. 2A-2C show MM scans of glioblastoma Patient MR. The first, second, third and fourth columns are, respectively, MM scans of a first, second, third and fourth observed lesion. Row A shows the status of the patient's lesions at baseline. Row B shows the status of the patient's lesions prior to the initiation of a second planned cycle of anti-B7-H3 antibody (hBRCA84D) administration. Row C shows the state of Lesions 1-5 at the time anti-B7-H3 antibody therapy was stopped. The status post administration of bevacizumab is shown in Row D of the Figures.
Figure 2B:
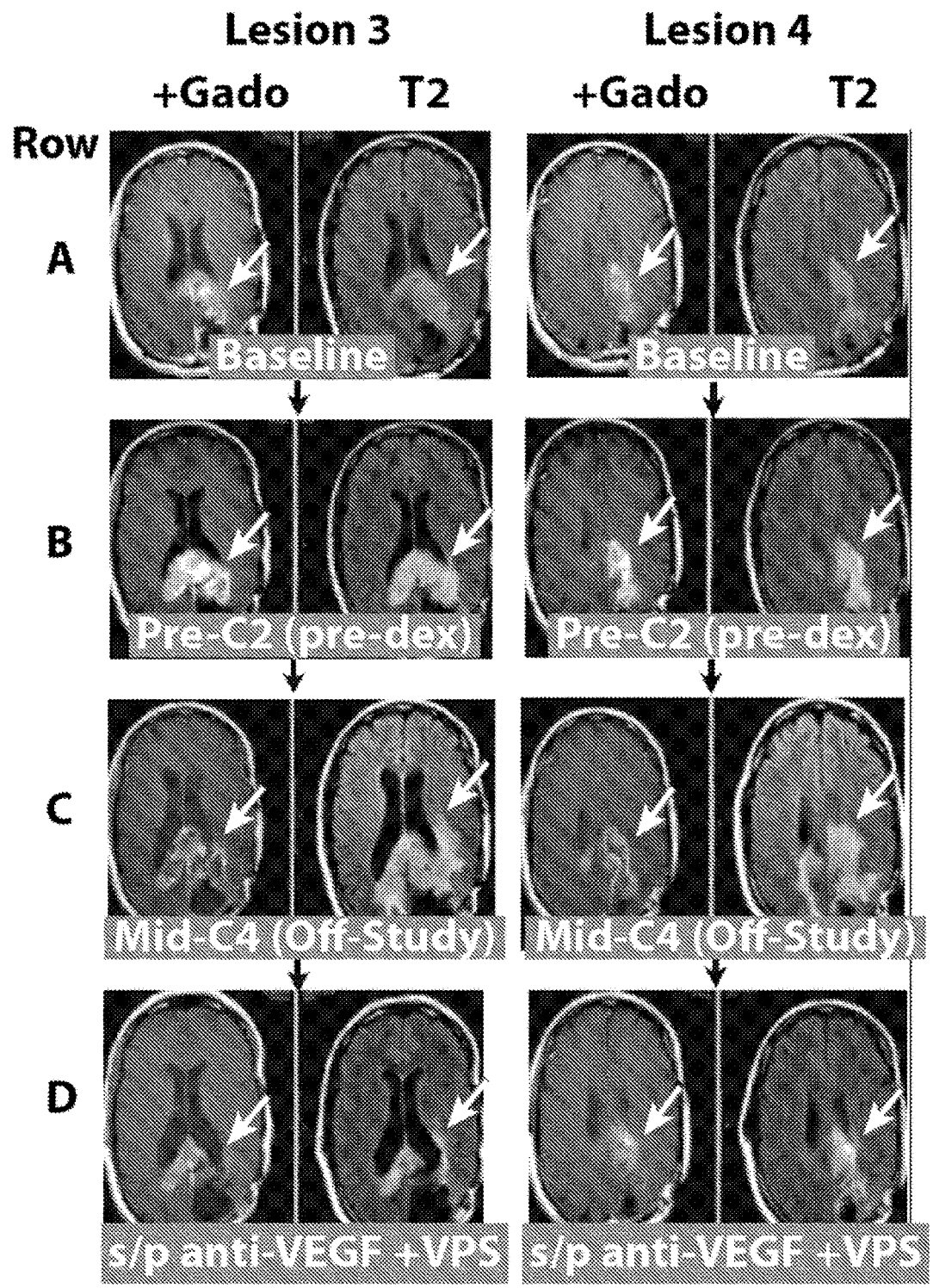
Figure 2C:
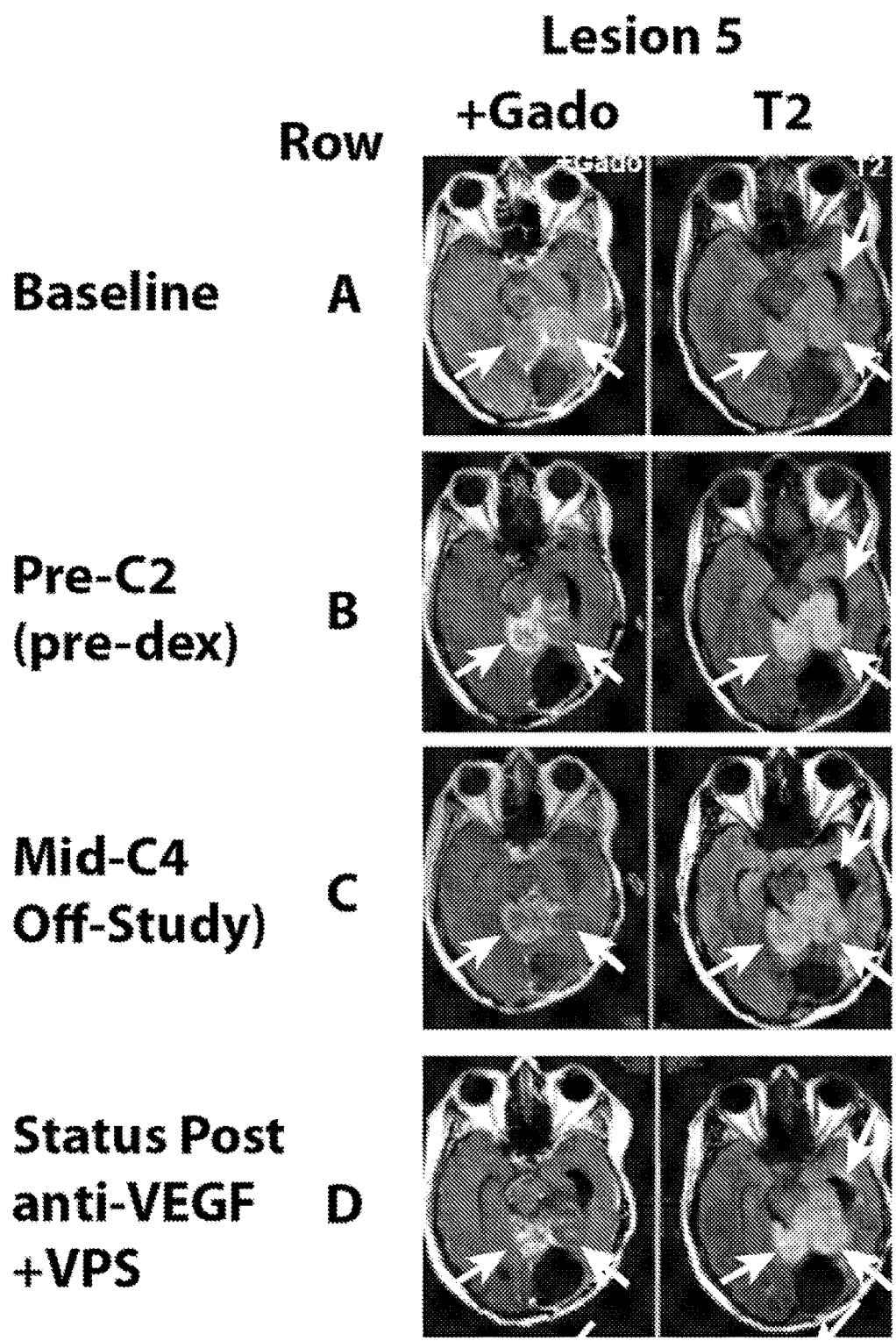
Figure 3:
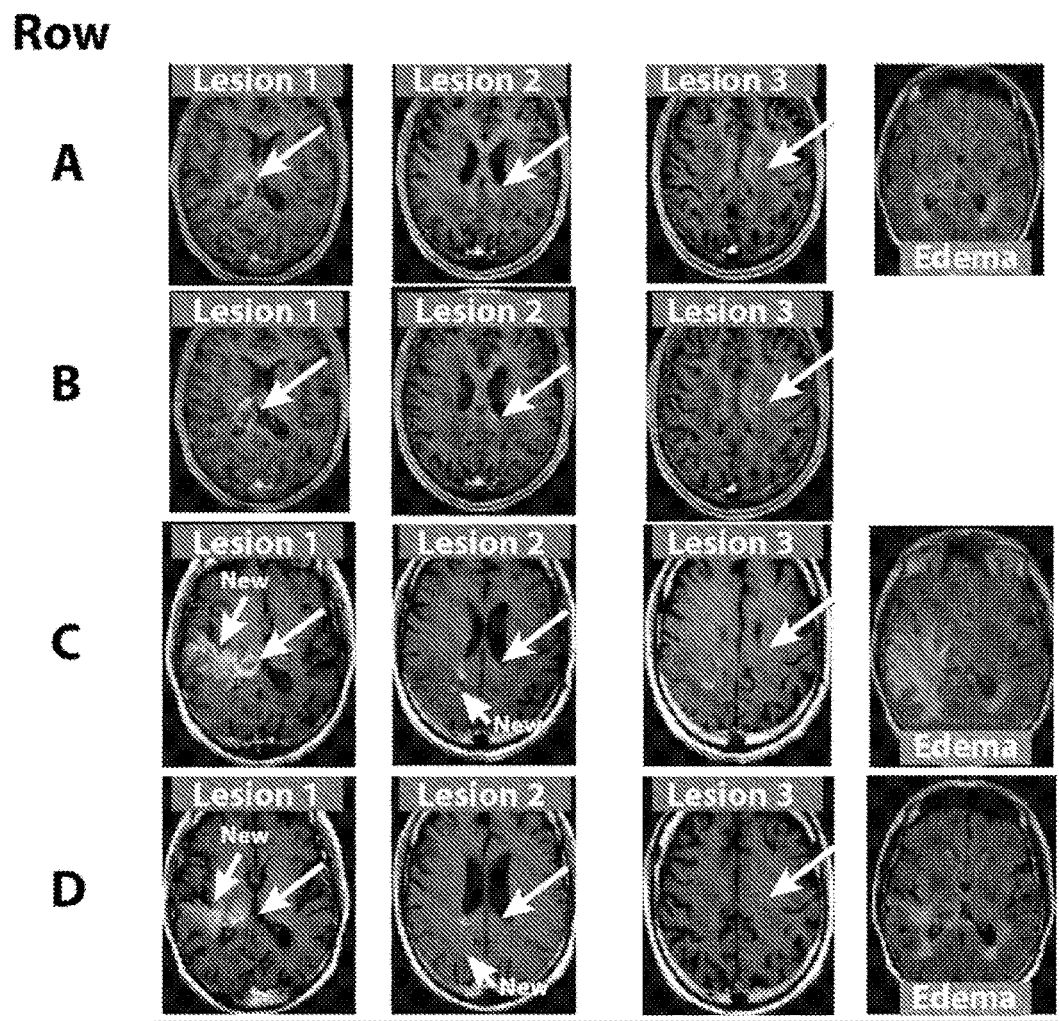
FIG. 3 shows MRI scans of glioblastoma Patient GC. Row A shows the status of the patient's lesions at baseline. Row B (images taken prior to the start of cycle 6) shows that the lesions were stable through 5-6 cycles of anti-B7-H3 antibody (hBRCA84D) administration, with a possible minor response. Row C (images taken at the end of cycle 6) show signs of progressive disease, including the occurrence of new lesions. The patient experienced cognitive decline and edema was noted in the patient's brain (Row C, fourth column). Row D shows MRI images taken after 2 doses of bevacizumab. As is evident, lesions and edema were found to decrease in size and extent. Cognition was observed to improve, but was not at baseline.

FIGS. 2A-2C show the clinical progression of Patient MR. Patient MR exhibited secondary glioblastoma and possessed glioblastoma characterized by the IDH1 mutant (Ichimura, K. et al. (2009) "*IDH1 Mutations Are Present In The Majority Of Common Adult Gliomas But Rare In Primary Glioblastomas,*" Neuro. Oncol. 11(4):341-347). A characteristic of glioblastoma associated with the IDH1 mutation is that such tumors are non-contrast enhanced (Carillo, J. A. et al. (2012) "*Relationship between Tumor Enhancement, Edema, IDH1 Mutational Status, MGMT Promoter Methylation, and Survival in Glioblastoma,*" Amer. J. Neuroradiol. 10.3174/ajnr. A2950, pages 1-7).

MRI scans of the patient's brain revealed 5 lesions. MRI scans of lesions 1-4 are shown in FIGS. 2A-2B; MRI scans of lesion 5 are shown in FIG. 2C. To assess the lesions of Patient MR, MRI imaging was done in the presence of the contrast agent, gadolinium (FIGS. 2A-2C, "GADO") with and without T2 weighting (FIGS. 2A-2C, T2). As will be appreciated, the signal in MRI images is high (bright) or low (dark), depending on the pulse sequence used, and the type of tissue in the image region of interest. Features appearing bright on a T2-weighted image include increased water, as in edema or inflammation. Features appearing dark on a T2-weighted image include calcification, fibrous tissue, protein-rich fluid, and flow void. Tumors of Patient MR had both contrast-enhancing and non-enhancing (T2 bright) components.

An initial cycle of humanized anti-B7-H3 antibody was administered at baseline. After the second cycle had started, dexamethasone was administered to the patient (2 mg bid). In the middle of Cycle 3, anti-B7-H3 antibody therapy was stopped and the patient was provided with 1 dose of bevacizumab and a ventriculoperitoneal shunt (VPS). The patient had a significant amount of anti-B7-H3 antibody at the time of bevacizumab administration.

In FIGS. 2A-2C, Row A shows the status of the patient's lesions at baseline. Row B shows the status of the patient's lesions prior to the initiation of a second planned cycle of anti-B7-H3 antibody administration. Row B of FIGS. 2A-2B reveal that Lesions 1-4 increased in size, and that increased edema in the brain (fourth column) was evident. The data is interpreted as showing pseudo-progression. Row C of FIGS. 2A-2B reveals the state of Lesions 1-4 at the time anti-B7-H3 antibody therapy was stopped. The patient was then provided with 1 dose of bevacizumab and a ventriculoperitoneal shunt was provided. The status post administration of bevacizumab is shown in Row D of the Figures. As seen in Row D of FIGS. 2A-2B, a dramatic reduction in lesion size and edema for Lesions 1-4 was observed.

As shown in FIG. 2C, Lesion 5 of the patient failed to respond to the therapy. Row A shows the status of Lesion 5 at baseline. Row B shows the status of Lesion 5 prior to the initiation of a second planned cycle of anti-B7-H3 antibody administration. Row C reveals the state of Lesion 5 at the time anti-B7-H3 antibody therapy was stopped. The status post administration of bevacizumab is shown in Row D. Typical of IDH-mutant gliomas (see lower right arrow) much of tumor was never previously enhancing. Most of the tumor developed marked enhancement with anti-B7-H3 antibody (cycle 2). Tumor size remained stable to decreased after 1 dose of bevacziumab. Lesion 5 (lower right arrow) never enhanced much with anti-B7-H3 antibody therapy and grew steadily throughout the course of treatment. Lesion 5 growth trapped left ventricle (see upper right arrow), and the patient needed a VP shunt. The patient's cognition and gait improved.

The data of FIGS. 2A-2C are interpreted as indicating that the combination treatment of bevacizumab and anti-B7-H3 antibody acted synergistically to improve the patient's condition with respect to Lesions 1-4, but that Lesion 5 grew steadily throughout, without any treatment effect. Lesions 1-4 developed marked enhancement after 1 cycle (having previously never had much enhancement, as is typical of IDH1-mutant gliomas). Treatment effect was symptomatic; the patient experienced neurological decline (ataxia and short term memory loss) upon going off study. After 1 dose of bevacizumab, most of tumor was stable to mildly decreased compared to baseline (see, e.g., Lesion 2). The treatment effect thus eventually caused tumor shrinkage; tumor heterogeneity resulted in mixed response.

Currently, the patient is neurologically improved from clinical nadir 5 months after the last dose of anti-B7-H3 antibody. The patient has been clinically stable for more than 10 months after the last dose of anti-B7-H3 antibody. The patient's overall survival is more than 3 years, 5 months from the date of diagnosis.

Patient GC

Figure 4:
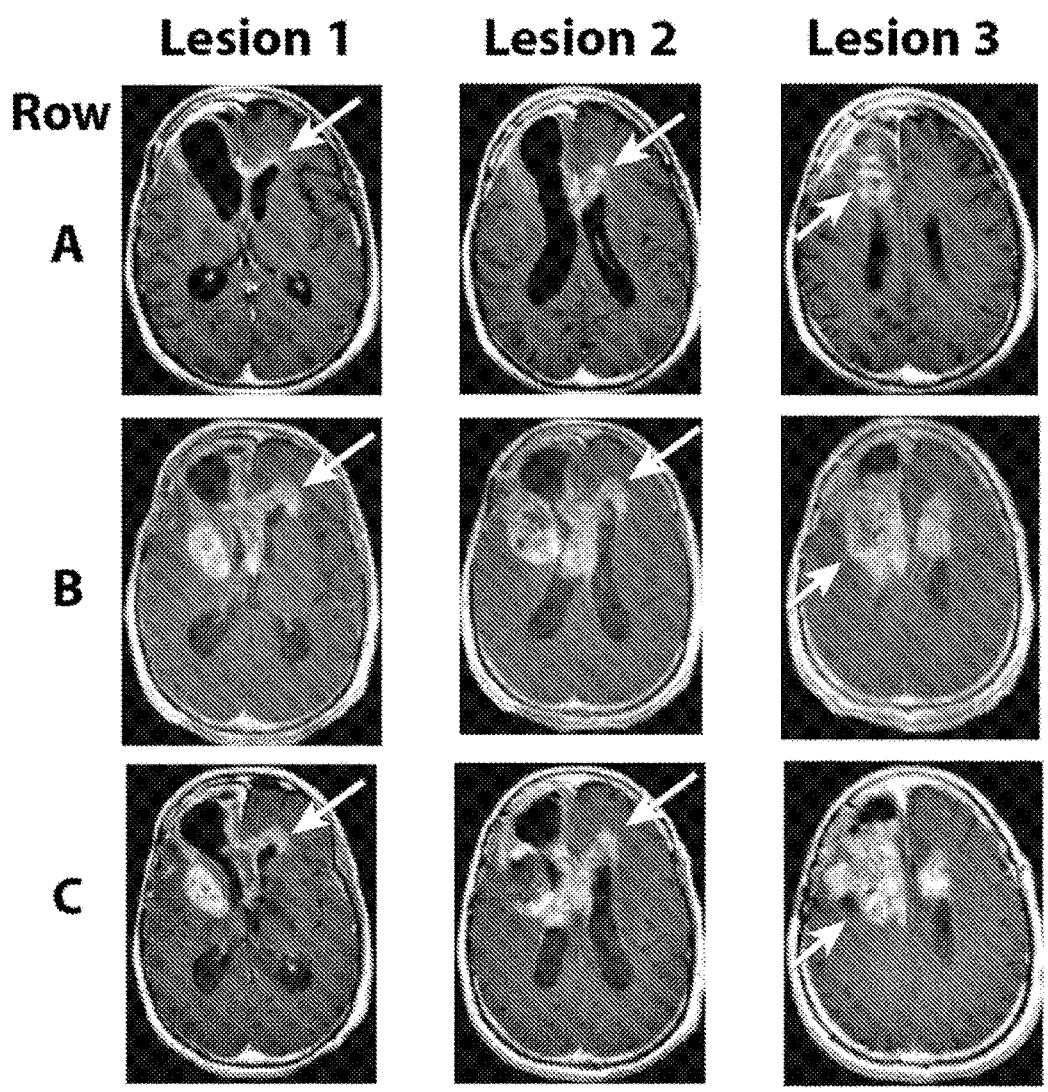
FIG. 4 shows MRI scans of glioblastoma Patient DK. Row A shows the status of the patient's lesions at baseline. Row B (images taken in the middle of cycle 2) shows progression and pseudo-progression of the disease. Row C (images taken post administration of 2 doses of bevacizumab shows a mild response, with cognition and gait mildly improved.

FIG. 4 shows the clinical progression of Patient GC. MRI scans of the patient's brain revealed 3 lesions. An initial cycle of humanized anti-B7-H3 antibody was administered at baseline. After cycle 1, markedly increased enhancement with cognitive and gait decline were observed.

Row A shows the status of the patient's lesions at baseline. Row B (images taken prior to the start of cycle 6) shows that the lesions were stable through 5-6 cycles of anti-B7-H3 antibody administration, with a possible minor response. Row C (images taken at the end of cycle 6) show signs of progressive disease, including the occurrence of new lesions. The patient experienced cognitive decline and edema was noted in the patient's brain (Row C, fourth column). Row D shows MRI images taken after 2 doses of bevacizumab. As is evident, lesions and edema were found to decrease in size and extent. Cognition was observed to improve, but was not at baseline.

The data of FIG. 4 are interpreted as indicating that the combination treatment of bevacizumab and anti-B7-H3 antibody acted synergistically to improve the patient's condition with respect to the observed lesions. The patient responded to bevacizumab treatment after anti-B7-H3 antibody treatment as indicated by the fact that the prior target lesions were smaller after bevacizumab treatment than prior to anti-B7-H3 antibody treatment. The patient's overall survival is more than 3 years from the date of diagnosis.

Patient DK

FIG. 4 shows the clinical progression of Patient DK. MRI scans of the patient's brain revealed 3 lesions. An initial cycle of humanized anti-B7-H3 antibody was administered at baseline. On the first day of cycle 2 (C2D1) treatment was amended to include the administration of dexamethasone (2 mg bid). Row A shows the status of the patient's lesions at baseline. Row B (images taken in the middle of cycle 2) shows progression and pseudo-progression of the disease.

Row C (images taken post administration of 2 doses of bevacizumab shows a mild response, with cognition and gait mildly improved.

The data of FIG. 4 are interpreted as indicating both pseudo-progression and progression, and that the combination treatment of bevacizumab and anti-B7-H3 antibody provided a mild response and acted synergistically to improve the patient's condition with respect to the observed lesions. The patient responded to bevacizumab treatment after anti-B7-H3 antibody treatment as indicated by the fact that the prior target lesions were smaller after bevacizumab treatment than prior to anti-B7-H3 antibody treatment.

The patient was in declining health in a hospice 10 weeks after the last dose of anti-B7-H3 antibody. The patient's overall survival is more than 1 year, 10 months from the date of diagnosis.

Patient JK

Figure 5:
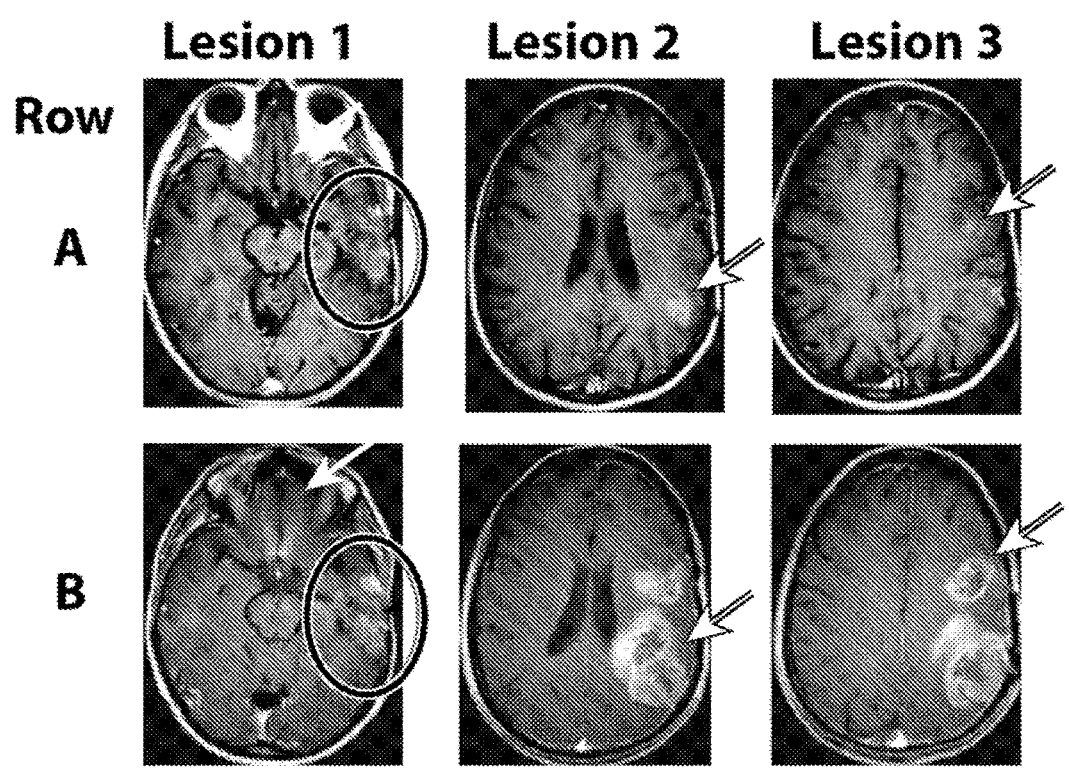
FIG. 5 shows MRI scans of glioblastoma Patient JK. Row A shows the status of the patient's lesions at baseline. Row B (images taken prior to cycle 2) shows progression and pseudo-progression of the disease.

FIG. 5 shows the clinical progression of Patient JK. MRI scans of the patient's brain revealed 3 lesions. An initial cycle of humanized anti-B7-H3 antibody was administered at baseline. After cycle 1, treatment was amended to include the administration of dexamethasone (2 mg bid). A mild decline in language and right arm dexterity was observed. Row A shows the status of the patient's lesions at baseline. Row B (images taken prior to cycle 2) shows progression and pseudo-progression of the disease. After administration of bevacizumab and CCNU×1 month, the patient shows stable language and right arm dexterity. A further MRI scan is pending.

Patient DW

Figure 6:
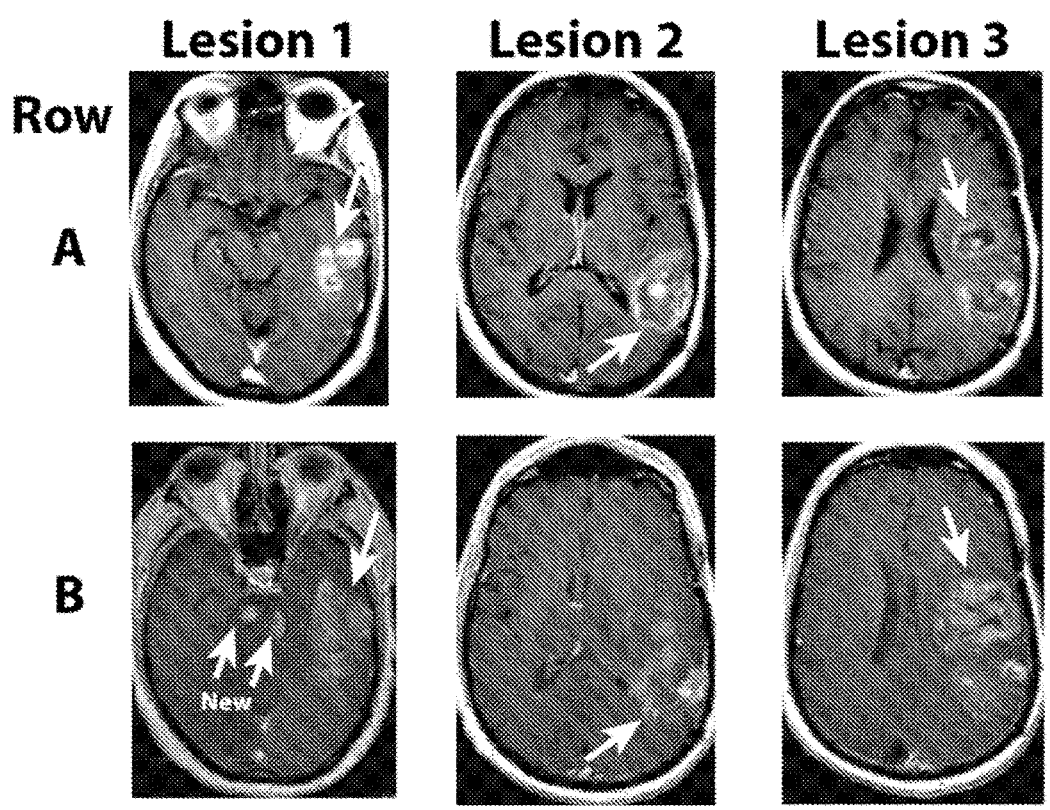
FIG. 6 shows MRI scans of glioblastoma Patient DW. Row A shows the status of the patient's lesions at baseline. Row B (images taken prior to cycle 2) shows progression of the disease.

FIG. 6 shows the clinical progression of Patient DW. MRI scans of the patient's brain revealed 3 lesions. An initial cycle of humanized anti-B7-H3 antibody was administered at baseline. Row A shows the status of the patient's lesions at baseline. After cycle 1, disease progression was noted with severe language and right arm and leg decline. The patient received 1 dose of bevacizumab, but continued to experience severe language and right arm and leg decline. Row B (images taken prior to cycle 2) shows progression of the disease. The patient succumbed to illness 5 weeks after the last dose of anti-B7-H3 antibody (overall survival was 14 months from diagnosis). The patient evidenced no clinical response to bevacizumab after anti-B7-H3 antibody treatment. The absence of response is possibly due to high baseline steroids or a particularly refractory disease.

Figure 7:
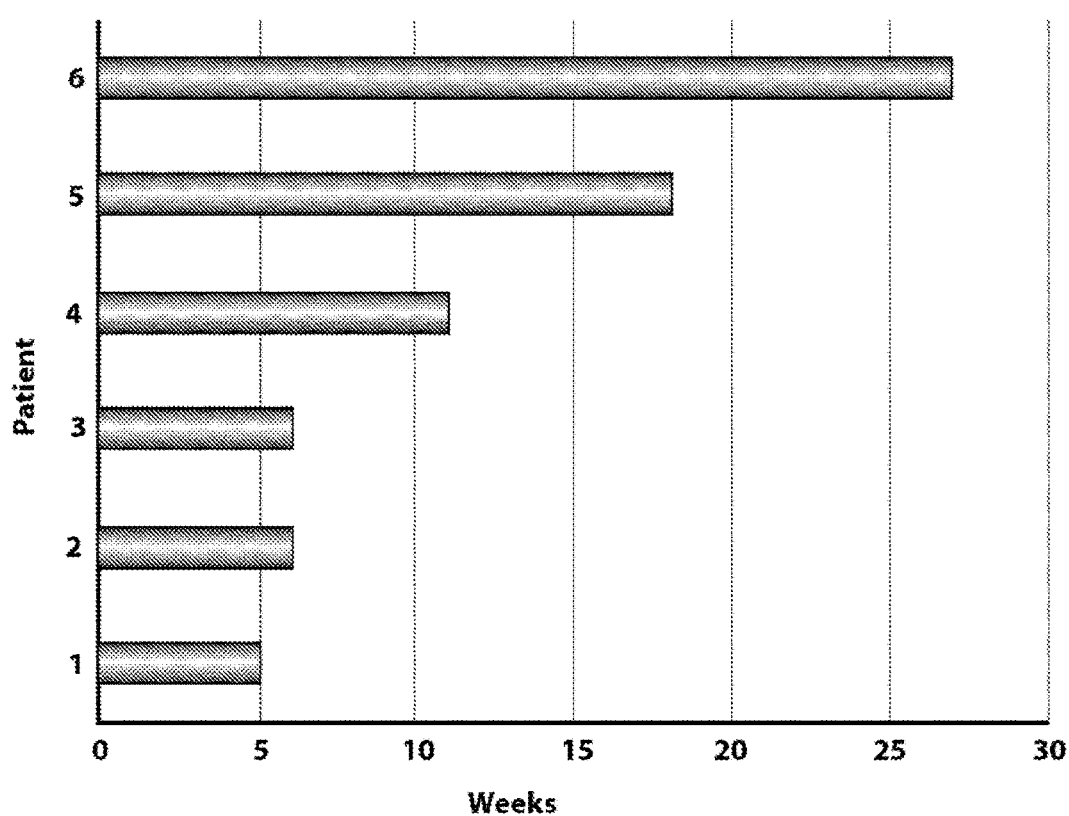
FIG. 7 shows the time on study for the 6 treated patients.

In conclusion, the data show that a treatment effect (increased enhancement) occurs (pseudo-progression). The treatment effect appears to be associated with tumor response and with observable neurological symptoms, which may not be completely reversible. Bevacizumab appears to synergize or perhaps reduce the treatment effect. A high baseline dose of dexamethasone appears to result in resistance. The anti-B7-H3 antibody treatment was well tolerated. FIG. 7 shows the time on study for the 6 treated patients.

Example 2

Evaluation of Patients Receiving Anti-B7-H3 Antibody

In the course of an ongoing clinical trial to assess the efficacy of anti-B7-H3 antibody therapy in the treatment of cancer, the levels of soluble B7-H3 ("sB7-H3") in the recipient patients was measured. The level of sB7-H3 in recipient patients prior to treatment was zero.

Figure 8:
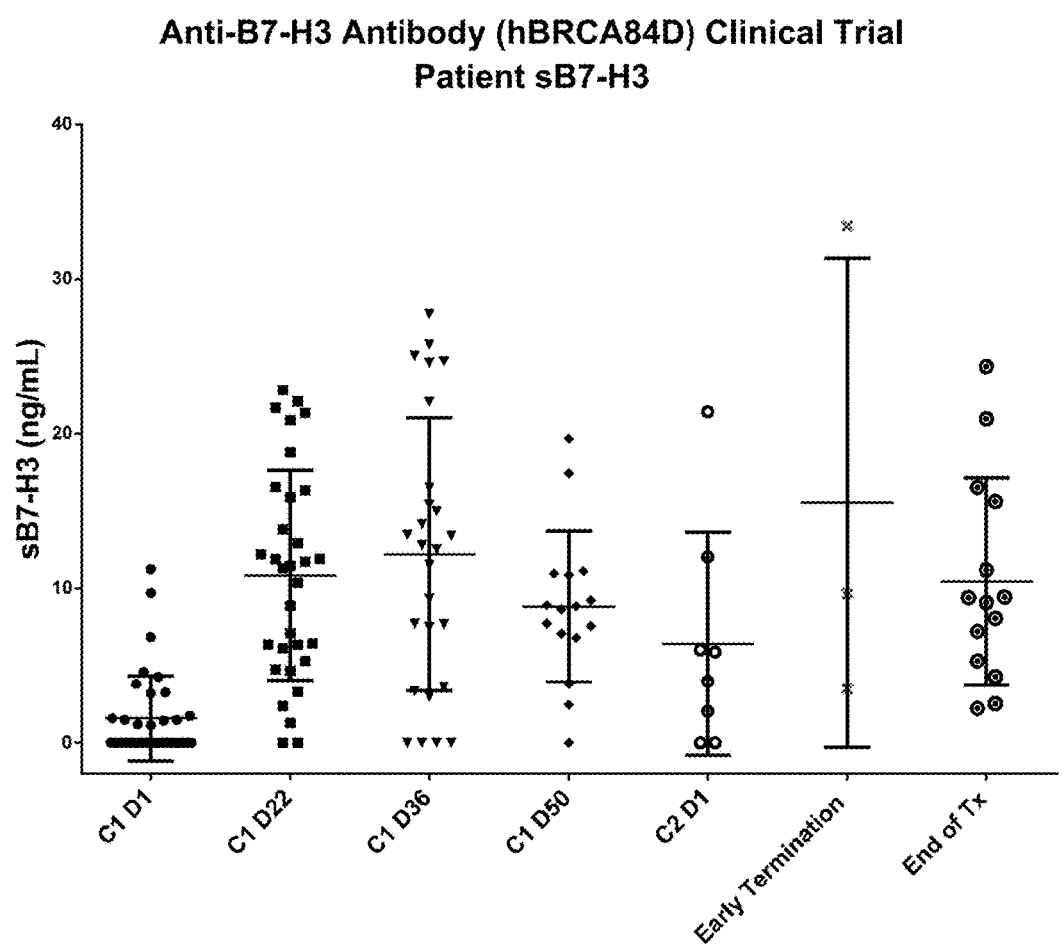
FIG. 8 shows the level of sB7-H3 in all patients receiving anti-B7-H3 antibody (hBRCA84D) at different cycles (C) and days (D) of treatment.
Figure 9:
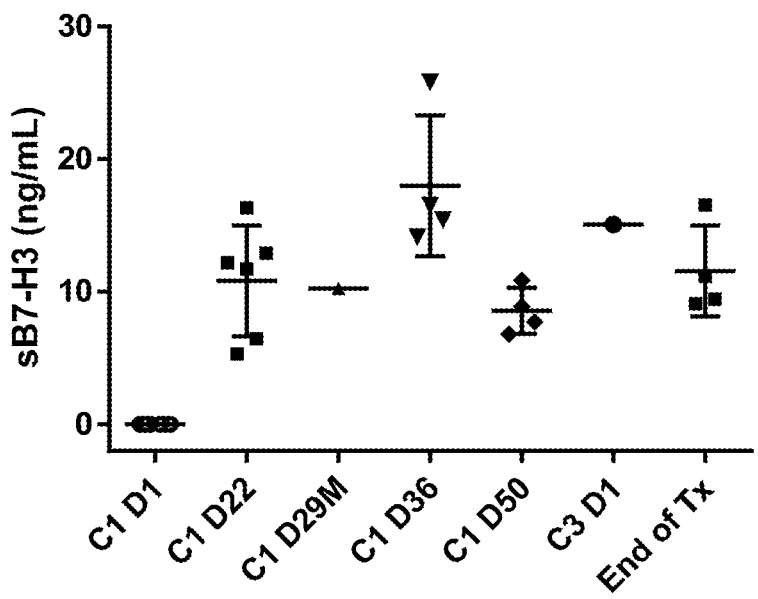
FIG. 9 shows the level of sB7-H3 in glioblastoma patients receiving anti-B7-H3 antibody (hBRCA84D) at different cycles (C) and days (D) of treatment.

As shown in FIG. 8 (all patients) and FIG. 9 (glioblastoma patients), the level of sB7-H3 in recipient patients increased throughout the first cycle of treatment, eventually declining as the treatment continues. This increase may reflect the death (and disruption) of tumor cells or the cleavage and release of membrane bound B7-H3, as a consequence of the therapy. The release of the sB7-H3 in recipient patients is a marker of progressive disease.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth

What is claimed is:

1. A method of treating glioblastoma comprising administering to a recipient patient in need thereof[1,1]:
   a) an antibody, an antibody fragment thereof, or a diabody that specifically binds B7-H3, wherein said antibody, antibody fragment thereof, or diabody that specifically binds B7-H3 comprises:
   (1) a light chain variable domain that comprises $CDR_1$ (SEQ ID NO: 7), $CDR_2$ (SEQ ID NO: 9) and $CDR_3$ (SEQ ID NO: 11), and a heavy chain variable domain that comprises $CDR_1$ (SEQ ID NO: 15), $CDR_2$ (SEQ ID NO: 17) and $CDR_3$ (SEQ ID NO: 19); or
   (2) a light chain variable domain that comprises $CDR_1$ (SEQ ID NO: 23), $CDR_2$ (SEQ ID NO: 25) and $CDR_3$ (SEQ ID NO: 27), and a heavy chain variable domain that comprises $CDR_1$ (SEQ ID NO: 31), $CDR_2$ (SEQ ID NO: 33) and $CDR_3$ (SEQ ID NO: 35); or
   (3) a light chain variable domain that comprises $CDR_1$ (SEQ ID NO: 39), $CDR_2$ (SEQ ID NO: 41) and CDR₃ (SEQ ID NO: 43), and a heavy chain variable domain that comprises CDR₁ (SEQ ID NO: 47), CDR₂ (SEQ ID NO: 49) and CDR₃ (SEQ ID NO: 51);
and
b) an antibody, or an antibody fragment thereof that specifically binds VEGF or VEGFR;
wherein said glioblastoma is characterized by cancer cells that express B7-H3.

2. The method of claim 1, wherein said antibody, or antibody fragment thereof that specifically binds VEGF or VEGFR is:
   (A) a VEGF antagonist; or
   (B) a VEGFR antagonist.

3. The method of claim 1, wherein said antibody, or antibody fragment thereof, that specifically binds VEGF or VEGFR:
   A. competes for VEGF binding with bevacizumab; or
   B. has the three heavy chain CDRs and the three light chain CDRs of bevacizumab.

4. The method of claim 1, wherein said antibody, antibody fragment thereof, or diabody that specifically binds B7-H3 is an anti-B7-H3 antibody having:
   (A) a light chain variable domain that comprises CDR₁ (SEQ ID NO: 39), CDR₂ (SEQ ID NO: 41) and CDR₃ (SEQ ID NO: 43) of the light chain of BRCA84D;
   (B) a heavy chain variable domain that comprises CDR₁ (SEQ ID NO: 47), CDR₂ (SEQ ID NO: 49) and CDR₃ (SEQ ID NO: 51) of the heavy chain of BRCA84D; and
   (C) an Fc region that comprises the substitutions: L235V, F243L, R292P, Y300L, and P396L.

5. The method of claim 4, wherein said antibody, antibody fragment thereof, or diabody that specifically binds B7-H3 is a humanized anti-B7-H3 antibody that comprises:
   (A) a variable light chain having the amino acid sequence of hBRCA84D-2 VL (SEQ ID NO:69); and
   (B) a variable heavy chain having the amino acid sequence of hBRCA84D-2 VH (SEQ ID NO:79);
and said antibody, or antibody fragment thereof, that specifically binds VEGF or VEGFR is bevacizumab.

6. The method of claim 1, wherein said antibody, antibody fragment thereof, or diabody that specifically binds B7-H3 and said antibody, or antibody fragment thereof, that specifically binds VEGF or VEGFR are administered to said patient concurrently.

7. The method of claim 1, wherein said antibody, antibody fragment thereof, or diabody that specifically binds B7-H3 and said antibody, or antibody fragment thereof, that specifically binds VEGF or VEGFR are administered to said patient sequentially, wherein the second of said antibody, antibody fragment thereof, or diabody that specifically binds B7-H3, or said antibody, or antibody fragment thereof, that specifically binds VEGF or VEGFR is administered to said patient within 5 half-lives after the administration of the first of said antibody, antibody fragment thereof, or diabody that specifically binds B7-H3, or said antibody, or antibody fragment thereof, that specifically binds VEGF or VEGFR.

8. The method of claim 1, wherein said antibody, antibody fragment thereof, or diabody that specifically binds B7-H3 comprises a light chain variable domain that comprises CDR₁ (SEQ ID NO: 7), CDR₂ (SEQ ID NO: 9) and CDR₃ (SEQ ID NO: 11), and a heavy chain variable domain that comprises CDR₁ (SEQ ID NO: 15), CDR₂ (SEQ ID NO: 17) and CDR₃ (SEQ ID NO: 19).

9. The method of claim 1, wherein said antibody, antibody fragment thereof, or diabody that specifically binds B7-H3 comprises a light chain variable domain that comprises CDR₁ (SEQ ID NO: 23), CDR₂ (SEQ ID NO: 25) and CDR₃ (SEQ ID NO: 27), and a heavy chain variable domain that comprises CDR₁ (SEQ ID NO: 31), CDR₂ (SEQ ID NO: 33) and CDR₃ (SEQ ID NO: 35).

10. The method of claim 1, wherein said antibody, antibody fragment thereof, or diabody that specifically binds B7-H3 comprises a light chain variable domain that comprises CDR₁ (SEQ ID NO: 39), CDR₂ (SEQ ID NO: 41) and CDR₃ (SEQ ID NO: 43), and a heavy chain variable domain that comprises CDR₁ (SEQ ID NO: 47), CDR₂ (SEQ ID NO: 49) and CDR₃ (SEQ ID NO: 51).

\* \* \* \* \*